(12) United States Patent
Yamaguchi et al.

(10) Patent No.: US 7,884,234 B2
(45) Date of Patent: Feb. 8, 2011

(54) N-PHENYLOXAMIDE DERIVATIVES

(75) Inventors: Youichi Yamaguchi, Kawasaki (JP); Takeshi Yanase, Tokyo (JP); Susumu Muto, Machida (JP); Akiko Itai, Tokyo (JP)

(73) Assignee: Institute of Medicinal Molecular Design, inc., Tokyo (JP)

( * ) Notice: Subject to any disclaimer, the term of this patent is extended or adjusted under 35 U.S.C. 154(b) by 333 days.

(21) Appl. No.: 11/870,741

(22) Filed: Oct. 11, 2007

(65) Prior Publication Data

US 2009/0215899 A9    Aug. 27, 2009

Related U.S. Application Data

(60) Provisional application No. 60/851,302, filed on Oct. 13, 2006.

(30) Foreign Application Priority Data

Oct. 12, 2006  (JP) ............................. 2006-278529

(51) Int. Cl.
*C07C 229/00* (2006.01)
(52) U.S. Cl. ....................... 562/456; 514/563
(58) Field of Classification Search ........................ None
See application file for complete search history.

(56) References Cited

U.S. PATENT DOCUMENTS

| | | | |
|---|---|---|---|
| 5,750,530 A | 5/1998 | Bryans et al. | |
| 5,869,501 A | 2/1999 | Hirayama et al. | |
| 5,891,877 A | 4/1999 | Brocchini et al. | |
| 6,589,970 B2 | 7/2003 | Commons et al. | |
| 6,599,925 B2 | 7/2003 | Elokdah et al. | |
| 6,800,654 B2 | 10/2004 | Mayers et al. | |
| 6,972,340 B2 | 12/2005 | Liu et al. | |
| 7,056,943 B2 | 6/2006 | Elokdah et al. | |
| 7,074,817 B2 | 7/2006 | Elokdah et al. | |
| 7,101,903 B2 | 9/2006 | Elokdah et al. | |
| 7,265,148 B2 | 9/2007 | Hu | |
| 7,291,639 B2 | 11/2007 | Elokdah | |
| 2002/0035137 A1 | 3/2002 | Liu et al. | |
| 2005/0070584 A1 | 3/2005 | Havran et al. | |
| 2005/0070585 A1 | 3/2005 | Elokdah et al. | |
| 2005/0096377 A1 | 5/2005 | Hu | |
| 2005/0119327 A1 | 6/2005 | Hu | |
| 2005/0124656 A1 | 6/2005 | Swinnen et al. | |
| 2005/0124664 A1* | 6/2005 | Sartori et al. ................ | 514/341 |
| 2005/0124667 A1 | 6/2005 | Sartori et al. | |
| 2005/0143384 A1 | 6/2005 | Sartori et al. | |
| 2007/0185118 A1 | 8/2007 | Hooft Van Huijsduijnen et al. | |
| 2007/0276011 A1 | 11/2007 | Muto et al. | |

FOREIGN PATENT DOCUMENTS

| | | |
|---|---|---|
| EP | 1666469 A1 | 6/2006 |
| GB | 2372740 A | 9/2002 |
| JP | 2004-531455 A | 10/2004 |
| JP | 2005-51661 A | 6/2005 |
| WO | 95/21832 A1 | 8/1995 |
| WO | 95/32190 A2 | 11/1995 |
| WO | 96/16940 A1 | 6/1996 |
| WO | WO 02/18323 A1 | 3/2002 |
| WO | WO 0218323 A2 * | 3/2002 |
| WO | 03/000253 A1 | 1/2003 |
| WO | 03/000258 A1 | 1/2003 |
| WO | 03/000649 A1 | 1/2003 |
| WO | 03/000671 A1 | 1/2003 |
| WO | 03/000684 A1 | 1/2003 |
| WO | 2004/052856 A1 | 6/2004 |
| WO | 2004/052893 A2 | 6/2004 |
| WO | 2005/030192 A1 | 4/2005 |
| WO | 2005/030204 A1 | 4/2005 |
| WO | 2005/030715 A1 | 4/2005 |

(Continued)

OTHER PUBLICATIONS

English Language Abstract of JP 2005-51661 A.

(Continued)

*Primary Examiner*—Sudhakar Katakam
(74) *Attorney, Agent, or Firm*—Greenblum & Bernstein, P.L.C.

(57) ABSTRACT

A compound represented by the following general formula (I) or a salt thereof, or a hydrate thereof or a solvate thereof having an inhibitory action against plasminogen activator inhibitor-1 (PAI-1):

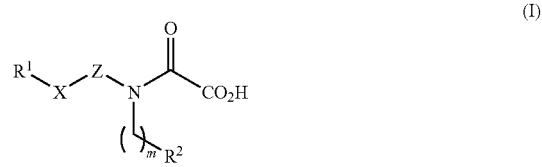

(I)

wherein $R^1$ represents a $C_{6-10}$ aryl group; or a $C_{6-10}$ aryl group substituted with a group or groups selected from the group consisting of a halogen atom, cyano group, nitro group, a $C_{1-6}$ alkyl group, a halogenated $C_{1-6}$ alkyl group, a $C_{1-6}$ alkoxy group, a halogenated $C_{1-6}$ alkoxy group and a $C_{1-6}$ alkylsulfanyl group, $R^2$ represents a $C_{6-10}$ aryl group; or a $C_{6-10}$ aryl group substituted with a group or groups selected from the group consisting of a halogen atom, hydroxy group, a $C_{1-6}$ alkyl group, a halogenated $C_{1-6}$ alkyl group, a $C_{1-6}$ alkoxy group, a halogenated $C_{1-6}$ alkoxy group, a $C_{1-6}$ alkylsulfanyl group and phenyl group, X represents a single bond or oxygen atom, Z represents a phenylene group or a substituted phenylene group, m represents 0 or 1.

7 Claims, No Drawings

FOREIGN PATENT DOCUMENTS

| WO | WO 2005/030716 A1 | 4/2005 |
|---|---|---|
| WO | WO 2005/030756 A1 | 4/2005 |
| WO | WO 03/064376 A1 | 8/2005 |
| WO | 2005/082347 A1 | 9/2005 |
| WO | WO 2005082347 A1 * | 9/2005 |

OTHER PUBLICATIONS

J. Schneiderman et al., "Increased type 1 plasminogen activator inhibitor gene expression in atherosclerotic human arteries", Proc. Natl. Acad. Sci. U.S.A., 1992, vol. 89, No. 15, pp. 6998-7002.

L.A. Erickson et al., "Development of venous occlusions in mice transgenic for the plasminogen activator inhibitor-1 gene", Nature, 1990, vol. 346, pp. 74-76.

F. Samad et al., "Tissue Distribution and Regulation of Plasminogen Activator Inhibitor-1 in Obese Mice", Molecular Medicine, 1996, vol. 2, No. 5, pp. 568-582.

K. Schaefer et al., "Disruption of the plasminogen activator inhibitor 1 gene reduces the adiposity and improves the metabolic profile of genetically obese and diabetic ob/ob mice", FASAB J., 2001, vol. 15, No. 10, pp. 1840-1842.

H. Tsuchiya et al., "The Antibody to Plasminogen Activator Inhibitor-1 Suppresses Pulmonary Metastases of Human Fibrosarcoma in Athymic Mice", Gen. Diagn. Pathol., 1995, vol. 141, No. 1, pp. 41-48.

K. Bajou et al., "Absence of host plasminogen activator inhibitor 1 prevents cancer invasion and vascularization", Nature Medicine, 1998, vol. 4, No. 8, pp. 923-928.

S. H. Cho et al., "Production of Plasminogen Activator Inhibitor-1 by Human Mast Cells and Its Possible Role in Asthma", The Journal of Immunology, 2000, vol. 165, No. 6, pp. 3154-3161.

K. O. Chad et al., "PAI-1 promotes extracellular matrix deposition in the airways of a murine asthma model", Biochemical and Biophysical Research Communications, 2002, vol. 294, No. 5, pp. 1155-1160.

P. Bjoerquist et al., "Identification of the Binding Site for a Low-Molecular-Weight Inhibitor of Plasminogen Activator Inhibitor Type 1 by Site-Directed Mutagenesis", Biochemistry, 1998, vol. 37, No. 5, pp. 1227-1234.

H. Elokdah et al., "Tiplaxtinin, a Novel, Orally Efficacious Inhibitor of Plasminogen Activator Inhibitor-1: Design, Synthesis, and Preclinical Characterization", J. Med. Chem., 2004, vol. 47, No. 14, pp. 3491-3494.

U.S. Appl. No. 11/870,718 (Yamaguchi et al.), filed Oct. 11, 2007 and entitled "Caboxylic Acid Derivatives".

* cited by examiner

N-PHENYLOXAMIDE DERIVATIVES

FIELD OF INVENTION

The present invention relates to N-phenyloxamic acid derivatives which are useful as inhibitors against plasminogen activator inhibitor-1 (hereinafter referred to as "PAI-1").

BACKGROUND ART

Blood coagulation system consists of a cascade reaction which comprises numbers of combinations of various kinds of proteases and precursors (substrates) thereof, and is regulated mainly depending upon blood endothelial cells. When the blood endothelial cells are disordered to collapse cascade regulation of the blood coagulation, a thrombotic tendency is increased to lead to stenosis or occlusion of blood vessels. The thrombus consists of blood components coagulated intravascularly, which components include fibrin, platelet, erythrocyte, leukocyte and the like.

Fibrinolytic system is a rather simple system as compared with the blood coagulation system. However, factors related to the fibrinolytic system are deeply involved not only in an intravascular dissolution of thrombus but also in various reactions occurring in tissues, such as movement or migration of cell; ovulation; cell proliferation; angiogenesis; reconstruction (remodeling) of tissue; inflammatory response and the like. The fibrinolytic system is driven by serine proteases. The plasminogen is converted into plasmin by a plasminogen activator (hereinafter referred to as "PA"); a tissue-type plasminogen activator (hereinafter referred to as "tPA"); or a urokinase-type plasminogen activator (hereinafter referred to as "uPA"), and the resulting plasmin degrades a fibrin thrombus and tissue protein. The fibrinolytic reaction is regulated and modulated by a plasminogen activator inhibitor-1 (PAI1), a specific inhibitory protein against plasminogen activator existing in vivo. PAI-1 forms a complex with PA in a ratio of one to one to inhibit actions thereof. PAI-1 released from an activated platelet binds to fibrin so as to exist around the fibrin in a concentrated form, especially at the site of thrombogenesis, and inhibits an activity of tPA effectively. Furthermore, PAI-1 accelerates hyperplasia of vascular wall to promote progress of cardiovascular lesion by inhibiting degradation of extracellular matrix by a protease. An activity of the fibrinolytic system is regulated by a balance between PA and PAI-1. Therefore, an increase or a decrease of production of PAI-1 in cells or fluctuation in the activity of PAI-1 molecule is reflected immediately in the activity of the fibrinolytic system in blood. Accordingly, a therapeutic effect for thrombotic diseases is expected by inhibiting PAI-1 activity followed by promoting the activation of PA.

PAI-1 binds to vitronectin, which is a cell adhesion molecule, to inhibit adhesion of cells to the extracellular matrix. Therefore, a therapeutic effect for diseases caused by movement or migration of cell is also expected. Furthermore, plasmin which is indirectly activated by an inhibition of PAI-1 is involved in an activation of transforming growth factor as a cell proliferation inhibitory cytokine or in an activation of collagenase. Therefore, a therapeutic effect for diseases caused by cell proliferation, angiogenesis, and remodeling of tissue is also expected.

It has been reported that an expression of PAI-1 is increased at the lesion of arteriosclerosis to increase risks of thrombotic diseases such as myocardial infarction, deep vein thrombosis (DVT) and disseminated intravascular coagulation (DIC) associated with sepsis (see, Non-Patent Document 1), and a PAI-1 transgenic mouse shows a thrombogenic tendency (see, Non-Patent Document 2).

It has also been reported that a mouse model of obesity shows a significantly higher blood level of PAI-1, and further reported that PAI-1 is synthesized not only in endothelial tissues and hepatic tissues but also in adipose tissues, and an amount of synthesized PAI-1 is rapidly increased, especially in visceral fat (see, Non-Patent Document 3). Furthermore, it has been reported that a PAI-1 gene knock out mouse model of obesity shows a decrease in body weight, and a lowering of blood levels of glucose and insulin (see, Non-Patent Document 4), suggesting a possibility that PAI-1 aggravates various symptoms caused by an accumulation of fats. It has been reported that PAI-1 exists specifically in cancerous tissues to be involved in regulation of physiological function of cancer cells, and that a PAI-1 antibody inhibits metastasis of cancer in a cancer model (see, Non-Patent Document 5). It has also been reported that, when a transplantation of malignant keratinocytes into PAI-1 knock out mouse is carried out, invasion of cancer and angiogenesis are inhibited (see, Non-Patent Document 6).

Furthermore, it has been reported that PAI-1 is secreted from mast cell (see, Non-Patent Document 7), and an accumulation of extracellular matrix in an airway of a mouse model of asthma is alleviated by PAI-1 knockout (see, Non-Patent Document 8).

An arterial lesion as an acute or a chronic rejection after cardiac or renal transplantation is considered to be caused by progressions such as progression of fibrogenesis of tissue, progression of thrombogenesis, progression of proliferation and remodeling of arterial endothelial cell. In experiments of murine cardiac transplantation, when the compound having inhibitory action against PAI-1 was administered, take of a graft was significantly prolonged and an incidence of vascular intimal thickening was reduced to about one third as compared with control group (see, Patent Document 1). Accordingly, the compounds that can inhibit PAI-1 are considered to have inhibitory effects against acute rejections and arterial lesions after organ transplantation such as cardiac transplantation, renal transplantation or the like.

Therefore, compounds having specific inhibitory action against PAI-1 are expected to be agents useful for diseases caused by thrombogenesis, fibrogenesis, accumulation of visceral fat, cell proliferation, angiogenesis, deposition and remodeling of extracellular matrix, and cell movement and migration.

As for compounds having inhibitory action against PAI-1, the compounds disclosed in Patent Documents 1 to 19 and Non-Patent Documents 9 to 10 are known. However, the structural feature of the compounds of the present invention described below is clearly distinguishable from those of the compounds disclosed in the aforementioned documents.

As for N-aralkyl-N-(aryl substituted phenyl)oxamic acid derivatives, the following 5 compounds are disclosed in Patent Documents 20 and 21.

({4-[(dodecylamino)carbonyl]benzyl}-4-phenoxyanilino)(oxo)acetic acid (Example 37)

[{4-[(dodecylamino)carbonyl]benzyl}(3-phenoxyphenyl)aminoyoxo)acetic acid (Example 232)

4'-acarboxycarbonyl){4-[dodecylamino)carbonyl]benzyl}amino)-1,1'-biphenyl-2-carboxylic acid (Example 237)

{(4-dibenzo[b,d]furan-4-ylphenyl)[4-(trifluoromethyl)benzyl]amino}(oxo)acetic acid (Example 271)

{(4-dibenzo[b,d]furan-4-ylphenyl)[4-(trifluoromethyl)benzyl]amino}(oxo)acetic acid, N-methyl-D-glucamine (Example 272)

However, no result of pharmacological test of the aforementioned 5 compounds is disclosed in each of the aforementioned patent documents. Furthermore, each of the aforementioned patent documents fails to teach nor suggest that N-aralkyl-N-(aryl substituted phenyl)oxamic acid derivatives have inhibitory action against PAI-1.

As for N-aryl-N-(aryl substituted phenyl)oxamic acid derivatives, the following 2 compounds are disclosed in Patent Document 22.

2((1,1'-biphenyl)-2-yl(carboxycarbonyl)amino)benzoic acid (Example 19)

2-((1,1'-biphenyl)-4-yl(carboxycarbonyl)amino)benzoic acid (Example 20)

However, the aforementioned patent document fails to teach nor suggest that N-aryl-N-(aryl substituted phenyl)oxamic acid derivatives have inhibitory action against PAI-1.

Non-Patent Document 1: Proc. Natl. Acad. Sci. U.S.A., Vol. 89, No. 15, pp. 6998-7002 (1992).

Non-Patent Document 2: Nature, Vol. 346, No. 6279, pp. 74-76 (1990).

Non-Patent Document 3: Mol. Med., Vol. 2, No. 5, pp. 568-582 (1996).

Non-Patent Document 4: FASEB J., Vol. 15, No. 10, pp. 1840-1842 (2001).

Non-Patent Document 5: Gen. Diagn. Pathol., Vol. 141, No. 1, pp. 41-48 (1995).

Non-Patent Document 6: Nat. Med., Vol. 4, No. 8, pp. 923-928 (1998).

Non-Patent Document 7: J. Immunol., Vol. 165, No. 6, pp. 3154-3161 (2000).

Non-Patent Document 8: Biochem. Biophys. Res. Commun., Vol. 294, No. 5, pp. 1155-1160 (2002).

Non-Patent Document 9: Biochemistry, Vol. 37, No. 5, pp. 1227-1234 (1998).

Non-Patent Document 10: J. Med. Chem., vol. 47, No. 14, pp. 3491-3494 (2004).

Patent Document 1: European Patent Application Publication No. EP 1666469

Patent Document 2: The pamphlet of International Publication No. WO95/32190

Patent Document 3: The pamphlet of International Publication No. WO95/21832

Patent Document 4: U. K. Patent Application Publication No. GB 2372740

Patent Document 5: The pamphlet of International Publication No. WO03/000253

Patent Document 6: The pamphlet of International Publication No. WO03/000258

Patent Document 7: The pamphlet of International Publication No. WO03/000649

Patent Document 8: The pamphlet of International Publication No. WO03/000671

Patent Document 9: The pamphlet of International Publication No. WO03/000684

Patent Document 10: The pamphlet of International Publication No. WO2004/052856

Patent Document 11: The pamphlet of International Publication No. WO2004/052893

Patent Document 12: The pamphlet of International Publication No. WO2005/030192

Patent Document 13: The pamphlet of International Publication No. WO2005/030204

Patent Document 14: The pamphlet of International Publication No. WO2005/030715

Patent Document 15: The pamphlet of International Publication No. WO2005/030716

Patent Document 16: The pamphlet of International Publication No. WO2005/030756

Patent Document 17: U.S. Patent Application Publication No. US 2005/0124664

Patent Document 18: U.S. Patent Application Publication No. US 2005/0124667

Patent Document 19: U.S. Patent Application Publication No. US 2005/0143384

Patent Document 20: The pamphlet of International Publication No. WO03/064376

Patent Document 21: The pamphlet of International Publication No. WO2005/082347

Patent Document 22: European Patent Publication No. EP 1313696

DISCLOSURE OF THE INVENTION

Problems to be solved by the invention

An object of the present invention is to provide a low molecular compound which is useful for preventive and/or therapeutic treatment of diseases with stenosis or occlusion caused by thrombus.

Another object of the present invention is to provide an antithrombotic compound with few hemorrhagic diatheses by selective inhibition of PAI-1 which is highly expressed in local lesions and a following indirect activation of PA.

Further object of the present invention is to provide a medicament which is provided in the form of injections as well as in a form of preparation depending on a target disease and a purpose of application by using the low molecular compound which inhibits PAI-1.

Still further object of the present invention is to provide low molecular compounds which are useful for preventive and/or therapeutic treatment of other diseases caused by an expression of PAI-1, an enhancement of PAI-1 activity, or a lowering of plasmin activity, for example, diseases caused by fibrogenesis, accumulation of visceral fat, cell proliferation, angiogenesis, deposition or remodeling of extracellular matrix, and cell movement and migration.

Means to solve the problems

The inventors of the present invention conducted various studies to solve the aforementioned objects. As a result, they found that N-aralkyl-N-(aryl substituted phenyl)oxamic acid derivatives, N-aryl-N-(aryl substituted phenyl)oxamic acid derivatives, N-aralkyl-N-(aryloxy substituted phenyl)oxamic acid derivatives and N-aryl-N-(aryloxy substituted phenyl) oxamic acid derivatives have strong inhibitory action against PAI-1 and achieved the present invention.

The present invention thus provides:

(1) a compound represented by the following general formula (I) or a salt thereof, or a hydrate thereof or a solvate thereof:

[Chemical formula 1]

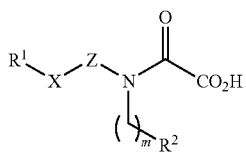

wherein $R^1$ represents a $C_{6-10}$ aryl group; or a $C_{6-10}$ aryl group substituted with a group or groups selected from the group consisting of a halogen atom, cyano group, nitro group, a $C_{1-6}$ alkyl group, a halogenated $C_{1-6}$ alkyl group, a $C_{1-6}$ alkoxy group, a halogenated $C_{1-6}$ alkoxy group and a $C_{1-6}$ alkylsulfanyl group, $R^2$ represents a $C_{6-10}$ aryl group; or a $C_{6-10}$ aryl group substituted with a group or groups selected from the group consisting of a halogen atom, hydroxy group, a $C_{1-6}$ alkyl group, a halogenated $C_{1-6}$ alkyl group, a $C_{1-6}$ alkoxy group, a halogenated $C_{1-6}$ alkoxy group, a $C_{1-6}$ alkylsulfanyl group and phenyl group, X represents a single bond or oxygen atom, Z represents a phenylene group or a substituted phenylene group, m represents 0 or 1.

According to preferred embodiments of the present invention, provided are:

(2) the compound according to the aforementioned (1) or a salt thereof, or a hydrate thereof or a solvate thereof, wherein Z is a phenylene group; or a phenylene group substituted with a group or groups selected from the group consisting of a halogen atom, a $C_{1-6}$ alkyl group, a halogenated $C_{1-6}$ alkyl group, a carboxy substituted $C_{1-6}$ alkyl group, a $C_{1-6}$ alkoxy group, a halogenated $C_{1-6}$ alkoxy group, a $C_{7-12}$ aralkyloxy group, a $C_{1-6}$ alkyl substituted $C_{7-12}$ aralkyloxy group and a di-$C_{1-6}$ alkylamino group.

From another aspect, the present invention provides:

(3) a medicament for preventive and/or therapeutic treatment of diseases caused by an expression of PAI-1 or an enhancement of PAI-1 activity, which comprises as an active ingredient a substance selected from the group consisting of a compound according to the aforementioned (1) or (2) and a pharmacologically acceptable salt thereof, and a hydrate thereof and a solvate thereof;

(4) a PAI-1 inhibitor which comprises as an active ingredient a substance selected from the group consisting of a compound according to the aforementioned (1) or (2) and a pharmacologically acceptable salt thereof, and a hydrate thereof and a solvate thereof;

(5) use of a substance selected from the group consisting of a compound according to the aforementioned (1) or (2) and a pharmacologically acceptable salt thereof, and a hydrate thereof and a solvate thereof for the manufacture of a PAI-1 inhibitor; and (6) use of a substance selected from the group consisting of a compound according to the aforementioned (1) or (2) and a pharmacologically acceptable salt thereof, and a hydrate thereof and a solvate thereof for the manufacture of a medicament for preventive and/or therapeutic treatment of diseases caused by an expression of PAI-1 or an enhancement of PAI-1 activity.

From further another aspect, the present invention provides a method of inhibiting PAI-1 in a mammal including a human, which comprises the step of administering a substance selected from the group consisting of a compound represented by the aforementioned general formula (I) and a pharmacologically acceptable salt thereof, and a hydrate thereof and a solvate thereof at a dose sufficient to inhibit PAI-1; a method of inhibiting PAI-1, which comprises the step of allowing a substance selected from the group consisting of a compound according to the aforementioned (1) and a pharmacologically acceptable salt thereof, and a hydrate thereof and a solvate thereof to act on PAI-1; and a method for preventive and/or therapeutic treatment of diseases caused by an expression of PAI-1 or an enhancement of PAI-1 activity in a mammal including a human, which comprises the step of administering a substance selected from the group consisting of a compound represented by the aforementioned general formula (I) and a pharmacologically acceptable salt thereof, and a hydrate thereof and a solvate thereof at a dose preventively and/or therapeutically sufficient to treat said diseases.

In the present specification, "allow to act on" means to allow a substance selected from the group consisting of a compound represented by the general formula (I) and a pharmacologically acceptable salt thereof, and a hydrate thereof and a solvate thereof to exhibit an inhibitory action against activation of PAI-1 by addition or administration thereof. The action may target PAI-1 or a cultured cell that produces PAI-1 or a cell within an individual. The aforementioned individual may be a human or other mammals.

BEST MODE FOR CARRYING OUT THE INVENTION

This application claims the benefit of priority to Japan Patent Application No. 2006-278529, filed on Oct. 12, 2006, and U.S. Provisional Application No. 60/851,302, filed on Oct. 13, 2006. All of the disclosures of the specifications of these applications are herein incorporated by reference.

The terms used in the present specification have the following meanings.

As the halogen atom, any of fluorine atom, chlorine atom, bromine atom or iodine atom may be used unless otherwise specifically referred to.

The "alkyl group" or an alkyl moiety of the substituents containing the alkyl moiety may be straight chain, branched chain, cyclic, or combination of these.

Examples of the "$C_{1-6}$ alkyl group" include, for example, n-pentyl group, isopentyl group, neopentyl group, tert-pentyl group, 1-ethylpropyl group, n-hexyl group, cyclopentyl group and cyclohexyl group, besides $C_{1-4}$ alkyl groups such as methyl group, ethyl group, n-propyl group, isopropyl group, n-butyl group, isobutyl group, sec-butyl group, tert-butyl group, cyclopropyl group, cyclobutyl group and (cyclopropyl)methyl group.

Examples of the "halogenated $C_{1-6}$ alkyl group" include, for example, perfluoropentyl group and perfluorohexyl group, besides halogenated $C_{1-4}$ alkyl groups such as chloromethyl group, bromomethyl group, fluoromethyl group, dichloromethyl group, dibromomethyl group, difluoromethyl group, trichloromethyl group, tribromomethyl group, trifluoromethyl group, 2,2,2-trifluoroethyl group, pentafluoroethyl group, heptafluoropropyl group, and nonafluorobutyl group.

Examples of the "carboxy substituted $C_{1-6}$ alkyl group" include, for example, carboxymethyl group, 2-carboxy-1-ethyl group, 3-carboxy-1-propyl group, 4-carboxy-1-butyl group, 5-carboxy-1-pentyl group and 6-carboxy-1-hexyl group.

Examples of the "$C_{1-6}$ alkoxy group" include, for example, n-pentyloxy group, isopentyloxy group, neopentyloxy group, tert-pentyloxy group, 1-ethylpropoxy group, n-hexyloxy group, cyclopentyloxy group and cyclohexyloxy group, besides $C_{1-4}$ alkoxy groups such as methoxy group, ethoxy group, n-propoxy group, isopropoxy group, n-butoxy group, isobutoxy group, sec-butoxy group, tert-butoxy group, cyclopropoxy group, cyclobutoxy group and (cyclopropyl)methoxy group.

Examples of the "halogenated $C_{1-6}$ alkoxy group" include, for example, perfluoropentyloxy group and perfluorohexyloxy group, besides halogenated $C_{1-4}$ alkoxy groups such as chloromethoxy group, bromomethoxy group, fluoromethoxy group, dichloromethoxy group, dibromomethoxy group, difluoromethoxy group, trichloromethoxy group, tribromomethoxy group, trifluoromethoxy group, 2,2,2-trifluoroethoxy group, pentafluoroethoxy group, heptafluoropropoxy group, and nonafluorobutoxy group.

Examples of the "$C_{7-12}$ aralkyloxy group" include, for example, benzyloxy group, 1-naphthyloxy group and 2-naphthyloxy group.

Examples of the "$C_{1-6}$ alkyl substituted $C_{7-12}$ aralkyloxy group" include, for example, 4-methylbenzyloxy group and 4-(tert-butyl)benzyloxy group.

Examples of the "$C_{1-6}$ alkylsulfanyl group" include, for example, n-pentylsulfanyl group, isopentylsulfanyl group, neopentylsulfanyl group, tert-pentylsulfanyl group, 1-ethylpropylsulfanyl group, n-hexylsulfanyl group, cyclopentylsulfanyl group and cyclohexylsulfanyl group, besides $C_{1-4}$ alkylsulfanyl groups such as methylsulfanyl group, ethylsulfanyl group, n-propylsulfanyl group, isopropylsulfanyl group, n-butylsulfanyl group, isobutylsulfanyl group, sec-butylsulfanyl group, tert-butylsulfanyl group, cyclopropylsulfanyl group, cyclobutylsulfanyl group and (cyclopropyl)methylsulfanyl group.

Examples of the "di-$C_{1-6}$ alkylamino group" include, for example, dimethylamino group, diethylamino group, di(n-propyl)amino group, diisopropylamino group, di(n-butyl)amino group, di(n-pentyl)amino group, di(n-hexyl)amino group and methyl(ethyl)amino group.

Examples of the "$C_{6-10}$ aryl group" include, for example, phenyl group, 1-naphthyl group and 2-naphthyl group.

Examples of the "phenylene group" include 1,4-phenylene group, 1,3-phenylene group and 1,2-phenylene group.

$R^1$ represents a $C_{6-10}$ aryl group or a substituted $C_{6-10}$ aryl group.

In the present specification, when a certain functional group is defined as "substituted", kinds, numbers, and positions of substituents existing in the functional groups are not particularly limited unless otherwise specifically referred to, and when the number of the substituents is two or more, their substituents may be the same or different. Examples of these substituents include, for example, halogen atoms, cyano group, nitro group, hydroxy group, sulfanyl group, a $C_{1-6}$ alkyl group, a $C_{3-7}$ cycloalkyl group (for example, cyclopropyl group), a $C_{1-6}$ alkylene group (for example, methylene group and ethylene group), a $C_{2-6}$ alkenyl group (for example, vinyl group and allyl group), a $C_{2-6}$ alkynyl group (for example, ethynyl group and propargyl group), a $C_{6-10}$ aryl group, a $C_{7-10}$ aralkyl group (for example, benzyl group and naphthylmethyl group), a $C_{1-6}$ alkoxy group, a $C_{3-7}$ cycloalkoxy group (for example, cyclopropyloxy group), a $C_{1-6}$ alkylenedioxy group (for example, methylenedioxy group and ethylenedioxy group), a $C_{2-6}$ alkenyloxy group (for example, allyloxy group), a $C_{2-6}$ alkynyloxy group (for example, propargyloxy group), a $C_{6-10}$ aryloxy group (for example, phenoxy group and naphthyloxy group), a $C_{7-12}$ aralkyloxy group (for example, benzyloxy group), formyl group, a $C_{2-7}$ alkanoyl group (for example, acetyl group, propionyl group and pivaloyl group), a $C_{7-11}$ aroyl group (for example, benzoyl group and napthoyl group), carboxy group, a $C_{2-7}$ alkoxycarbonyl group (for example, methoxycarbonyl group and ethoxycarbonyl group), carbamoyl group, a $C_{1-6}$ alkylsulfanyl group (for example, methylsulfanyl group), a $C_{6-10}$ arylsulfanyl group (for example, phenylsulfanyl group), a $C_{7-12}$ aralkysulfanyl group (for example, benzylsulfanyl group), sulfo group, a $C_{1-6}$ alkylsulfonyl group (for example, methanesulfonyl group), a $C_{6-10}$ arylsulfonyl group (for example, benzenesulfonyl group), sulfamoyl group, amino group, a $C_{1-6}$ alkylamino group (for example, methylamino group), a di-$C_{1-6}$ alkylamino group (for example, dimethylamino group), formylamino group, a $C_{2-7}$ alkanolamino group (for example, acetylamino group), a $C_{7-11}$ arylamino group (for example, benzoylamino group), a $C_{2-7}$ alkoxycarbonylamino group (for example, methoxycarbonylamino group), a $C_{1-6}$ alkylsulfonylamino group (for example, methanesulfonylamino group), a $C_{6-10}$ arylsulfonylamino group (for example, benzenesulfonylamino group), amidino group, guanidino group, oxo group, thioxo group (for example, benzenesulfonylamino group (for example, a 5 to 14-membered heteroaryl group such as furyl group, thienyl group, pyrrolyl group, isoxazolyl group, isothiazolyl group, pyrazolyl group, oxazolyl group, thiazolyl group, imidazoyl group, pyridyl group, pyrimidinyl group, pyrazinyl group, pyridazinyl group, benzo[b]furyl group, benzo[b]thienyl group, indolizinyl group, indolyl group, isoindolyl group, indazoyl group, purinyl group, quinolyl group, isoquinolyl group, naphthyridinyl group, quinoxalinyl group, quinazolinyl group, cinnolinyl group, pteridinyl group, carbazolyl group, β-carbolinyl group, phenoxazinyl group and phenothiazinyl group; a 5 to 10-membered partly saturated heterocyclic group such as pyrrolinyl group, imidazolinyl group, pyrazolinyl group, chromanyl group, isochromanyl group, indolinyl group, isoindolinyl group, tetrahydroquinolyl group and tetrahydroisoquinolyl group; and a 3 to 7-remembered completely saturated heterocyclic group such as aziridinyl group, azetidinyl group, pyrrolidinyl group, imidazolidinyl group, pyrazolidinyl group, oxazolidinyl group, thiazolidinyl group, piperidinyl group, piperazinyl group, morpholinyl group, thiomorpholinyl group, azepanyl group, 1,4-diazepanyl group, 1,4-oxazepanyl group, 1,4-thiazepanyl group, tetrahydrofuranyl group, tetrahydrothiophenyl group, tetrahydropyranyl group and tetrahydrothiopyranyl group). These substituents may further be substituted with the aforementioned substituents. Examples of these substituents include, for example, a halogenated $C_{1-6}$ alkyl group, a halogenated $C_{1-6}$ alkoxy group, a $C_{3-7}$ cycloalkyl substituted $C_{1-6}$ alkyl group (for example, cyclopropylmethyl group), a hydroxy substituted $C_{1-6}$ alkyl group (for example, hydroxymethyl group), a carboxy substituted $C_{1-6}$ alkyl group (for example, carboxymethyl group).

$R^1$ is preferably a $C_{6-10}$ aryl group; or a $C_{6-10}$ aryl group substituted with a group or groups selected from the group consisting of a halogen atom, cyano group, nitro group, a $C_{1-6}$ alkyl group, a halogenated $C_{1-6}$ alkyl group, a $C_{1-6}$ alkoxy group, a halogenated $C_{1-6}$ alkoxy group and a $C_{1-6}$ alkylsulfanyl group.

When $R^1$ is a $C_{6-10}$ aryl group substituted with a group or groups selected from the group consisting of a halogen atom, cyano group, nitro group, a $C_{1-6}$ alkyl group, a halogenated $C_{1-6}$ alkyl group, a $C_{1-6}$ alkoxy group, a halogenated $C_{1-6}$ alkoxy group and a $C_{1-6}$ alkylsulfanyl group, the number of the said substituents may be one to five. Furthermore, when the number of the said substituents is two or more, their substituents may be the same or different.

$R^1$ is preferably a group represented by the following formula (II):

[Chemical formula 2]

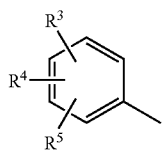

(II)

wherein $R^3$, $R^4$ and $R^5$ independently represent hydrogen atom, a halogen atom, cyano group, nitro group, a $C_{1-4}$ alkyl group, a halogenated $C_{1-4}$ alkyl group, a $C_{1-4}$ alkoxy group, a halogenated $C_{1-4}$ alkoxy group or a $C_{1-4}$ alkylsulfanyl group.

$R^3$, $R^4$ and $R^5$ are preferably the following (a).

(a) $R^3$ is hydrogen atom, a halogen atom, cyano group, nitro group, a $C_{1-4}$ alkyl group, a halogenated $C_{1-4}$ alkyl group, a $C_{1-4}$ alkoxy group, a halogenated $C_{1-4}$ alkoxy group or a $C_{1-4}$ alkylsulfanyl group, $R^4$ is hydrogen atom, $R^5$ is hydrogen atom.

$R^1$ is preferably any one of the following groups.

[Chemical formula 3]

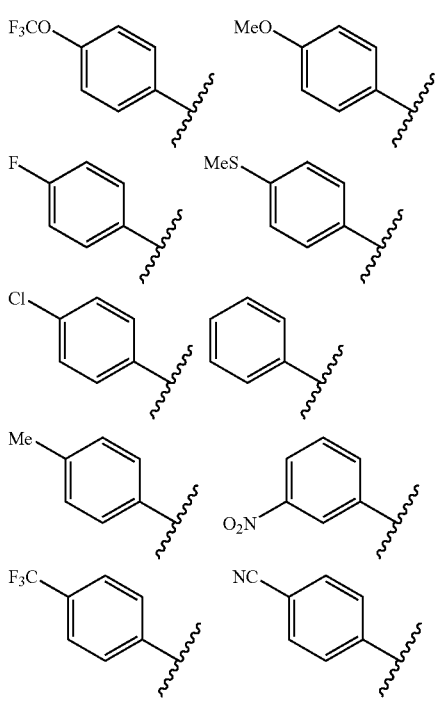

-continued

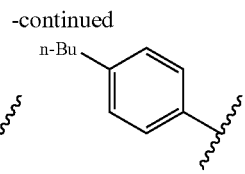

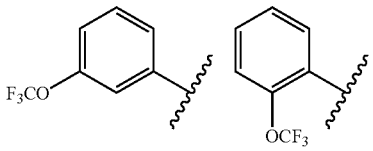

$R^2$ represents a $C_{6-10}$ aryl group or a substituted $C_{6-10}$ aryl group.

$R^2$ is preferably a $C_{6-10}$ aryl group; or a $C_{6-30}$ aryl group substituted with a group or groups selected from the group consisting of a halogen atom, hydroxy group, a $C_{1-6}$ alkyl group, a halogenated $C_{1-6}$ alkyl group, a $C_{1-6}$ alkoxy group, a halogenated $C_{1-6}$ alkoxy group, a $C_{1-6}$ alkylsulfanyl group and phenyl group.

When $R^2$ is a $C_{6-10}$ aryl group substituted with a group or groups selected from the group consisting of a halogen atom, hydroxy group, a $C_{1-6}$ alkyl group, a halogenated $C_{1-6}$ alkyl group, a $C_{1-6}$ alkoxy group, a halogenated $C_{1-6}$ alkoxy group, a $C_{1-6}$ alkylsulfanyl group and phenyl group, the number of the said substituents may be one to five. Furthermore, when the number of the said substituents is two or more, their substituents may be the same or different.

$R^2$ is preferably a group represented by the following formula (III):

[Chemical formula 4]

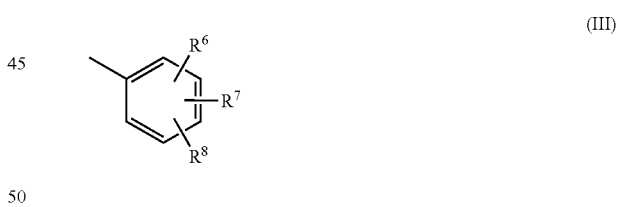

(III)

wherein $R^6$, $R^7$ and $R^8$ independently represent hydrogen atom, a halogen atom, hydroxy group, a $C_{1-4}$ alkyl group, a halogenated $C_{1-4}$ alkyl group, a $C_{1-4}$ alkoxy group, a halogenated $C_{1-4}$ alkoxy group, a $C_{1-4}$ alkylsulfanyl group or phenyl group.

$R^6$, $R^7$ and $R^8$ are preferably the following (a).

(a) $R^6$ is hydrogen atom, a halogen atom, hydroxy group, a $C_{1-4}$ alkyl group, a halogenated $C_{1-4}$ alkyl group, a $C_{1-4}$ alkoxy group, a halogenated $C_{1-4}$ alkoxy group, a $C_{1-4}$ alkylsulfanyl group or a $C_{6-10}$ aryl group, $R^7$ is hydrogen atom, a halogen atom or a $C_{1-4}$ alkyl group, $R^8$ is hydrogen atom.

$R^2$ is preferably any one of the following groups.

[Chemical formula 5]

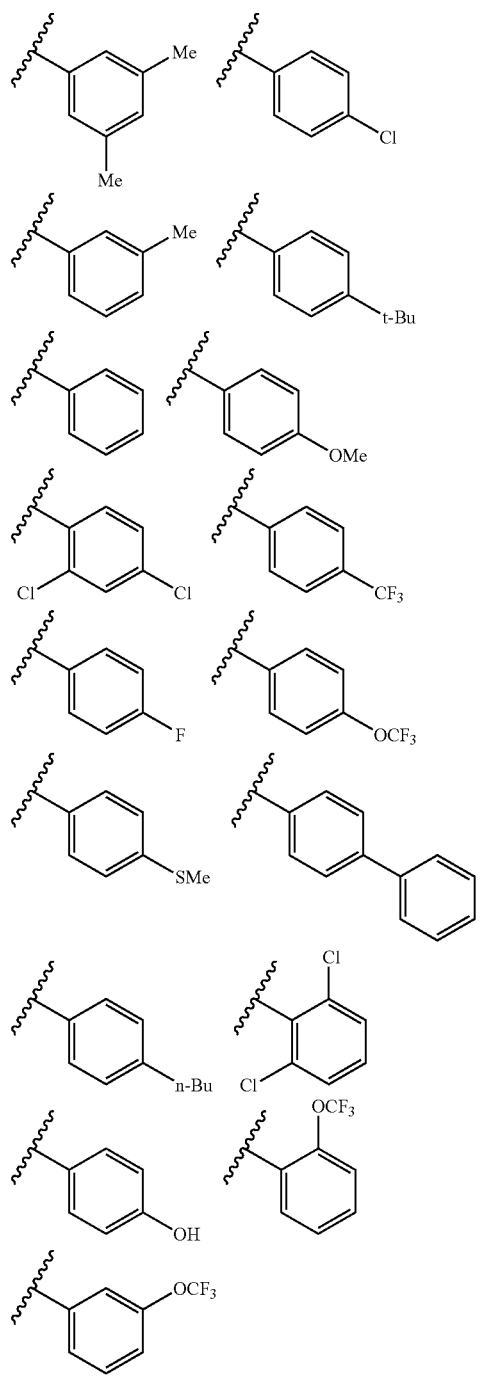

X represents a single bond or oxygen atom. m represents 0 or 1.

Z represents a phenylene group or a substituted phenylene group.

Z is preferably a phenylene group; or a phenylene group substituted with a group or groups selected from the group consisting of a halogen atom, a $C_{1-6}$ alkyl group, a halogenated $C_{1-6}$ alkyl group, a carboxy substituted $C_{1-6}$ alkyl group, a $C_{1-6}$ alkoxy group, a halogenated $C_{1-6}$ alkoxy group, a $C_{7-12}$ aralkyloxy group, a $C_{1-6}$ alkyl substituted $C_{7-12}$ aralkyloxy group and a di-$C_{1-6}$ alkylamino group.

When Z is a phenylene group substituted with a group or groups selected from the group consisting of a halogen atom, a $C_{1-6}$ alkyl group, a halogenated $C_{1-6}$ alkyl group, a carboxy substituted $C_{1-6}$ alkyl group, a $C_{1-6}$ alkoxy group, a halogenated $C_{1-6}$ alkoxy group, a $C_{7-12}$ aralkyloxy group, a $C_{1-6}$ alkyl substituted $C_{7-12}$ aralkyloxy group and a di-$C_{1-6}$ alkylamino group, the number of the said substituents may be one to four. Furthermore, when the number of the said substituents is two or more, their substituents may be the same or different.

Z is preferably any one of the following groups wherein the bond at the left end binds to X and the bond at the right end binds to the nitrogen atom.

[Chemical formula 6]

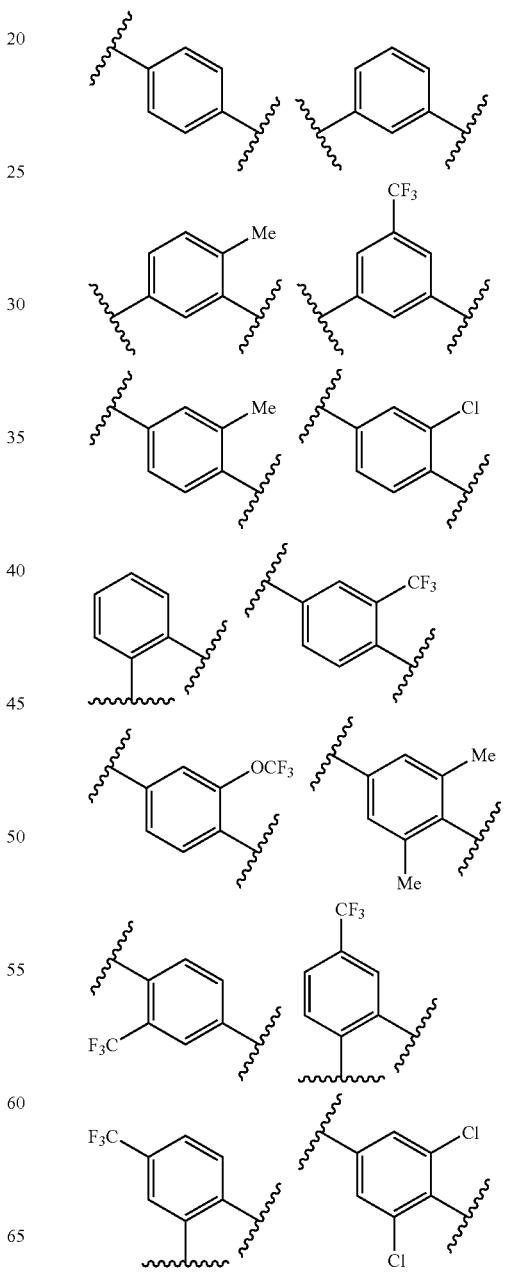

-continued

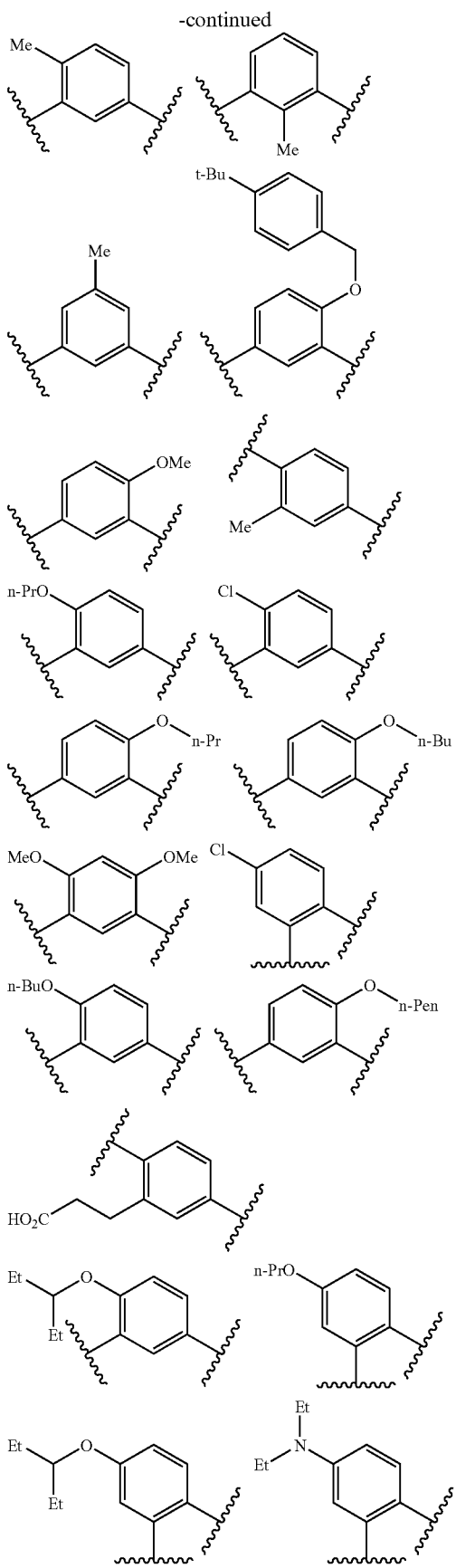
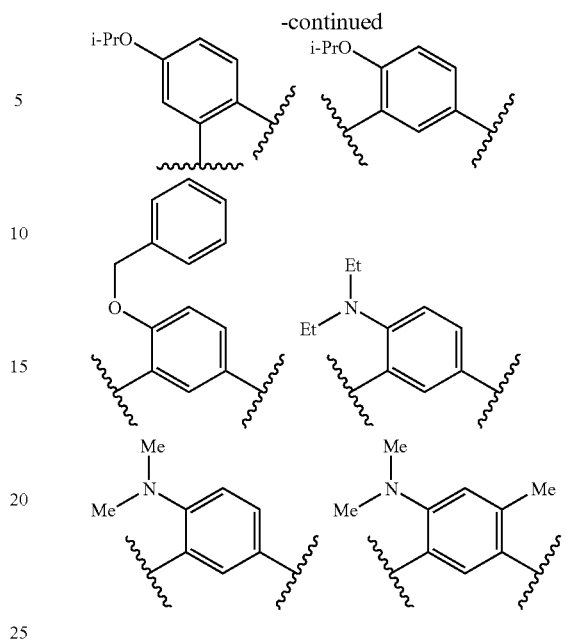

The compounds represented by the aforementioned formula (I) may form salts. Examples of pharmacologically acceptable salts include, when acidic groups exist, metal salts such as lithium salt, sodium salt, potassium salt, magnesium salt, calcium salts, or ammonium salts such as ammonium salt, methylammonium salt, dimethylammonium salt, trimethylammonium salt, dicyclohexylammonium salt, and when basic groups exist, mineral acid salts such as hydrochloride, hydrobromide (salt of hydrobromic acid), hydrosulfate, nitrate, phosphate, or organic acid salts such as methane sulfonate, benzene sulfonate, para-toluene sulfonate, acetate, propionate, tartrate, fumarate, maleate, malate, oxalate, succinate, citrate, benzoate, mandelate, cinnamate, lactate. Salts may sometimes be formed with amino acids such as glycine. As active ingredients of the medicament of the present invention, pharmacologically acceptable salts may also be suitably used.

The compounds or salts thereof represented by the aforementioned formula (I) may exist as hydrates or solvates. As active ingredients of the medicament of the present invention, any of the aforementioned substances may be used. Furthermore, the compounds represented by the aforementioned formula (I) may sometimes have one or more asymmetric carbons, and may exist as steric isomers such as optically active substance and diastereomer. As active ingredients of the medicament of the present invention, pure forms of stereoisomers, arbitrary mixture of enantiomers or diastereomers, and racemates may be used.

Furthermore, when the compounds represented by the aforementioned formula (I) may exist as a tautomer. As active ingredients of the medicament of the present invention, pure forms of tautomers or a mixture thereof may be used. When the compounds represented by the aforementioned formula (I) have olefinic double bonds, the configuration may be in either E or Z, and as active ingredients of the medicament of the present invention, geometrical isomer in either of the configurations or a mixture thereof may be used.

Examples of the preferred compounds as active ingredients of the medicaments of the present invention are shown below. However, the active ingredients of the medicaments of the present invention are not limited to the following compounds.

The abbreviations used in the following tables have the following meanings. Me: methyl group, Et: ethyl group, n-Pr: n-propyl group, n-Bu: n-butyl group, t-Bu: tert-butyl group, n-Pen: n-pentyl group, OMe: methoxy group, n-PrO: n-propoxy group, i-PrO: isopropoxy group, n-BuO: n-butoxy group, SMe: methylsulfanyl group.

TABLE 1

$$R^1-X-Z-N(-\underset{m}{(\phantom{x})}R^2)-C(=O)-CO_2H$$

| Compound Number | R¹ | Z (*) | R² | X | m |
|---|---|---|---|---|---|
| 1 | F₃CO-C₆H₄- | -C₆H₄- | 3,5-diMe-C₆H₃- | single bond | 1 |
| 2 | F₃CO-C₆H₄- | -C₆H₄- | 4-Cl-C₆H₄- | single bond | 1 |
| 3 | F₃CO-C₆H₄- | -C₆H₄- | 3-Me-C₆H₄- | single bond | 1 |
| 4 | MeO-C₆H₄- | -C₆H₄- | 4-t-Bu-C₆H₄- | single bond | 1 |
| 5 | F-C₆H₄- | -C₆H₄- | 4-t-Bu-C₆H₄- | single bond | 1 |
| 6 | F₃CO-C₆H₄- | -C₆H₄- | C₆H₅- | single bond | 1 |
| 7 | F₃CO-C₆H₄- | -C₆H₄- | 4-t-Bu-C₆H₄- | single bond | 0 |
| 8 | F₃CO-C₆H₄- | -C₆H₄- | 4-t-Bu-C₆H₄- | single bond | 1 |
| 9 | F₃CO-C₆H₄- | -m-C₆H₄- | 4-t-Bu-C₆H₄- | single bond | 1 |
| 10 | F₃CO-C₆H₄- | -C₆H₄- | 4-OMe-C₆H₄- | single bond | 1 |

TABLE 1-continued

| Compound Number | R¹ | Z (*) | R² | X | m |
|---|---|---|---|---|---|
| 11 | 4-F₃CO-phenyl | phenyl (1,4) | 4-t-Bu-phenyl | O | 1 |
| 12 | 4-F₃CO-phenyl | phenyl (1,4) | 4-t-Bu-phenyl | single bond | 1 |
| 13 | 4-MeS-phenyl | phenyl (1,4) | 4-t-Bu-phenyl | single bond | 1 |
| 14 | 4-Cl-phenyl | phenyl (1,4) | 4-t-Bu-phenyl | single bond | 1 |
| 15 | 4-F₃CO-phenyl | 2-Me-phenyl (1,4) | 4-t-Bu-phenyl | single bond | 1 |
| 16 | phenyl | 2-Me-phenyl (1,4) | 4-t-Bu-phenyl | single bond | 1 |
| 17 | 3-O₂N-phenyl | 2-Me-phenyl (1,4) | 4-t-Bu-phenyl | single bond | 1 |
| 18 | 4-F₃CO-phenyl | 3-CF₃-phenyl (1,5) | 4-t-Bu-phenyl | single bond | 1 |
| 19 | phenyl | 3-CF₃-phenyl (1,5) | 4-t-Bu-phenyl | single bond | 1 |
| 20 | 4-Me-phenyl | phenyl (1,4) | 4-t-Bu-phenyl | single bond | 1 |
| 21 | 3-O₂N-phenyl | phenyl (1,4) | 4-t-Bu-phenyl | single bond | 1 |

TABLE 1-continued

Structure: R¹-X-Z-N(-(CH₂)ₘ-R²)-C(=O)-CO₂H

| Compound Number | R¹ | Z (*) | R² | X | m |
|---|---|---|---|---|---|
| 22 | 4-F₃CO-C₆H₄- | 1,4-phenylene | 4-Me-C₆H₄- | single bond | 1 |
| 23 | 4-F₃CO-C₆H₄- | 1,4-phenylene | 2,4-diCl-C₆H₃- | single bond | 1 |
| 24 | 4-F₃C-C₆H₄- | 1,4-phenylene | 4-t-Bu-C₆H₄- | single bond | 1 |
| 25 | 4-F₃CO-C₆H₄- | 2-Me-1,4-phenylene | 4-t-Bu-C₆H₄- | single bond | 1 |
| 26 | 4-F₃CO-C₆H₄- | 2-Cl-1,4-phenylene | 4-t-Bu-C₆H₄- | single bond | 1 |
| 27 | 4-F₃CO-C₆H₄- | 1,2-phenylene | 4-t-Bu-C₆H₄- | single bond | 1 |
| 28 | 4-NC-C₆H₄- | 1,4-phenylene | 4-t-Bu-C₆H₄- | single bond | 1 |
| 29 | 4-F₃CO-C₆H₄- | 2-CF₃-1,4-phenylene | 4-t-Bu-C₆H₄- | single bond | 1 |
| 30 | 4-F₃CO-C₆H₄- | 2-OCF₃-1,4-phenylene | 4-t-Bu-C₆H₄- | single bond | 1 |
| 31 | 4-F₃CO-C₆H₄- | 2,6-diMe-1,4-phenylene | 4-t-Bu-C₆H₄- | single bond | 1 |

TABLE 1-continued

| Compound Number | R¹ | Z (*) | R² | X | m |
|---|---|---|---|---|---|
| 32 | F₃CO-C₆H₄- | 1,2-phenylene | 4-t-Bu-C₆H₄- | O | 1 |
| 33 | F₃CO-C₆H₄- | 1,4-phenylene | C₆H₅- | O | 1 |
| 34 | F₃CO-C₆H₄- | 1,4-phenylene | 4-CF₃-C₆H₄- | single bond | 1 |
| 35 | F₃CO-C₆H₄- | 1,4-phenylene | 4-F-C₆H₄- | single bond | 1 |
| 36 | t-Bu-C₆H₄- | 1,4-phenylene | C₆H₅- | single bond | 1 |
| 37 | F₃CO-C₆H₄- | 1,2-phenylene | 4-t-Bu-C₆H₄- | single bond | 0 |
| 38 | F₃CO-C₆H₄- | 1,3-phenylene | 4-t-Bu-C₆H₄- | single bond | 0 |
| 39 | F₃CO-C₆H₄- | 1,4-phenylene | 4-OCF₃-C₆H₄- | single bond | 1 |
| 40 | F₃CO-C₆H₄- | 1,4-phenylene | 4-SMe-C₆H₄- | single bond | 1 |
| 41 | F₃CO-C₆H₄- | 1,4-phenylene | 4-biphenyl | single bond | 1 |

TABLE 1-continued $$R^1\text{-}X\text{-}Z\text{-}N(\text{-}CO\text{-}CO_2H)\text{-}(CH_2)_m\text{-}R^2$$

| Compound Number | R¹ | Z (*) | R² | X | m |
|---|---|---|---|---|---|
| 42 | 4-t-Bu-C₆H₄- | 1,4-C₆H₄ | 4-OCF₃-C₆H₄- | single bond | 1 |
| 43 | 4-t-Bu-C₆H₄- | 1,4-C₆H₄ | 4-t-Bu-C₆H₄- | single bond | 1 |
| 44 | 4-n-Bu-C₆H₄- | 1,4-C₆H₄ | 4-t-Bu-C₆H₄- | single bond | 1 |
| 45 | 4-F₃CO-C₆H₄- | 1,4-C₆H₄ | 4-t-Bu-C₆H₄- | O | 0 |
| 46 | 4-F₃CO-C₆H₄- | 3-CF₃-1,4-C₆H₃ | 4-t-Bu-C₆H₄- | single bond | 1 |
| 47 | 4-F₃CO-C₆H₄- | 1,4-C₆H₄ | 4-n-Bu-C₆H₄- | single bond | 1 |
| 48 | 4-F₃CO-C₆H₄- | 4-CF₃-1,2-C₆H₃ | 4-t-Bu-C₆H₄- | single bond | 1 |
| 49 | 4-F₃CO-C₆H₄- | 4-CF₃-1,2-C₆H₃ | 4-t-Bu-C₆H₄- | single bond | 1 |
| 50 | 4-F₃CO-C₆H₄- | 4-t-Bu-1,4-C₆H₄ | 4-t-Bu-C₆H₄- | O | 0 |
| 51 | 4-F₃CO-C₆H₄- | 1,4-C₆H₄ | 2,6-Cl₂-C₆H₃- | single bond | 1 |

TABLE 1-continued $$R^1-X-Z-N(-CO-CO_2H)-(CH_2)_m-R^2$$

| Compound Number | R¹ | Z (*) | R² | X | m |
|---|---|---|---|---|---|
| 52 | F₃CO-C₆H₄- | C₆H₄ (1,3) | 4-t-Bu-C₆H₄- | O | 1 |
| 53 | F₃CO-C₆H₄- | 2,6-Cl₂-C₆H₃- | 4-t-Bu-C₆H₄- | single bond | 1 |
| 54 | F₃CO-C₆H₄- | 2-CF₃-C₆H₃- | 4-t-Bu-C₆H₄- | O | 1 |
| 55 | F₃CO-C₆H₄- | 3-CF₃-C₆H₃ (1,5) | 4-t-Bu-C₆H₄- | O | 1 |
| 56 | F₃CO-C₆H₄- | 2-Me-C₆H₃- | 4-t-Bu-C₆H₄- | single bond | 1 |
| 57 | F₃CO-C₆H₄- | 2-Me-C₆H₃- | 4-t-Bu-C₆H₄- | single bond | 1 |
| 58 | F₃CO-C₆H₄- | 3-Me-C₆H₃ (1,5) | 4-t-Bu-C₆H₄- | single bond | 1 |
| 59 | F₃CO-C₆H₄- | 4-t-Bu-C₆H₄-CH₂-O-(2,4-Me₂-C₆H₃)- | C₆H₅- | single bond | 1 |
| 60 | F₃CO-C₆H₄- | 2,6-Cl₂-C₆H₃- | C₆H₅- | single bond | 1 |

TABLE 1-continued

[Structure: R¹−X−Z−N(−(CH₂)ₘ−R²)−C(=O)−CO₂H]

| Compound Number | R¹ | Z (*) | R² | X | m |
|---|---|---|---|---|---|
| 61 | F₃CO—C₆H₄— | —C₆H₄— | —C₆H₄—OH | single bond | 1 |
| 62 | F₃CO—C₆H₄— | 2-OMe-C₆H₃— | —C₆H₄—t-Bu | single bond | 1 |
| 63 | C₆H₅— | —C₆H₄— | —C₆H₄—OCF₃ | single bond | 1 |
| 64 | F₃CO—C₆H₄— | 2-Me-C₆H₃— | —C₆H₄—t-Bu | single bond | 1 |
| 65 | F₃CO—C₆H₄— | 2-n-PrO-C₆H₃— | —C₆H₄—t-Bu | single bond | 1 |
| 66 | F₃CO—C₆H₄— | 2-Cl-C₆H₃— | —C₆H₄—t-Bu | single bond | 1 |
| 67 | F₃CO—C₆H₄— | 2-Me-C₆H₃— | —C₆H₄—t-Bu | O | 1 |
| 68 | F₃CO—C₆H₄— | 2-(O-n-Pr)-C₆H₃— | —C₆H₄—t-Bu | single bond | 1 |
| 69 | F₃CO—C₆H₄— | 2-(O-n-Bu)-C₆H₃— | —C₆H₄—t-Bu | single bond | 1 |
| 70 | F₃CO—C₆H₄— | 2,5-(MeO)₂-C₆H₂— | —C₆H₄—t-Bu | single bond | 1 |
| 71 | F₃CO—C₆H₄— | 5-Cl-2-Me-C₆H₂— | —C₆H₄—t-Bu | O | 1 |

TABLE 1-continued
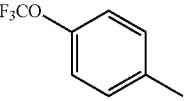
| Compound Number | R¹ | Z (*) | R² | X | m |
|---|---|---|---|---|---|
| 72 | 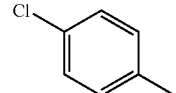 | 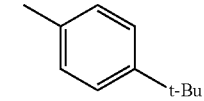 | 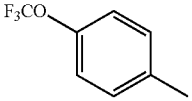 | single bond | 1 |
| 73 | 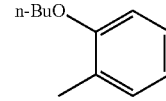 | 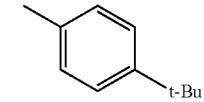 | 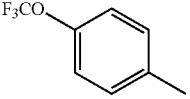 | single bond | 1 |
| 74 | 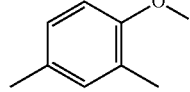 | 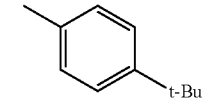 | 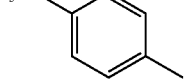 | single bond | 1 |
| 75 | 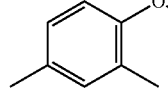 | 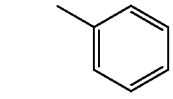 | 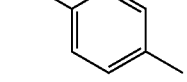 | single bond | 1 |
| 76 | 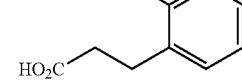 | 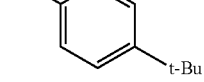 | 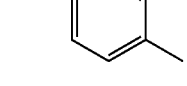 | single bond | 1 |
| 77 | 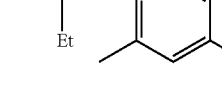 | 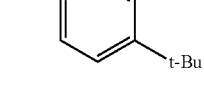 | 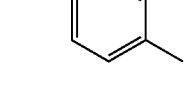 | single bond | 1 |
| 78 | 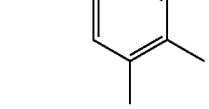 | 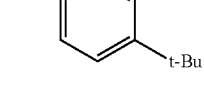 | 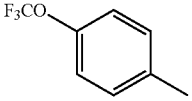 | single bond | 1 |
| 79 | 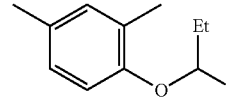 | 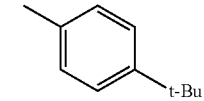 | 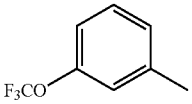 | single bond | 1 |
| 80 | 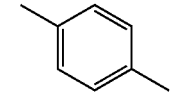 | 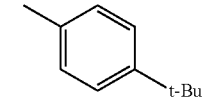 | 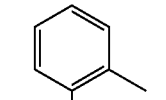 | single bond | 1 |
| 81 | 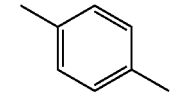 | 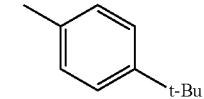 | | single bond | 1 |

TABLE 1-continued

| Compound Number | R¹ | Z (*) | R² | X | m |
|---|---|---|---|---|---|
| 82 | t-Bu-C₆H₄- | -C₆H₄- | 2-OCF₃-C₆H₄- | single bond | 1 |
| 83 | t-Bu-C₆H₄- | -C₆H₄- | 3-OCF₃-C₆H₄- | single bond | 1 |
| 84 | t-Bu-C₆H₄- | -C₆H₄- | 4-Cl-C₆H₄- | single bond | 1 |
| 85 | t-Bu-C₆H₄- | -C₆H₄- | 4-CF₃-C₆H₄- | single bond | 1 |
| 86 | t-Bu-C₆H₄- | -C₆H₄- | 4-n-Bu-C₆H₄- | single bond | 1 |
| 87 | F₃CO-C₆H₄- | 3,4-diMe-C₆H₃-O-CH(Et)₂ | 4-t-Bu-C₆H₄- | single bond | 1 |
| 88 | F₃CO-C₆H₄- | 3,4-diMe-C₆H₃-O-CH(Et)₂ | 4-t-Bu-C₆H₄- | single bond | 1 |
| 89 | F₃CO-C₆H₄- | 3,4-diMe-C₆H₃-O-i-Pr | 4-t-Bu-C₆H₄- | single bond | 1 |
| 90 | F₃CO-C₆H₄- | 2,4-diMe-C₆H₃-O-n-Pr | C₆H₅- | single bond | 1 |
| 91 | F₃CO-C₆H₄- | 2,4-diMe-C₆H₃-O-i-Pr | 4-t-Bu-C₆H₄- | single bond | 1 |

TABLE 1-continued

| Compound Number | R¹ | Z (*) | R² | X | m |
|---|---|---|---|---|---|
| 92 | F₃CO-phenyl- | -CH(CH₂OPh(2,4-diMe))- with benzyl | 4-methylphenyl | single bond | 1 |
| 93 | F₃CO-phenyl- | -CH(aryl-NEt₂)- (2,4-dimethyl-NEt₂-phenyl) | 4-methylphenyl | single bond | 1 |
| 94 | F₃CO-phenyl- | -CH(aryl-NMe₂)- (2,4-dimethyl-NMe₂-phenyl) | 4-methylphenyl | single bond | 1 |
| 95 | F₃CO-phenyl- | -CH(aryl-NMe₂)- (2,4,5-trimethyl-NMe₂-phenyl) | 4-methylphenyl | single bond | 1 |

☐ Compound No. 1, 2, 3 and 12: sodium salt
(*) The bond at the left end binds to X and the bond at the right end binds to the nitrogen atom.

The compounds represented by the general formula (I) can be prepared, for example, by methods shown below.

The compounds represented by the general formula (I), wherein X is a single bond, m is 1, can be prepared, for example, by a method shown below.

[Chemical formula 7]

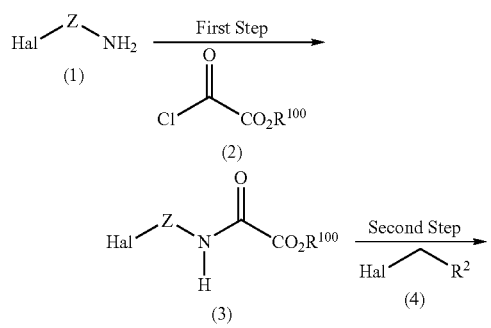

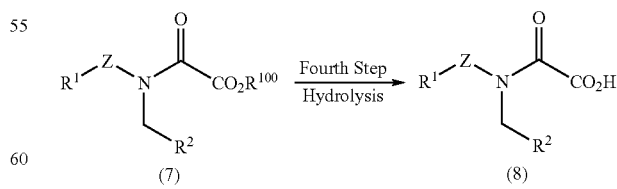

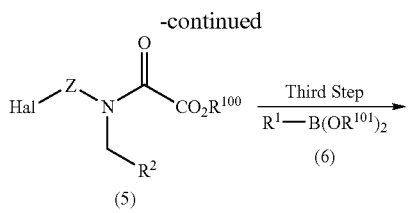

wherein Hal represents a halogen atom; $R^{100}$ represents a $C_{1-4}$ alkyl group or the like; $R^{101}$ represents hydrogen atom, a $C_{1-4}$ alkyl group or the like; each of $R^1$, $R^2$ and Z has the same meanings as that described above.

<First Step>

The N-(halophenyl)oxamic acid ester derivative (3) can be prepared by reacting the haloaniline derivative (1) with the chloroglyoxylic acid ester (2). This reaction is carried out in a solvent, in the presence of a base, at a reaction temperature of from 0° to 180°, preferably at a temperature of from 0° to the boiling point of the solvent.

As the base, examples include inorganic bases such as potassium carbonate, sodium carbonate and sodium hydrogencarbonate; and organic bases such as triethylamine and diisopropylethylamine.

As the solvent, any solvent can be used as long as it does not inhibit the reaction, and examples include, for example, halogenated solvents such as dichloromethane, dichloroethane and chloroform; ethers such as tetrahydrofuran, 1,2-dimethoxyethane and 1,4-dioxane; or a mixed solvent thereof.

<Second Step>

The N-aralkyl-N-(halophenyl)oxamic acid ester derivative (5) can be prepared by reacting the N-(halophenyl)oxamic acid ester derivative (3) obtained in the first step with the aralkyl halide derivative (4). This reaction is carried out in a solvent, in the presence of a base, at a reaction temperature of from 0° to 180°, preferably at a temperature of from 0° to the boiling point of the solvent. Crown ethers such as 18-crown-6 may be added.

As the base, examples include inorganic bases such as sodium hydride, potassium hydride, potassium carbonate, sodium carbonate and sodium hydrogencarbonate; and organic bases such as triethylamine and diisopropylethylamine.

As the solvent, any solvent can be used as long as it does not inhibit the reaction, and examples include, for example, halogenated solvents such as dichloromethane, dichloroethane and chloroform; ethers such as tetrahydrofuran, 1,2-dimethoxyethane and 1,4-dioxane; acetonitrile; or a mixed solvent thereof.

<Third Step>

The N-aralkyl-N-(aryl substituted phenyl)oxamic acid ester derivative (7) can be prepared by reacting the N-aralkyl-N-(halophenyl)oxamic acid ester derivative (5) obtained in the second step with the arylboronic acid derivative (6). This reaction is carried out in a solvent, in the presence of a catalytic amount of a transition metal complex, in the presence or absence of a base, at a reaction temperature of from 0° to 180°, preferably at a temperature of from 0° to the boiling point of the solvent.

As the transition metal complex, examples include, for example, [1,1-bis(diphenylphosphino)ferrocene]dichloropalladium (II), tetrakis(triphenylphosphine)palladium and the like.

As the base, examples include inorganic bases such as potassium carbonate, sodium carbonate and sodium hydrogencarbonate; and organic bases such as triethylamine and diisopropylethylamine.

As the solvent, any solvent can be used as long as it does not inhibit the reaction, and examples include, for example, ethers such as tetrahydrofuran, 1,2-dimethoxyethane and 1,4-dioxane; amides such as dimethylformamide and N-methylpyrrolidone; aromatic solvents such as benzene and toluene; alcohols such as methanol and ethanol; water; or a mixed solvent thereof.

<Fourth Step>

The final target compound (8) can be prepared by the hydrolysis of the N-aralkyl-N-(aryl substituted phenyl)oxamic acid ester derivative (7) obtained in the third step. This reaction is carried out in a solvent, in the presence of a base, at a reaction temperature of from 0° to 180°, preferably at a temperature of from 0° to the boiling point of the solvent. The reaction may be carried out under ultrasound irradiation.

As the base, examples include, for example, inorganic bases such as sodium hydroxide, potassium hydroxide, potassium carbonate and sodium carbonate.

As the solvent, any solvent can be used as long as it does not inhibit the reaction, and examples include, for example, ethers such as tetrahydrofuran, 1,2-dimethoxyethane and 1,4-dioxane; alcohols such as methanol and ethanol; water; or a mixed solvent thereof.

When the aftertreatment is carried out under acidic condition, the free form of the oxamic acid can be obtained. When the aftertreatment is carried out under basic condition, the salt of the oxamic acid can be obtained.

The aforementioned N-aralkyl-N-(halophenyl)oxamic acid ester derivative (5) can also be prepared by a method shown below.

[Chemical Formula 8]

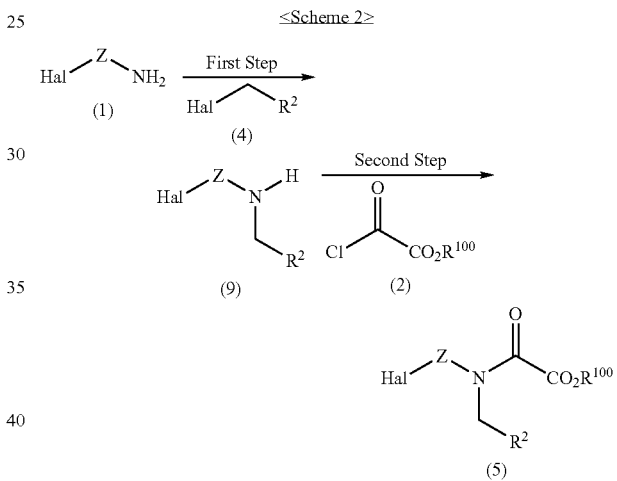

wherein Hal represents a halogen atom; $R^{100}$ represents a $C_{1-4}$ alkyl group or the like; each of $R^2$ and Z has the same meanings as that described above.

<First Step>

The N-(aralkyl)-haloaniline derivative (9) can be prepared by reacting the haloaniline derivative (1) with the aralkyl halide derivative (4). This reaction is carried out in a solvent, in the presence of a base, at a reaction temperature of from 0° to 180°, preferably at a temperature of from 0° to the boiling point of the solvent. Crown ethers such as 18-crown-6 may be added.

As the base, examples include inorganic bases such as potassium carbonate, sodium carbonate and sodium hydrogencarbonate; and organic bases such as triethylamine and diisopropylethylamine.

As the solvent, any solvent can be used as long as it does not inhibit the reaction, and examples include, for example, halogenated solvents such as dichloromethane, dichloroethane and chloroform; ethers such as tetrahydrofuran, 1,2-dimethoxyethane and 1,4-dioxane; amides such as dimethylformamide and N-methylpyrrolidone; or a mixed solvent thereof.

<Second Step>

The N-aralkyl-N-(halophenyl)oxamic acid ester derivative (5) can be prepared by reacting the N-(aralkyl)-haloaniline derivative (9) obtained in the first step with the chloroglyoxylic acid ester(2). This reaction is carried out in a solvent, in the presence of a base, at a reaction temperature of from 0° to 180°, preferably at a temperature of from 0° to the boiling point of the solvent.

As the base, examples include inorganic bases such as potassium carbonate, sodium carbonate and sodium hydrogencarbonate; and organic bases such as triethylamine and diisopropylethylamine.

As the solvent, any solvent can be used as long as it does not inhibit the reaction, and examples include, for example, halogenated solvents such as dichloromethane, dichloroethane and chloroform; ethers such as tetrahydrofuran, 1,2-dimethoxyethane and 1,4-dioxane; or a mixed solvent thereof.

The aforementioned N-aralkyl-N-(aryl substituted phenyl) oxamic acid ester derivative (7) can also be prepared by a method shown below.

[Chemical Formula 9]

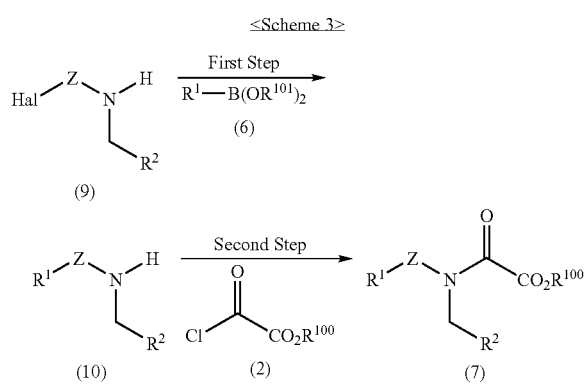

wherein Hal represents a halogen atom; $R^{100}$ represents a $C_{1-4}$ alkyl group or the like; $R^{101}$ represents hydrogen atom, a $C_{1-4}$ alkyl group or the like; each of $R^1$, $R^2$ and Z has the same meanings as that described above.

<First Step>

The N-(aralkyl)-aryl substituted aniline derivative (10) can be prepared by reacting the N-(aralkyl)-haloaniline derivative (9) with the arylboronic acid derivative (6). This reaction is carried out in a solvent, in the presence of a catalytic amount of a transition metal complex, in the presence or absence of a base, at a reaction temperature of from 0° to 180°, preferably at a temperature of from 0° to the boiling point of the solvent.

As the transition metal complex, examples include, for example, [1,1-bis(diphenylphosphino)ferrocene]dichloropalladium (II), tetrakis(triphenylphosphine)palladium and the like.

As the base, examples include inorganic bases such as potassium carbonate, sodium carbonate and sodium hydrogencarbonate; and organic bases such as triethylamine and diisopropylethylamine.

As the solvent, any solvent can be used as long as it does not inhibit the reaction, and examples include, for example, ethers such as tetrahydrofuran, 1,2-dimethoxyethane and 1,4-dioxane; amides such as dimethylformamide and N-methylpyrrolidone; aromatic solvents such as benzene and toluene; alcohols such as methanol and ethanol; water; or a mixed solvent thereof.

<Second Step>

The N-aralkyl-N-(aryl substituted phenyl)oxamic acid ester derivative (7) can be prepared by reacting the N-(aralkyl)-aryl substituted aniline derivative (10) obtained in the first step with the chloroglyoxylic acid ester (2). This reaction is carried out in a solvent, in the presence of a base, at a reaction temperature of from 0° to 180°, preferably at a temperature of from 0° to the boiling point of the solvent.

As the base, examples include inorganic bases such as potassium carbonate, sodium carbonate and sodium hydrogencarbonate; and organic bases such as triethylamine and diisopropylethylamine.

As the solvent, any solvent can be used as long as it does not inhibit the reaction, and examples include, for example, halogenated solvents such as dichloromethane, dichloroethane and chloroform; ethers such as tetrahydrofuran, 1,2-dimethoxyethane and 1,4-dioxane; or a mixed solvent thereof.

The aforementioned N-aralkyl-N-(aryl substituted phenyl) oxamic acid ester derivative (7) can also be prepared by a method shown below.

[Chemical Formula 10]

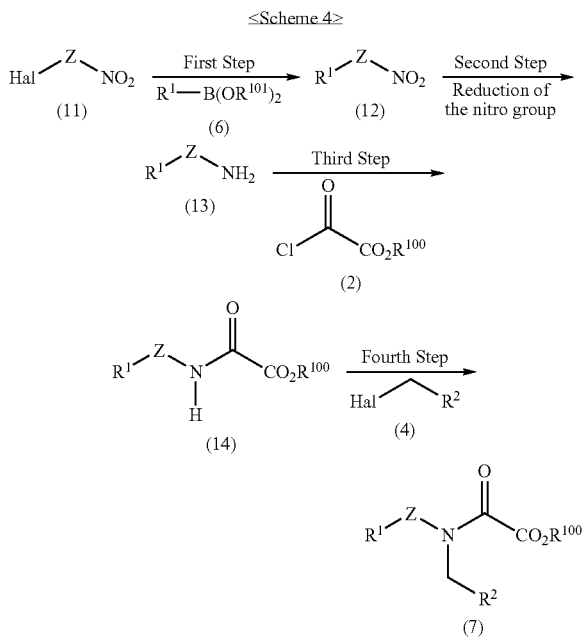

wherein Hal represents a halogen atom; $R^{100}$ represents a $C_{1-4}$ alkyl group or the like; $R^{101}$ represents hydrogen atom, a $C_{1-4}$ alkyl group or the like; each of $R^1$, $R^2$ and Z has the same meanings as that described above.

<First Step>

The aryl substituted nitrobenzene derivative (12) can be prepared by reacting the halo-nitrobenzene derivative (11) with the arylboronic acid derivative (6). This reaction is carried out in a solvent, in the presence of a catalytic amount of a transition metal complex, in the presence or absence of a base, at a reaction temperature of from 0° to 180°, preferably at a temperature of from 0° to the boiling point of the solvent.

As the transition metal complex, examples include, for example, [1,1-bis(diphenylphosphino)ferrocene]dichloropalladium (II), tetrakis(triphenylphosphine)palladium and the like.

As the base, examples include inorganic bases such as potassium carbonate, sodium carbonate and sodium hydrogencarbonate; and organic bases such as triethylamine and diisopropylethylamine.

As the solvent, any solvent can be used as long as it does not inhibit the reaction, and examples include, for example, ethers such as tetrahydrofuran, 1,2-dimethoxyethane and 1,4-dioxane; amides such as dimethylformamide and N-methylpyrrolidone; aromatic solvents such as benzene and toluene; alcohols such as methanol and ethanol; water; or a mixed solvent thereof.

<Second Step>

The aryl substituted aniline derivative (13) can be prepared by the reduction of the nitro group of the aryl substituted nitrobenzene derivative (12) obtained in the first step. This reaction is carried out in a solvent under hydrogen atmosphere, in the presence of a catalytic amount of a transition metal, at a reaction temperature of from 0° to 180°, preferably at a temperature of from 0° to the boiling point of the solvent.

As the transition metal, examples include, for example, palladium-activated charcoal, platinum-activated charcoal and the like.

As the solvent, any solvent can be used as long as it does not inhibit the reaction, and examples include, for example, ethers such as tetrahydrofuran, 1,2-dimethoxyethane and 1,4-dioxane; alcohols such as methanol and ethanol; water; or a mixed solvent thereof.

<Third Step>

The N-(aryl substituted phenyl)oxamic acid ester derivative (14) can be prepared by reacting the aryl substituted aniline derivative (13) obtained in the second step with the ester of chloroglyoxylic acid (2). This reaction is carried out in a solvent, in the presence of a base, at a reaction temperature of from 0° to 180°, preferably at a temperature of from 0° to the boiling point of the solvent.

As the base, examples include inorganic bases such as potassium carbonate, sodium carbonate and sodium hydrogencarbonate; and organic bases such as triethylamine and diisopropylethylamine.

As the solvent, any solvent can be used as long as it does not inhibit the reaction, and examples include, for example, halogenated solvents such as dichloromethane, dichloroethane and chloroform; ethers such as tetrahydrofuran, 1,2-dimethoxyethane and 1,4-dioxane; or a mixed solvent thereof.

<Fourth Step>

The N-aralkyl-N-(aryl substituted phenyl)oxamic acid ester derivative (7) can be prepared by reacting the N-(aryl substituted phenyl)oxamic acid ester derivative (14) obtained in the third step with the aralkyl halide derivative (4). This reaction is carried out in a solvent, in the presence of a base, at a reaction temperature of from 0° to 180°, preferably at a temperature of from 0° to the boiling point of the solvent. Crown ethers such as 18-crown-6 may be added.

As the base, examples include inorganic bases such as sodium hydride, potassium hydride, potassium carbonate, sodium carbonate and sodium hydrogencarbonate; and organic bases such as triethylamine and diisopropylethylamine.

As the solvent, any solvent can be used as long as it does not inhibit the reaction, and examples include, for example, halogenated solvents such as dichloromethane, dichloroethane and chloroform; ethers such as tetrahydrofuran, 1,2-dimethoxyethane and 1,4-dioxane; acetonitrile; or a mixed solvent thereof.

In the compounds represented by the general formula (I), the compounds wherein X is oxygen atom and m is 1 can be prepared, for example, by using the aryloxy-substituted nitrobenzene derivative ($R^1$—O—Z—$NO_2$) obtained by reacting the halo-nitrobenzene derivative (11) with the hydroxyaryl derivative ($R^1$—OH) or the aryloxy-substituted aniline derivative ($R^1$—O—Z—$NH_2$), instead of the aryl-substituted nitrobenzene derivative (12) or the aryl-substituted aniline derivative (13) in scheme 4.

The compounds represented by the general formula (I), wherein X is a single bond, m is 0, can be prepared, for example, by a method shown below.

[Chemical Formula 11]

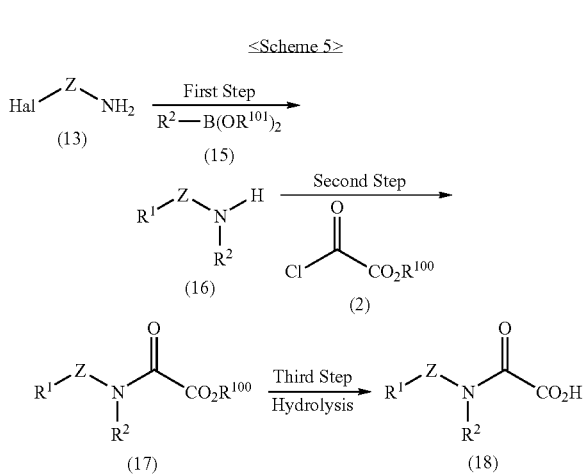

wherein Hal represents a halogen atom; $R^{100}$ represents a $C_{1-4}$ alkyl group or the like; $R^{101}$ represents hydrogen atom, a $C_{1-4}$ alkyl group or the like; each of $R^1$, $R^2$ and Z has the same meanings as that described above.

<First Step>

The N-(aryl)-aryl substituted aniline derivative (16) can be prepared by reacting the aryl substituted aniline derivative (13) with the arylboronic acid derivative (15). This reaction is carried out, for example, in a solvent, in the presence of copper(II) acetate and a base, at a reaction temperature of from 0° to 180°, preferably at a temperature of from 0° to the boiling point of the solvent.

As the base, examples include, for example, organic bases such as triethylamine and diisopropylethylamine.

As the solvent, any solvent can be used as long as it does not inhibit the reaction, and examples include, for example, halogenated solvents such as dichloromethane, dichloroethane and chloroform; pyridine; or a mixed solvent thereof.

<Second Step>

The N-aryl-N-(aryl substituted phenyl)oxamic acid ester derivative (17) can be prepared by reacting the N-(aryl)-aryl substituted aniline derivative (16) obtained in the first step with the chloroglyoxylic acid ester (2). This reaction is carried out in a solvent, in the presence of a base, at a reaction temperature of from 0° to 180°, preferably at a temperature of from 0° to the boiling point of the solvent.

As the base, examples include inorganic bases such as potassium carbonate, sodium carbonate and sodium hydrogencarbonate; and organic bases such as triethylamine and diisopropylethylamine.

As the solvent, any solvent can be used as long as it does not inhibit the reaction, and examples include, for example, halogenated solvents such as dichloromethane, dichloroethane and chloroform; ethers such as tetrahydrofuran, 1,2-dimethoxyethane and 1,4-dioxane; or a mixed solvent thereof.

<Third Step>

The final target compound (18) can be prepared by the hydrolysis of the N-aryl-N-(aryl substituted phenyl)oxamic acid ester derivative (17) obtained in the second step. This reaction is carried out in a solvent, in the presence of a base, at a reaction temperature of from 0° to 180°, preferably at a temperature of from 0° to the boiling point of the solvent. The reaction may be carried out under ultrasound irradiation.

As the base, examples include, for example, inorganic bases such as sodium hydroxide, potassium hydroxide, potassium carbonate and sodium carbonate.

As the solvent, any solvent can be used as long as it does not inhibit the reaction, and examples include, for example, ethers such as tetrahydrofuran, 1,2-dimethoxyethane and 1,4-dioxane; alcohols such as methanol and ethanol; water; or a mixed solvent thereof.

When the aftertreatment is carried out under acidic condition, the free form of the oxamic acid can be obtained. When the aftertreatment is carried out under basic condition, the salt of the oxamic acid can be obtained.

In the compounds represented by the general formula (I), the compounds wherein X is oxygen atom and m is 0 can be prepared, for example, by using the aryloxy-substituted aniline derivative ($R^1$—O—Z—$NH_2$) instead of the aryl-substituted aniline derivative (13) in scheme 5.

The compounds represented by the general formula (I), wherein X is oxygen atom, Z is a 1,2-phenylene group, a substituted 1,2-phenylene group, a 1,4-phenylene group or a substituted 1,4-phenylene group, m is 1, can be prepared, for example, by a method shown below.

[Chemical Formula 12]

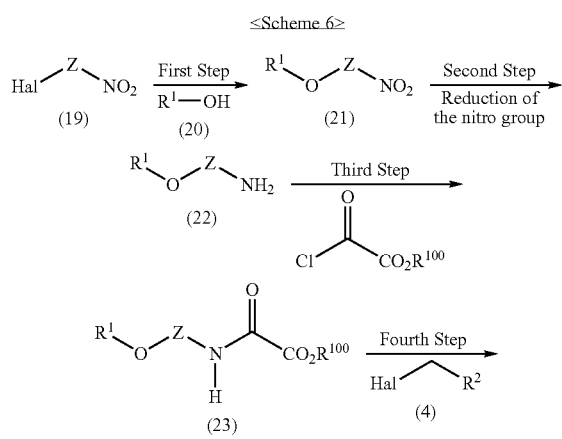

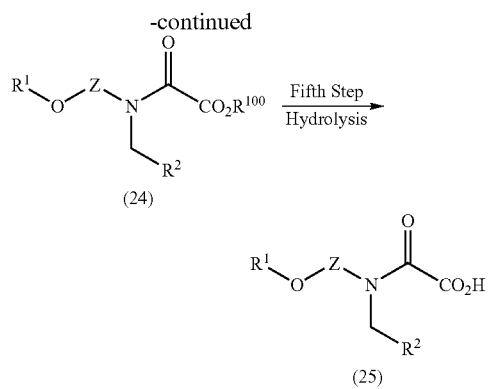

wherein Hal represents a halogen atom; $R^{100}$ represents a $C_{1-4}$ alkyl group or the like; $R^{101}$ represents hydrogen atom, a $C_{1-4}$ alkyl group or the like; z represents a 1,4-phenylene group or a substituted 1,4-phenylene group; each of $R^1$ and $R^2$ has the same meanings as that described above.

<First Step>

The 4-aryloxy-1-nitrobenzene derivative (21) can be prepared by reacting the 4-halo-1-nitrobenzene derivative (19) with the hydroxyaryl derivative (20). This reaction is carried out in a solvent, in the presence of a base, at a reaction temperature of from 0° to 180°, preferably at a temperature of from 0° to the boiling point of the solvent.

As the base, examples include inorganic bases such as sodium hydride, potassium hydride, potassium carbonate, sodium carbonate and sodium hydrogencarbonate; and organic bases such as triethylamine and diisopropylethylamine.

As the solvent, any solvent can be used as long as it does not inhibit the reaction, and examples include, for example, halogenated solvents such as dichloromethane, dichloroethane and chloroform; ethers such as tetrahydrofuran, 1,2-dimethoxyethane and 1,4-dioxane; amides such as dimethylformamide and N-methylpyrrolidone; or a mixed solvent thereof.

<Second Step>

The 4-(aryloxy)aniline derivative (22) can be prepared by the reduction of the nitro group of the 4-aryloxy-1-nitrobenzene derivative (21) obtained in the first step. This reaction is carried out in a solvent under hydrogen atmosphere, in the presence of a catalytic amount of a transition metal, at a reaction temperature of from 0° to 180°, preferably at a temperature of from 0° to the boiling point of the solvent.

As the transition metal, examples include, for example, palladium-activated charcoal, platinum-activated charcoal and the like.

As the solvent, any solvent can be used as long as it does not inhibit the reaction, and examples include, for example, ethers such as tetrahydrofuran, 1,2-dimethoxyethane and 1,4-dioxane; alcohols such as methanol and ethanol; water; or a mixed solvent thereof.

<Third Step>

The N-[4-(aryloxy)phenyl]oxamic acid ester derivative (23) can be prepared by reacting the 4-(aryloxy)aniline derivative (22) obtained in the second step with the chloroglyoxylic acid ester (2). This reaction is carried out in a solvent, in the presence of a base, at a reaction temperature of from 0° to 180°, preferably at a temperature of from 0° to the boiling point of the solvent.

As the base, examples include inorganic bases such as potassium carbonate, sodium carbonate and sodium hydrogencarbonate; and organic bases such as triethylamine and diisopropylethylamine.

As the solvent, any solvent can be used as long as it does not inhibit the reaction, and examples include, for example, halogenated solvents such as dichloromethane, dichloroethane and chloroform; ethers such as tetrahydrofuran, 1,2-dimethoxyethane and 1,4-dioxane; or a mixed solvent thereof.

<Fourth Step>

The N-aralkyl-N-[4-(aryloxy)phenyl]oxamic acid ester derivative (24) can be prepared by reacting the N-[4-(aryloxy)phenyl]oxamic acid ester derivative (23) obtained in the third step with the aralkyl halide derivative (4). This reaction is carried out in a solvent, in the presence of a base, at a reaction temperature of from 0° to 180°, preferably at a temperature of from 0° to the boiling point of the solvent. Crown ethers such as 18-crown-6 may be added.

As the base, examples include inorganic bases such as sodium hydride, potassium hydride, potassium carbonate, sodium carbonate and sodium hydrogencarbonate; and organic bases such as triethylamine and diisopropylethylamine.

As the solvent, any solvent can be used as long as it does not inhibit the reaction, and examples include, for example, halogenated solvents such as dichloromethane, dichloroethane and chloroform; ethers such as tetrahydrofuran, 1,2-dimethoxyethane and 1,4-dioxane; acetonitrile; or a mixed solvent thereof.

<Fifth Step>

The final target compound (25) can be prepared by the hydrolysis of the N-aralkyl-N-[4-(aryloxy)phenyl]oxamic acid ester derivative (24) obtained in the fourth step. This reaction is carried out in a solvent, in the presence of a base, at a reaction temperature of from 0° to 180°, preferably at a temperature of from 0° to the boiling point of the solvent. The reaction may be carried out under ultrasound irradiation.

As the base, examples include, for example, inorganic bases such as sodium hydroxide, potassium hydroxide, potassium carbonate and sodium carbonate.

As the solvent, any solvent can be used as long as it does not inhibit the reaction, and examples include, for example, ethers such as tetrahydrofuran, 1,2-dimethoxyethane and 1,4-dioxane; alcohols such as methanol and ethanol; water; or a mixed solvent thereof.

When the aftertreatment is carried out under acidic condition, the free form of the oxamic acid can be obtained. When the aftertreatment is carried out under basic condition, the salt of the oxamic acid can be obtained.

In the examples of the specification, preparation methods of typical compounds included in the general formula (I) are explained in details. Therefore, those skilled in the art can prepare any compound included in the general formula (I) by referring to the explanations of the aforementioned general preparation methods and of specific preparation methods of the examples, selecting appropriate reaction raw materials, reaction reagents, and reaction conditions, and by adding appropriate modification and alteration of these methods, if necessary.

The medicament of the present invention can be used for prophylactic and/or therapeutic treatment of diseases caused by an expression of PAI-1 or an enhancement of PAI-1 activity. The term "therapeutic treatment" used in the present specification includes prevention of progression of diseases and the term "prophylactic treatment" includes the prevention of reoccurrence. The medicament of the present invention can be used, for example, for prophylactic and/or therapeutic treatment of diseases caused by thrombogenesis, fibrogenesis, accumulation of visceral fat, angiogenesis, deposition and remodeling of extracellular matrix, proliferation, movement, infiltration, and migration of cell (for example, tumor cell and vascular endothelial cell), and tissue remodeling (for example, cardiac remodeling and vascular remodeling).

More specifically, the medicament of the present invention can be used for prophylactic and/or therapeutic treatment of one or more diseases selected from ischemic cerebrovascular diseases such as cerebral thrombosis, cerebral embolism, cerebral infarction, transient ischemic attack, cerebral stroke and vascular dementia; ischemic heart diseases such as angina, myocardial infarction, intraatrial thrombosis caused by atrial fibrillation, and heart failure; thrombotic pulmonary diseases such as pulmonary thrombosis and pulmonary embolism; venous occlusive diseases such as deep vein thrombosis (DVT) and thrombophlebitis; peripheral arterial occlusive diseases such as acute arterial occlusion and chronic arterial occlusion; thrombus after bypass vascular transplantation; disseminated intravascular coagulation (DIC); acute coronary occlusion and restenosis after percutaneous transluminal coronary angioplasty (PTCA); angiopathy and thromboses caused by immune disorder such as antiphospholipid syndrome; angiopathy and thromboses caused by congenital thrombotic tendency such as genetic abnormality; thrombotic renal diseases such as renal thrombosis and renal embolism; nephropathy caused by metabolic diseases; arteriosclerosis; thrombotic diseases, thrombosis, fibrotic diseases, blood coagulation, ischemic diseases, heart attack, deep-seated thrombosis, pulmonary thromboembolism, venous thromboembolism, nephrosclerosis, metabolic syndrome, aldosterone tissue disorder, organ failure, economy-class syndrome, endotoxic shock, allergic diseases, vascular events such as cerebrovascular event and cardiovascular event, angiitis, nonbacterial thrombotic endocarditis; severe infectious diseases such as sepsis; fibrin-dependent pain in arthritis; diabetic complications such as retinopathy, nephropathy, neurosis, peripheral circulatory disturbance; hypertension; diabetes; hyperinsulinemia; hypercholesteremia; insulin resistant disorder; hyperlipidemia; obesity; tumors including solid cancers such as lung cancer, pancreatic cancer, colon cancer, gastric cancer, prostate cancer, breast cancer, cervical cancer and ovarian cancer; tumor invasion; tumor metastasis; asthma; tissue fibrosis such as hepatic cirrhosis, pulmonary fibrosis, renal fibrosis and interstitial cystitis; acute rejections and arterial lesions after organ transplantation such as cardiac transplantation and renal transplantation. Moreover, the medicament of the present invention is effective in healing of wounds and bedsores because the medicament of the present invention can prevent and improve thrombus formation.

As the active ingredient of the medicament on the present invention, 1 or more kinds of substances selected from the group consisting of the compound represented by the general formula (I) and a pharmacologically acceptable salt thereof, and a hydrate thereof and a solvate thereof may be used. The aforementioned substance, per se, may be administered as the medicament of the present invention, however, preferably, the medicament of the present invention is provided in the form of a pharmaceutical composition comprising the aforementioned substance which is an active ingredient together with one or more pharmacologically acceptable pharmaceutical additives. In the aforementioned pharmaceutical compositions, a ratio of the active ingredient to the pharmaceutical additives is 1 weight % to 90 weight %.

The pharmaceutical compositions of the present invention may be administered as pharmaceutical compositions for oral administration, for example, granules, subtilized granules, powders, hard capsules, soft capsules, syrup, emulsion, suspension, or solution, or may be administered as pharmaceutical compositions for parenteral administration, for example, injections for intravenous administration, intramuscular administration, or subcutaneous administration, drops, suppositories, percutaneous absorbent, transmucosal absorption preparations, nasal drops, ear drops, instillation, and inhalants. Preparations made as pharmaceutical compositions in a form of powder may be dissolved when necessary and used as injections or drip infusions.

For preparation of pharmaceutical compositions, solid or liquid pharmaceutical additives may be used. Pharmaceutical additives may either be organic or inorganic. When an oral solid preparation is prepared, an excipient is added to the active ingredient, and further binders, disintegrator, lubricant, colorant, corrigent are added, if necessary, preparations in the forms of tablets, coating tablets, granules, powders, capsules and the like may be manufactured by common procedures. Examples of the excipient include lactose, sucrose, saccharose, glucose, corn starch, starch, talc, sorbit, crystal cellulose, dextrin, kaolin, calcium carbonate, and silicon dioxide. Examples of the binder include, for example, polyvinyl alcohol, polyvinyl ether, ethyl cellulose, methyl cellulose, gum Arabic, tragacanth, gelatine, shellac, hydroxypropyl cellulose, hydroxypropyl methyl cellulose, calcium citrate, dextrin, and pectin. Examples of the lubricant include, for example, magnesium stearate, talc, polyethylene glycol, silica, and hydrogenated vegetable oil. As the coloring agent, any material can be used which are approved to be added to ordinary pharmaceuticals. As the corrigent, cocoa powder, menthol, aromatic acid, peppermint oil, d-borneol, cinnamon powder and the like can be used. These tables and granules may be applied with sugarcoating, gelatine coating, or an appropriate coating, if necessary. Preservatives, antioxidant and the like may be added, if required.

For liquid preparations for oral administration such as emulsions, syrups, suspensions, and solutions, ordinary used inactive diluents, for example, water or vegetable oil may be used. For these preparations, besides inactive diluents, adjuvants such as wetting agents, suspending aids, sweating agents, flavoring agents, coloring agents or preservatives may be blended. After a liquid preparation is manufactured, the preparation may be filled in capsules made of a absorbable substance such as gelatin. Examples of solvents or suspending agents used for the preparations of parenteral administration such as injections or suppositories include, for example, water, propylene glycol, polyethylene glycol, benzyl alcohol, ethyl oleate, and lecithin. Examples of base materials used for preparation of suppositories include, for example, cacao butter, emulsified cacao butter, lauric fat, and witepsol. Methods for preparation of the aforementioned preparations are not limited, and any method ordinarily used in the art may be used.

When the composition are prepared in the form of injections, carriers such as, for example, diluents including water, ethanol, macrogol, propyleneglycol, citric acid, acetic acid, phosphoric acid, lactic acid, sodium lactate, sulfuric acid and sodium hydroxide, pH modifiers and buffer solutions including sodium citrate, sodium acetate and sodium phosphate, stabilizers such as sodium pyrosulfite, ethylenediaminetetraacetic acid, thioglycolic acid and thiolactate may be used. For the preparation, a sufficient amount of a salt, glucose, mannitol or glycerin may be blended in the preparation to manufacture an isotonic solution, and an ordinary solubilizer, a soothing agent, or a topical anesthetic may be used.

When the preparation in the form of an ointment such as a paste, a cream, and a gel is manufactured, an ordinarily used base material, a stabilizer, a wetting agent, and a preservative may be blended, if necessary, and may be prepared by mixing the components by a common method. As the base material, for example, white petrolatum, polyethylene, paraffin, glycerin, cellulose derivatives, polyethylene glycol, silicon, and bentonite may be used. As the preservative, paraoxy methyl benzoate, paraoxy ethyl benzoate, paraoxy propyl benzoate and the like may be used. When the preparation in the form of a patch is manufactured, the aforementioned ointment, cream gel, or paste and the like may be applied by a common method to an ordinary support. As the support, fabric made of cotton, span rayon, and synthetic fibersor or nonwoven fabric, and a film or a foam sheet such as made of soft vinyl chloride, polyethylene, and polyurethane and the like may be preferably used.

A dose of the medicament of the present invention is not particularly limited. For oral administration, a dose may generally be 0.01 to 5,000 mg per day for an adult as the weight of the compound of the present invention. It is preferred to increase or decrease the above dose appropriately depending on the age, pathological conditions, and symptoms of a patient. The above dose may be administered once a day or 2 to 3 times a day as divided portions with proper intervals, or intermittent administration for every several days may be acceptable. When the medicament is used as an injection, the dose may be 0.001 to 100 mg per day for an adult as the weight of the compound of the present invention.

Oral or parenteral administration of the medicament of the present invention may be carried out preoperatively, when the medicament of the present invention is used for prophylactic and/or therapeutic treatment of intravascular lesions after vascular transplantation or organ transplantation, or after blood circulation restoration, whose examples include, for example, thrombus after bypass vascular transplantation, acute coronary occlusion and restenosis after percutaneous transluminal coronary angioplasty, arterial lesions after organ transplantation such as cardiac transplantation and renal transplantation and the like. Furthermore, oral or parenteral administration of the medicament of the present invention may be carried out intraoperatively and/or postoperatively in addition to the aforementioned preoperative administration, if necessary.

EXAMPLES

The present invention will be explained more specifically with reference to the following examples. However the scope of the present invention is not limited to the following examples. In the present examples, compounds wherein the groups and numeric values shown on Table 1 are selected as $R^1$, $R^2$, X, Z and m of the compound represented by the general formula (I) are prepared.

In the following, the structure of the intermediate prepared in each example is shown, respectively.

TABLE 2

| Example | Structure |
|---|---|
| 1(1) | 4-Br-C6H4-NH-CH2-(3,5-diMe-C6H3) |
| 1(2) | 4-Br-C6H4-N(C(O)CO2Me)-CH2-(3,5-diMe-C6H3) |
| 1(3) | 4-(F3CO)-C6H4-C6H4-N(C(O)CO2Me)-CH2-(3,5-diMe-C6H3) |
| 2(1) | 4-Br-C6H4-NH-CH2-(4-Cl-C6H4) |
| 2(2) | 4-Br-C6H4-N(C(O)CO2Me)-CH2-(4-Cl-C6H4) |
| 2(3) | 4-(F3CO)-C6H4-C6H4-N(C(O)CO2Me)-CH2-(4-Cl-C6H4) |
| 3(1) | 4-(F3CO)-C6H4-C6H4-NO2 |
| 3(2) | 4-(F3CO)-C6H4-C6H4-NH2 |
| 3(3) | 4-(F3CO)-C6H4-C6H4-NH-C(O)CO2Me |
| 3(4) | 4-(F3CO)-C6H4-C6H4-N(C(O)CO2Me)-CH2-(3-Me-C6H4) |
| 4(1) | 4-Br-C6H4-NH-C(O)CO2Me |

TABLE 2-continued

| Example | Structure |
|---|---|
| 4(2) | 4-bromophenyl-N-(4-tert-butylbenzyl)-N-(methoxycarbonylcarbonyl)aniline |
| 4(3) | 4'-methoxy-biphenyl-4-yl-N-(4-tert-butylbenzyl)-N-(methoxycarbonylcarbonyl)amine |
| 5(1) | 4'-fluoro-biphenyl-4-yl-N-(4-tert-butylbenzyl)-N-(methoxycarbonylcarbonyl)amine |
| 6(1) | N-benzyl-4-bromoaniline |
| 6(2) | N-benzyl-4'-(trifluoromethoxy)biphenyl-4-amine |
| 6(3) | N-benzyl-N-(methoxycarbonylcarbonyl)-4'-(trifluoromethoxy)biphenyl-4-amine |
| 7(1) | N-(4-tert-butylphenyl)-4'-(trifluoromethoxy)biphenyl-4-amine |
| 7(2) | N-(4-tert-butylphenyl)-N-(methoxycarbonylcarbonyl)-4'-(trifluoromethoxy)biphenyl-4-amine |
| 8(1) | N-(4-tert-butylbenzyl)-N-(methoxycarbonylcarbonyl)-4'-(trifluoromethoxy)biphenyl-4-amine |
| 9(1) | N-(4-tert-butylbenzyl)-3-bromoaniline |

TABLE 2-continued

| Example | Structure |
|---|---|
| 9(2) | 4'-(trifluoromethoxy)-N-(4-tert-butylbenzyl)-[1,1'-biphenyl]-3-amine |
| 9(3) | methyl 2-(N-(4-tert-butylbenzyl)-4'-(trifluoromethoxy)-[1,1'-biphenyl]-3-ylamino)-2-oxoacetate |
| 10(1) | methyl 2-(N-(4-methoxybenzyl)-4'-(trifluoromethoxy)-[1,1'-biphenyl]-4-ylamino)-2-oxoacetate |
| 11(1) | 1-(4-nitrophenoxy)-4-(trifluoromethoxy)benzene |
| 11(2) | 4-(4-(trifluoromethoxy)phenoxy)aniline |
| 11(3) | methyl 2-oxo-2-(4-(4-(trifluoromethoxy)phenoxy)phenylamino)acetate |
| 11(4) | methyl 2-(N-(4-tert-butylbenzyl)-4-(4-(trifluoromethoxy)phenoxy)phenylamino)-2-oxoacetate |

TABLE 2-continued

| Example | Structure |
|---|---|
| 13(1) | methyl 2-(N-(4-tert-butylbenzyl)-4'-(methylthio)-[1,1'-biphenyl]-4-ylamino)-2-oxoacetate |
| 14(1) | methyl 2-(N-(4-tert-butylbenzyl)-4'-chloro-[1,1'-biphenyl]-4-ylamino)-2-oxoacetate |
| 15(1) | 5-bromo-N-(4-tert-butylbenzyl)-2-methylaniline |
| 15(2) | methyl 2-(5-bromo-N-(4-tert-butylbenzyl)-2-methylphenylamino)-2-oxoacetate |
| 15(3) | methyl 2-(N-(4-tert-butylbenzyl)-6-methyl-4'-(trifluoromethoxy)-[1,1'-biphenyl]-3-ylamino)-2-oxoacetate |

TABLE 2-continued

| Example | Structure |
|---|---|
| 16(1) | 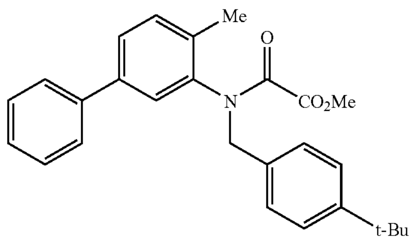 |
| 17(1) | 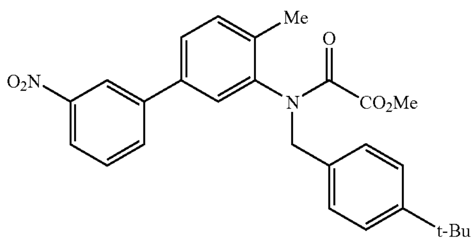 |
| 18(1) | 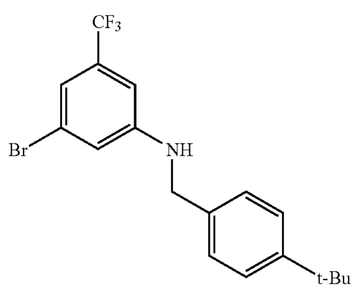 |
| 18(2) | 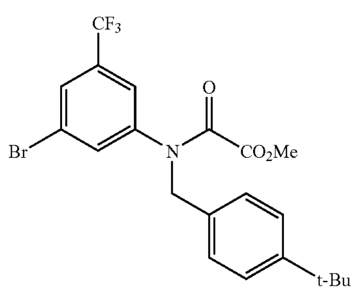 |
| 18(3) | 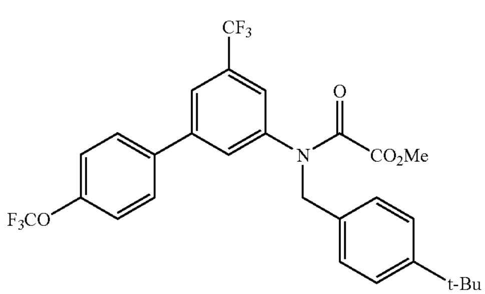 |
| 19(1) | |
| 20(1) | |
| 21(1) | |
| 22(1) | |
| 23(1) | |

TABLE 2-continued
| Example | Structure |
|---|---|
| 24(1) | 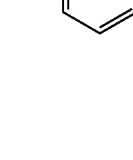 |
| 25(1) | 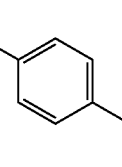 |
| 25(2) |  |
| 25(3) | 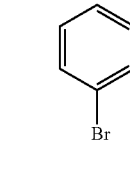 |
| 26(1) | 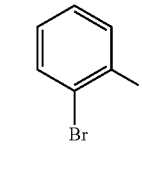 |
| 26(2) | 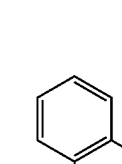 |
| 26(3) | 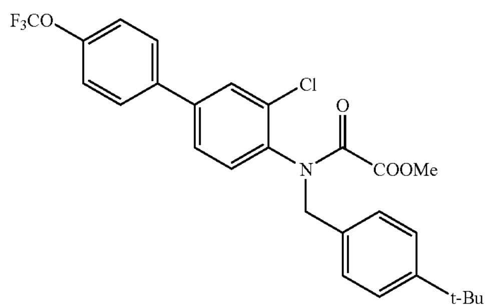 |
| 27(1) | 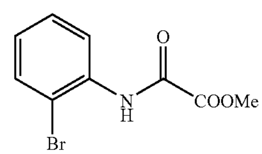 |
| 27(2) | 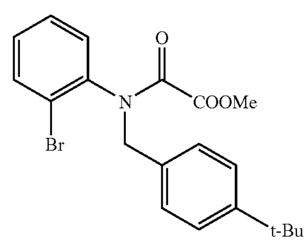 |
| 27(3) | 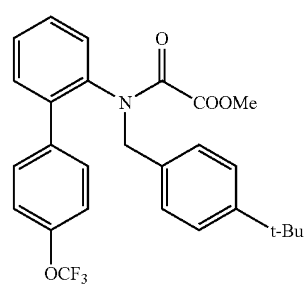 |
| 28(1) | 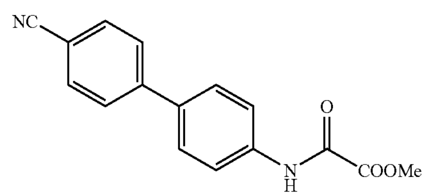 |

TABLE 2-continued
| Example | Structure |
|---|---|
| 28(2) | 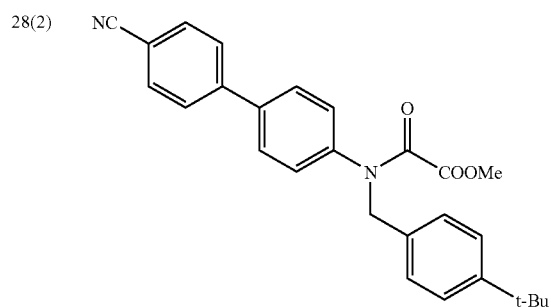 |
| 29(1) | 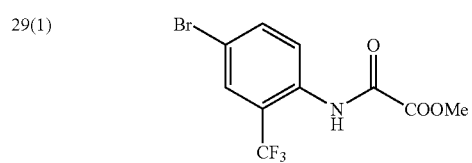 |
| 29(2) | 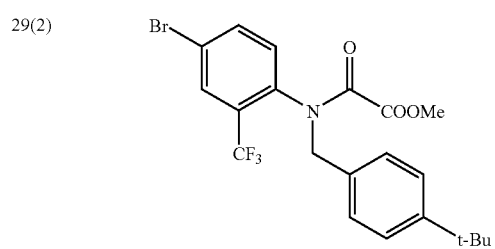 |
| 29(3) | 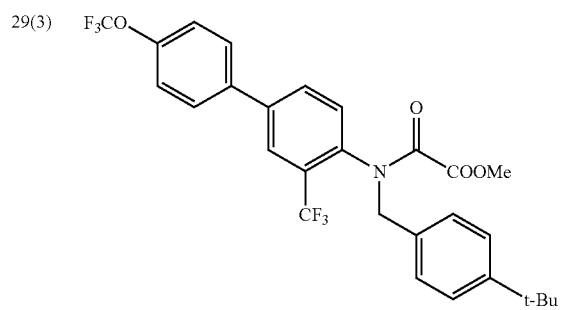 |
| 30(1) | 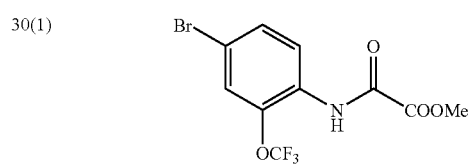 |
| 30(2) | 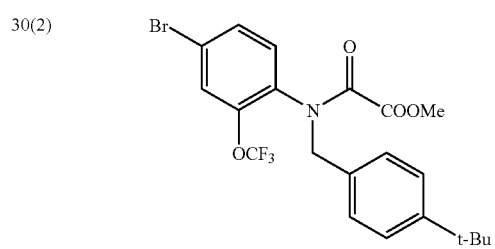 |
TABLE 2-continued
| Example | Structure |
|---|---|
| 30(3) | 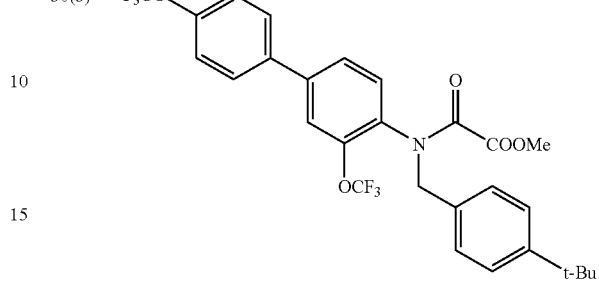 |
| 31(1) | 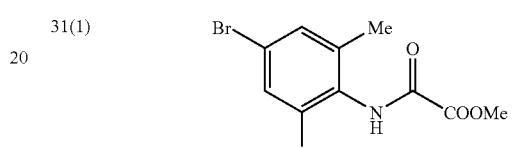 |
| 31(2) | 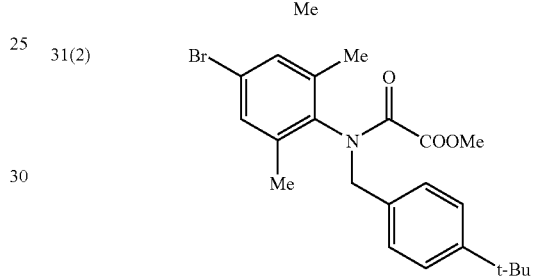 |
| 31(3) | 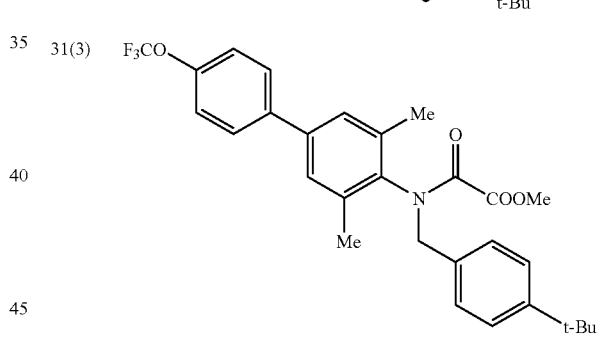 |
| 32(1) | 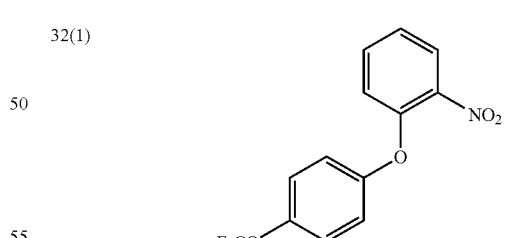 |
| 32(2) | 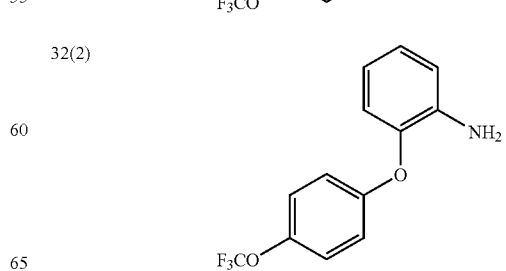 |

TABLE 2-continued
| Example | Structure |
|---|---|
| 32(3) | 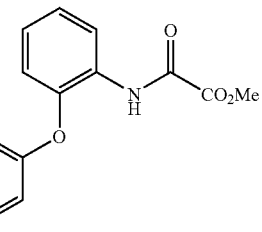 |
| 32(4) | 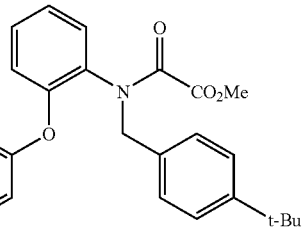 |
| 33(1) | 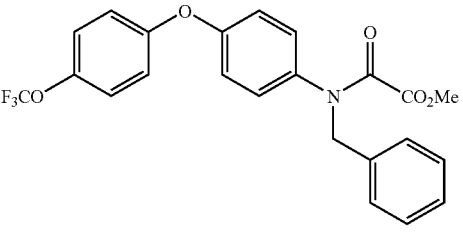 |
| 34(1) | 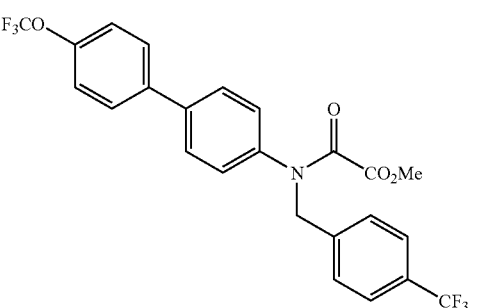 |
| 35(1) | 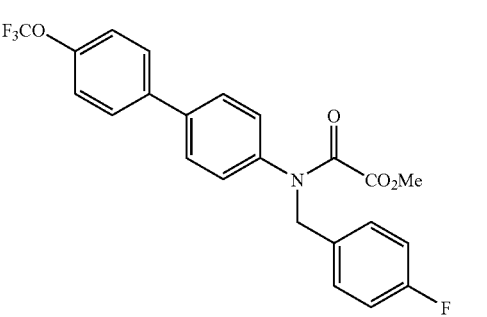 |
| 36(1) | 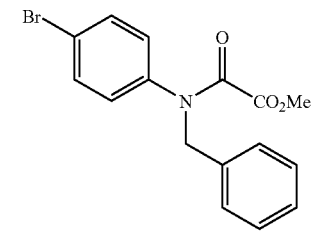 |
| 36(2) | 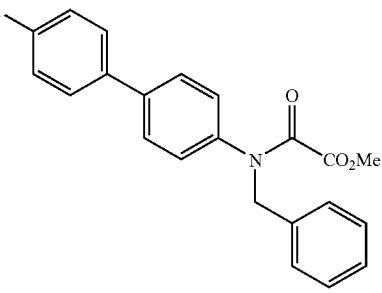 |
| 37(1) | 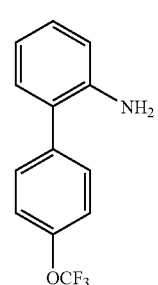 |
| 37(2) | 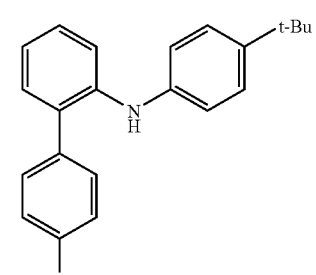 |
| 37(3) | 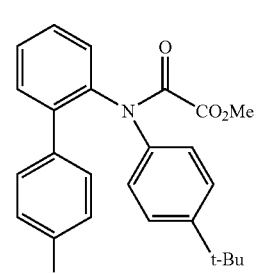 |

TABLE 2-continued

| Example | Structure |
|---|---|
| 38(1) | 4'-(trifluoromethoxy)-[1,1'-biphenyl]-3-amine |
| 38(2) | N-(4-tert-butylphenyl)-4'-(trifluoromethoxy)-[1,1'-biphenyl]-3-amine |
| 38(3) | methyl 2-[N-(4-tert-butylphenyl)-4'-(trifluoromethoxy)-[1,1'-biphenyl]-3-yl)amino]-2-oxoacetate |
| 39(1) | methyl 2-oxo-2-[N-(4-(trifluoromethoxy)benzyl)-4'-(trifluoromethoxy)-[1,1'-biphenyl]-4-yl)amino]acetate |
| 40(1) | methyl 2-[N-(4-(methylthio)benzyl)-4'-(trifluoromethoxy)-[1,1'-biphenyl]-4-yl)amino]-2-oxoacetate |
| 41(1) | methyl 2-[N-(4-biphenylmethyl)-4'-(trifluoromethoxy)-[1,1'-biphenyl]-4-yl)amino]-2-oxoacetate |
| 42(1) | methyl 2-[(4-bromophenyl)(4-(trifluoromethoxy)benzyl)amino]-2-oxoacetate |
| 42(2) | methyl 2-[4'-tert-butyl-[1,1'-biphenyl]-4-yl)(4-(trifluoromethoxy)benzyl)amino]-2-oxoacetate |
| 43(1) | methyl 2-[4'-tert-butyl-[1,1'-biphenyl]-4-yl)(4-tert-butylbenzyl)amino]-2-oxoacetate |
| 44(1) | methyl 2-[4'-n-butyl-[1,1'-biphenyl]-4-yl)(4-tert-butylbenzyl)amino]-2-oxoacetate |

TABLE 2-continued

| Example | Structure |
|---|---|
| 45(1) | 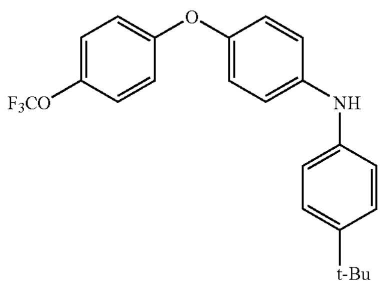 |
| 45(2) | 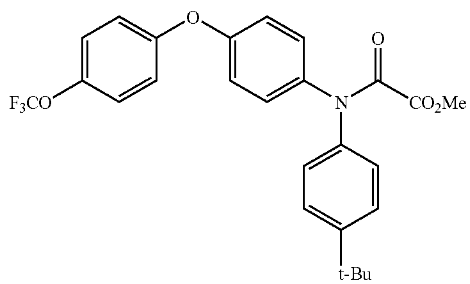 |
| 46(1) | 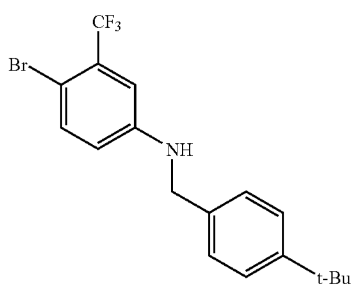 |
| 46(2) | 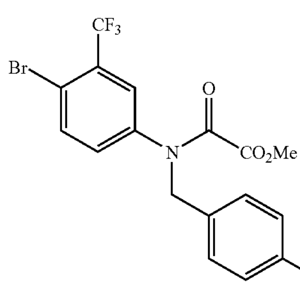 |
| 46(3) | 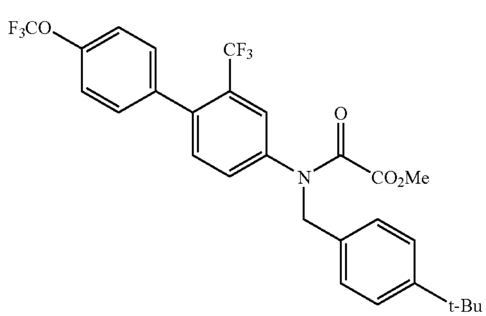 |
| 47(1) | |
| 47(2) | |
| 48(1) | |
| 48(2) | |
| 48(3) | |

TABLE 2-continued

| Example | Structure |
|---|---|
| 49(1) | 4-(trifluoromethyl)-4'-(trifluoromethoxy)-[1,1'-biphenyl]-2-amine |
| 49(2) | methyl 2-((4-(trifluoromethyl)-4'-(trifluoromethoxy)-[1,1'-biphenyl]-2-yl)amino)-2-oxoacetate |
| 49(3) | methyl 2-((4-tert-butylbenzyl)(4-(trifluoromethyl)-4'-(trifluoromethoxy)-[1,1'-biphenyl]-2-yl)amino)-2-oxoacetate |
| 50(1) | 1-(4-(trifluoromethoxy)phenoxy)-3-nitrobenzene |
| 50(2) | 3-(4-(trifluoromethoxy)phenoxy)aniline |
| 50(3) | N-(4-tert-butylphenyl)-3-(4-(trifluoromethoxy)phenoxy)aniline |
| 50(4) | methyl 2-((4-tert-butylphenyl)(3-(4-(trifluoromethoxy)phenoxy)phenyl)amino)-2-oxoacetate |
| 51(1) | N-(2,6-dichlorobenzyl)-4-bromoaniline |
| 51(2) | N-(2,6-dichlorobenzyl)-4'-(trifluoromethoxy)-[1,1'-biphenyl]-4-amine |
| 51(3) | methyl 2-((2,6-dichlorobenzyl)(4'-(trifluoromethoxy)-[1,1'-biphenyl]-4-yl)amino)-2-oxoacetate |
| 52(1) | methyl 2-((3-(4-(trifluoromethoxy)phenoxy)phenyl)amino)-2-oxoacetate |
| 52(2) | methyl 2-((4-tert-butylbenzyl)(3-(4-(trifluoromethoxy)phenoxy)phenyl)amino)-2-oxoacetate |

TABLE 2-continued

| Example | Structure |
|---|---|
| 53(1) | 4-bromo-2,6-dichloro-N-(4-tert-butylbenzyl)aniline |
| 53(2) | 3,5-dichloro-4'-(trifluoromethoxy)-N-(4-tert-butylbenzyl)-[1,1'-biphenyl]-4-amine |
| 53(3) | methyl 2-(N-(4-tert-butylbenzyl)-3,5-dichloro-4'-(trifluoromethoxy)-[1,1'-biphenyl]-4-ylamino)-2-oxoacetate |
| 54(1) | 4-(4-(trifluoromethoxy)phenoxy)-2-(trifluoromethyl)-1-nitrobenzene |
| 54(2) | 4-(4-(trifluoromethoxy)phenoxy)-2-(trifluoromethyl)aniline |
| 54(3) | methyl 2-oxo-2-(4-(4-(trifluoromethoxy)phenoxy)-2-(trifluoromethyl)phenylamino)acetate |
| 54(4) | methyl 2-(N-(4-tert-butylbenzyl)-4-(4-(trifluoromethoxy)phenoxy)-2-(trifluoromethyl)phenylamino)-2-oxoacetate |
| 55(1) | 1-(4-(trifluoromethoxy)phenoxy)-3-nitro-5-(trifluoromethyl)benzene |
| 55(2) | 3-(4-(trifluoromethoxy)phenoxy)-5-(trifluoromethyl)aniline |
| 55(3) | methyl 2-oxo-2-(3-(4-(trifluoromethoxy)phenoxy)-5-(trifluoromethyl)phenylamino)acetate |
| 55(4) | methyl 2-(N-(4-tert-butylbenzyl)-3-(4-(trifluoromethoxy)phenoxy)-5-(trifluoromethyl)phenylamino)-2-oxoacetate |
| 56(1) | methyl 2-(3-bromo-4-methylphenylamino)-2-oxoacetate |
| 56(2) | methyl 2-(N-(4-tert-butylbenzyl)-3-bromo-4-methylphenylamino)-2-oxoacetate |

TABLE 2-continued

| Example | Structure |
|---|---|
| 56(3) | 4-OCF3-phenyl-2-Me-phenyl-N(CH2-4-t-Bu-phenyl)-C(O)COOMe |
| 57(1) | 3-Br-2-Me-phenyl-NH-CH2-4-t-Bu-phenyl |
| 57(2) | 3-Br-2-Me-phenyl-N(CH2-4-t-Bu-phenyl)-C(O)CO2Me |

TABLE 3

| Example | Structure |
|---|---|
| 57(3) | 4-F3CO-phenyl-2-Me-phenyl-N(CH2-4-t-Bu-phenyl)-C(O)CO2Me |
| 58(1) | 3-Br-5-Me-phenyl-NH-CH2-4-t-Bu-phenyl |
| 58(2) | 4-F3CO-phenyl-5-Me-phenyl-NH-CH2-4-t-Bu-phenyl |
| 58(3) | 4-F3CO-phenyl-5-Me-phenyl-N(CH2-4-t-Bu-phenyl)-C(O)CO2Me |
| 59(1) | 4-Br-2-NO2-phenyl-O-CH2-4-t-Bu-phenyl |
| 59(2) | 4-F3CO-phenyl-3-NO2-phenyl-O-CH2-4-t-Bu-phenyl |
| 59(3) | 4-F3CO-phenyl-3-NH2-phenyl-O-CH2-4-t-Bu-phenyl |

TABLE 3-continued
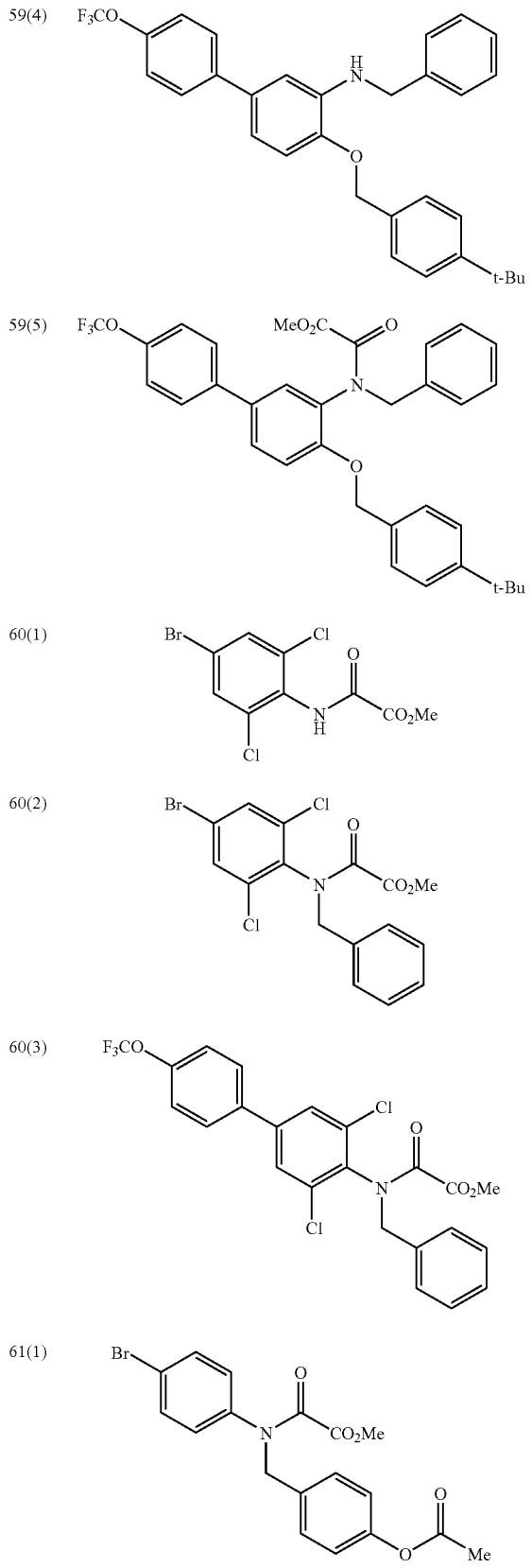
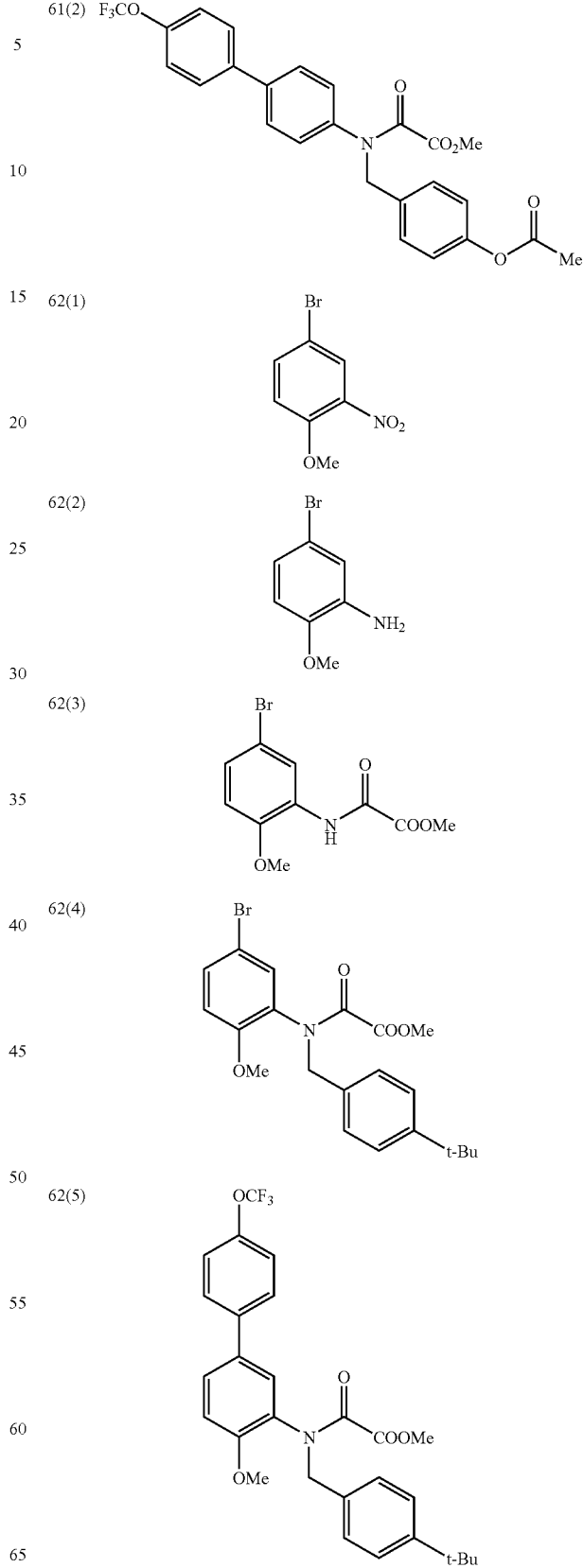

TABLE 3-continued
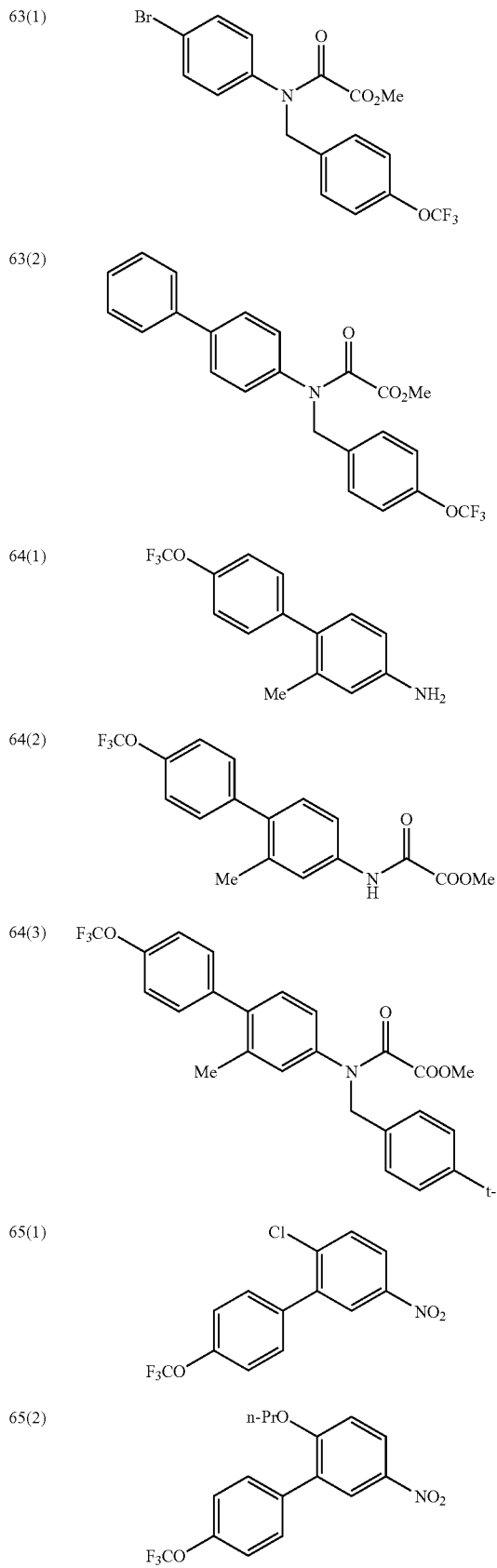
TABLE 3-continued
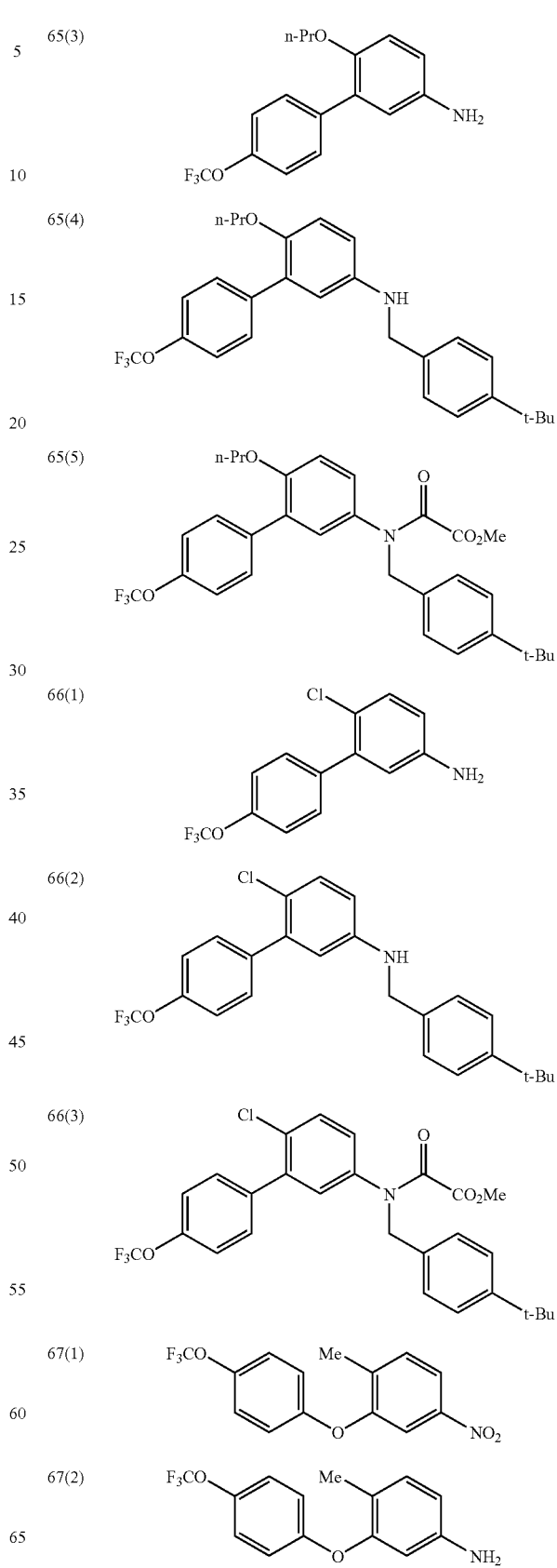

TABLE 3-continued
67(3) 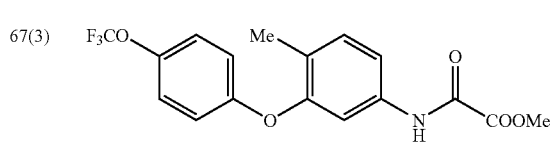
67(4) 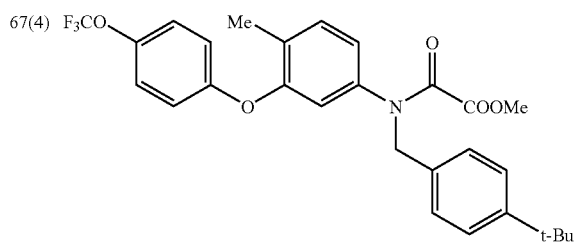
68(1) 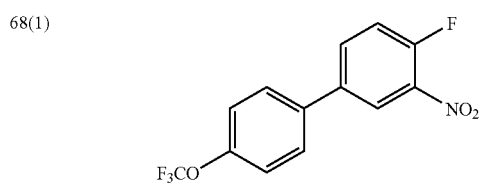
68(2) 
68(3) 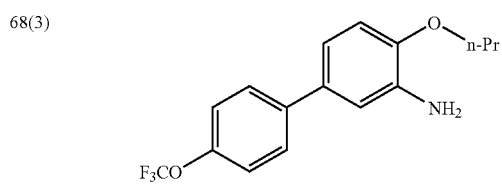
68(4) 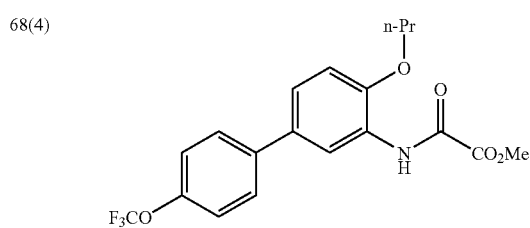
68(5) 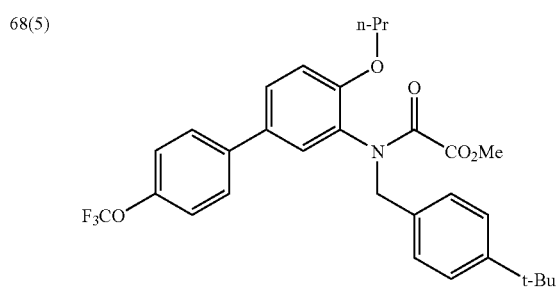
TABLE 3-continued
69(1) 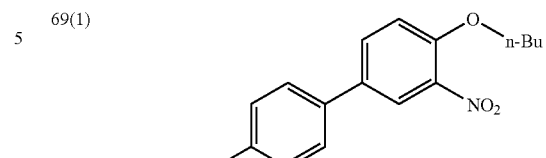
69(2) 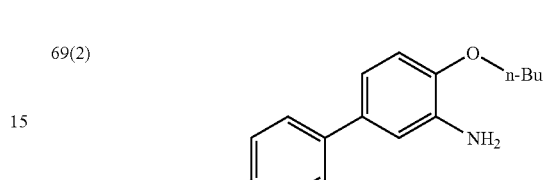
69(3) 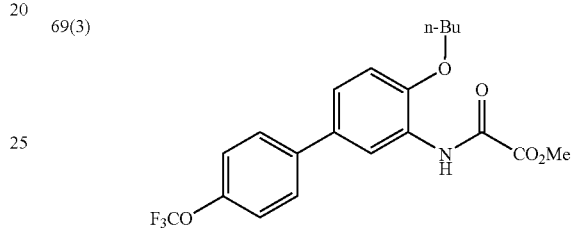
69(4) 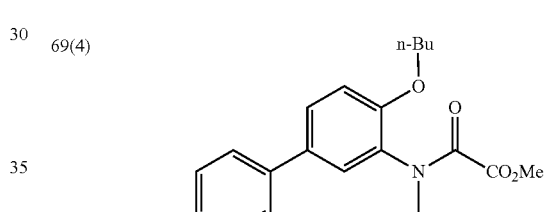
70(1) 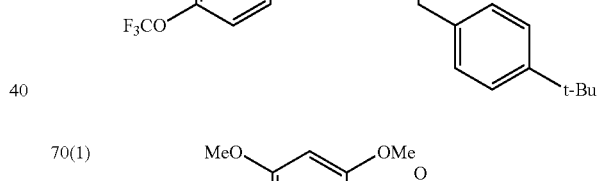
70(2) 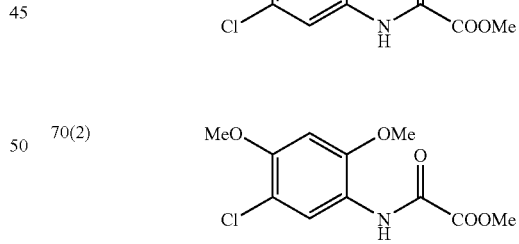
70(3) 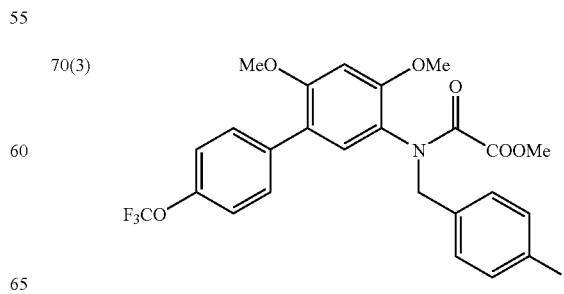

TABLE 3-continued
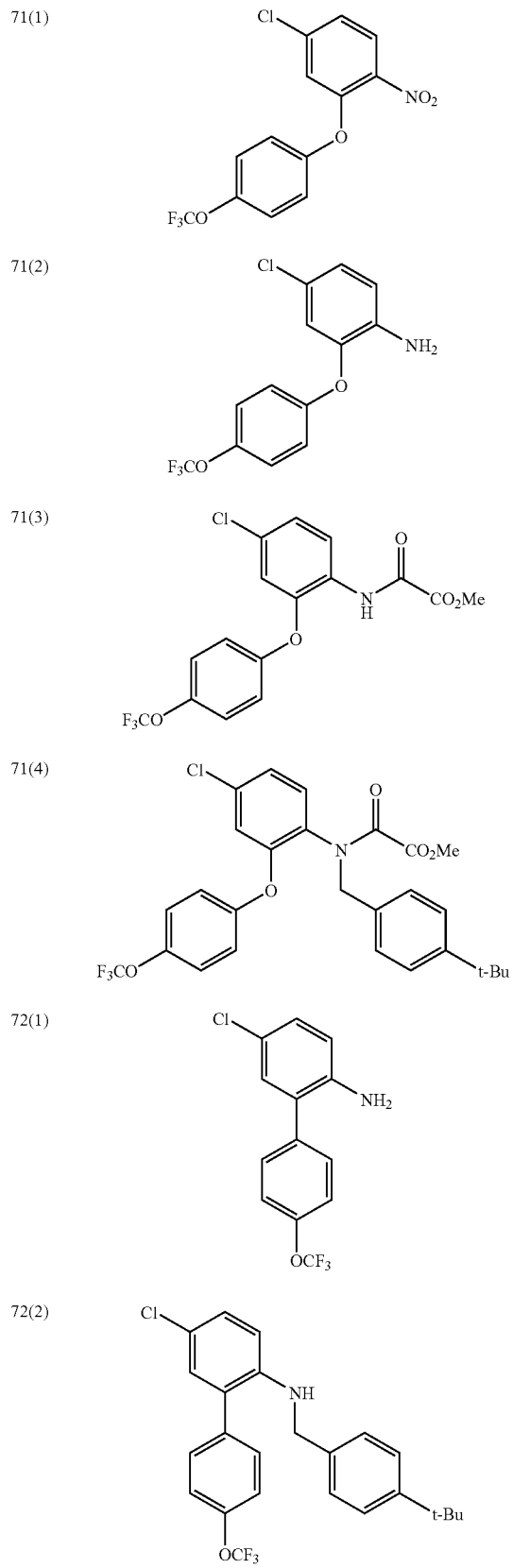
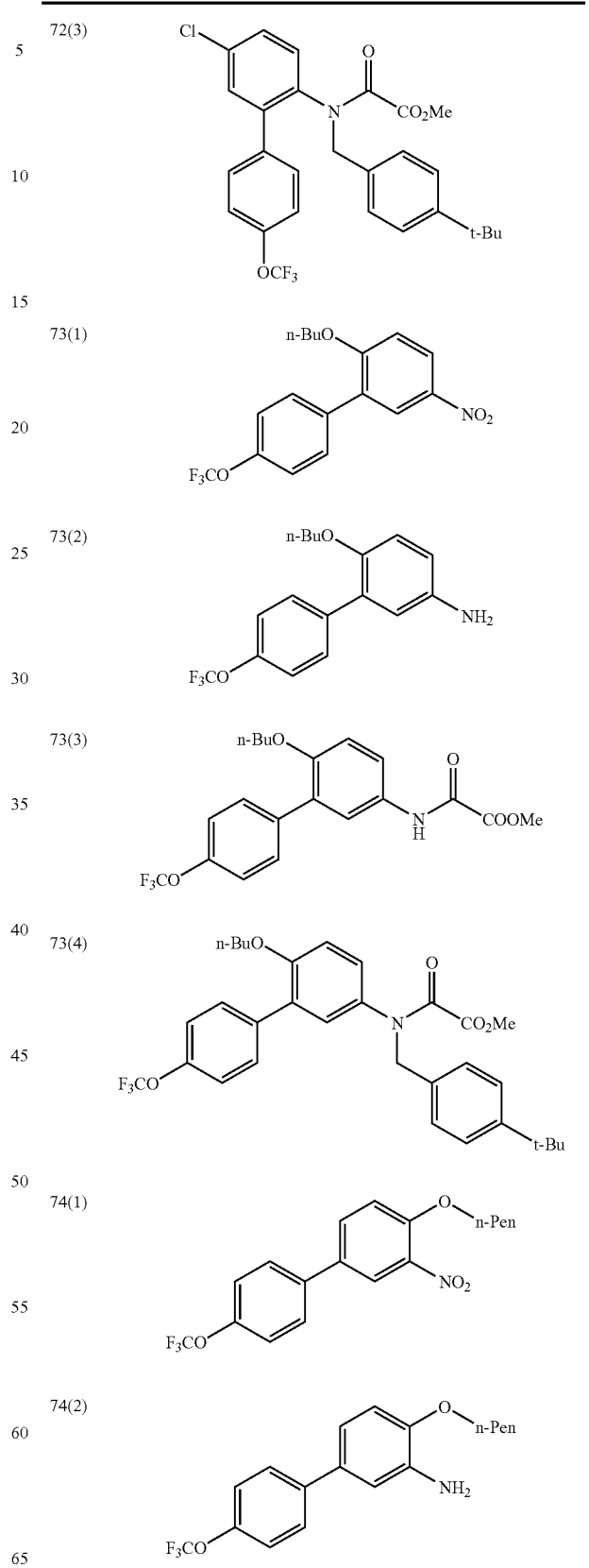

TABLE 3-continued
| 74(3) | 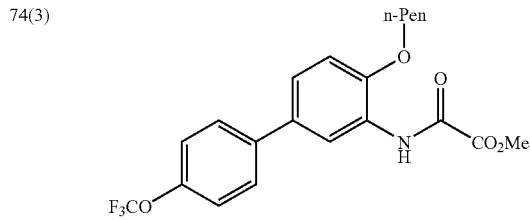 |
| 74(4) | 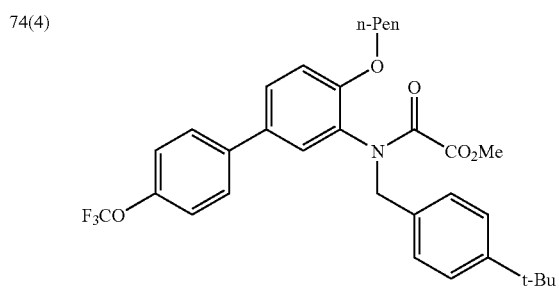 |
| 75(1) | 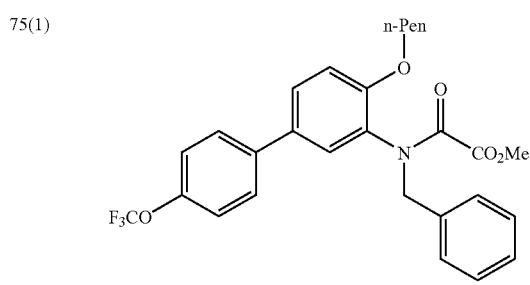 |
| 76(1) | 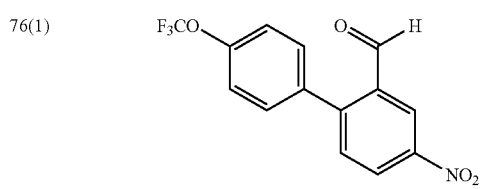 |
| 76(2) | 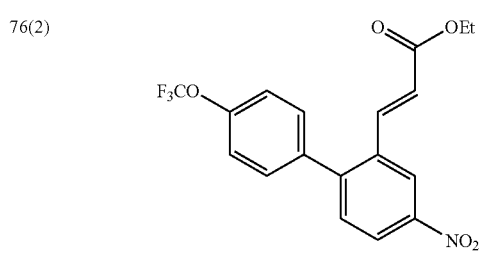 |
| 76(3) | 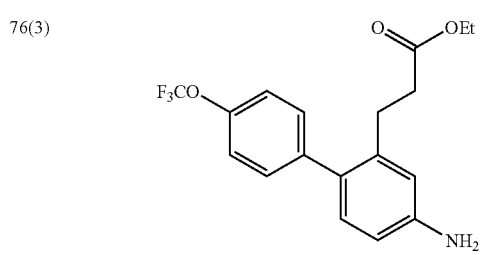 |
TABLE 3-continued
| 76(4) | 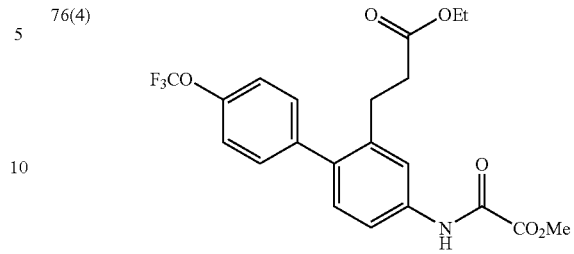 |
| 76(5) | 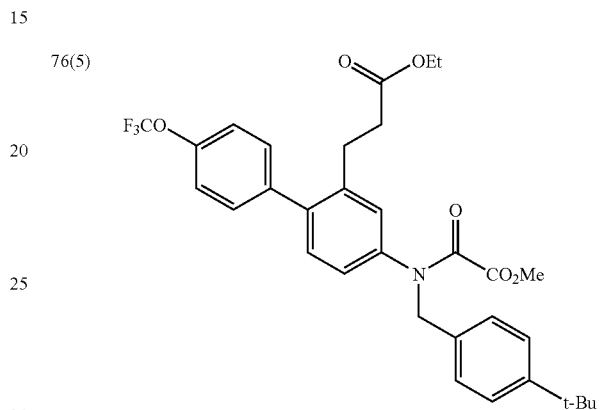 |
| 77(1) | 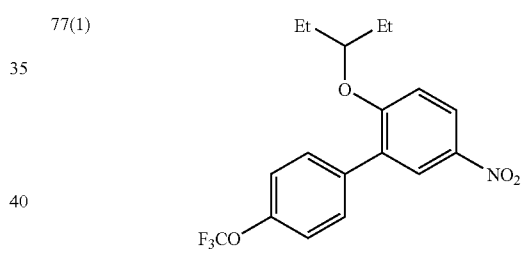 |
| 77(2) | 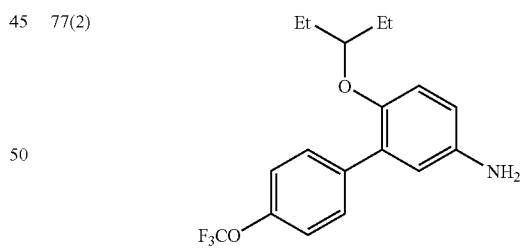 |
| 77(3) | 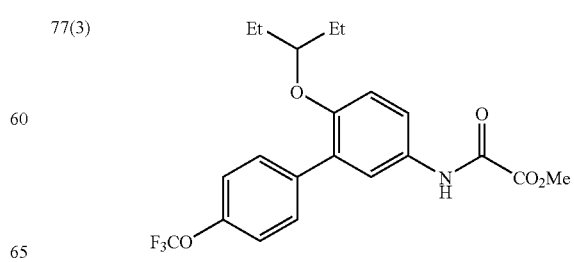 |

TABLE 3-continued
77(4) 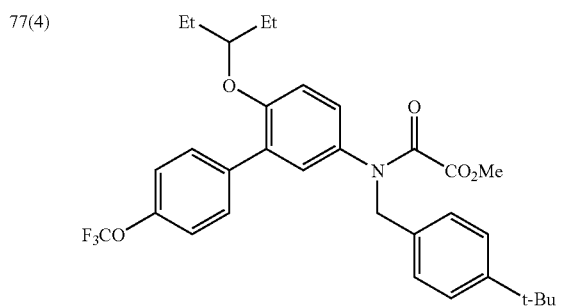
78(1) 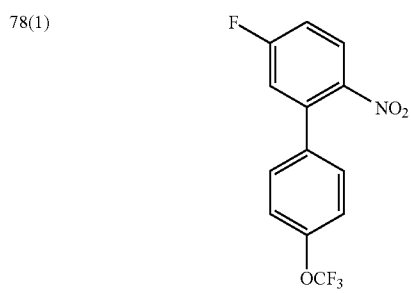
78(2) 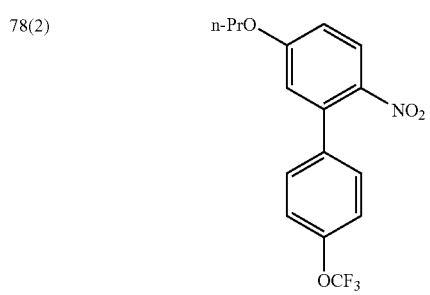
78(3) 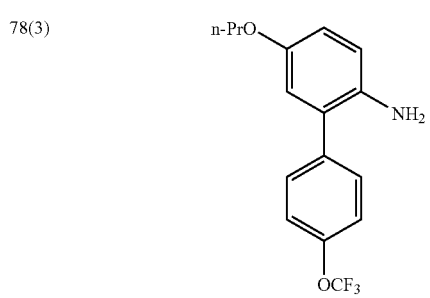
78(4) 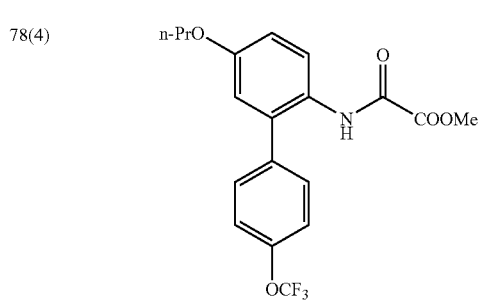
TABLE 3-continued
78(5) 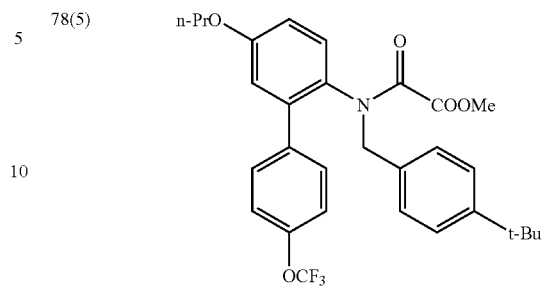
79(1) 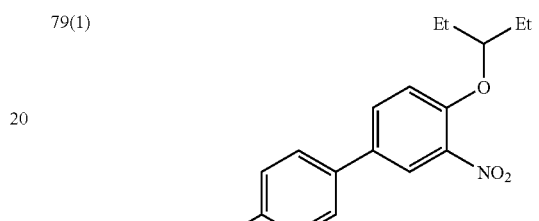
79(2) 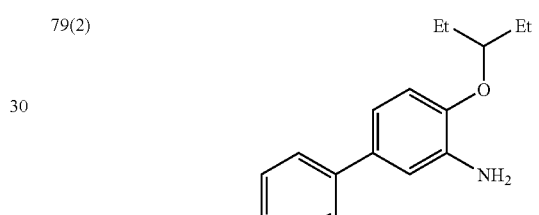
79(3) 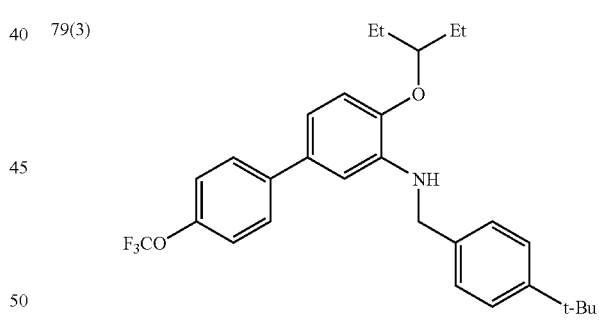
79(4) 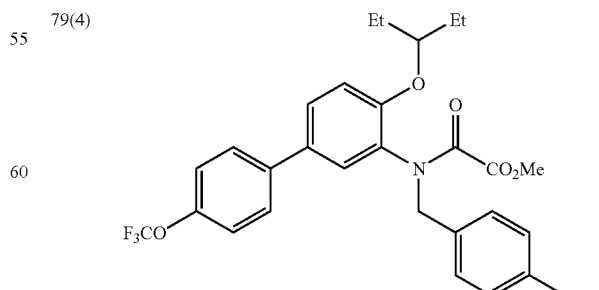

TABLE 3-continued
| 80(1) | 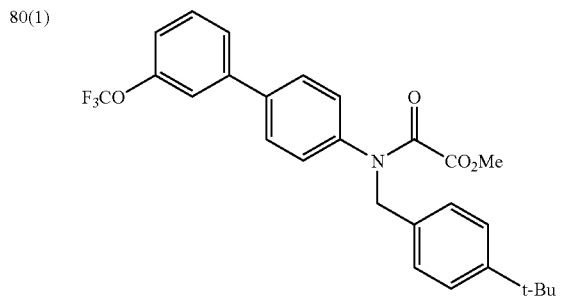 |
| 81(1) | 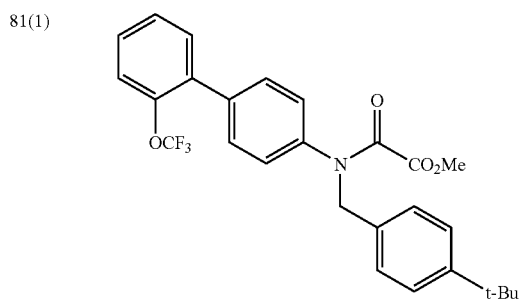 |
| 82(1) | 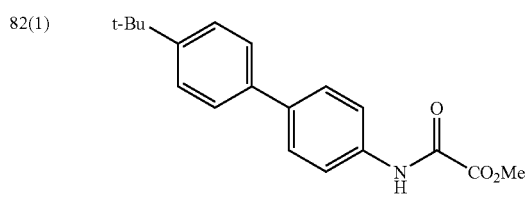 |
| 82(2) | 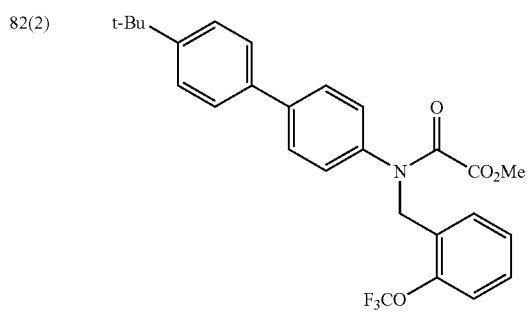 |
| 83(1) | 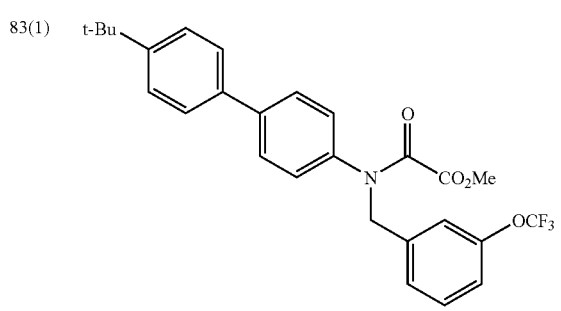 |
| 84(1) | 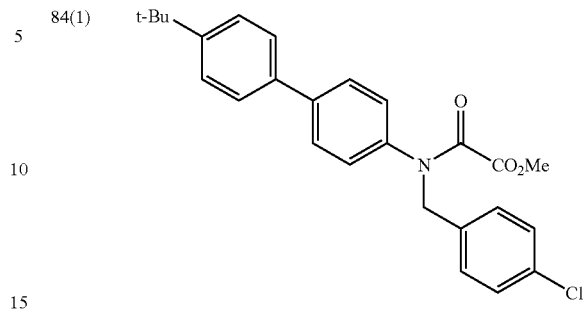 |
| 85(1) | 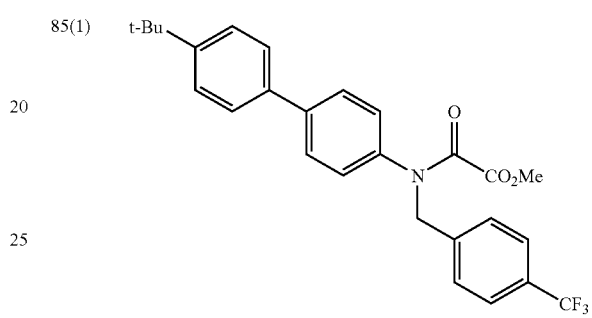 |
| 86(1) | 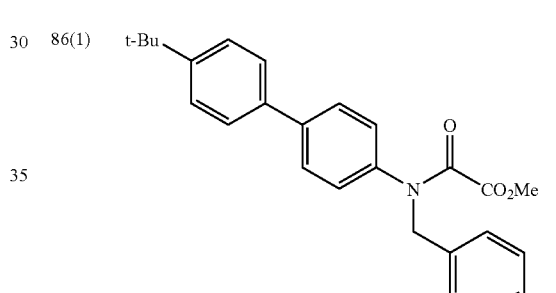 |
| 87(1) | 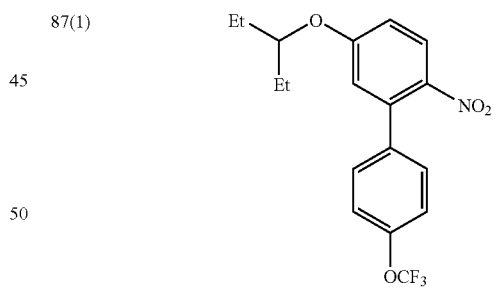 |
| 87(2) | 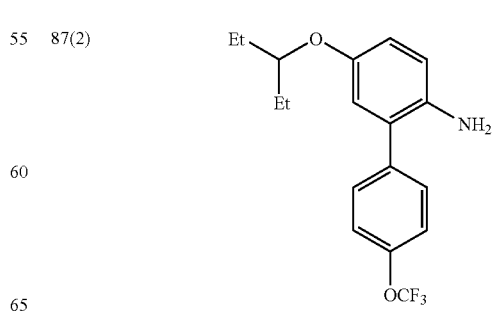 |

TABLE 3-continued
87(3) 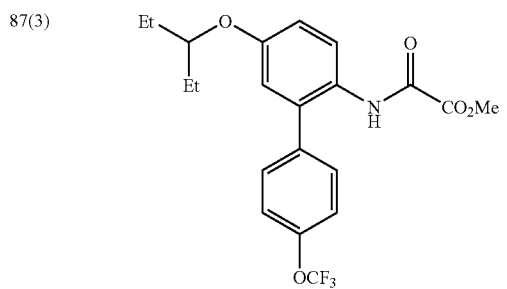
87(4) 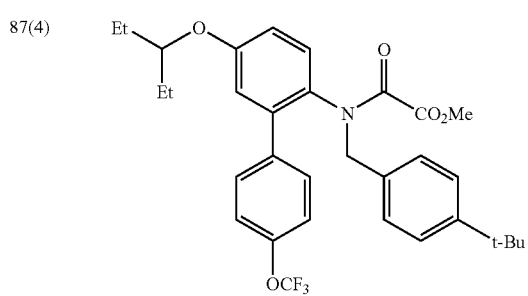
88(1) 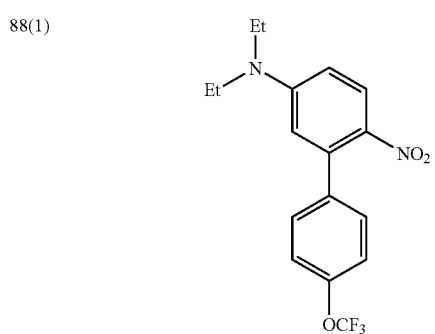
88(2) 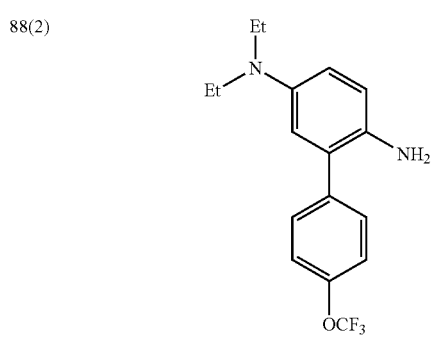
88(3) 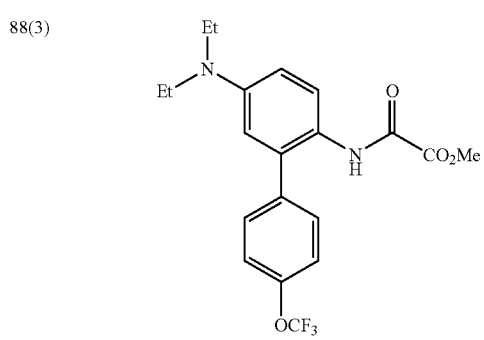
TABLE 3-continued
88(4) 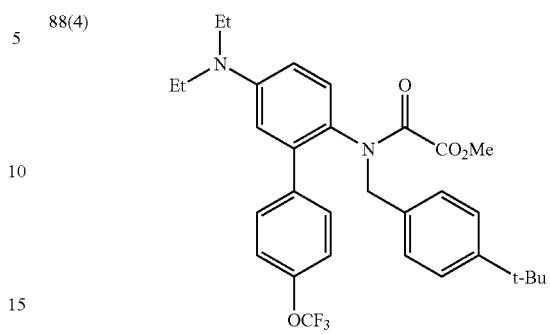
89(1) 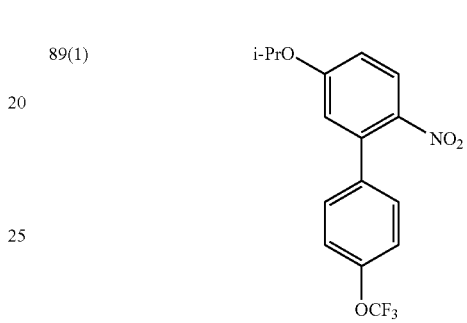
89(2) 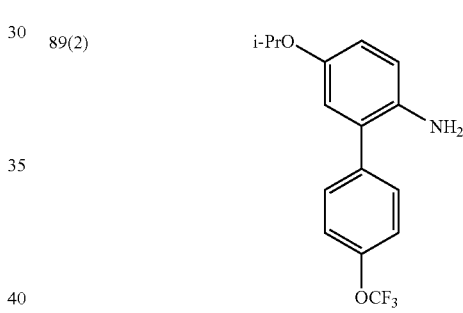
89(3) 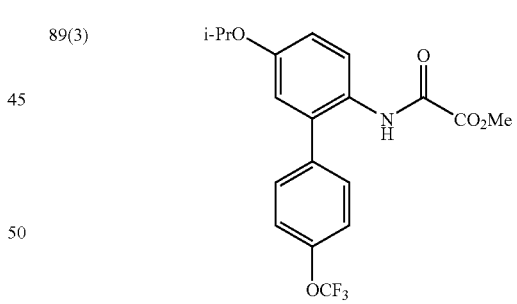
89(4) 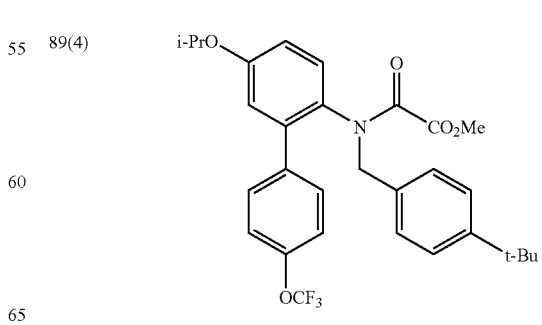

TABLE 3-continued
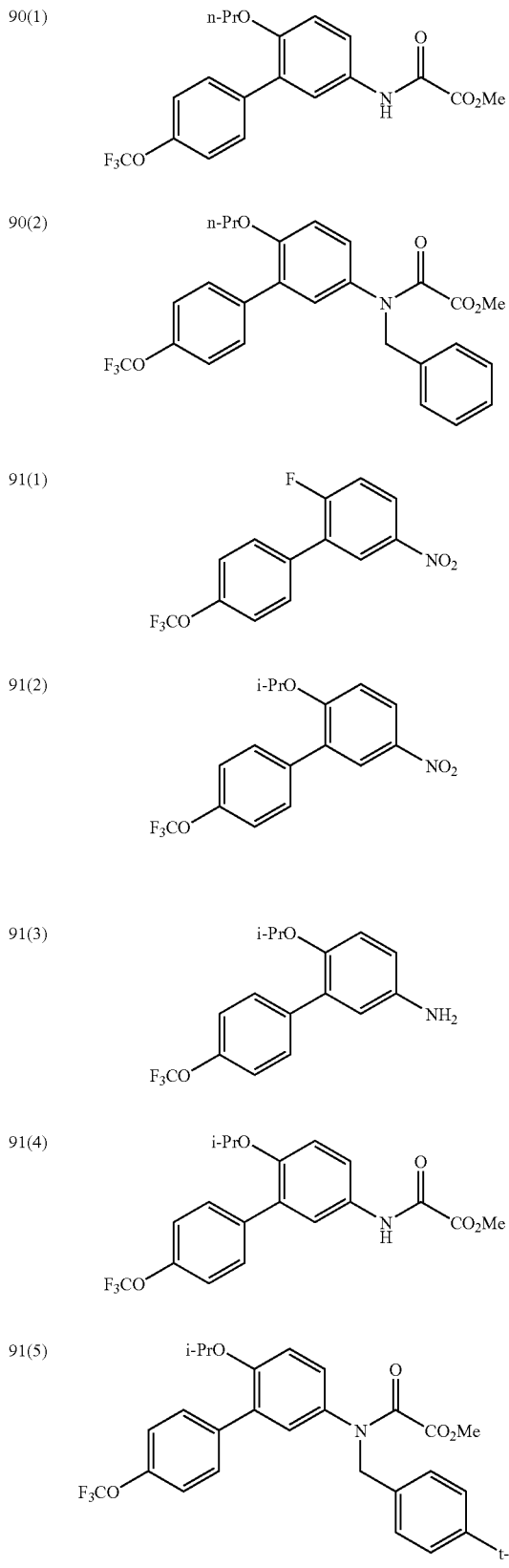
TABLE 3-continued
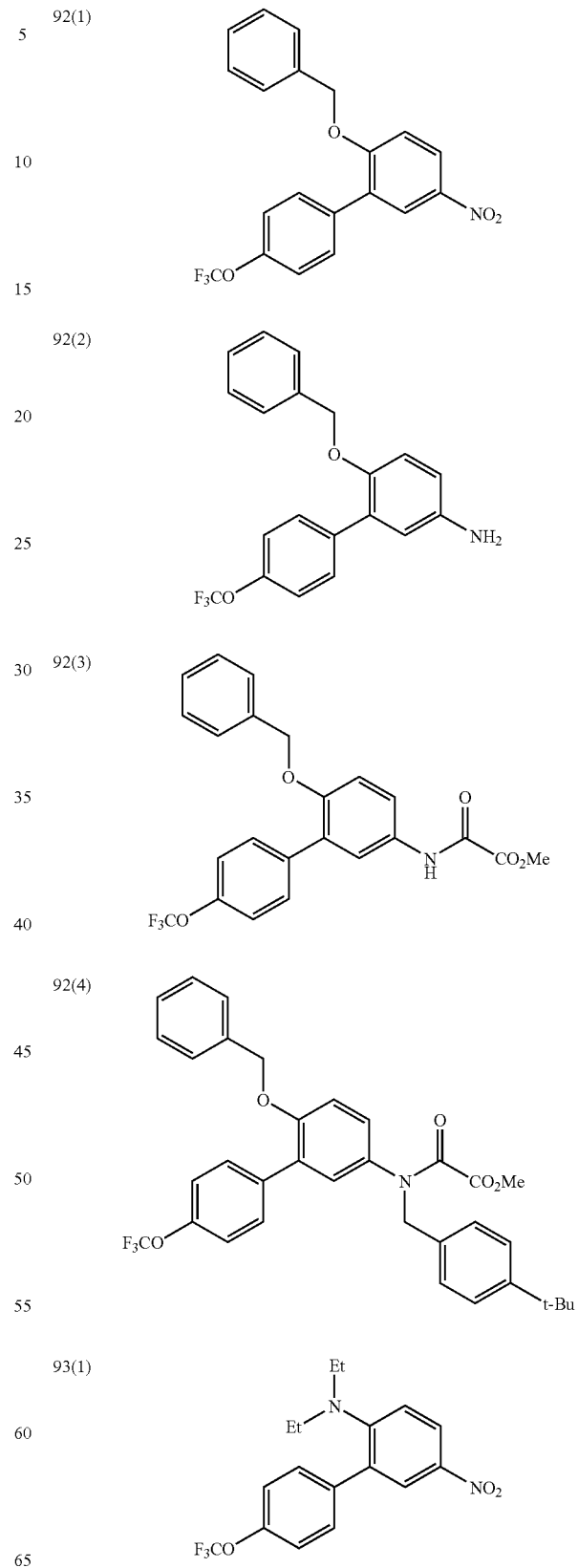

TABLE 3-continued
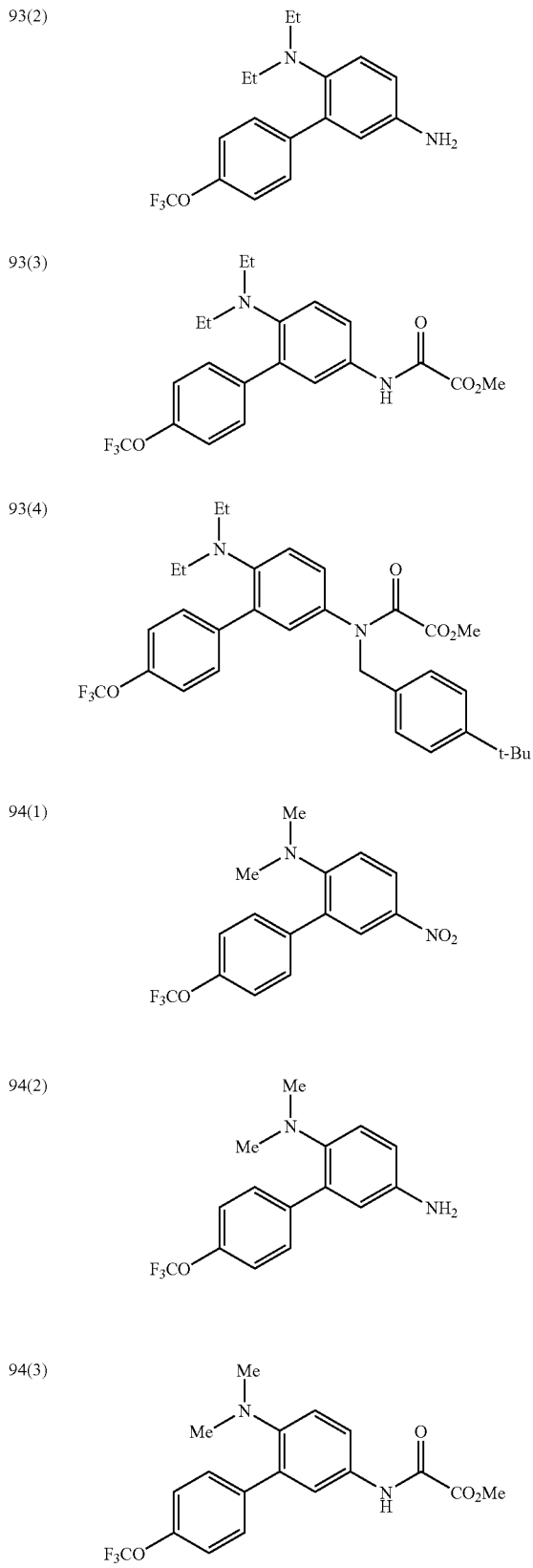
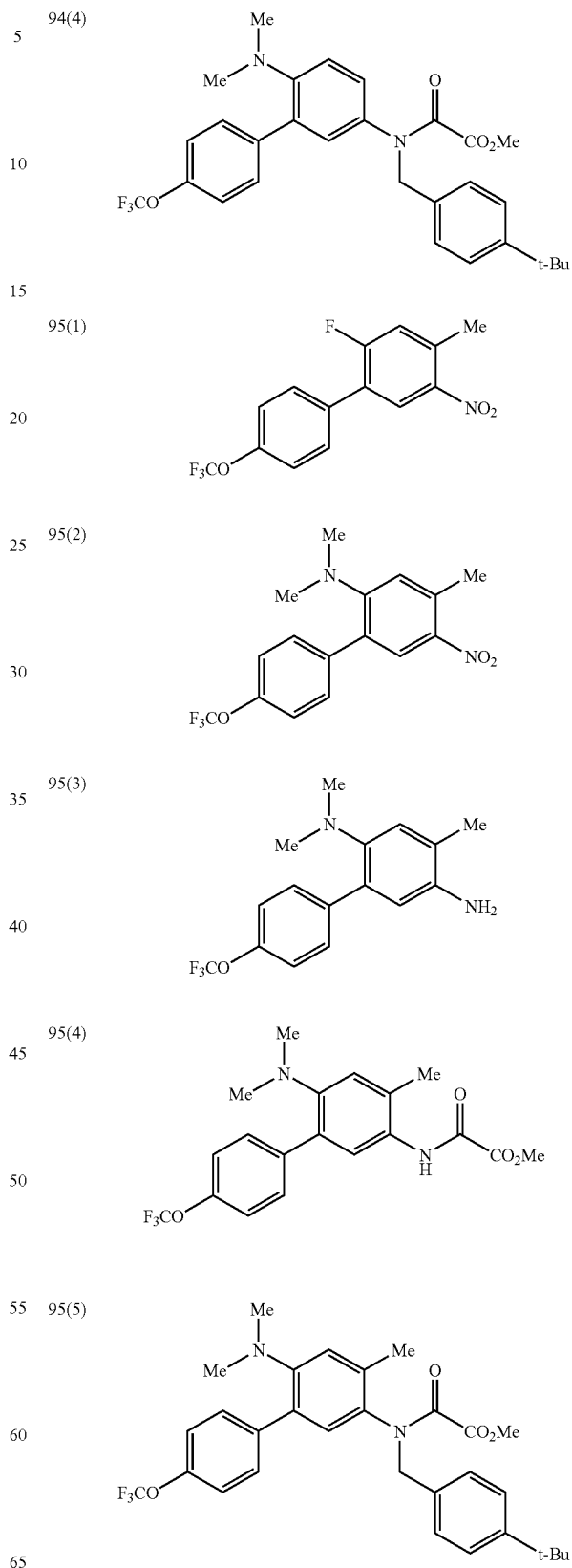

Example 1

Preparation of N-(3,5-dimethylbenzyl)-N-[4'-(trifluoromethoxy)biphenyl-4-yl]oxamic Acid Sodium Salt (Compound No. 1)

(1) Preparation of 4-bromo-N-(3,5-dimethylbenzyl)aniline

A mixture of 3,5-dimethylbenzyl bromide (1.59 g, 7.986 mmol), 4-bromoaniline (1.374 g, 7.986 mmol), potassium carbonate (5.519 g, 39.93 mmol) and N,N-dimethylformamide (6.5 ml) was stirred at 80° for 2 hours under argon atmosphere. The reaction mixture was cooled to room temperature, diluted with water, and extracted with ethyl acetate. The organic layer was washed with water and saturated brine, and dried over anhydrous sodium sulfate. The residue obtained by evaporation of the solvent under reduced pressure was purified by column chromatography on silica gel (n-hexane:ethyl acetate=15:1) to give the title compound (2.106 g, 57.2%) as a pale yellow oil.

$^1$H-NMR (CDCl$_3$) δ: 2.30 (6H, s), 4.00 (1H, brs), 4.20 (2H, s), 6.47-6.53 (2H, m), 6.90-6.98 (3H, m), 7.21-7.26 (2H, m).

(2) Preparation of Methyl N-(4-bromophenyl)-N-(3,5-dimethylbenzyl)oxamate

Methyl chloroglyoxylate (0.566 ml, 6.16 mmol) was added dropwise to a mixture of 4-bromo-N-(3,5-dimethylbenzyl)aniline (1.49 g, 5.13 mmol), triethylamine (1.08 ml, 7.70 mmol) and dichloromethane (20 ml) at 0°, and the mixture was stirred at room temperature for 1 hour. The reaction mixture was diluted with water, and extracted with ethyl acetate. The organic layer was washed with saturated brine, and dried over anhydrous sodium sulfate. The residue obtained by evaporation of the solvent under reduced pressure was purified by column chromatography on silica gel (n-hexane:ethyl acetate=3:1) to give the title compound (1.66 g, 86%) as a pale yellow oil.

$^1$H-NMR (CDCl$_3$) δ: 2.26 (6H, s), 3.59 (3H, s), 4.84 (2H, s), 6.80 (2H, s), 6.90 (1H, s), 6.70-6.92 (2H, m), 7.40-7.46 (2H, m).

(3) Preparation of Methyl N-(3,5-dimethylbenzyl)-N-[4'-(trifluoromethoxy)biphenyl-4-yl]oxamate A mixture of methyl N-(4-bromophenyl)-N-(3,5-dimethylbenzyl)oxamate (707 mg, 1.88 mmol), 4-(trifluoromethoxy)phenylboronic acid (500 mg, 2.44 mmol), [1,1-bis(diphenylphosphino)ferrocene]dichloropalladium(II) (300 mg, 0.357 mmol), potassium carbonate (389 mg, 2.82 mmol), dioxane (10 ml) and water (1 ml) was stirred at 80° for 4 hours. The reaction mixture was cooled to room temperature, and filtered through celite. The residue obtained by concentration of the filtrate under reduced pressure was purified by column chromatography on silica gel (n-hexane:ethyl acetate=10:1) to give the title compound (630 mg, 73%) as a light brown oil.

$^1$H-NMR (CDCl$_3$) δ: 2.26 (6H, s), 3.59 (3H, s), 4.90 (2H, s), 6.85 (2H, s), 6.91 (1H, s), 7.12-7.17 (2H, m), 7.25-7.31 (2H, m), 7.46-7.52 (2H, m), 7.53-7.59 (2H, m).

(4) Preparation of N-(3,5-dimethylbenzyl)-N-[4'-(trifluoromethoxy)biphenyl-4-yl]oxamic Acid Sodium Salt (Compound No. 1)

A mixture of methyl N-(3,5-dimethylbenzyl)-N-[4'-(trifluoromethoxy)biphenyl-4-yl]oxamate (200 mg, 0.437 mmol), 2N aqueous sodium hydroxide (2 ml) and water (1 ml) was irradiated with ultrasound for 5 minutes. The reaction mixture was diluted with water, and extracted with ethyl acetate. The organic layer was washed with saturated brine, and dried over anhydrous sodium sulfate. The solvent was evaporated under reduced pressure to give the title compound (130 mg, 66%) as a white solid.

$^1$H-NMR (DMSO-d$_6$) δ: 2.20 (6H, s), 4.87 (2H, s), 6.78-7.00 (3H, m), 7.30-7.37 (2H, m), 7.39-7.45 (2H, m), 7.51-7.59 (2H, m), 7.70-7.77 (2H, m).

Example 2

Preparation of N-(4-chlorobenzyl)-N-[4'-(trifluoromethoxy)biphenyl-4-yl]oxamic Acid Sodium Salt (Compound No. 2)

(1) Preparation of 4-bromo-N-(4-chlorobenzyl)aniline

The title compound was obtained in the same manner as the Example 1(1) using the following raw materials.
Raw materials: 4-chlorobenzyl chloride and 4-bromoaniline.
Yield: 21% (white solid).
$^1$H-NMR (CDCl$_3$) δ: 4.10 (1H, brs), 4.25-4.31 (2H, m), 6.44-6.51 (2H, m), 7.20-7.34 (6H, m).

(2) Preparation of Methyl N-(4-bromophenyl)-N-(4-chlorobenzyl)oxamate

The title compound was obtained in the same manner as the Example 1(2) using the following raw materials.
Raw materials: 4-bromo-N-(4-chlorobenzyl)aniline and methyl chloroglyoxylate.
Yield: 96% (colorless oil).
$^1$H-NMR (CDCl$_3$) δ: 3.59 (3H, s), 4.88 (2H, s), 6.88-6.94 (2H, m), 7.12-7.17 (2H, m), 7.24-7.30 (2H, m), 7.42-7.48 (2H, m).

(3) Preparation of Methyl N-(4-chlorobenzyl)-N-[4'-(trifluoromethoxy)biphenyl-4-yl]oxamate The title compound was obtained in the same manner as the Example 1(3) using the following raw materials.
Raw materials: methyl N-(4-bromophenyl)-N-(4-chlorobenzyl)oxamate and 4-(trifluoromethoxy)phenylboronic acid.
Yield: 28% (light brown oil).
$^1$H-NMR (CDCl$_3$) δ: 3.59 (3H, s), 4.94 (2H, s), 7.09-7.22 (4H, m), 7.24-7.32 (4H, m), 7.47-7.59 (4H, m).

(4) Preparation of N-(4-chlorobenzyl)-N-[4'-(trifluoromethoxy)biphenyl-4-yl]oxamic Acid Sodium Salt (Compound No. 2)

The title compound was obtained in the same manner as the Example 1(4) using the following raw material.
Raw material: methyl N-(4-chlorobenzyl)-N-[4'-(trifluoromethoxy)biphenyl-4-yl]oxamate.
Yield: 93% (white solid).
$^1$H-NMR (DMSO-d$_6$) δ: 4.91 (2H, s), 7.20-7.38 (6H, m), 7.38-7.48 (2H, m), 7.52-7.63 (2H, m), 7.71-7.82 (2H, m).

Example 3

Preparation of N-(3-methylbenzyl)-N-[4'-(trifluoromethoxy)biphenyl-4-yl]oxamic Acid Sodium Salt (Compound No. 3)

(1) Preparation of 4-nitro-4'-(trifluoromethoxy)biphenyl

The title compound was obtained in the same manner as the Example 1(3) using the following raw materials.

Raw materials: 4-bromonitrobenzene and 4-(trifluoromethoxy)phenylboronic acid.

Yield: 98% (white solid).

$^1$H-NMR (CDCl$_3$) δ: 7.32-7.38 (2H, m), 7.62-7.68 (2H, m), 7.69-7.75 (2H, m), 8.29-8.35 (2H, m).

(2) Preparation of 4-amino-4'-(trifluoromethoxy)biphenyl

A mixture of 4-nitro-4'-(trifluoromethoxy)biphenyl (6.41 g, 22.6 mmol), 10% platinum-activated charcoal (150 mg) and methanol (50 ml) was stirred for 16 hours under hydrogen atmosphere. The reaction mixture was filtered through celite. The filtrate was concentrated under reduced pressure to give the title compound (5.48 g, 96%) as a white solid.

$^1$H-NMR (CDCl$_3$) δ: 3.75 (2H, brs), 6.73-6.78 (2H, m), 7.23 (2H, d, J=8.4 Hz), 7.35-7.40 (2H, m), 7.50-7.55 (2H, m).

(3) Preparation of methyl N-[4'-(trifluoromethoxy)biphenyl-4-yl]oxamate

A solution of methyl chloroglyoxylate (2.98 ml, 32.4 mmol) in dichloromethane (10 ml) was added dropwise at a slow speed to a mixture of 4-amino-4'-(trifluoromethoxy)biphenyl (5.476 g, 21.6 mmol), sodium hydrogencarbonate (3.62 g, 43.2 mmol), dichloromethane (40 ml) and water (40 ml), and stirred at 0° for 2 hours. The reaction mixture was diluted with water, and extracted with ethyl acetate. The organic layer was washed with saturated brine, and dried over anhydrous sodium sulfate. The solvent was evaporated under reduced pressure to give the title compound (6.71 g, 91.5%) as a white solid.

$^1$H-NMR (DMSO-d$_6$) δ: 3.87 (3H, s), 7.41-7.48 (2H, m), 7.67-7.73 (2H, m), 7.76-7.82 (2H, m), 7.84-7.91 (2H, m), 10.94 (1H, s).

(4) Preparation of Methyl N-(3-methylbenzyl)-N-[4'-(trifluoromethoxy)biphenyl-4-yl]oxamate A mixture of methyl N-[4'-(trifluoromethoxy)biphenyl-4-yl]oxamate (250 mg, 0.737 mmol), 3-methylbenzyl bromide (0.299 ml, 2.21 mmol), potassium carbonate (306 mg, 2.21 mmol), 18-crown-6 (20 mg, 0.074 mmol) and acetonitrile (10 ml) was stirred at 50° for 3 hors under argon atmosphere. The reaction mixture was cooled to room temperature, diluted with water, and extracted with ethyl acetate. The organic layer was washed with saturated brine, and dried over anhydrous sodium sulfate. The residue obtained by evaporation of the solvent under reduced pressure was purified by column chromatography on silica gel (n-hexane:ethyl acetate=2:1) to give the title compound (320 mg, 98%) as a colorless oil.

$^1$H-NMR (CDCl$_3$) δ: 2.32 (3H, s), 3.59 (3H, s), 4.95 (2H, s), 7.02-7.32 (8H, m), 7.46-7.52 (2H, m), 7.52-7.59 (2H, m).

(5) Preparation of N-(3-methylbenzyl)-N-[4'-(trifluoromethoxy)biphenyl-4-yl]oxamic Acid Sodium Salt (Compound No. 3)

The title compound was obtained in the same manner as the Example 1(4) using the following raw material.

Raw material: methyl N-(3-methylbenzyl)-N-[4'-(trifluoromethoxy)biphenyl-4-yl]oxamate.

Yield: 93% (white solid).

$^1$H-NMR (DMSO-d$_6$) δ: 2.25 (3H, s), 4.92 (2H, s), 6.95-7.23 (4H, m), 7.30-7.38 (2H, m), 7.39-7.44 (2H, m), 7.52-7.60 (2H, m), 7.70-7.77 (2H, m).

Example 4

Preparation of N-[4-(tert-butyl)benzyl]-N-(4'-methoxybiphenyl-4-yl)oxamic Acid (Compound No. 4)

(1) Preparation of Methyl N-(4-bromophenyl)oxamate

The title compound was obtained in the same manner as the Example 1(2) using the following raw materials.

Raw materials: 4-bromoaniline and methyl chloroglyoxylate.

Yield: 68.9% (white solid).

$^1$H-NMR (CDCl$_3$) δ: 3.98 (3H, s), 7.47-7.57 (4H, m), 8.85 (1H, brs).

(2) Preparation of Methyl N-(4-bromophenyl)-N-[4-(tert-butyl)benzyl]oxamate The title compound was obtained in the same manner as the Example 3(4) using the following raw materials.

Raw materials: methyl N-(4-bromophenyl)oxamate and 4-(tert-butyl)benzyl bromide.

Yield: 99.0% (colorless oil).

$^1$H-NMR (CDCl$_3$) δ: 1.28 (9H, s), 3.58 (3H, s), 4.88 (2H, s), 6.93 (2H, d, J=8.1 Hz), 7.12 (2H, d, J=8.1 Hz), 7.30 (2H, d, J=8.1 Hz), 7.43 (2H, d, J=8.1 Hz).

(3) Preparation of Methyl N-[4-(tert-butyl)benzyl]-N-(4'-methoxybiphenyl-4-yl)oxamate The title compound was obtained in the same manner as the Example 1(3) using the following raw materials.

Raw materials: methyl N-(4-bromophenyl)-N-[4-(tert-butyl)benzyl]oxamate and 4-methoxyphenylboronic acid.

Yield: 100% (colorless oil).

$^1$H-NMR (CDCl$_3$) δ: 1.32 (9H, m), 3.57 (3H, s), 3.84 (3H, s), 4.93 (2H, s), 6.96 (2H, d, J=9.0 Hz), 7.01 (2H, d, J=8.4 Hz), 7.18 (2H, d, J=8.7 Hz), 7.31 (2H, d, J=8.4 Hz), 7.46-7.52 (4H, m).

(4) Preparation of N-[4-(tert-butyl)benzyl]-N-(4'-methoxybiphenyl-4-yl)oxamic Acid (Compound No. 4)

A mixture of methyl N-[4-(tert-butyl)benzyl]-N-(4'-methoxybiphenyl-4-yl)oxamate (230 mg, 0.533 mmol), methanol (1.5 ml), 2N aqueous sodium hydroxide (0.8 ml) and tetrahydrofuran (1.5 ml) was stirred at room temperature for 10 minutes. The reaction mixture was adjusted to pH 5-6 by addition of 2N hydrochloric acid, and extracted with ethyl acetate. The organic layer was washed with saturated brine, and dried over anhydrous sodium sulfate. The solvent was evaporated under reduced pressure to give the title compound (160 mg, 71.9%) as a white solid.

¹H-NMR (DMSO-d₆) δ: 1.25 (9H, s), 3.79 (3H, s), 4.93 (2H, s), 7.01 (2H, d, J=8.7 Hz), 7.16 (2H, d, J=8.4 Hz), 7.27 (2H, d, J=8.7 Hz), 7.35 (2H, d, J=8.4 Hz), 7.59-7.65 (4H, m).

Example 5

Preparation of N-[4-(tert-butyl)benzyl]-N-(4'-fluoro-biphenyl-4-yl)oxamic Acid (Compound No. 5).

(1) Preparation of Methyl N-[4-(tert-butyl)benzyl]-N-(4'-fluorobiphenyl-4-yl)oxamate The title compound was obtained in the same manner as the Example 1(3) using the following raw materials.
Raw materials: methyl N-(4-bromophenyl)-N-[4-(tert-butyl)benzyl]oxamate (compound of Example 4(2)) and 4-fluorophenylboronic acid.
Yield: 100% (colorless oil).
¹H-NMR (CDCl₃) δ: 1.30 (9H, s), 3.58 (3H, s), 4.94 (2H, s), 7.09-7.19 (6H, m), 7.31 (2H, d, J=7.8 Hz), 7.47-7.54 (4H, m).

(2) Preparation of N-[4-(tert-butyl)benzyl]-N-(4'-fluorobiphenyl-4-yl)oxamic Acid (Compound No. 5)

The title compound was obtained in the same manner as the Example 4(4) using the following raw material.
Raw material: methyl N-[4-(tert-butyl)benzyl]-N-(4'-fluorobiphenyl-4-yl)oxamate.
Yield: 71.6% (white solid).
¹H-NMR (DMSO-d₆) δ: 1.25 (9H, s), 4.95 (2H, s), 7.16 (2H, d, J=8.4 Hz), 7.25-7.36 (6H, m), 7.66-7.73 (4H, m).

Example 6

Preparation of N-benzyl-N-[4'-(trifluoromethoxy)biphenyl-4-yl]oxamic Acid (Compound No. 6).

(1) Preparation of N-benzyl-4-bromoaniline

The title compound was obtained in the same manner as the Example 1(1) using the following raw materials.
Raw materials: 4-bromoaniline and benzyl bromide.
Yield: 72.4% (colorless oil).
¹H-NMR (CDCl₃) δ: 4.30 (2H, s), 4.62 (1H, s), 6.47-6.52 (2H, m), 7.20-7.37 (7H, m).

(2) Preparation of 4-benzylamino-4'-(trifluoromethoxy)biphenyl

The title compound was obtained in the same manner as the Example 1(3) using the following raw materials.
Raw materials: N-benzyl-4-bromoaniline and 4-(trifluoromethoxy)phenylboronic acid.
Yield: 41.8% (white solid).
¹H-NMR (CDCl₃) δ: 4.14-4.21 (1H, m), 4.38 (2H, d, J=5.1 Hz), 6.68-6.72 (2H, m), 7.20-7.34 (4H, m), 7.36-7.41 (5H, m), 7.49-7.54 (2H, m).

(3) Preparation of Methyl N-benzyl-N-[4'-(trifluoromethoxy)biphenyl-4-yl]oxamate The title compound was obtained in the same manner as the Example 1(2) using the following raw materials.
Raw materials: 4-benzylamino-4'-(trifluoromethoxy)biphenyl and methyl chloroglyoxylate.
Yield: 100.0% (colorless oil).
¹H-NMR (CDCl₃) δ: 3.59 (3H, s), 4.98 (2H, s), 7.14 (2H, d, J=8.4 Hz), 7.25-7.31 (7H, m), 7.49 (2H, d, J=8.4 Hz), 7.56 (2H, d, J=8.4 Hz).

(4) Preparation of N-benzyl-N-[4'-(trifluoromethoxy)biphenyl-4-yl]oxamic Acid (Compound No. 6)

The title compound was obtained in the same manner as the Example 4(4) using the following raw material.
Raw material: methyl N-benzyl-N-[4'-(trifluoromethoxy)biphenyl-4-yl]oxamate.
Yield: 57.8% (yellow solid).
¹H-NMR (DMSO-d₆) δ: 5.00 (2H, s), 7.22-7.33 (7H, m), 7.44 (2H, d, J=8.4 Hz), 7.70 (2H, d, J=8.4 Hz), 7.78 (2H, d, J=8.4 Hz).

Example 7

Preparation of N-[4-(tert-butyl)phenyl]-N-[4'-(trifluoromethoxy)biphenyl-4-yl]oxamic Acid (Compound No. 7)

(1) Preparation of 4-[4-(tert-butyl)phenyl]amino-4'-(trifluoromethoxy)biphenyl

A mixture of 4-amino-4'-(trifluoromethoxy)biphenyl (compound of Example 3(2); 112 mg, 0.442 mmol), 4-(tert-butyl)phenylboronic acid (87 mg, 0.486 mmol), copper(II) acetate (40 mg, 0.221 mmol), triethylamine (0.061 ml, 0.884 mmol) and pyridine (3.0 ml) was stirred at 50° for 2 hours. The reaction mixture was cooled to room temperature and filtered through celite. The filtrate was diluted with 1N hydrochloric acid (10 ml), and extracted with ethyl acetate. The organic layer was dried over anhydrous sodium sulfate. The residue obtained by evaporation of the solvent under reduced pressure was purified by column chromatography on silica gel (n-hexane:ethyl acetate=1:1) to give the title compound (50 mg, 29%) as a pale yellow solid.
¹H-NMR (CDCl₃) δ: 1.32 (9H, s), 5.73 (1H, s), 7.05-7.12 (4H, m), 7.22-7.27 (2H, m), 7.29-7.36 (2H, m), 7.41-7.47 (2H, m), 7.52-7.58 (2H, m).

(2) Preparation of Methyl N-[4-(tert-butyl)phenyl]-N-[4'-(trifluoromethoxy)biphenyl-4-yl]oxamate The title compound was obtained in the same manner as the Example 1(2) using the following raw materials.
Raw materials: 4-[4-(tert-butyl)phenyl]amino-4'-(trifluoromethoxy)biphenyl and methyl chloroglyoxylate.
Yield: 88% (pale yellow oil).
This compound was obtained as a mixture of the rotational isomers (3:2).
Major isomer: ¹H-NMR (CDCl₃) δ: 1.33 (9H, s), 3.60 (3H, s), 7.20-7.46 (8H, m), 7.51-7.62 (4H, m).
Minor isomer: ¹H-NMR (CDCl₃) δ: 1.31 (9H, s), 3.65 (3H, s), 7.20-7.46 (8H, m), 7.51-7.62 (4H, m).

(3) Preparation of N-[4-(tert-butyl)phenyl]-N-[4'-(trifluoromethoxy)biphenyl-4-yl]oxamic Acid (Compound No. 7).

The title compound was obtained in the same manner as the Example 4(4) using the following raw material.
Raw material: methyl N-[4-(tert-butyl)phenyl]-N-[4'-(trifluoromethoxy)biphenyl-4-yl]oxamate.
Yield: 96% (light brown solid).

This compound was obtained as a mixture of the rotational isomers.

¹H-NMR (DMSO-d₆) δ: 1.25-1.31 (9H, m), 7.06-7.55 (8H, m), 7.66-7.86 (4H, m).

Example 8

Preparation of N-[4-(tert-butyl)benzyl]-N-[4'-(trifluoromethoxy)biphenyl-4-yl]oxamic Acid (Compound No. 8)

(1) Preparation of Methyl N-[4-(tert-butyl)benzyl]-N-[4'-(trifluoromethoxy)biphenyl-4-yl]oxamate The title compound was obtained in the same manner as the Example 3(4) using the following raw materials.

Raw materials: methyl N-[4'-(trifluoromethoxy)biphenyl-4-yl]oxamate (compound of Example 3(3)) and 4-(tert-butyl)benzyl bromide.

Yield: 100% (colorless oil).

¹H-NMR (CDCl₃) δ: 1.30 (9H, s), 3.58 (3H, s), 4.95 (2H, s), 7.14-7.20 (4H, m), 7.25-7.34 (4H, m), 7.48-7.59 (4H, m).

(2) Preparation of N-[4-(tert-butyl)benzyl]-N-[4'-(trifluoromethoxy)biphenyl-4-yl]oxamic Acid (Compound No. 8)

The title compound was obtained in the same manner as the Example 4(4) using the following raw material.

Raw material: methyl N-[4-(tert-butyl)benzyl]-N-[4'-(trifluoromethoxy)biphenyl-4-yl]oxamate.

Yield: 86.7% (white solid).

¹H-NMR (DMSO-d₆) δ: 1.23 (9H, s), 4.91 (2H, s), 7.15-7.60 (8H, m), 7.57 (2H, d, J=8.4 Hz), 7.73 (2H, d, J=9.0 Hz).

Example 9

Preparation of N-[4-(tert-butyl)benzyl]-N-[4'-(trifluoromethoxy)biphenyl-3-yl]oxamic Acid (Compound No. 9)

(1) Preparation of 3-bromo-N-[4-(tert-butyl)benzyl]aniline

The title compound was obtained in the same manner as the Example 1(1) using the following raw materials.

Raw materials: 3-bromoaniline and 4-(tert-butyl)benzyl bromide.

Yield: 66.4% (pale yellow oil).

¹H-NMR (CDCl₃) δ: 1.32 (9H, s), 4.04 (1H, brs), 4.25 (2H, d, J=4.8 Hz), 6.51-6.55 (1H, m), 6.78 (1H, t, J=1.8 Hz), 6.80-6.83 (1H, m), 7.00 (1H, t, J=8.1 Hz), 7.28 (2H, d, J=8.4 Hz), 7.36-7.39 (2H, m).

(2) Preparation of 3-[4-(tert-butyl)benzyl]amino-4'-(trifluoromethoxy)biphenyl

The title compound was obtained in the same manner as the Example 1(3) using the following raw materials.

Raw materials: 3-bromo-N-[4-(tert-butyl)benzyl]aniline and 4-(trifluoromethoxy)phenylboronic acid.

Yield: 86.7% (yellow solid).

¹H-NMR (CDCl₃) δ: 1.33 (9H, s), 4.12 (2H, d, J=7.2 Hz), 4.34 (1H, s), 6.63-6.67 (1H, m), 6.80-6.81 (1H, m), 6.87-6.91 (1H, m), 7.22-7.29 (3H, m), 7.33 (2H, d, J=8.1 Hz), 7.39 (2H, d, J=8.1 Hz), 7.52-7.57 (2H, m).

(3) Preparation of methyl N-[4-(tert-butyl)benzyl]-N-[4'-(trifluoromethoxy)biphenyl-3-yl]oxamate The title compound was obtained in the same manner as the Example 1(2) using the following raw materials.

Raw materials: 3-[4-(tert-butyl)benzyl]amino-4'-(trifluoromethoxy)biphenyl and methyl chloroglyoxylate.

Yield: 87.5% (white solid).

¹H-NMR (CDCl₃) δ: 1.30 (9H, s), 3.55 (3H, s), 4.95 (2H, s), 7.11-7.13 (2H, m), 7.17 (2H, d, J=8.1 Hz), 7.25 (2H, d, J=8.1 Hz), 7.31-7.34 (2H, m), 7.38-7.44 (3H, m), 7.48-7.52 (1H, m).

(4) Preparation of N-[4-(tert-butyl)benzyl]-N-[4'-(trifluoromethoxy)biphenyl-3-yl]oxamic Acid (Compound No. 9)

The title compound was obtained in the same manner as the Example 4(4) using the following raw material.

Raw material: methyl N-[4-(tert-butyl)benzyl]-N-[4'-(trifluoromethoxy)biphenyl-3-yl]oxamate.

Yield: 32.3% (white solid).

¹H-NMR (DMSO-d₆) δ: 1.22 (9H, s), 4.95 (2H, s), 7.16 (2H, d, J=7.8 Hz), 7.26-7.33 (3H, m); 7.38-7.43 (3H, m), 7.51-7.53 (2H, m), 7.68 (2H, d, J=8.4 Hz).

Example 10

Preparation of N-(4-methoxybenzyl)-N-[4'-(trifluoromethoxy)biphenyl-4-yl]oxamic Acid (Compound No. 10)

(1) Preparation of Methyl N-(4-methoxybenzyl)-N-[4'-(trifluoromethoxy)biphenyl-4-yl]oxamate The title compound was obtained in the same manner as the Example 3(4) using the following raw materials.

Raw materials: methyl N-[4'-(trifluoromethoxy)biphenyl-4-yl]oxamate (compound of Example 3(3)) and 4-methoxybenzyl bromide.

Yield: 82.7% (colorless oil).

¹H-NMR (CDCl₃) δ: 3.57 (3H, s), 3.79 (3H, s), 4.91 (2H, s), 6.82 (2H, d, J=8.4 Hz), 7.11 (2H, d, J=8.4 Hz), 7.16 (2H, d, J=8.7 Hz), 7.28 (2H, d, J=8.4 Hz), 7.49 (2H, d, J=8.4 Hz), 7.56 (2H, d, J=8.7 Hz).

(2) Preparation of N-(4-methoxybenzyl)-N-[4'-(trifluoromethoxy)biphenyl-4-yl]oxamic Acid (Compound No. 10)

The title compound was obtained in the same manner as the Example 4(4) using the following raw material.

Raw material: methyl N-(4-methoxybenzyl)-N-[4'-(trifluoromethoxy)biphenyl-4-yl]oxamate.

Yield: 55.8% (white solid).

¹H-NMR (DMSO-d₆) δ: 3.69 (3H, s), 4.87 (2H, s), 6.80-6.89 (2H, m), 7.10-7.38 (4H, m), 7.42 (2H, d, J=8.4 Hz), 7.55 (2H, d, J=8.4 Hz), 7.74 (2H, d, J=8.4 Hz).

Example 11

Preparation of N-[4-(tert-butyl)benzyl]-N-{4-[4-(trifluoromethoxy)phenoxy]phenyl}oxamic Acid (Compound No. 11)

(1) Preparation of 1-nitro-4-[4-(trifluoromethoxy)phenoxy]benzene

A mixture of 4-(trifluoromethoxy)phenol (2.50 g, 14.036 mmol), 4-fluoro-1-nitrobenzene (1.98 g, 14.036 mmol), potassium carbonate (2.90 g, 20.982 mmol) and N,N-dimethylacetamide (15 ml) was stirred at 160° for 2 hours under argon atmosphere. The reaction mixture was cooled to room temperature, diluted with water, and extracted with ethyl acetate. The organic layer was washed with water and saturated brine, and dried over anhydrous sodium sulfate. The residue obtained by evaporation of the solvent under reduced pressure was purified by column chromatography on silica gel (n-hexane:ethyl acetate=10:1) to give the title compound (4.18 g, 100%) as a pale yellow solid.

$^1$H-NMR (CDCl$_3$) δ: 7.02-7.06 (2H, m), 7.10-7.14 (2H, m), 7.26-7.31 (2H, m), 8.21-8.25 (2H, m).

(2) Preparation of 4-[4-(trifluoromethoxy)phenoxy]aniline

A mixture of 1-nitro-4-[4-(trifluoromethoxy)phenoxy]benzene (4.18 g, 13.970 mmol), 10% platinum-activated charcoal (270 mg) and ethanol (40 ml) was stirred for 3 hours under hydrogen atmosphere. The reaction mixture was filtered through celite. The residue obtained by concentration of the filtrate under reduced pressure was purified by column chromatography on silica gel (n-hexane:ethyl acetate=3:1) to give the title compound (3.54 g, 93.9%) as a yellow oil.

$^1$H-NMR (CDCl$_3$) δ: 3.61 (2H, s), 6.67-6.70 (2H, m), 6.85-6.88 (2H, m), 6.89-6.92 (2H, m), 7.12 (2H, t, J=9.0 Hz).

(3) Preparation of methyl N-{4-[4-(trifluoromethoxy)phenoxy]phenyl}oxamate

The title compound was obtained in the same manner as the Example 3(3) using the following raw materials.

Raw materials: 4-[4-(trifluoromethoxy)phenoxy]aniline and methyl chloroglyoxylate.

Yield: 96.9% (white solid).

$^1$H-NMR (CDCl$_3$) δ: 3.98 (3H, s), 6.97-7.05 (4H, m), 7.16-7.22 (2H, m), 7.62-7.65 (2H, m), 8.85 (1H, brs).

(4) Preparation of Methyl N-[4-(tert-butyl)benzyl]-N-{4-[4-(trifluoromethoxy)phenoxy]phenyl}oxamate The title compound was obtained in the same manner as the Example 3(4) using the following raw materials.

Raw materials: methyl N-{4-[4-(trifluoromethoxy)phenoxy]phenyl}oxamate and 4-(tert-butyl)benzyl bromide.

Yield: 92.0% (colorless oil).

$^1$H-NMR (CDCl$_3$) δ: 1.30 (9H, s), 3.59 (3H, s), 4.88 (2H, s), 6.88-6.91 (2H, m), 6.98-7.01 (2H, m), 7.03-7.06 (2H, m), 7.16 (2H, d, J=8.4 Hz), 7.20 (2H, d, J=8.4 Hz), 7.30-7.33 (2H, m).

(5) Preparation of N-[4-(tert-butyl)benzyl]-N-{4-[4-(trifluoromethoxy)phenoxy]phenyl}oxamic Acid (Compound No. 11)

The title compound was obtained in the same manner as the Example 4(4) using the following raw material.

Raw material: methyl N-[4-(tert-butyl)benzyl]-N-{4-[4-(trifluoromethoxy)phenoxy]phenyl}oxamate.

Yield: 78.5% (yellow solid).

$^1$H-NMR (CDCl$_3$) δ: 1.23 (9H, s), 4.80 (2H, s), 5.83 (1H, brs), 6.75 (2H, d, J=8.4 Hz), 6.89-6.97 (4H, m), 7.08-7.13 (4H, m), 7.23 (2H, d, J=7.2 Hz).

Example 12

Preparation of N-[4-(tert-butyl)benzyl]-N-[4'-(trifluoromethoxy)biphenyl-4-yl]oxamic Acid Sodium Salt (Compound No. 12)

The title compound was obtained in the same manner as the Example 1(4) using the following raw material.

Raw material: methyl N-[4-(tert-butyl)benzyl]-N-[4'-(trifluoromethoxy)biphenyl-4-yl]oxamate (compound of Example 8(1)).

Yield: 56.5% (white solid).

$^1$H-NMR (DMSO-d$_6$) δ: 1.24 (9H, s), 4.89 (2H, s), 7.18-7.43 (8H, m), 7.54-7.57 (2H, m), 7.72-7.77 (2H, m).

Example 13

Preparation of N-[4-(tert-butyl)benzyl]-N-[4'-(methylsulfanyl)biphenyl-4-yl]oxamic Acid (Compound No. 13)

(1) Preparation of methyl N-[4-(tert-butyl)benzyl]-N-[4'-(methylsulfanyl)buphenyl-4-yl]oxamate The title compound was obtained in the same manner as the Example 1(3) using the following raw materials.

Raw materials: methyl N-(4-bromophenyl)-N-[4-(tert-butyl)benzyl]oxamate (compound of Example 4(2)) and 4-(methylsulfanyl)phenylboronic acid.

Yield: 81.2% (colorless oil).

$^1$H-NMR (CDCl$_3$) δ: 1.30 (9H, s), 2.52 (3H, s), 3.58 (3H, s), 4.94 (2H, s), 7.11-7.38 (4H, m), 7.28-7.36 (4H, m), 7.45-7.54 (4H, m).

(2) Preparation of N-[4-(tert-butyl)benzyl]-N-[4'-(methylsulfanyl)biphenyl-4-yl]oxamic Acid (Compound No. 13)

The title compound was obtained in the same manner as the Example 4(4) using the following raw material.

Raw material: methyl N-[4-(tert-butyl)benzyl]-N-[4'-(methylsulfanyl)biphenyl-4-yl]oxamate.

Yield: 94.2% (white solid).

$^1$H-NMR (DMSO-d$_6$) δ: 1.24 (9H, s), 2.51 (3H, s), 4.93 (2H, s), 7.13-7.18 (2H, m), 7.28-7.36 (6H, m), 7.58-7.66 (4H, m).

Example 14

Preparation of N-[4-(tert-butyl)benzyl]-N-(4'-chlorobiphenyl-4-yl)oxamic Acid (Compound No. 14)

(1) Preparation of Methyl N-[4-(tert-butyl)benzyl]-N-(4'-chlorobiphenyl-4-yl)oxamate The title compound was obtained in the same manner as the Example 1(3) using the following raw materials.

Raw materials: methyl N-(4-bromophenyl)-N-[4-(tert-butyl)benzyl]oxamate (compound of Example 4(2)) and 4-chlorophenylboronic acid.

Yield: 88.0% (light brown oil).

$^1$H-NMR (DMSO-$d_6$) δ: 1.30 (9H, s), 3.59 (2H, s), 4.94 (2H, s), 7.09-7.54 (12H, m).

(2) Preparation of N-[4-(tert-butyl)benzyl]-N-(4'-chlorobiphenyl-4-yl)oxamic Acid (Compound No. 14)

The title compound was obtained in the same manner as the Example 4(4) using the following raw material.

Raw material: methyl N-[4-(tert-butyl)benzyl]-N-(4'-chlorobiphenyl-4-yl)oxamate.

Yield: 44.0% (white solid).

$^1$H-NMR (DMSO-$d_6$) δ: 1.24 (9H, s), 4.89 (2H, s), 7.02-7.74 (12H, m).

Example 15

Preparation of N-[4-(tert-butyl)benzyl]-N-[4-methyl-4'-(trifluoromethoxy)biphenyl-3-yl]oxamic Acid (Compound No. 15)

(1) Preparation of 5-bromo-N-[4-(tert-butyl)benzyl]-2-methylaniline

The title compound was obtained in the same manner as the Example 1(1) using the following raw materials.

Raw materials: 5-bromo-2-methylaniline and 4-(tert-butyl)benzyl bromide.

Yield: 71.8% (colorless oil).

$^1$H-NMR (CDCl$_3$) δ: 1.33 (9H, s), 2.08 (3H, s), 3.81 (1H, brs), 4.28 (2H, d, J=4.8 Hz), 6.75-6.92 (2H, m), 6.88-6.92 (1H, m), 7.28-7.32 (2H, m), 4.28 (2H, d, J=4.8 Hz).

(2) Preparation of methyl N-(5-bromo-2-methylphenyl)-N-[4-(tert-butyl)benzyl]oxamate The title compound was obtained in the same manner as the Example 3(3) using the following raw material.

Raw material: 5-bromo-N-[4-(tert-butyl)benzyl]-2-methylaniline. Yield: 94.8% (colorless oil).

$^1$H-NMR (CDCl$_3$) δ: 1.30 (9H, s), 2.07 (3H, s), 3.54 (3H, s), 4.35 (1H, d, J=13.8 Hz), 5.20 (1H, d, J=13.8 Hz), 6.91 (1H, d, J=2.1 Hz), 7.07-7.13 (3H, m), 7.28-7.33 (2H, m), 7.35 (1H, dd, J=2.1, 8.4 Hz).

(3) Preparation of Methyl N-[4-(tert-butyl)benzyl]-N-[4-methyl-4'-(trifluoromethoxy)biphenyl-3-yl] oxamate The title compound was obtained in the same manner as the Example 1(3) using the following raw materials.

Raw materials: methyl N-(5-bromo-2-methylphenyl)-N-[4-(tert-butyl)benzyl]oxamate and 4-(trifluoromethoxy)phenylboronic acid.

Yield: 80.0% (colorless oil).

$^1$H-NMR (CDCl$_3$) δ: 1.30 (9H, s), 2.27 (3H, s), 3.48 (3H, s), 4.14 (1H, d, J=13.5 Hz), 5.51 (1H, d, J=13.5 Hz), 6.75 (1H, d, J=1.8 Hz), 7.11-7.20 (4H, m), 7.24-7.34 (5H, m), 7.42 (1H, dd, J=1.8, 7.8 Hz).

(4) Preparation of N-[4-(tert-butyl)benzyl]-N-[4-methyl-4'-(trifluoromethoxy)biphenyl-3-yl]oxamic Acid (Compound No. 15)

The title compound was obtained in the same manner as the Example 4(4) using the following raw material.

Raw material: methyl N-[4-(tert-butyl)benzyl]-N-[4-methyl-4'-(trifluoromethoxy)biphenyl-3-yl]oxamate.

Yield: 37.0% (white solid).

This compound was obtained as a mixture of the rotational isomers.

Major isomer: $^1$H-NMR (DMSO-$d_6$) δ: 1.24 (9H, s), 2.19 (3H, s), 4.32 (1H, d, J=14.1 Hz), 5.26 (1H, d, J=14.1 Hz), 6.93 (1H, d, J=1.8 Hz), 7.07-7.20 (2H, m), 7.29-7.50 (7H, m), 6.93 (1H, dd, J=1.8, 10.2 Hz).

Minor isomer: $^1$H-NMR (DMSO-$d_6$) δ: 1.23 (9H, s), 1.97 (3H, s), 4.60 (1H, d, J=14.1 Hz), 4.96 (1H, d, J=14.1 Hz), 6.80-7.60 (11H, m).

Example 16

Preparation of N-[4-(tert-butyl)benzyl]-N-(4-methylbiphenyl-3-yl)oxamic Acid (Compound No. 16)

(1) Preparation of Methyl N-[4-(tert-butyl)benzyl]-N-(4-methylbiphenyl-3-yl)oxamate The title compound was obtained in the same manner as the Example 1(3) using the following raw materials.

Raw materials: methyl N-(5-bromo-2-methylphenyl)-N-[4-(tert-butyl)benzyl]oxamate (compound of Example 15(2)) and phenylboronic acid.

Yield: 98.3% (pale yellow oil).

$^1$H-NMR (CDCl$_3$) δ: 1.31 (9H, s), 2.26 (3H, s), 3.47 (3H, s), 4.17 (1H, d, J=13.8 Hz), 5.49 (1H, d, J=13.8 Hz), 6.81 (1H, d, J=1.8 Hz), 7.13-7.17 (2H, m), 7.23-7.38 (8H, m), 7.45 (1H, dd, J=1.8, 7.5 Hz).

(2) Preparation of N-[4-(tert-butyl)benzyl]-N-(4-methylbiphenyl-3-yl)oxamic Acid (Compound No. 16)

The title compound was obtained in the same manner as the Example 4(4) using the following raw material.

Raw material: methyl N-[4-(tert-butyl)benzyl]-N-(4-methylbiphenyl-3-yl)oxamate.

Yield: 44.3% (white solid).

This compound was obtained as a mixture of the rotational isomers.

Major isomer: $^1$H-NMR (DMSO-d$_6$) δ: 1.27 (9H, s), 2.22 (3H, s), 4.23 (1H, d, J=14.4 Hz), 5.33 (1H, d, J=14.4 Hz), 6.85 (1H, d, J=1.8 Hz), 7.12-7.16 (2H, m), 7.28-7.41 (8H, m), 7.54 (1H, dd, J=1.8, 8.1 Hz).

Minor isomer: $^1$H-NMR (DMSO-d$_6$) δ: 1.26 (9H, s), 2.00 (3H, s), 4.55 (1H, d, J=15.0 Hz), 4.97 (1H, d, J=15.0 Hz), 6.73-7.60 (12H, m).

Example 17

Preparation of N-[4-(tert-butyl)benzyl]-N-(4-methyl-3'-nitrobiphenyl-3-yl)oxamic Acid (Compound No. 17)

(1) Preparation of methyl N-[4-(tert-butyl)benzyl]-N-(4-methyl-3'-nitrobiphenyl-3-yl)oxamate The title compound was obtained in the same manner as the Example 1(3) using the following raw materials.

Raw materials: methyl N-(5-bromo-2-methylphenyl)-N-[4-(tert-butyl)benzyl]oxamate (compound of Example 15(2)) and 3-nitrophenylboronic acid.

Yield: 52.1% (colorless oil).

$^1$H-NMR (CDCl$_3$) δ: 1.30 (9H, s), 2.28 (3H, s), 3.51 (3H, s), 4.20 (1H, d, J=14.1 Hz), 5.49 (1H, d, J=14.1 Hz), 6.89 (1H, d, J=2.1 Hz), 7.11-7.21 (2H, m), 7.29-7.42 (3H, m), 7.45-7.55 (3H, m), 8.13-8.26 (2H, m).

(2) Preparation of N-[4-(tert-butyl)benzyl]-N-(4-methyl-3'-nitrobiphenyl-3-yl)oxamic Acid (Compound No. 17)

The title compound was obtained in the same manner as the Example 4(4) using the following raw material.

Raw material: methyl N-[4-(tert-butyl)benzyl]-N-(4-methyl-3'-nitrobiphenyl-3-yl)oxamate.

Yield: 96.5% (pale white solid).

This compound was obtained as a mixture of the rotational isomers.

Major isomer: $^1$H-NMR (DMSO-d$_6$) δ: 1.24 (9H, s), 2.26 (3H, s), 3.99 (1H, d, J=13.8 Hz), 5.29 (1H, d, J=13.8 Hz), 7.01 (1H, d, J=1.8 Hz), 7.12-8.24 (10H, m).

Minor isomer: $^1$H-NMR (DMSO-d$_6$) δ: 1.23 (9H, s), 3.31 (3H, s), 4.54 (1H, d, J=15.3 Hz), 4.98 (1H, d, J=15.3 Hz), 7.08 (1H, d, J=1.8 Hz), 7.10-8.24 (10H, m).

Example 18

Preparation of N-[4-(tert-butyl)benzyl]-N-[4'-(trifluoromethoxy)-5-(trifluoromethyl)biphenyl-3-yl]oxamic Acid (Compound No. 18)

(1) Preparation of 3-bromo-N-[4-(tert-butyl)benzyl]-5-(trifluoromethyl)aniline

The title compound was obtained in the same manner as the Example 1(1) using the following raw materials.

Raw materials: 3-bromo-5-(trifluoromethyl)aniline and 4-(tert-butyl)benzyl bromide.

Yield: 99.9% (colorless oil).

$^1$H-NMR (CDCl$_3$) δ: 1.33 (9H, s), 4.27 (2H, s), 4.59 (1H, s), 6.73-6.75 (1H, m), 6.87-6.89 (1H, m), 7.03-7.05 (1H, m), 7.23-7.28 (2H, m), 7.36-7.41 (2H, m).

(2) Preparation of Methyl N-[3-bromo-5-(trifluoromethyl)phenyl]-N-[4-(tert-butyl)benzyl]oxamate The title compound was obtained in the same manner as the Example 3(3) using the following raw materials.

Raw materials: 3-bromo-N-[4-(tert-butyl)benzyl]-5-(trifluoromethyl)aniline and methyl chloroglyoxylate.

Yield: 65.5% (colorless oil).

$^1$H-NMR (CDCl$_3$) δ: 1.30 (9H, s), 3.63 (3H, s), 4.92 (2H, s), 7.09-7.18 (3H, m), 7.30-7.36 (2H, m), 7.39-7.42 (1H, m), 7.69-7.71 (1H, m).

(3) Preparation of Methyl N-[4-(tert-butyl)benzyl]-N-[4'-(trifluoromethoxy)-5-(trifluoromethyl)biphenyl-3-yl]oxamate The title compound was obtained in the same manner as the Example 1(3) using the following raw materials.

Raw materials: methyl N-[3-bromo-5-(trifluoromethyl)phenyl]-N-[4-(tert-butyl)benzyl]oxamate and 4-(trifluoromethoxy)phenylboronic acid.

Yield: 75.7% (colorless oil).

$^1$H-NMR (CDCl$_3$) δ: 1.30 (9H, s), 3.59 (3H, s), 4.97 (2H, s), 7.13-7.17 (2H, m), 7.26-7.45 (8H, m), 7.72-7.74 (1H, m).

(4) Preparation of N-[4-(tert-butyl)benzyl]-N-[4'-(trifluoromethoxy)-5-(trifluoromethyl)biphenyl-3-yl]oxamic Acid (Compound No. 18)

The title compound was obtained in the same manner as the Example 4(4) using the following raw material.

Raw material: methyl N-[4-(tert-butyl)benzyl]-N-[4'-(trifluoromethoxy)-5-(trifluoromethyl)biphenyl-3-yl]oxamate Yield: 43.5% (white solid).

$^1$H-NMR (DMSO-d$_6$) δ: 1.22 (9H, s), 4.97 (2H, s), 7.10-7.22 (2H, m), 7.29 (1H, d, J=8.4 Hz), 7.46 (2H, d, J=8.7 Hz), 7.57-7.61 (2H, m), 7.72-7.90 (4H, m).

Example 19

Preparation of N-[4-(tert-butyl)benzyl]-N-[5-(trifluoromethyl)biphenyl-3-yl]oxamic Acid (Compound No. 19)

(1) Preparation of methyl N-[4-(tert-butyl)benzyl]-N-[5-(trifluoromethyl)biphenyl-3-yl]oxamate The title compound was obtained in the same manner as the Example 1(3) using the following raw materials.

Raw materials: methyl N-[3-bromo-5-(trifluoromethyl)phenyl]-N-[4-(tert-butyl)benzyl]oxamate (compound of Example 18(2)) and phenylboronic acid.

Yield: 91.1% (white solid).

$^1$H-NMR (CDCl$_3$) δ: 1.30 (9H, s), 3.58 (3H, s), 4.97 (2H, s), 7.13-7.18 (2H, m), 7.26-7.46 (9H, m), 7.75-7.77 (1H, m).

(2) Preparation of N-[4-(tert-butyl)benzyl]-N-[5-(trifluoromethyl)biphenyl-3-yl]oxamic Acid (Compound No. 19)

The title compound was obtained in the same manner as the Example 4(4) using the following raw material.

Raw material: methyl N-[4-(tert-butyl)benzyl]-N-[5-(trifluoromethyl)biphenyl-3-yl]oxamate.

Yield: 24.9% (white solid).

$^1$H-NMR (DMSO-d$_6$) δ: 1.23 (9H, s), 4.97 (2H, s), 7.10-7.24 (2H, m), 7.30 (2H, d, J=7.8 Hz), 7.38-7.51 (3H; m), 7.53-7.64 (3H, m), 7.69-7.73 (1H, m), 7.74-7.82 (1H, m).

Example 20

Preparation of N-[4-(tert-butyl)benzyl]-N-(4'-methylbiphenyl-4-yl)oxamic Acid (Compound No. 20)

(1) Preparation of Methyl N-[4-(tert-butyl)benzyl]-N-(4'-methylbiphenyl-4-yl)oxamate The title compound was obtained in the same manner as the Example 1(3) using the following raw materials.
Raw materials: methyl N-(4-bromophenyl)-N-[4-(tert-butyl)benzyl]oxamate (compound of Example 4(2)) and 4-methylphenylboronic acid.
Yield: 91.3% (colorless oil).
$^1$H-NMR (CDCl$_3$) δ: 1.30 (9H, s), 2.39 (3H, s), 3.57 (3H, s), 4.93 (2H, s), 7.05-7.38 (8H, m), 7.38-7.60 (4H, m).

(2) Preparation of N-[4-(tert-butyl)benzyl]-N-(4'-methylbiphenyl-4-yl)oxamic Acid (Compound No. 20)

The title compound was obtained in the same manner as the Example 4(4) using the following raw material.
Raw material: methyl N-[4-(tert-butyl)benzyl]-N-(4'-methylbiphenyl-4-yl)oxamate.
Yield: 99.9% (white solid).
$^1$H-NMR (DMSO-d$_6$) δ: 1.24 (9H, s), 2.32 (3H, s), 4.87 (2H, s), 7.06-7.45 (8H, m), 7.51 (4H, d, J=8.0 Hz).

Example 21

Preparation of N-[4-(tert-butyl)benzyl]-N-(3'-nitrobiphenyl-4-yl)oxamic Acid (Compound No. 21)

(1) Preparation of Methyl N-[4-(tert-butyl)benzyl]-N-(3'-nitrobiphenyl-4-yl)oxamate The title compound was obtained in the same manner as the Example 1(3) using the following raw materials.
Raw materials: methyl N-(4-bromophenyl)-N-[4-(tert-butyl)benzyl]oxamate (compound of Example 4(2)) and 3-nitrophenylboronic acid.
Yield: 59.3% (white solid).
$^1$H-NMR (CDCl$_3$) δ: 1.30 (9H, s), 3.61 (3H, s), 4.96 (2H, s), 7.13-7.25 (4H, m), 7.29-7.39 (2H, m), 7.54-7.68 (3H, m), 7.84-7.94 (1H, m), 8.18-8.27 (1H, m), 8.38-8.46 (1H, m).

(2) Preparation of N-[4-(tert-butyl)benzyl]-N-(3'-nitrobiphenyl-4-yl)oxamic Acid (Compound No. 21)

The title compound was obtained in the same manner as the Example 4(4) using the following raw material.
Raw material: methyl N-[4-(tert-butyl)benzyl]-N-(3'-nitrobiphenyl-4-yl)oxamate.
Yield: 99.9% (yellow solid).
$^1$H-NMR (DMSO-d$_6$) δ: 1.24 (9H, s), 4.91 (2H, s), 7.09-7.27 (2H, m), 7.29 (2H, d, J=8.2 Hz), 7.43 (2H, d, J=8.5 Hz), 7.67 (2H, d, J=8.5 Hz), 7.73 (1H, t, J=8.2 Hz), 8.06-8.22 (2H, m) 8.36-8.44 (1H, m).

Example 22

Preparation of N-(4-methylbenzyl)-N-[4'-(trifluoromethoxy)biphenyl-4-yl]oxamic Acid (Compound No. 22)

(1) Preparation of Methyl N-(4-methylbenzyl)-N-[4'-(trifluoromethoxy)biphenyl-4-yl]oxamate The title compound was obtained in the same manner as the Example 3(4) using the following raw materials.
Raw materials: methyl N-[4'-(trifluoromethoxy)biphenyl-4-yl]oxamate (compound of Example 3(3)) and 4-methylbenzyl chloride.
Yield: 24.1% (white solid).
$^1$H-NMR (CDCl$_3$) δ: 2.31 (3H, s), 3.57 (3H, s), 4.94 (2H, s), 7.06-7.17 (6H, m), 7.27 (2H, d, J=8.8 Hz), 7.49 (2H, d, J=8.8 Hz), 7.55 (2H, d, J=8.8 Hz).

(2) Preparation of N-(4-methylbenzyl)-N-[4'-(trifluoromethoxy)biphenyl-4-yl]oxamic Acid (Compound No. 22)

The title compound was obtained in the same manner as the Example 4(4) using the following raw material.
Raw material: methyl N-(4-methylbenzyl)-N-[4'-(trifluoromethoxy)biphenyl-4-yl]oxamate.
Yield: 86.9% (white solid).
$^1$H-NMR (DMSO-d$_6$) δ: 2.23 (3H, s), 4.88 (2H, s), 6.98-7.48 (8H, m), 7.48-7.63 (2H, m) 7.73 (2H, d, J=8.5 Hz).

Example 23

Preparation of N-(2,4-dichlorobenzyl)-N-[4'-(trifluoromethoxy)biphenyl-4-yl]oxamic Acid (Compound No. 23)

(1) Preparation of Methyl N-(2,4-dichlorobenzyl)-N-[4'-(trifluoromethoxy)biphenyl-4-yl]oxamate The title compound was obtained in the same manner as the Example 1(3) using the following raw materials.
Raw materials: methyl N-[4'-(trifluoromethoxy)biphenyl-4-yl]oxamate (compound of Example 3(3)) and 2,4-dichlorobenzyl chloride.
Yield: 59.5% (colorless oil).
$^1$H-NMR (CDCl$_3$) δ: 3.61 (3H, s), 5.11 (2H, s), 7.14-7.42 (7H, m), 7.51 (2H, d, J=8.8 Hz), 7.56 (2H, d, J=8.8 Hz).

(2) Preparation of N-(2,4-dichlorobenzyl)-N-[4'-(trifluoromethoxy)biphenyl-4-yl]oxamic Acid (Compound No. 23)

The title compound was obtained in the same manner as the Example 4(4) using the following raw material.
Raw material: methyl N-(2,4-dichlorobenzyl)-N-[4'-(trifluoromethoxy)biphenyl-4-yl]oxamate.
Yield: 98.8% (white solid).
$^1$H-NMR (DMSO-d$_6$) δ: 4.94 (2H, s), 7.33-7.48 (6H, m), 7.53-7.63 (3H, m), 7.75 (2H, d, J=8.8 Hz).

Example 24

Preparation of N-[4-(tert-butyl)benzyl]-N-[4'-(trifluoromethyl)phenyl-4-yl]oxamic Acid (Compound No. 24)

(1) Preparation of Methyl N-[4-(tert-butyl)benzyl]-N-[4'-(trifluoromethyl)phenyl-4-yl]oxamate The title compound was obtained in the same manner as the Example 1(3) using the following raw materials.

Raw materials: methyl N-(4-bromophenyl)-N-[4-(tert-butyl)benzyl]oxamate (compound of Example 4(2)) and 4-(trifluoromethyl)boronic acid.

Yield: 55.7% (white solid).

$^1$H-NMR (CDCl$_3$) δ: 1.30 (9H, s), 3.60 (3H, s), 4.95 (2H, s), 7.18 (4H, d, J=8.1 Hz), 7.32 (2H, d, J=8.1 Hz), 7.55 (2H, d, J=8.7 Hz), 7.62-7.76 (4H, m).

(2) Preparation of N-[4-(tert-butyl)benzyl]-N-[4'-(trifluoromethyl)phenyl-4-yl]oxamic Acid (Compound No. 24)

The title compound was obtained in the same manner as the Example 4(4) using the following raw material.

Raw material: methyl N-[4-(tert-butyl)benzyl]-N-[4'-(trifluoromethyl)phenyl-4-yl]oxamate.

Yield: 99.5% (white solid).

$^1$H-NMR (DMSO-d$_6$) δ: 1.23 (9H, s), 4.90 (2H, s), 7.09-7.36 (4H, m), 7.41 (2H, d, J=8.5 Hz), 7.63 (2H, d, J=8.5 Hz), 7.78 (2H, d, J=8.5 Hz), 7.85 (2H, d, J=8.5 Hz).

Example 25

Preparation of N-[4-(tert-butyl)benzyl]-N-[3-methyl-4'-(trifluoromethoxy)biphenyl-4-yl]oxamic Acid (Compound No. 25)

(1) Preparation of 4-bromo-N-[4-(tert-butyl)benzyl]-2-methylaniline

The title compound was obtained in the same manner as the Example 1(1) using the following raw materials.

Raw materials: 4-bromo-2-methylaniline and 4-(tert-butyl)benzyl bromide.

Yield: 55.8% (white solid).

$^1$H-NMR (DMSO-d$_6$) δ: 1.33 (9H, s), 2.12 (3H, s), 3.82 (1H, brs), 4.30 (2H, s), 6.49 (1H, d, J=9.3 Hz), 7.12-7.21 (2H, m), 7.23-7.33 (2H, m), 7.34-7.43 (2H, m).

(2) Preparation of Methyl N-(4-bromo-2-methylphenyl)-N-[4-(tert-butyl)benzyl]oxamate The title compound was obtained in the same manner as the Example 3(3) using the following raw materials.

Raw materials: 4-bromo-N-[4-(tert-butyl)benzyl]-2-methylaniline and methyl chloroglyoxylate.

Yield: 80.2% (colorless oil).

$^1$H-NMR (CDCl$_3$) δ: 1.29 (9H, s), 2.13 (3H, s), 3.52 (3H, s), 4.26 (1H, d, J=14.0 Hz), 5.24 (1H, d, J=14.0 Hz), 6.64 (1H, d, J=8.5 Hz), 7.04-7.15 (2H, m), 7.15-7.23 (1H, m), 7.23-7.34 (2H, m), 7.34-7.44 (1H, m).

(3) Preparation of Methyl N-[4-(tert-butyl)benzyl]-N-[3-methyl-4'-(trifluoromethoxy)biphenyl-4-yl]oxamate The title compound was obtained in the same manner as the Example 1(3) using the following raw materials.

Raw materials: methyl N-(4-bromo-2-methylphenyl)-N-[4-(tert-butyl)benzyl]oxamate and 4-(trifluoromethoxy)phenylboronic acid.

Yield: 66.9% (white solid).

$^1$H-NMR (CDCl$_3$) δ: 1.30 (9H, s), 2.23 (3H, s), 3.52 (3H, s), 4.33 (1H, d, J=14.1 Hz), 5.29 (1H, d, J=14.1 Hz), 6.78-6.86 (1H, m), 6.88 (1H, d, J=8.2 Hz), 7.09 (1H, d, J=8.8 Hz), 7.16 (2H, d, J=8.2 Hz), 7.20-7.36 (3H, m), 7.42 (1H, s), 7.52-7.61 (2H, m).

(4) Preparation of N-[4-(tert-butyl)benzyl]-N-[3-methyl-4'-(trifluoromethoxy)biphenyl-4-yl]oxamic Acid (Compound No. 25)

The title compound was obtained in the same manner as the Example 4(4) using the following raw material.

Raw material: methyl N-[4-(tert-butyl)benzyl]-N-[3-methyl-4'-(trifluoromethoxy)biphenyl-4-yl]oxamate Yield: 41.1% (white solid).

This compound was obtained as a mixture of the rotational isomers.

Major isomer: $^1$H-NMR (DMSO-d$_6$) δ: 1.26 (9H, s), 2.24 (3H, s), 4.10 (1H, d, J=13.8 Hz), 5.13 (1H, d, J=13.8 Hz), 6.94 (1H, d, J=8.2 Hz), 7.14 (1H, d, J=8.0 Hz), 7.21-7.56 (7H, m), 7.75 (2H, d, J=8.8 Hz).

Minor isomer: $^1$H-NMR (DMSO-d$_6$) δ: 1.23 (9H, s), 1.98 (3H, s), 4.48-4.74 (1H, m), 4.74-4.98 (1H, m), 6.90-7.86 (11H, m).

Example 26

Preparation of N-[4-(tert-butyl)benzyl]-N-[3-chloro-4'-(trifluoromethoxy)biphenyl-4-yl]oxamic Acid (Compound No. 26)

(1) Preparation of 4-bromo-N-[4-(tert-butyl)benzyl]-2-chloroaniline

The title compound was obtained in the same manner as the Example 1(1) using the following raw materials.

Raw materials: 4-bromo-2-chloroaniline and 4-(tert-butyl)benzyl bromide.

Yield: 43.7% (white solid).

$^1$H-NMR (CDCl$_3$) δ: 1.32 (9H, s), 4.33 (2H, s), 4.70 (1H, brs), 6.52 (1H, d, J=8.8 Hz), 7.18 (1H, d, J=2.2, 8.8 Hz), 7.27 (2H, d, J=8.0 Hz), 7.34-7.43 (3H, m).

(2) Preparation of Methyl N-(4-bromo-2-chlorophenyl)-N-[4-(tert-butyl)benzyl]oxamate The title compound was obtained in the same manner as the Example 3(3) using the following raw materials.

Raw materials: 4-bromo-N-[4-(tert-butyl)benzyl]-2-chloroaniline and methyl chloroglyoxylate.

Yield: 88.3% (colorless oil).

$^1$H-NMR (CDCl$_3$) δ: 1.29 (9H, s), 3.59 (3H, s), 4.17 (1H, d, J=14.4 Hz), 5.51 (1H, d, J=14.4 Hz), 6.71 (1H, d, J=8.5 Hz), 7.06-7.18 (2H, m), 7.21-7.36 (3H, m), 7.63 (1H, d, J=2.2 Hz).

(3) Preparation of Methyl N-[4-(tert-butyl)benzyl]-N-[3-chloro-4'-(trifluoromethoxy)biphenyl-4-yl]oxamate The title compound was obtained in the same manner as the Example 1(3) using the following raw materials.

Raw materials: methyl N-(4-bromo-2-chlorophenyl)-N-[4-(tert-butyl)benzyl]oxamate and 4-(trifluoromethoxy)phenylboronic acid.

Yield: 43.9% (white solid).

$^1$H-NMR (CDCl$_3$) δ: 1.29 (9H, s), 3.59 (3H, s), 4.25 (1H, d, J=14.4 Hz), 5.56 (1H, d, J=14.4 Hz), 6.95 (1H, d, J=7.8 Hz), 7.17 (2H, d, J=8.1 Hz), 7.24-7.37 (5H, m), 7.51-7.60 (2H, m), 7.66 (1H, d, J=1.8 Hz).

(4) Preparation of N-[4-(tert-butyl)benzyl]-N-[3-chloro-4'-(trifluoromethoxy)biphenyl-4-yl]oxamic Acid (Compound No. 26)

The title compound was obtained in the same manner as the Example 4(4) using the following raw material.

Raw material: methyl

N-[4-(tert-butyl)benzyl]-N-[3-chloro-4'-(trifluoromethoxy)biphenyl-4-yl]oxamate

Yield: 92.1% (white solid).

This compound was obtained as a mixture of the rotational isomers.

Major isomer: $^1$H-NMR (DMSO-d$_6$) δ: 1.24 (9H, s), 4.06 (1H, d, J=14.7 Hz), 5.39 (1H, d, J=14.7 Hz), 7.08-7.22 (2H, m), 7.22-7.39 (3H, m), 7.39-7.58 (3H, m), 7.74-7.88 (3H, m).

Minor isomer: $^1$H-NMR (DMSO-d$_6$) δ: 1.23 (9H, s), 4.38-4.84 (1H, m), 4.84-5.28 (1H, m), 7.02-7.88 (11H, m).

Example 27

Preparation of N-[4-(tert-butyl)benzyl]-N-[4'-(trifluoromethoxy)biphenyl-2-yl]oxamic Acid (Compound No. 27)

(1) Preparation of Methyl N-(2-bromophenyl)oxamate

The title compound was obtained in the same manner as the Example 3(3) using the following raw materials.

Raw materials: 2-bromoaniline and methyl chloroglyoxylate.

Yield: 98.5% (white solid).

$^1$H-NMR (CDCl$_3$) δ: 4.00 (3H, s), 7.04-7.61 (3H, m), 8.41-8.44 (1H, m), 9.48 (1H, brs).

(2) Preparation of Methyl N-(2-bromophenyl)-N-[4-(tert-butyl)benzyl]oxamate The title compound was obtained in the same manner as the Example 1(1) using the following raw materials.

Raw materials: methyl N-(2-bromophenyl)oxamate and 4-(tert-butyl)benzyl bromide.

Yield: 25.6% (colorless oil).

$^1$H-NMR (CDCl$_3$) δ: 1.29 (9H, s), 3.55 (3H, s), 4.18 (1H, d, J=14.1 Hz), 5.56 (1H, d, J=14.1 Hz), 6.82-6.86 (1H, m), 7.11-7.30 (6H, m), 7.63-7.67 (1H, m).

(3) Preparation of methyl N-[4-(tert-butyl)benzyl]-N-[4'-(trifluoromethoxy)biphenyl-2-yl]oxamate The title compound was obtained in the same manner as the Example 1(3) using the following raw materials.

Raw materials: methyl N-(2-bromophenyl)-N-[4-(tert-butyl)benzyl]oxamate and 4-(trifluoromethoxy)phenylboronic acid.

Yield: 80.0% (colorless oil).

$^1$H-NMR (CDCl$_3$) δ: 1.25 (9H, s), 3.47 (1H, d, J=14.1 Hz), 3.63 (3H, s), 5.10 (1H, d, J=14.1 Hz), 6.82-6.86 (1H, m), 6.91-6.95 (2H, m), 7.17-7.42 (7H, m), 7.59-7.65 (2H, m).

(4) Preparation of N-[4-(tert-butyl)benzyl]-N-[4'-(trifluoromethoxy)biphenyl-2-yl]oxamic Acid (Compound No. 27)

The title compound was obtained in the same manner as the Example 4(4) using the following raw material.

Raw material: methyl N-[4-(tert-butyl)benzyl]-N-[4'-(trifluoromethoxy)biphenyl-2-yl]oxamate.

Yield: 66.9% (white solid).

$^1$H-NMR (DMSO-d$_6$) δ: 1.20 (9H, s), 3.14 (1H, d, J=14.7 Hz), 4.82 (1H, d, J=14.7 Hz), 6.86 (2H, d, J=8.1 Hz), 7.05-7.36 (6H, m), 7.43 (2H, d, J=8.4 Hz), 8.05 (2H, d, J=8.7 Hz).

Example 28

Preparation of N-[4-(tert-butyl)benzyl]-N-(4'-cyanobiphenyl-4-yl)oxamic Acid (Compound No. 28)

(1) Preparation of Methyl N-(4'-cyanobiphenyl-4-yl)oxamate

The title compound was obtained in the same manner as the Example 3(3) using the following raw materials.

Raw materials: 4-(4-aminophenyl)benzonitrile and methyl chloroglyoxylate.

Yield: 80.9% (white solid).

$^1$H-NMR (DMSO-d$_6$) δ: 3.87 (3H, s), 7.77-7.94 (8H, m), 10.98 (1H, brs).

(2) Preparation of Methyl N-[4-(tert-butyl)benzyl]-N-(4'-cyanobiphenyl-4-yl)oxamate The title compound was obtained in the same manner as the Example 1(1) using the following raw materials.

Raw materials: methyl N-(4'-cyanobiphenyl-4-yl)oxamate and 4-(tert-butyl)benzyl bromide.

Yield: 77.7% (pale yellow oil).

$^1$H-NMR (CDCl$_3$) δ: 1.30 (9H, s), 3.60 (3H, s), 4.95 (2H, s), 7.15-7.22 (4H, m), 7.32 (2H, d, J=8.4 Hz), 7.54 (2H, d, J=8.1 Hz), 7.65 (2H, d, J=7.8 Hz), 7.73 (2H, d, J=7.8 Hz).

(3) Preparation of N-[4-(tert-butyl)benzyl]-N-(4'-cyanobiphenyl-4-yl)oxamic Acid (Compound No. 28)

The title compound was obtained in the same manner as the Example 1(3) using the following raw material.

Raw material: methyl N-[4-(tert-butyl)benzyl]-N-(4'-cyanobiphenyl-4-yl)oxamate.

Yield: 48.7% (white solid).

$^1$H-NMR (DMSO-d$_6$) δ: 1.23 (9H, s), 4.91 (2H, s), 7.12-7.34 (4H, m), 7.42 (2H, d, J=8.7 Hz), 7.64 (2H, d, J=8.7 Hz), 7.82-7.92 (4H, m).

Example 29

Preparation of N-[4-(tert-butyl)benzyl]-N-[4'-(trifluoromethoxy)-3-(trifluoromethyl)biphenyl-4-yl]oxamic Acid (Compound No. 29)

(1) Preparation of Methyl N-[4-bromo-2-(trifluoromethyl)phenyl]oxamate

The title compound was obtained in the same manner as the Example 3(3) using the following raw materials.
Raw materials: 4-bromo-2-(trifluoromethyl)aniline and methyl chloroglyoxylate.
Yield: 71.9% (white solid).
$^1$H-NMR (CDCl$_3$) δ: 4.00 (3H, s), 7.73 (1H, dd, J=2.1, 8.7 Hz), 7.79 (1H, d, J=2.1 Hz), 8.29 (1H, d, J=8.7 Hz), 9.30 (1H, brs).

(2) Preparation of Methyl N-[4-bromo-2-(trifluoromethyl)phenyl]-N-[4-(tert-butyl)benzyl]oxamate The title compound was obtained in the same manner as the Example 1(1) using the following raw materials.
Raw materials: methyl N-[4-bromo-2-(trifluoromethyl)phenyl]oxamate and 4-(tert-butyl)benzyl bromide.
Yield: 70.2% (colorless oil).
$^1$H-NMR (CDCl$_3$) δ: 1.31 (9H, s), 3.61 (3H, s), 3.91 (1H, d, J=14.7 Hz), 5.76 (1H, d, J=14.7 Hz), 6.66 (1H, d, J=8.7 Hz), 7.12-7.17 (2H, m), 7.29-7.36 (2H, m), 7.52 (1H, dd, J=2.4, 8.7 Hz), 7.86 (1H, d, J=2.4 Hz).

(3) Preparation of Methyl N-[4-(tert-butyl)benzyl]-N-[4'-(trifluoromethoxy)-3-(trifluoromethyl)biphenyl-4-yl]oxamate The title compound was obtained in the same manner as the Example 1(3) using the following raw materials.
Raw materials: methyl N-[4-bromo-2-(trifluoromethyl)phenyl]-N-[4-(tert-butyl)benzyl]oxamate and 4-(trifluoromethoxy)phenylboronic acid.
Yield: 44.6% (colorless oil).
$^1$H-NMR (CDCl$_3$) δ: 1.31 (9H, s), 3.60 (3H, s), 3.99 (1H, d, J=14.4 Hz), 5.79 (1H, d, J=14.4 Hz), 6.91 (1H, d, J=8.4 Hz), 7.16-7.21 (2H, m), 7.27-7.36 (4H, m), 7.54-7.63 (3H, m), 7.90 (1H, d, J=2.1 Hz).

(4) Preparation of N-[4-(tert-butyl)benzyl]-N-[4'-(trifluoromethoxy)-3-(trifluoromethyl)biphenyl-4-yl]oxamic Acid (Compound No. 29)

The title compound was obtained in the same manner as the Example 4(4) using the following raw material.
Raw material: methyl N-[4-(tert-butyl)benzyl]-N-[4'-(trifluoromethoxy)-3-(trifluoromethyl)biphenyl-4-yl]oxamate Yield: 66.7% (white solid).
This compound was obtained as a mixture of the rotational isomers.
Major isomer: $^1$H-NMR (DMSO-d$_6$) δ: 1.26 (9H, s), 3.86 (1H, d, J=14.7 Hz), 5.51 (1H, d, J=14.7 Hz), 7.08-7.80 (11H, m).
Minor isomer: $^1$H-NMR (DMSO-d$_6$) δ: 1.25 (9H, s), 4.26 (1H, d, J=15.3 Hz), 5.33 (1H, d, J=15.3 Hz), 6.79 (1H, d, J=8.4 Hz), 7.08-7.80 (10H, m).

Example 30

Preparation of N-[4-(tert-butyl)benzyl]-N-[3,4'-bis(trifluoromethoxy)biphenyl-4-yl]oxamic Acid (Compound No. 30)

(1) Preparation of Methyl N-[4-bromo-2-(trifluoromethoxy)phenyl]oxamate

The title compound was obtained in the same manner as the Example 3(3) using the following raw materials.
Raw materials: 4-bromo-2-(trifluoromethoxy)aniline and methyl chloroglyoxylate.
Yield: 80.7% (white solid).
$^1$H-NMR (CDCl$_3$) δ: 4.00 (3H, s), 7.47-7.50 (2H, m), 8.36-8.41 (1H, m), 9.21 (1H, brs).

(2) Preparation of Methyl N-[4-bromo-2-(trifluoromethoxy)phenyl]-N-[4-(tert-butyl)benzyl]oxamate The title compound was obtained in the same manner as the Example 1(1) using the following raw materials.
Raw materials: methyl N-[4-bromo-2-(trifluoromethoxy)phenyl]oxamate and 4-(tert-butyl)benzyl bromide.
Yield: 89.9% (colorless oil).
$^1$H-NMR (CDCl$_3$) δ: 1.29 (9H, s), 3.61 (3H, s), 4.31 (1H, d, J=14.7 Hz), 5.37 (1H, d, J=14.7 Hz), 6.84 (1H, d, J=8.7 Hz), 7.08-7.13 (2H, m), 7.25-7.32 (3H, m), 7.43-7.46 (1H, m).

(3) Preparation of Methyl N-[4-(tert-butyl)benzyl]-N-[3,4'-bis(trifluoromethoxy)biphenyl-4-yl]oxamate The title compound was obtained in the same manner as the Example 1(3) using the following raw materials.
Raw materials: methyl N-[4-bromo-2-(trifluoromethoxy)phenyl]-N-[4-(tert-butyl)benzyl]oxamate and 4-(trifluoromethoxy)phenylboronic acid.
Yield: 44.7% (colorless oil).
$^1$H-NMR (CDCl$_3$) δ: 1.29 (9H, s), 3.61 (3H, s), 4.37 (1H, d, J=14.4 Hz), 5.44 (1H, d, J=14.4 Hz), 7.06 (1H, d, J=8.1 Hz), 7.14-7.17 (2H, m), 7.26-7.35 (5H, m), 7.43-7.48 (1H, m), 7.53-7.58 (2H, m).

(4) Preparation of N-[4-(tert-butyl)benzyl]-N-[3,4'-bis(trifluoromethoxy)biphenyl-4-yl]oxamic Acid (Compound No. 30)

The title compound was obtained in the same manner as the Example 4(4) using the following raw material.
Raw material: methyl N-[4-(tert-butyl)benzyl]-N-[3,4'-bis(trifluoromethoxy)biphenyl-4-yl]oxamate.
Yield: 47.6% (white solid).
This compound was obtained as a mixture of the rotational isomers.
Major isomer: $^1$H-NMR (DMSO-d$_6$) δ: 1.24 (9H, s), 4.84 (2H, s), 7.07-7.80 (11H, m).
Minor isomer: $^1$H-NMR (DMSO-d$_6$) δ: 1.22 (9H, s), 4.77 (2H,$), 7.07-7.80 (11H, m).

Example 31

Preparation of N-[4-(tert-butyl)benzyl]-N-[4'-(trifluoromethoxy)-3,5-dimethylbiphenyl-4-yl]oxamic Acid (Compound No. 31)

(1) Preparation of Methyl N-(4-bromo-2,6-dimethylphenyl)oxamate

The title compound was obtained in the same manner as the Example 3(3) using the following raw materials.

Raw materials: 4-bromo-2,6-dimethylaniline and methyl chloroglyoxylate.

Yield: 73.0% (white solid).

$^1$H-NMR (CDCl$_3$) δ: 2.22 (6H, s), 3.99 (3H, s), 7.26 (2H, d, J=1.5 Hz), 8.32 (1H, brs).

(2) Preparation of Methyl N-(4-bromo-2,6-dimethylphenyl)-N-[4-(tert-butyl)benzyl]oxamate The title compound was obtained in the same manner as the Example 1(1) using the following raw materials.

Raw materials: methyl N-(4-bromo-2,6-dimethylphenyl)oxamate and 4-(tert-butyl)benzyl bromide.

Yield: 89.1% (colorless oil).

$^1$H-NMR (CDCl$_3$) δ: 1.29 (9H, s), 1.88 (6H, s), 3.51 (3H, s), 4.72 (2H, s), 7.11-7.15 (2H, m), 7.16-7.18 (2H, m), 7.25-7.30 (2H, m).

(3) Preparation of Methyl N-[4-(tert-butyl)benzyl]-N-[4'-(trifluoromethoxy)-3,5-dimethylbiphenyl-4-yl]oxamate The title compound was obtained in the same manner as the Example 1(3) using the following raw materials.

Raw materials: methyl N-(4-bromo-2,6-dimethylphenyl)-N-[4-(tert-butyl)benzyl]oxamate and 4-(trifluoromethoxy)phenylboronic acid.

Yield: 79.4% (colorless oil).

$^1$H-NMR (CDCl$_3$) δ: 1.29 (9H, s), 1.97 (6H, s), 3.51 (3H, s), 4.78 (2H, s), 7.16-7.22 (4H, m), 7.25-7.30 (4H, m), 7.55-7.61 (2H, m).

(4) Preparation of N-[4-(tert-butyl)benzyl]-N-[4'-(trifluoromethoxy)-3,5-dimethylbiphenyl-4-yl]oxamic Acid (Compound No. 31)

The title compound was obtained in the same manner as the Example 4(4) using the following raw material.

Raw material: methyl N-[4-(tert-butyl)benzyl]-N-[4'-(trifluoromethoxy)-3,5-dimethylbiphenyl-4-yl]oxamate Yield: 51.7% (white solid).

This compound was obtained as a mixture of the rotational isomers.

Major isomer: $^1$H-NMR (DMSO-d$_6$) δ: 1.25 (9H, s), 1.99 (6H, s), 4.55 (2H, s), 7.13-7.77 (10H, m).

Minor isomer: $^1$H-NMR (DMSO-d$_6$) δ: 1.23 (9H, s), 1.85 (6H, s), 4.62 (2H, s), 7.13-7.77 (10H, m).

Example 32

Preparation of N-[4-(tert-butyl)benzyl]-N-{2-[4-(trifluoromethoxy)phenoxy]phenyl}oxamic Acid (Compound No. 32)

(1) Preparation of 1-nitro-2-[4-(trifluoromethoxy)phenoxy]benzene

The title compound was obtained in the same manner as the Example 11(1) using the following raw materials.

Raw materials: 2-fluoro-1-nitrobenzene and 4-(trifluoromethoxy)phenol.

Yield: 94% (yellow oil).

$^1$H-NMR (CDCl$_3$) δ: 7.02-7.09 (3H, m), 7.20-7.30 (3H, m), 7.52-7.60 (1H, m), 7.98 (1H, dd, J=1.5, 8.1 Hz).

(2) Preparation of 2-[4-(trifluoromethoxy)phenoxy]aniline

The title compound was obtained in the same manner as the Example 3(2) using the following raw material.

Raw material: 1-nitro-2-[4-(trifluoromethoxy)phenoxy]benzene.

Yield: 98% (colorless oil).

$^1$H-NMR (CDCl$_3$) δ: 3.78 (2H, brs), 6.70-6.78 (1H, m), 6.84 (1H, dd, J=1.8, 8.1 Hz), 6.88 (1H, dd, J=1.5, 8.1 Hz), 6.93-6.99 (2H, m), 7.01 (1H, dt, J=1.5, 8.1 Hz), 7.12-7.18 (2H, m).

(3) Preparation of methyl N-{2-[4-(trifluoromethoxy)phenoxy]phenyl}oxamate

The title compound was obtained in the same manner as the Example 3(3) using the following raw materials.

Raw materials: 2-[4-(trifluoromethoxy)phenoxy]aniline and methyl chloroglyoxylate.

Yield: 96% (white solid).

$^1$H-NMR (CDCl$_3$) δ: 3.96 (3H, s), 6.89 (1H, dd, J=1.8, 8.1 Hz), 7.03-7.26 (6H, m), 8.79 (1H, dd, J=1.8, 7.8 Hz), 9.43 (1H, brs).

(4) Preparation of Methyl N-[4-(tert-butyl)benzyl]-N-{2-[4-(trifluoromethoxy)phenoxy]phenyl}oxamate The title compound was obtained in the same manner as the Example 3(4) using the following raw materials.

Raw materials: methyl N-{2-[4-(trifluoromethoxy)phenoxy]phenyl}oxamate and 4-(tert-butyl)benzyl bromide.

Yield: 93% (colorless oil).

$^1$H-NMR (CDCl$_3$) δ: 1.28 (9H, s), 3.62 (3H, s), 4.72 (1H, d, J=14.4 Hz), 5.13 (1H, d, J=14.4 Hz), 6.78 (1H, dd, J=1.5, 8.4 Hz), 6.85-6.93 (2H, m), 6.97-7.10 (2H, m), 7.12-7.28 (7H, m).

(5) Preparation of N-[4-(tert-butyl)benzyl]-N-{2-[4-(trifluoromethoxy)phenoxy]phenyl}oxamic Acid (Compound No. 32)

The title compound was obtained in the same manner as the Example 4(4) using the following raw material.

Raw material: methyl N-[4-(tert-butyl)benzyl]-N-{2-[4-(trifluoromethoxy)phenoxy]phenyl}oxamate.

Yield: 84% (white solid).

$^1$H-NMR (DMSO-d$_6$) δ: 1.24 (9H, s), 4.64 (1H, d, J=15.0 Hz), 5.03 (1H, d, J=15.0 Hz), 6.80-6.86 (1H, m), 6.98-7.04 (2H, m), 7.06-7.36 (7H, m), 7.37-7.44 (2H, m), 13.95 (1H, brs).

Example 33

Preparation of N-benzyl-N-{4-[4-(trifluoromethoxy)phenoxy]phenyl}oxamic Acid (Compound No. 33).

(1) Preparation of Methyl N-benzyl-N-{4-[4-(trifluoromethoxy)phenoxy]phenyl}oxamate The title compound was obtained in the same manner as the Example 3(4) using the following raw materials.

Raw materials: methyl N-{4-[4-(trifluoromethoxy)phenoxy]phenyl}oxamate (compound of Example 11(3)) and benzyl bromide.

Yield: 92% (colorless oil).

$^1$H-NMR (CDCl$_3$) δ: 3.60 (3H, s), 4.92 (2H, s), 6.85-6.92 (2H, m), 6.96-7.05 (4H, m), 7.17-7.35 (7H, m).

(2) Preparation of N-benzyl-N-{4-[4-(trifluoromethoxy)phenoxy]phenyl}oxamic Acid (Compound No. 33)

The title compound was obtained in the same manner as the Example 4(4) using the following raw material.

Raw material: methyl N-benzyl-N-{4-[4-(trifluoromethoxy)phenoxy]phenyl}oxamate.

Yield: 93% (white solid).

$^1$H-NMR (CDCl$_3$) δ: 4.89 (2H, s), 5.71 (1H, brs), 6.82-7.02 (6H, m), 7.14-7.23 (4H, m), 7.24-7.31 (3H, m).

Example 34

Preparation of N-[4'-(trifluoromethoxy)biphenyl-4-yl]-N-[4-(trifluoromethyl)benzyl]oxamic Acid (Compound No. 34)

(1) Preparation of Methyl N-[4'-(trifluoromethoxy)biphenyl-4-yl]-N-[4-(trifluoromethyl)benzyl]oxamate The title compound was obtained in the same manner as the Example 3(4) using the following raw materials.

Raw materials: methyl N-[4'-(trifluoromethoxy)biphenyl-4-yl]oxamate (compound of Example 3(3)) and 4-trifluoromethylbenzyl chloride.

Yield: 37.4% (colorless oil).

$^1$H-NMR (CDCl$_3$) δ: 3.61 (3H, s), 5.03 (2H, s), 7.10-7.20 (2H, m), 7.24-7.34 (2H, m), 7.36-7.45 (2H, m), 7.48-7.65 (6H, m).

(2) Preparation of N-[4'-(trifluoromethoxy)biphenyl-4-yl]-N-[4-(trifluoromethyl)benzyl]oxamic Acid (Compound No. 34)

The title compound was obtained in the same manner as the Example 4(4) using the following raw material.

Raw material: methyl N-[4'-(trifluoromethoxy)biphenyl-4-yl]-N-[4-(trifluoromethyl)benzyl]oxamate.

Yield: 98.1% (white solid).

$^1$H-NMR (DMSO-d$_6$) δ: 5.02 (2H, s), 7.30-7.84 (12H, m).

Example 35

Preparation of N-(4-fluorobenzyl)-N-[4'-(trifluoromethoxy)biphenyl-4-yl]oxamic Acid (Compound No. 35)

(1) Preparation of Methyl N-(4-fluorobenzyl)-N-[4'-(trifluoromethoxy)biphenyl-4-yl]oxamate The title compound was obtained in the same manner as the Example 1(1) using the following raw materials.

Raw materials: methyl N-[4'-(trifluoromethoxy)biphenyl-4-yl]oxamate (compound of Example 3(3)) and 4-fluorobenzyl chloride.

Yield: 67.6% (colorless oil).

$^1$H-NMR (CDCl$_3$) δ: 3.59 (3H, s), 4.94 (2H, s), 6.96-7.02 (2H, m), 7.10-7.13 (2H, m), 7.20-7.25 (2H, m), 7.26-7.33 (2H, m), 7.48-7.53 (2H, m), 7.54-7.58 (2H, m).

(2) Preparation of N-(4-fluorobenzyl)-N-[4'-(trifluoromethoxy)biphenyl-4-yl]oxamic Acid (Compound No. 35)

The title compound was obtained in the same manner as the Example 4(4) using the following raw material.

Raw material: methyl N-(4-fluorobenzyl)-N-[4'-(trifluoromethoxy)biphenyl-4-yl]oxamate.

Yield: 64.5% (white solid).

$^1$H-NMR (DMSO-d$_6$) δ: 4.89 (2H, s), 7.06-7.12 (2H, m), 7.24-7.34 (4H, m), 7.42 (2H, d, J=8.7 Hz), 7.55 (2H, d, J=8.1 Hz), 7.74 (2H, d, J=8.7 Hz).

Example 36

Preparation of N-benzyl-N-[4'-(tert-butyl)biphenyl-4-yl]oxamic Acid (Compound No. 36)

(1) Preparation of Methyl N-(4-bromophenyl)-N-benzyloxamate

The title compound was obtained in the same manner as the Example 1(1) using the following raw materials.

Raw materials: methyl N-(4-bromophenyl)oxamate (compound of Example 4(1)) and benzyl chloride.

Yield: 60.2% (colorless oil).

$^1$H-NMR (CDCl$_3$) δ: 3.59 (3H, s), 4.92 (2H, s), 6.89-6.94 (2H, m), 7.18-7.23 (2H, m), 7.26-7.30 (3H, m), 7.40-7.45 (2H, m).

(2) Preparation of methyl N-benzyl-N-[4'-(tert-butyl)biphenyl-4-yl]oxamate

The title compound was obtained in the same manner as the Example 1(3) using the following raw materials.

Raw materials: methyl N-(4-bromophenyl)-N-benzyloxamate and 4-(tert-butyl)phenylboronic acid.

Yield: 86.5% (yellow oil).

$^1$H-NMR (CDCl$_3$) δ: 1.35 (9H, s), 3.56 (3H, s), 4.97 (2H, s), 7.09-7.12 (2H, m), 7.23-7.31 (4H, m), 7.43-7.54 (7H, m).

(3) Preparation of N-benzyl-N-[4'-(tert-butyl)biphenyl-4-yl]oxamic Acid (Compound No. 36)

The title compound was obtained in the same manner as the Example 4(4) using the following raw material.

Raw material: methyl N-benzyl-N-[4'-(tert-butyl)biphenyl-4-yl]oxamate.

Yield: 65.9% (white solid).

$^1$H-NMR (DMSO-d$_6$) δ: 1.30 (9H, s), 4.95 (2H, s), 7.22-7.36 (7H, m), 7.45 (2H, d, J=8.4 Hz), 7.53-7.56 (4H, m).

Example 37

Preparation of N-[2-(tert-butyl)phenyl]-N-[4'-(trifluoromethoxy)biphenyl-2-yl]oxamic Acid (Compound No. 37)

(1) Preparation of 2-amino-4'-(trifluoromethoxy)biphenyl

The title compound was obtained in the same manner as the Example 1(3) using the following raw materials.

Raw materials: 2-bromoaniline and 4-(trifluoromethoxy)phenylboronic acid.

Yield: 83% (red-brown solid).

$^1$H-NMR (CDCl$_3$) δ: 3.77 (2H, brs), 6.78 (1H, dd, J=1.2, 9.0 Hz), 6.84 (1H, dt, J=1.2, 7.5 Hz), 7.10 (1H, dd, J=1.5, 7.5 Hz), 7.15-7.21 (1H, m), 7.27-7.32 (2H, m), 7.45-7.52 (2H, m).

(2) Preparation of 2-[4-(tert-butyl)phenyl]amino-4'-(trifluoromethoxy)biphenyl

A mixture of 2-amino-4'-(trifluoromethoxy)biphenyl (633 mg, 2.50 mmol), 1-bromo-4-(tert-butyl)benzene (533 mg, 2.50 mmol), rac-2,2'-bis(diphenylphosphino)-1,1'-binaphthyl (124 mg, 0.2 mmol), bis(dibenzylideneacetone)palladium (0) (72 mg, 0.125 mmol), potassium tert-butoxide (1.68 g, 15.0 mmol) and toluene (10 ml) was stirred at 60° for 5 hours under argon atmosphere. After the reaction mixture was cooled to room temperature, saturated aqueous ammonium chloride. The mixture was filtered through celite and extracted with ethyl acetate. The residue obtained by evaporation of the solvent under reduced pressure was purified by column chromatography on silica gel (n-hexane:ethyl acetate=5:1) to give the title compound (857 mg, 89%) as a brown oil.

$^1$H-NMR (CDCl$_3$) δ: 1.31 (9H, s), 5.44 (1H, s), 6.93-7.04 (3H, m), 7.18-7.38 (7H, m), 7.46-7.52 (2H, m).

(3) Preparation of methyl N-[2-(tert-butyl)phenyl]-N-[4'-(trifluoromethoxy)biphenyl-2-yl]oxamate The title compound was obtained in the same manner as the Example 3(3) using the following raw materials.

Raw materials: 2-[4-(tert-butyl)phenyl]amino-4'-(trifluoromethoxy)biphenyl and methyl chloroglyoxylate.

Yield: 44% (white solid).

This compound was obtained as a mixture of the rotational isomers.

Major isomer: $^1$H-NMR (CDCl$_3$) δ: 1.19 (9H, s), 3.71 (3H, s), 6.53-6.59 (2H, m), 7.00-7.11 (3H, m), 7.13-7.24 (3H, m), 7.29-7.36 (1H, m), 7.39-7.51 (3H, m).

Minor isomer: $^1$H-NMR (CDCl$_3$) δ: 1.21 (9H, s), 3.58 (3H, s), 6.58-6.65 (2H, m), 7.00-7.11 (3H, m), 7.13-7.24 (3H, m), 7.29-7.36 (1H, m), 7.39-7.51 (3H, m).

(4) Preparation of N-[2-(tert-butyl)phenyl]-N-[4'-(trifluoromethoxy)biphenyl-2-yl]oxamic Acid (Compound No. 37)

The title compound was obtained in the same manner as the Example 4(4) using the following raw material.

Raw material: methyl N-[2-(tert-butyl)phenyl]-N-[4'-(trifluoromethoxy)biphenyl-2-yl]oxamate.

Yield: 94% (light brown solid).

This compound was obtained as a mixture of the rotational isomers.

Major isomer: $^1$H-NMR (DMSO-d$_6$) δ: 1.15 (9H, s), 6.48-6.56 (2H, m), 7.00-7.62 (10H, m), 14.21 (1H, brs).

Minor isomer: $^1$H-NMR (DMSO-d$_6$) δ: 1.18 (9H, s), 6.67-6.73 (2H, m), 7.00-7.62 (10H, m), 14.21 (1H, brs).

Example 38

Preparation of N-[4-(tert-butyl)phenyl]-N-[4'-(trifluoromethoxy)biphenyl-3-yl]oxamic Acid (Compound No. 38)

(1) Preparation of 3-amino-4'-(trifluoromethoxy)biphenyl

The title compound was obtained in the same manner as the Example 1(3) using the following raw materials.

Raw materials: 3-bromoaniline and 4-(trifluoromethoxy)phenylboronic acid.

Yield: 83% (pale yellow oil).

$^1$H-NMR (CDCl$_3$) δ: 3.76 (2H, brs), 6.70 (1H, ddd, J=1.8, 2.1, 8.1 Hz), 6.86 (1H, dd, J=1.8, 2.1 Hz), 6.94 (1H, ddd, J=0.9, 1.8, 7.5 Hz), 7.20-7.29 (3H, m), 7.53-7.59 (2H, m).

(2) Preparation of 3-[4-(tert-butyl)phenyl]amino-4'-(trifluoromethoxy)biphenyl

The title compound was obtained in the same manner as the Example 37(2) using the following raw materials.

Raw materials: 3-amino-4'-(trifluoromethoxy)biphenyl and 1-bromo-4-(tert-butyl)benzene.

Yield: 90% (brown oil).

$^1$H-NMR (CDCl$_3$) δ: 1.32 (9H, s), 5.73 (1H, s), 7.00-7.11 (3H, m), 7.17-7.35 (7H, m), 7.54-7.60 (2H, m).

(3) Preparation of Methyl N-[4-(tert-butyl)phenyl]-N-[4'-(trifluoromethoxy)biphenyl-3-yl]oxamate The title compound was obtained in the same manner as the Example 3(3) using the following raw materials.

Raw materials: 3-[4-(tert-butyl)phenyl]amino-4'-(trifluoromethoxy)biphenyl and methyl chloroglyoxylate.

Yield: 73% (light brown solid).

This compound was obtained as a mixture of the rotational isomers.

Major isomer: $^1$H-NMR (CDCl$_3$) δ: 1.31 (9H, s), 3.61 (3H, s), 7.20-7.34 (5H, m), 7.36-7.62 (7H, m).

Minor isomer: $^1$H-NMR (CDCl$_3$) δ: 1.30 (9H, s), 3.62 (3H, s), 7.20-7.34 (5H, m), 7.36-7.62 (7H, m).

(4) Preparation of N-[4-(tert-butyl)phenyl]-N-[4'-(trifluoromethoxy)biphenyl-3-yl]oxamic Acid (Compound No. 38)

The title compound was obtained in the same manner as the Example 4(4) using the following raw material.
Raw material: methyl N-[4-(tert-butyl)phenyl]-N-[4'-(trifluoromethoxy)biphenyl-3-yl]oxamate.
Yield: 71% (white solid).
This compound was obtained as a mixture of the rotational isomers.
$^1$H-NMR (DMSO-$d_6$) δ: 1.27 (9H, s), 7.17-7.31 (7H, m), 7.35-7.58 (5H, m), 14.17 (1H, brs).

Example 39

Preparation of N-[4-(trifluoromethoxy)benzyl]-N-[4'-(trifluoromethoxy)biphenyl-4-yl]oxamic Acid (Compound No. 39)

(1) Preparation of Methyl N-[4-(trifluoromethoxy)benzyl]-N-[4'-(trifluoromethoxy)biphenyl-4-yl]oxamate The title compound was obtained in the same manner as the Example 3(4) using the following raw materials.
Raw materials: methyl N-[4'-(trifluoromethoxy)biphenyl-4-yl]oxamate (compound of Example 3(3)) and 4-(trifluoromethoxy)benzyl bromide.
Yield: 81.5% (colorless oil).
$^1$H-NMR (CDCl$_3$) δ: 3.60 (3H, s), 4.98 (2H, s), 7.10-7.21 (4H, m), 7.24-7.35 (4H, m), 7.48-7.62 (4H, m).

(2) Preparation of N-[4-(trifluoromethoxy)benzyl]-N-[4'-(trifluoromethoxy)biphenyl-4-yl]oxamic Acid (Compound No. 39)

The title compound was obtained in the same manner as the Example 4(4) using the following raw material.
Raw material: methyl N-[4-(trifluoromethoxy)benzyl]-N-[4'-(trifluoromethoxy)biphenyl-4-yl]oxamate Yield: 72.6% (white solid).
$^1$H-NMR (DMSO-$d_6$) δ: 4.98 (2H, s), 7.20-7.67 (10H, m), 7.67-7.81 (2H, m).

Example 40

Preparation of N-[4-(methylsulfanyl)benzyl]-N-[4'-(trifluoromethoxy)biphenyl-4-yl]oxamic Acid (Compound No. 40)

(1) Preparation of Methyl N-[4-(methylsulfanyl)benzyl]-N-[4'-(trifluoromethoxy)biphenyl-4-yl]oxamate The title compound was obtained in the same manner as the Example 3(4) using the following raw materials.
Raw materials: methyl N-[4'-(trifluoromethoxy)biphenyl-4-yl]oxamate (compound of Example 3(3)) and 4-(methylsulfanyl)benzyl chloride.
Yield: 34.3% (colorless oil).
$^1$H-NMR (CDCl$_3$) δ: 2.64 (3H, s), 3.58 (3H, s), 4.93 (2H, s), 7.09-7.21 (6H, m), 7.24-7.33 (2H, m), 7.46-7.61 (4H, m).

(2) Preparation of N-[4-(methylsulfanyl)benzyl]-N-[4'-(trifluoromethoxy)biphenyl-4-yl]oxamic Acid (Compound No. 40)

The title compound was obtained in the same manner as the Example 4(4) using the following raw material.
Raw material: methyl N-[4-(methylsulfanyl)benzyl]-N-[4'-(trifluoromethoxy)biphenyl-4-yl]oxamate.
Yield: 97.9% (white solid).
$^1$H-NMR (DMSO-$d_6$) δ: 2.42 (3H, m), 4.90 (2H, s), 7.06-7.50 (8H, m), 7.57 (2H, d, J=8.5 Hz), 7.74 (2H, d, J=8.5 Hz).

Example 41

Preparation of N-[4-phenylbenzyl]-N-[4'-(trifluoromethoxy)biphenyl-4-yl]oxamic Acid (Compound No. 41)

(1) Preparation of methyl N-[4-phenylbenzyl]-N-[4'-(trifluoromethoxy)biphenyl-4-yl]oxamate The title compound was obtained in the same manner as the Example 3(4) using the following raw materials.
Raw materials: methyl N-[4'-(trifluoromethoxy)biphenyl-4-yl]oxamate (compound of Example 3(3)) and 4-phenylbenzyl bromide.
Yield: 45.6% (white solid).
$^1$H-NMR (CDCl$_3$) δ: 3.60 (3H, s), 5.02 (2H, s), 7.13-7.22 (2H, m), 7.22-7.64 (15H, m).

(2) Preparation of N-[4-phenylbenzyl]-N-[4'-(trifluoromethoxy)biphenyl-4-yl]oxamic Acid (Compound No. 41)

The title compound was obtained in the same manner as the Example 4(4) using the following raw material.
Raw material: methyl N-[4-phenylbenzyl]-N-[4'-(trifluoromethoxy)biphenyl-4-yl]oxamate.
Yield: 87.9% (white solid).
$^1$H-NMR (DMSO-$d_6$) δ: 5.00 (2H, s), 7.26-7.52 (9H, m), 7.52-7.70 (6H, m), 7.75 (2H, d, J=9.0 Hz).

Example 42

Preparation of N-[4-(trifluoromethoxy)benzyl]-N-[4'-(tert-butyl)biphenyl-4-yl]oxamic Acid (Compound No. 42)

(1) Preparation of Methyl N-(4-bromophenyl)-N-[4-(tert-butyl)benzyl]oxamate The title compound was obtained in the same manner as the Example 3(4) using the following raw materials.
Raw materials: methyl N-(4-bromophenyl)oxamate (compound of Example 4(1)) and 4-(trifluoromethyl) bromide.
Yield: 91.8% (colorless oil).
$^1$H-NMR (CDCl$_3$) δ: 3.60 (3H, s), 4.91 (2H, s), 6.87-6.97 (2H, m), 7.08-7.19 (2H, m), 7.19-7.32 (2H, m), 7.40-7.53 (2H, m).

(2) Preparation of methyl N-[4-(trifluoromethoxy)benzyl]-N-[4'-(tert-butyl)biphenyl-4-yl]oxamate The title compound was obtained in the same manner as the Example 1(3) using the following raw materials.
Raw materials: methyl N-(4-bromophenyl)-N-[4-(tert-butyl)benzyl]oxamate and 4-(tert-butyl)boronic acid.

Yield: 28.5% (white solid).

¹H-NMR (CDCl₃) δ: 1.35 (9H, s), 3.57 (3H, s), 4.97 (2H, s), 7.01-7.20 (4H, m), 7.22-7.35 (2H, m), 7.38-7.60 (6H, m).

(3) Preparation of N-[4-(trifluoromethoxy)benzyl]-N-[4'-(tert-butyl)biphenyl-4-yl]oxamic Acid (Compound No. 42)

The title compound was obtained in the same manner as the Example 4(4) using the following raw material.

Raw material: methyl N-[4-(trifluoromethoxy)benzyl]-N-[4'-(tert-butyl)biphenyl-4-yl]oxamate.

Yield: 93.5% (white solid).

¹H-NMR (DMSO-d₆) δ: 1.30 (9H, s), 4.94 (2H, s), 7.20-7.66 (12H, m).

Example 43

Preparation of N-[4-(tert-butyl)benzyl]-N-[4'-(tert-butyl)biphenyl-4-yl]oxamic Acid (Compound No. 43)

(1) Preparation of methyl N-[4-(tert-butyl)benzyl]-N-[4'-(tert-butyl)biphenyl-4-yl]oxamate The title compound was obtained in the same manner as the Example 1(3) using the following raw materials.

Raw materials: methyl N-(4-bromophenyl)-N-[4-(tert-butyl)benzyl]oxamate (compound of Example 4(2)) and 4-(tert-butyl)phenylboronic acid.

Yield: 99.9% (yellow oil).

¹H-NMR (CDCl₃) δ: 1.30 (9H, s), 1.35 (9H, s), 3.56 (3H, s), 4.94 (2H, s), 7.13 (2H, d, J=8.7 Hz), 7.18 (2H, d, J=8.1 Hz), 7.30-7.33 (2H, m), 7.42-7.54 (6H, m).

(2) Preparation of N-[4-(tert-butyl)benzyl]-N-[4'-(tert-butyl)biphenyl-4-yl]oxamic Acid (Compound No. 43)

The title compound was obtained in the same manner as the Example 4(4) using the following raw material.

Raw material: methyl N-[4-(tert-butyl)benzyl]-N-[4'-(tert-butyl)biphenyl-4-yl]oxamate.

Yield: 62.8% (white solid).

¹H-NMR (DMSO-d₆) δ: 1.23 (9H, s), 1.30 (9H, s), 4.89 (2H, s), 7.14-7.37 (6H, m), 7.42-7.55 (6H, m).

Example 44

Preparation of N-[4-(tert-butyl)benzyl]-N-(4'-butylbiphenyl-4-yl)oxamic Acid (Compound No. 44)

(1) Preparation of Methyl N-[4-(tert-butyl)benzyl]-N-(4'-butylbiphenyl-4-yl)oxamate The title compound was obtained in the same manner as the Example 1(3) using the following raw materials.

Raw materials: methyl N-(4-bromophenyl)-N-[4-(tert-butyl)benzyl]oxamate (compound of Example 4(2)) and 4-(tert-butyl)phenylboronic acid.

Yield: 99.9% (yellow oil).

¹H-NMR (CDCl₃) δ: 0.93 (3H, t, J=7.2 Hz), 1.30 (9H, s), 1.54-1.62 (4H, m), 2.65 (2H, t, J=8.1 Hz), 3.57 (3H, s), 4.94 (2H, s), 7.11-7.14 (2H, m), 7.17-7.20 (2H, m), 7.23-7.27 (2H, m), 7.29-7.33 (2H, m), 7.42-7.49 (2H, m), 7.50-7.73 (2H, m).

(2) Preparation of N-[4-(tert-butyl)benzyl]-N-(4'-butylbiphenyl-4-yl)oxamic acid (compound No. 44)

The title compound was obtained in the same manner as the Example 4(4) using the following raw material.

Raw material: methyl N-[4-(tert-butyl)benzyl]-N-(4'-butylbiphenyl-4-yl)oxamate.

Yield: 56.7% (white solid).

¹H-NMR (DMSO-d₆) δ: 0.90 (3H, t, J=7.2 Hz), 1.24-1.37 (11H, m), 1.52-1.62 (2H, m), 2.59 (2H, d, J=2.7 Hz), 4.90 (2H, s), 7.15-7.35 (8H, m), 7.51-7.57 (4H, m).

Example 45

Preparation of N-[4-(tert-butyl)phenyl]-N-{4-[4-(trifluoromethoxy)phenoxy]phenyl}oxamic Acid (Compound No. 45)

(1) Preparation of N-[4-(tert-butyl)phenyl]-4-[4-(trifluoromethoxy)phenoxy]aniline The title compound was obtained in the same manner as the Example 37(2) using the following raw materials.

Raw materials: 4-[4-(trifluoromethoxy)phenoxy]aniline (compound of Example 11(2)) and 1-bromo-4-(tert-butyl)benzene.

Yield: 69% (brown solid).

¹H-NMR (CDCl₃) δ: 1.31 (9H, s), 5.59 (1H, brs), 6.91-7.08 (8H, m), 7.12-7.19 (2H, m), 7.27-7.33 (2H, m).

(2) Preparation of Methyl N-[4-(tert-butyl)phenyl]-N-{4-[4-(trifluoromethoxy)phenoxy]phenyl}oxamate The title compound was obtained in the same manner as the Example 3(3) using the following raw materials.

Raw materials: N-[4-(tert-butyl)phenyl]-4-[4-(trifluoromethoxy)phenoxy]aniline and methyl chloroglyoxylate.

Yield: 90% (light brown oil).

This compound was obtained as a mixture of the rotational isomers.

Major isomer: ¹H-NMR (CDCl₃) δ: 1.32 (9H, s), 3.60 (3H, s), 6.96-7.07 (4H, m), 7.16-7.32 (6H, m), 7.36-7.44 (2H, m).

Minor isomer: ¹H-NMR (CDCl₃) δ: 1.30 (9H, s), 3.66 (3H, s), 6.96-7.07 (4H, m), 7.16-7.32 (6H, m), 7.36-7.44 (2H, m).

(3) Preparation of N-[4-(tert-butyl)phenyl]-N-{4-[4-(trifluoromethoxy)phenoxy]phenyl}oxamic Acid (Compound No. 45)

The title compound was obtained in the same manner as the Example 4(4) using the following raw material.

Raw material: methyl N-[4-(tert-butyl)phenyl]-N-{4-[4-(trifluoromethoxy)phenoxy]phenyl}oxamate.

Yield: 83% (white solid).

This compound was obtained as a mixture of the rotational isomers.

Major isomer: ¹H-NMR (DMSO-d₆) δ: 1.28 (9H, s), 7.05-7.19 (4H, m), 7.19-7.50 (8H, m), 14.15 (1H, brs).

Minor isomer: ¹H-NMR (DMSO-d₆) δ: 1.26 (9H, s), 6.93-7.06 (4H, m), 7.19-7.50 (8H, m), 14.15 (1H, brs).

Example 46

Preparation of N-[4-(tert-butyl)benzyl]-N-[4'-(trifluoromethoxy)-2-(trifluoromethyl)biphenyl-4-yl]oxamic Acid (Compound No. 46)

(1) Preparation of 4-bromo-N-[4-(tert-butyl)benzyl]-3-(trifluoromethyl)aniline The title compound was obtained in the same manner as the Example 1(1) using the following raw materials.
Raw materials: 4-bromo-3-(trifluoromethyl)aniline and 4-(tert-butyl)benzyl bromide.
Yield: 64.3% (yellow oil).
$^1$H-NMR (CDCl$_3$) δ: 1.31 (9H, s), 4.28 (2H, s), 4.59 (1H, brs), 6.61 (1H, dd, J=2.7, 9.0 Hz), 6.95 (1H, d, J=2.7 Hz), 7.26-7.28 (2H, m), 7.34-7.43 (3H, m).

(2) Preparation of Methyl N-[4-bromo-3-(trifluoromethyl)phenyl]-N-[4-(tert-butyl)benzyl]oxamate The title compound was obtained in the same manner as the Example 3(3) using the following raw materials.
Raw materials: 4-bromo-N-[4-(tert-butyl)benzyl]-3-(trifluoromethyl)aniline and methyl chloroglyoxylate.
Yield: 76.5% (colorless oil).
$^1$H-NMR (CDCl$_3$) δ: 1.29 (9H, s), 3.60 (3H, s), 4.91 (2H, s), 7.08-7.13 (3H, m), 7.31-7.34 (3H, m), 7.65 (1H, d, J=8.7 Hz).

(3) Preparation of Methyl N-[4-(tert-butyl)benzyl]-N-[4'-(trifluoromethoxy)-2-(trifluoromethyl)biphenyl-4-yl]oxamate The title compound was obtained in the same manner as the Example 1(3) using the following raw materials.
Raw materials: methyl N-[4-bromo-3-(trifluoromethyl)phenyl]-N-[4-(tert-butyl)benzyl]oxamate and 4-(trifluoromethoxy)phenylboronic acid.
Yield: 8.8% (colorless oil).
$^1$H-NMR (CDCl$_3$) δ: 1.30 (9H, s), 3.65 (3H, s), 4.98 (2H, s), 6.81-6.84 (2H, m), 7.05-7.11 (2H, m), 7.16-7.41 (7H, m).

(4) Preparation of N-[4-(tert-butyl)benzyl]-N-[4'-(trifluoromethoxy)-2-(trifluoromethyl)biphenyl-4-yl]oxamic Acid (Compound No. 46)

The title compound was obtained in the same manner as the Example 4(4) using the following raw material.
Raw material: methyl N-[4-(tert-butyl)benzyl]-N-[4'-(trifluoromethoxy)-2-(trifluoromethyl)biphenyl-4-yl]oxamate.
Yield: 62.7% (white solid).
$^1$H-NMR (DMSO-d$_6$) δ: 1.24 (9H, s), 4.93 (2H, s), 7.18-7.24 (2H, m), 7.30-7.35 (3H, m), 7.40-7.44 (4H, m), 7.58-7.61 (1H, m), 7.73 (1H, brs).

Example 47

Preparation of N-(4-butylbenzyl)-N-[4'-(trifluoromethoxy)biphenyl-4-yl]oxamic Acid (Compound No. 47)

(1) Preparation of 4-butylbenzyl Chloride

Methanesulfonyl chloride (3.069 g, 26.791 mmol) was added to a solution of 4-butylbenzyl alcohol (4.000 g, 24.355 mmol) in dichloromethane (120 mL) at 0° under argon atmosphere. Triethylamine (2.711 g, 26.791 mmol) was added dropwise at a slow speed to this mixture, and stirred at room temperature overnight. The solvent was evaporated under reduced pressure and the residue was diluted with ethyl acetate. The organic layer was washed with saturated brine, and dried over anhydrous sodium sulfate. The residue obtained by evaporation of the solvent under reduced pressure was purified by column chromatography on silica gel (n-hexane) to give the title compound (3.64 g, 82%) as a colorless oil.
$^1$H-NMR (CDCl$_3$) δ: 0.92 (3H, t, J=7.5 Hz), 1.35 (2H, sext, J=7.5 Hz), 1.52-1.64 (2H, m), 2.60 (2H, t, J=7.5 Hz), 4.57 (2H, s), 7.15-7.18 (2H, m), 7.25-7.30 (2H, m).

(2) Preparation of Methyl N-(4-butylbenzyl)-N-[4'-(trifluoromethoxy)biphenyl-4-yl]oxamate The title compound was obtained in the same manner as the Example 1(1) using the following raw materials.
Raw materials: methyl N-[4'-(trifluoromethoxy)biphenyl-4-yl]oxamate (compound of Example 3(3)) and 4-butylbenzyl chloride.
Yield: 83.6% (colorless oil).
$^1$H-NMR (CDCl$_3$) δ: 0.89-0.95 (3H, m), 1.30-1.39 (2H, m), 1.52-1.57 (2H, m), 2.58 (2H, t, J=7.8 Hz), 3.58 (3H, s), 4.94 (2H, s), 7.09-7.16 (6H, m), 7.26-7.30 (2H, m), 7.47-7.51 (2H, m), 7.54-7.60 (2H, m).

(3) Preparation of N-(4-butylbenzyl)-N-[4'-(trifluoromethoxy)biphenyl-4-yl]oxamic Acid (Compound No. 47)

The title compound was obtained in the same manner as the Example 4(4) using the following raw material.
Raw material: methyl N-(4-butylbenzyl)-N-[4'-(trifluoromethoxy)biphenyl-4-yl]oxamate.
Yield: 84.2% (light pink solid).
$^1$H-NMR (DMSO-d$_6$) δ: 0.87 (3H, t, J=4.5 Hz), 1.20-1.33 (2H, m), 1.45-1.50 (2H, m), 3.30-3.37 (2H, m), 4.87 (2H, s), 7.06-7.22 (4H, m), 7.34 (2H, d, J=8.1 Hz), 7.41 (2H, d, J=8.1 Hz), 7.54 (2H, d, J=8.4 Hz), 7.71-7.76 (2H, m).

Example 48

Preparation of N-[4-(tert-butyl)benzyl]-N-[4'-(trifluoromethoxy)-4-(trifluoromethyl)biphenyl-2-yl]oxamic Acid (Compound No. 48)

(1) Preparation of 2-amino-4'-(trifluoromethoxy)-4-(trifluoromethyl)biphenyl The title compound was obtained in the same manner as the Example 1(3) using the following raw materials.
Raw materials: 2-bromo-5-(trifluoromethyl)aniline and 4-(trifluoromethoxy)phenylboronic acid.
Yield: 99% (white solid).
$^1$H-NMR (CDCl$_3$) δ: 4.02 (2H, brs), 6.78 (1H, d, J=8.7 Hz), 7.29-7.36 (3H, m), 7.37-7.44 (1H, m), 7.44-7.51 (2H, m).

(2) Preparation of Methyl N-[4'-(trifluoromethoxy)-4-(trifluoromethyl)biphenyl-2-yl]oxamate The title compound was obtained in the same manner as the Example 3(3) using the following raw materials.
Raw materials: 2-amino-4'-(trifluoromethoxy)-4-(trifluoromethyl)biphenyl and methyl chloroglyoxylate.

Yield: 99% (white solid).

$^1$H-NMR (CDCl$_3$) δ: 3.92 (3H, s), 7.38-7.47 (5H, m), 7.50-7.56 (1H, m), 8.76-8.79 (1H, m), 9.02 (1H, brs).

(3) Preparation of Methyl N-[4-(tert-butyl)benzyl]-N-[4'-(trifluoromethoxy)-4-(trifluoromethyl)biphenyl-2-yl]oxamate The title compound was obtained in the same manner as the Example 3(4) using the following raw materials.

Raw materials: methyl N-[4'-(trifluoromethoxy)-4-(trifluoromethyl)biphenyl-2-yl]oxamate and 4-(tert-butyl)benzyl bromide.

Yield: 73% (white solid).

This compound was obtained as a mixture of the rotational isomers.

Major isomer: $^1$H-NMR (CDCl$_3$) δ: 1.25 (9H, s), 3.43 (1H, d, J=14.4 Hz), 3.66 (3H, s), 5.20 (1H, d, J=14.4 Hz), 6.82-6.98 (3H, m), 7.16-7.58 (2H, m), 7.32-7.40 (2H, m), 7.51 (1H, d, J=7.8 Hz), 7.60-7.69 (3H, m).

Minor isomer: $^1$H-NMR (CDCl$_3$) δ: 1.27 (9H, s), 3.43 (1H, d, J=14.4 Hz), 3.90 (3H, s), 5.20 (1H, d, J=14.4 Hz), 6.82-7.69 (11H, m).

(4) Preparation of N-[4-(tert-butyl)benzyl]-N-[4'-(trifluoromethoxy)-4-(trifluoromethyl)biphenyl-2-yl]oxamic Acid (Compound No. 48)

The title compound was obtained in the same manner as the Example 4(4) using the following raw material.

Raw material: methyl

N-[4-(tert-butyl)benzyl]-N-[4'-(trifluoromethoxy)-4-(trifluoromethyl)biphenyl-2-yl]oxamate Yield: 93% (white solid).

This compound was obtained as a mixture of the rotational isomers.

Major isomer: $^1$H-NMR (DMSO-d$_6$) δ: 1.21 (9H, s), 3.42 (1H, d, J=14.4 Hz), 5.03 (1H, d, J=14.4 Hz), 6.83-6.94 (2H, m), 7.00-7.09 (1H, m), 7.15-7.44 (3H, m), 7.60-7.87 (5H, m), 14.67 (1H, brs).

Minor isomer: $^1$H-NMR (DMSO-d$_6$) δ: 1.22 (9H, s), 4.01-4.18 (1H, m), 4.57-4.70 (1H, m), 6.84-7.87 (11H, m), 14.67 (1H, brs).

Example 49

Preparation of N-[4-(tert-butyl)benzyl]-N-[4'-trifluoromethoxy-5-(trifluoromethyl)biphenyl-2-yl]oxamic Acid (Compound No. 49).

(1) Preparation of 2-amino-4'-trifluoromethoxy-5-(trifluoromethyl)biphenyl

The title compound was obtained in the same manner as the Example 1(3) using the following raw materials.

Raw materials: 2-bromo-4-(trifluoromethyl)aniline and 4-(trifluoromethoxy)phenylboronic acid.

Yield: 98% (light brown oil).

$^1$H-NMR (CDCl$_3$) δ: 4.02 (2H, brs), 6.78 (1H, d, J=8.7 Hz), 7.29-7.36 (3H, m), 7.37-7.44 (1H, m), 7.44-7.51 (2H, m).

(2) Preparation of methyl N-[4'-trifluoromethoxy-5-(trifluoromethyl)biphenyl-2-yl]oxamate The title compound was obtained in the same manner as the Example 3(3) using the following raw materials.

Raw materials: 2-amino-4'-trifluoromethoxy-5-(trifluoromethyl)biphenyl and methyl chloroglyoxylate.

Yield: 94% (white solid).

$^1$H-NMR (CDCl$_3$) δ: 3.92 (3H, s), 7.38-7.50 (4H, m), 7.54-7.58 (1H, m), 7.67-7.75 (1H, m), 8.63 (1H, d, J=8.4 Hz), 9.08 (1H, brs).

(3) Preparation of Methyl N-[4-(tert-butyl)benzyl]-N-[4'-trifluoromethoxy-5-(trifluoromethyl)biphenyl-2-yl]oxamate The title compound was obtained in the same manner as the Example 3(4) using the following raw materials.

Raw materials: methyl N-[4'-trifluoromethoxy-5-(trifluoromethyl)biphenyl-2-yl]oxamate and 4-(tert-butyl)benzyl bromide.

Yield: 84% (white solid).

This compound was obtained as a mixture of the rotational isomers.

Major isomer: $^1$H-NMR (CDCl$_3$) δ: 1.26 (9H, s), 3.50 (1H, d, J=14.4 Hz), 3.67 (3H, s), 5.14 (1H, d, J=14.4 Hz), 6.85-7.00 (3H, m), 7.15-7.51 (5H, m), 7.55-7.67 (3H, m).

Minor isomer: $^1$H-NMR (CDCl$_3$) δ: 1.28 (9H, s), 3.50 (1H, d, J=14.4 Hz), 3.88 (3H, s), 5.14 (1H, d, J=14.4 Hz), 6.85-7.67 (11H, m).

(4) Preparation of N-[4-(tert-butyl)benzyl]-N-[4'-trifluoromethoxy-5-(trifluoromethyl)biphenyl-2-yl]oxamic Acid (Compound No. 49)

The title compound was obtained in the same manner as the Example 4(4) using the following raw material.

Raw material: methyl

N-[4-(tert-butyl)benzyl]-N-[4'-trifluoromethoxy-5-(trifluoromethyl)biphenyl-2-yl]oxamate Yield: 94% (white solid).

This compound was obtained as a mixture of the rotational isomers.

Major isomer: $^1$H-NMR (DMSO-d$_6$) δ: 1.22 (9H, s), 3.42 (1H, d, J=14.7 Hz), 4.91 (1H, d, J=14.7 Hz), 6.89-6.98 (2H, m), 7.17-7.42 (3H, m), 7.51-7.59 (2H, m), 7.70-7.86 (4H, m), 14.48 (1H, brs).

Minor isomer: $^1$H-NMR (DMSO-d$_6$) δ: 1.23 (9H, s), 4.12-4.30 (1H, m), 4.47-4.70 (1H, m), 6.89-7.86 (11H, m), 14.48 (1H, brs).

Example 50

Preparation of N-[4-(tert-butyl)phenyl]-N-{3-[4-(trifluoromethoxy)phenoxy]phenyl}oxamic Acid (Compound No. 50)

(1) Preparation of 1-nitro-3-[4-(trifluoromethoxy)phenoxy]benzene

The title compound was obtained in the same manner as the Example 11(1) using the following raw materials.

Raw materials: 1,3-dinitrobenzene and 4-(trifluoromethoxy)phenol.

Yield: 74% (pale yellow oil).

¹H-NMR (CDCl₃) δ: 7.05-7.11 (2H, m), 7.23-7.30 (2H, m), 7.33 (1H, ddd, J=0.9, 2.4, 8.4 Hz), 7.52 (1H, t, J=8.4 Hz), 7.82 (1H, t, J=2.4 Hz), 7.98 (1H, ddd, J=0.9, 2.4, 8.4 Hz).

(2) Preparation of 3-[4-(trifluoromethoxy)phenoxy]aniline

The title compound was obtained in the same manner as the Example 3(2) using the following raw material.

Raw material: 1-nitro-3-[4-(trifluoromethoxy)phenoxy]benzene.

Yield: 98% (colorless oil).

¹H-NMR (CDCl₃) δ: 3.73 (2H, brs), 6.33 (1H, t, J=2.4 Hz), 6.39 (1H, ddd, J=0.9, 2.4, 8.1 Hz), 6.45 (1H, ddd, J=0.9, 2.4, 8.1 Hz), 6.98-7.04 (2H, m), 7.11 (1H, t, J=8.1 Hz), 7.13-7.20 (2H, m).

(3) Preparation of N-[4-(tert-butyl)phenyl]-3-[4-(trifluoromethoxy)phenoxy]aniline The title compound was obtained in the same manner as the Example 37(2) using the following raw materials.

Raw materials: 3-[4-(trifluoromethoxy)phenoxy]aniline and 1-bromo-4-(tert-butyl)benzene.

Yield: 69% (orange oil).

¹H-NMR (CDCl₃) δ: 1.30 (9H, s), 5.69 (1H, brs), 6.48 (1H, ddd, J=0.9, 2.1, 8.4 Hz), 6.69 (1H, t, J=2.4 Hz), 6.76 (1H, ddd, J=0.9, 2.4, 8.4 Hz), 6.98-7.06 (4H, m), 7.13-7.22 (3H, m), 7.27-7.32 (2H, m).

(4) Preparation of Methyl N-[4-(tert-butyl)phenyl]-N-{3-[4-(trifluoromethoxy)phenoxy]phenyl}oxamate The title compound was obtained in the same manner as the Example 3(3) using the following raw materials.

Raw materials: N-[4-(tert-butyl)phenyl]-3-[4-(trifluoromethoxy)phenoxy]aniline and methyl chloroglyoxylate.

Yield: 84% (pale yellow solid).

This compound was obtained as a mixture of the rotational isomers.

Major isomer: ¹H-NMR (CDCl₃) δ: 1.31 (9H, m), 3.58 (3H, s), 6.87-7.25 (9H, m), 7.29-7.44 (3H, m).

Minor isomer: ¹H-NMR (CDCl₃) δ: 1.31 (9H, m), 3.66 (3H, s), 6.87-7.25 (9H, m), 7.29-7.44 (3H, m).

(5) Preparation of N-[4-(tert-butyl)phenyl]-N-{3-[4-(trifluoromethoxy)phenoxy]phenyl}oxamic Acid (Compound No. 50)

The title compound was obtained in the same manner as the Example 4(4) using the following raw material.

Raw material: methyl N-[4-(tert-butyl)phenyl]-N-{3-[4-(trifluoromethoxy)phenoxy]phenyl}oxamate.

Yield: 94% (white solid).

This compound was obtained as a mixture of the rotational isomers.

¹H-NMR (DMSO-d₆) δ: 1.27 (9H, s), 6.90-7.35 (6H, m), 7.36-7.50 (6H, m), 14.24 (1H, brs).

Example 51

Preparation of N-(2,6-dichlorobenzyl)-N-[4'-(trifluoromethoxy)biphenyl-4-yl]oxamic Acid (Compound No. 51)

(1) Preparation of 5-bromo-N-(2,6-dichlorobenzyl)aniline

The title compound was obtained in the same manner as the Example 1(1) using the following raw materials.

Raw materials: 4-bromo-aniline and 2,6-dibromobenzyl chloride.

Yield: 41.0% (white solid).

¹H-NMR (CDCl₃) δ: 4.02 (1H, brs), 4.55 (2H, s), 6.62-6.67 (2H, m), 7.15-7.21 (1H, m), 7.24-7.29 (2H, m), 7.33 (2H, d, J=7.8 Hz).

(2) Preparation of 4-(2,6-dichlorobenzyl)amino-4'-(trifluoromethoxy)biphenyl The title compound was obtained in the same manner as the Example 1(3) using the following raw materials.

Raw materials: 4-bromo-N-(2,6-dichlorobenzyl)aniline and 4-(trifluoromethoxy)phenylboronic acid.

Yield: 36.3% (white solid).

¹H-NMR (CDCl₃) δ: 4.13 (1H, brs), 4.64 (2H, s), 6.82-6.86 (2H, m), 7.16-7.25 (3H, m), 7.34 (2H, d, J=7.8 Hz), 7.40-7.45 (2H, m), 7.50-7.55 (2H, m).

(3) Preparation of Methyl N-(2,6-dichlorobenzyl)-N-[4'-(trifluoromethoxy)biphenyl-4-yl]oxamate The title compound was obtained in the same manner as the Example 3(3) using the following raw materials.

Raw materials: 3-(2,6-dichlorobenzyl)amino-4'-(trifluoromethoxy)biphenyl and methyl chloroglyoxylate.

Yield: 99.9% (colorless oil).

¹H-NMR (CDCl₃) δ: 3.56 (3H, s), 5.38 (2H, s), 7.06-7.12 (1H, m), 7.15-7.22 (4H, m), 7.25-7.27 (2H, m), 7.38-7.42 (2H, m), 7.51-7.55 (2H, m).

(4) Preparation of N-(2,6-dichlorobenzyl)-N-[4'-(trifluoromethoxy)biphenyl-4-yl]oxamic Acid (Compound No. 51)

The title compound was obtained in the same manner as the Example 4(4) using the following raw material.

Raw material: methyl N-(2,6-dichlorobenzyl)-N-[4'-(trifluoromethoxy)biphenyl-4-yl]oxamate.

Yield: 67.8% (white solid).

¹H-NMR (DMSO-d₆) δ: 5.24 (2H, s), 7.23-7.27 (3H, m), 7.35-7.42 (4H, m), 7.57 (2H, d, J=8.1 Hz), 7.72 (2H, d, J=8.4 Hz).

Example 52

Preparation of N-[4-(tert-butyl)benzyl]-N-{3-[4-(trifluoromethoxy)phenoxy]phenyl}oxamic Acid (Compound No. 52)

(1) Preparation of Methyl N-{3-[4-(trifluoromethoxy)phenoxy]phenyl}oxamate

The title compound was obtained in the same manner as the Example 3(3) using the following raw materials.

Raw materials: 3-[4-(trifluoromethoxy)phenoxy]aniline (compound of Example 50(2)) and methyl chloroglyoxylate.

Yield: 71% (white solid).

¹H-NMR (CDCl₃) δ: 3.97 (3H, s), 6.80-6.88 (1H, m), 7.00-7.07 (2H, m), 7.17-7.24 (2H, m), 7.33-7.42 (3H, m), 8.84 (1H, brs).

(2) Preparation of Methyl N-[4-(tert-butyl)benzyl]-N-{3-[4-(trifluoromethoxy)phenoxy]phenyl}oxamate The title compound was obtained in the same manner as the Example 3(4) using the following raw materials.
Raw materials: methyl N-{3-[4-(trifluoromethoxy)phenoxy]phenyl}oxamate and 4-(tert-butyl)benzyl bromide.
Yield: 93% (colorless oil).
¹H-NMR (CDCl₃) δ: 1.29 (9H, s), 3.60 (3H, s), 4.90 (2H, s), 6.73 (1H, t, J=2.4 Hz), 6.84-6.98 (4H, m), 7.11-7.23 (4H, m), 7.25-7.32 (3H, m).

(3) Preparation of N-[4-(tert-butyl)benzyl]-N-{3-[4-(trifluoromethoxy)phenoxy]phenyl}oxamic Acid (Compound No. 52)

The title compound was obtained in the same manner as the Example 4(4) using the following raw material.
Raw material: methyl N-[4-(tert-butyl)benzyl]-N-{3-[4-(trifluoromethoxy)phenoxy]phenyl}oxamate.
Yield: 90.8% (colorless oil).
¹H-NMR (DMSO-d₆) δ: 1.23 (9H, s), 4.88 (2H, s), 6.88 (1H, brs), 6.95-7.12 (6H, m), 7.30 (2H, d, J=7.8 Hz), 7.35-7.40 (3H, m).

Example 53

Preparation of N-[4-(tert-butyl)benzyl]-N-[3,5-dichloro-4'-(trifluoromethoxy)biphenyl-4-yl]oxamic Acid (Compound No. 53)

(1) Preparation of 4-bromo-N-[4-(tert-butyl)benzyl]-2,6-dichloroaniline

The title compound was obtained in the same manner as the Example 1(1) using the following raw materials.
Raw materials: 4-bromo-2,6-dichloroaniline and 4-(tert-butyl)benzyl bromide.
Yield: 20.2% (red oil).
¹H-NMR (CDCl₃) δ: 1.31 (9H, s), 4.23 (1H, brs), 4.44 (2H, s), 7.29-7.38 (6H, m).

(2) Preparation of 4-[4-(tert-butyl)benzyl]amino-3,5-dichloro-4'-(trifluoromethoxy)biphenyl The title compound was obtained in the same manner as the Example 1(3) using the following raw materials.
Raw materials: 4-bromo-N-[4-(tert-butyl)benzyl]-2,6-dichloroaniline and 4-(trifluoromethoxy)phenylboronic acid.
Yield: 42.3% (white solid).
¹H-NMR (CDCl₃) δ: 1.33 (9H, s), 4.34 (1H, brs), 4.52 (2H, s), 7.25-7.29 (2H, m), 7.34-7.41 (4H, m), 7.45 (2H, s), 7.50-7.53 (2H, m).

(3) Preparation of Methyl N-[4-(tert-butyl)benzyl]-N-[3,5-dichloro-4'-(trifluoromethoxy)biphenyl-4-yl]oxamate The title compound was obtained in the same manner as the Example 3(3) using the following raw materials.
Raw materials: 4-[4-(tert-butyl)benzyl]amino-3,5-dichloro-4'-(trifluoromethoxy)biphenyl and methyl chloroglyoxylate.

Yield: 99.9% (colorless oil).
¹H-NMR (CDCl₃) δ: 1.27 (9H, s), 3.68 (3H, s), 4.93 (2H, s), 7.16-7.20 (2H, m), 7.22-7.26 (2H, m), 7.29-7.33 (2H, m), 7.49 (2H, s), 7.55-7.58 (2H, m).

(4) Preparation of N-[4-(tert-butyl)benzyl]-N-[3,5-dichloro-4'-(trifluoromethoxy)biphenyl-4-yl]oxamic Acid (Compound No. 53)

The title compound was obtained in the same manner as the Example 4(4) using the following raw material.
Raw material: methyl N-[4-(tert-butyl)benzyl]-N-[3,5-dichloro-4'-(trifluoromethoxy)biphenyl-4-yl]oxamate Yield: 31.3% (light orange solid).
This compound was obtained as a mixture of the rotational isomers.
Major isomer: ¹H-NMR (DMSO-d₆) δ: 1.22 (9H, s), 4.80 (2H, s), 7.17-7.29 (4H, m), 7.44-7.47 (2H, m), 7.76-7.77 (2H, m), 7.86 (2H, d, J=8.4 Hz).
Minor isomer: ¹H-NMR (DMSO-d₆) δ: 1.22 (9H, s), 4.73 (2H, s), 7.17-7.29 (4H, m), 7.44-7.47 (2H, m), 7.76-7.77 (2H, m), 7.86 (2H, d, J=8.4 Hz).

Example 54

Preparation of N-[4-(tert-butyl)benzyl]-N-{4-[4-(trifluoromethoxy)phenoxy]-2-(trifluoromethyl)phenyl}oxamic Acid (Compound No. 54)

(1) Preparation of 1-nitro-4-[4-(trifluoromethoxy)phenoxy]-2-(trifluoromethyl)benzene The title compound was obtained in the same manner as the Example 11(1) using the following raw materials.
Raw materials: 4-fluoro-1-nitro-2-(trifluoromethyl)benzene and 4-(trifluoromethoxy)phenol.
Yield: 88% (pale yellow oil).
¹H-NMR (CDCl₃) δ: 7.10-7.19 (3H, m), 7.29-7.36 (2H, m), 7.41 (1H, d, J=3.0 Hz), 7.98 (1H, d, J=9.0 Hz).

(2) Preparation of 4-[4-(trifluoromethoxy)phenoxy]-2-(trifluoromethyl)aniline

The title compound was obtained in the same manner as the Example 3(2) using the following raw material.
Raw material: 1-nitro-4-[4-(trifluoromethoxy)phenoxy]-2-(trifluoromethyl)benzene.
Yield: 99% (gray oil).
¹H-NMR (CDCl₃) δ: 4.10 (2H, brs), 6.76 (1H, d, J=9.0 Hz), 6.88-6.94 (2H, m), 7.03 (1H, dd, J=2.7, 8.7 Hz), 7.12-7.19 (3H, m).

(3) Preparation of methyl N-{4-[4-(trifluoromethoxy)phenoxy]-2-(trifluoromethyl)phenyl}oxamate The title compound was obtained in the same manner as the Example 3(3) using the following raw materials.
Raw materials: 4-[4-(trifluoromethoxy)phenoxy]-2-(trifluoromethyl)aniline and methyl chloroglyoxylate.
Yield: 95% (white solid).
¹H-NMR (CDCl₃) δ: 4.01 (3H, s), 7.01-7.07 (2H, m), 7.18-7.27 (3H, m), 7.32 (1H, d, J=2.7 Hz), 8.26 (1H, d, J=9.0 Hz), 9.22 (1H, brs).

(4) Preparation of Methyl N-[4-(tert-butyl)benzyl]-N-{4-[4-(trifluoromethoxy)phenoxy]-2-(trifluoromethyl)phenyl}oxamate The title compound was obtained in the same manner as the Example 3(4) using the following raw materials.
Raw materials: methyl N-{4-[4-(trifluoromethoxy)phenoxy]-2-(trifluoromethyl)phenyl}oxamate and 4-(tert-butyl)benzyl bromide.
Yield: 94% (colorless oil).
This compound was obtained as a mixture of the rotational isomers.
Major isomer: $^1$H-NMR (CDCl$_3$) δ: 1.30 (9H, s), 3.62 (3H, s), 3.65 (1H, d, J=14.4 Hz), 5.75 (1H, d, J=14.4 Hz), 6.78 (1H, d, J=9.0 Hz), 6.92 (1H, dd, J=3.0, 9.0 Hz), 7.02-7.08 (2H, m), 7.13-7.20 (2H, m), 7.21-7.37 (5H, m).
Minor isomer: $^1$H-NMR (CDCl$_3$) δ: 1.30 (9H, s), 3.94 (3H, s), 4.36 (1H, d, J=14.4 Hz), 5.11 (1H, d, J=14.4 Hz), 6.72 (1H, d, J=9.0 Hz), 6.89-6.96 (1H, m), 7.02-7.08 (2H, m), 7.13-7.20 (2H, m), 7.21-7.37 (5H, m).

(5) Preparation of N-[4-(tert-butyl)benzyl]-N-[4-{4-(trifluoromethoxy)phenoxy]-2-(trifluoromethyl)phenyl}oxamic Acid (Compound No. 54)

The title compound was obtained in the same manner as the Example 4(4) using the following raw material.
Raw material: methyl N-[4-(tert-butyl)benzyl]-N-{4-[4-(trifluoromethoxy)phenoxy]-2-(trifluoromethyl)phenyl}oxamate.
Yield: 91% (white solid).
This compound was obtained as a mixture of the rotational isomers.
Major isomer: $^1$H-NMR (CDCl$_3$) δ: 1.24 (9H, s), 4.05 (1H, d, J=14.4 Hz), 5.39 (1H, d, J=14.4 Hz), 6.99 (1H, d, J=8.4 Hz), 7.12-7.23 (5H, m), 7.30-7.36 (2H, m), 7.40-7.48 (3H, m), 14.00 (1H, brs).
Minor isomer: $^1$H-NMR (CDCl$_3$) δ: 1.23 (9H, s), 4.42 (1H, d, J=15.6 Hz), 5.03 (1H, d, J=15.6 Hz), 6.90 (1H, d, J=8.4 Hz), 7.12-7.23 (5H, m), 7.30-7.36 (2H, m), 7.40-7.48 (3H, m), 14.00 (1H, brs).

Example 55

Preparation of N-[4-(tert-butyl)benzyl]-N-{3-[4-(trifluoromethoxy)phenoxy]-5-(trifluoromethyl)phenyl}oxamic Acid (Compound No. 55)

(1) Preparation of 1-nitro-3-[4-(trifluoromethoxy)phenoxy]-3-(trifluoromethyl)benzene The title compound was obtained in the same manner as the Example 11(1) using the following raw materials.
Raw materials: 1,3-dinitro-5-(trifluoromethyl)benzene and 4-(trifluoromethoxy)phenol.
Yield: 75% (orange oil).
$^1$H-NMR (CDCl$_3$) δ: 7.09-7.16 (2H, m), 7.30-7.36 (2H, m), 7.57 (1H, brs), 7.95 (1H, t, J=2.1 Hz), 8.22 (1H, brs).

(2) Preparation of 3-[4-(trifluoromethoxy)phenoxy]-5-(trifluoromethyl)aniline The title compound was obtained in the same manner as the Example 3(2) using the following raw material.
Raw material: 1-nitro-3-[4-(trifluoromethoxy)phenoxy]-3-(trifluoromethyl)benzene.
Yield: 99% (pale yellow oil).

$^1$H-NMR (CDCl$_3$) δ: 3.90 (2H, brs), 6.42 (1H, t, J=2.4 Hz), 6.61 (1H, brs), 6.65 (1H, brs), 7.00-7.05 (2H, m), 7.18-7.24 (2H, m).

(3) Preparation of methyl N-{3-[4-(trifluoromethoxy)phenoxy]-5-(trifluoromethyl)phenyl]oxamate The title compound was obtained in the same manner as the Example 3(3) using the following raw materials.
Raw materials: 3-[4-(trifluoromethoxy)phenoxy]-5-(trifluoromethyl)aniline and methyl chloroglyoxylate.
Yield: 7% (pale yellow oil).
$^1$H-NMR (CDCl$_3$) δ: 3.98 (3H, s), 7.04-7.10 (3H, m), 7.22-7.29 (2H, m), 7.57-7.63 (2H, m), 8.96 (1H, brs).

(4) Preparation of Methyl N-[4-(tert-butyl)benzyl]-N-{3-[4-(trifluoromethoxy)phenoxy]-5-(trifluoromethyl)phenyl}oxamate The title compound was obtained in the same manner as the Example 3(4) using the following raw materials.
Raw materials: methyl N-{3-[4-(trifluoromethoxy)phenoxy]-5-(trifluoromethyl)phenyl}oxamate and 4-(tert-butyl)benzyl bromide.
Yield: 85% (colorless oil).
$^1$H-NMR (CDCl$_3$) δ: 1.29 (9H, s), 3.64 (3H, s), 4.90 (2H, s), 6.86 (1H, t, J=2.1 Hz), 6.92-7.00 (2H, m), 7.02 (1H, brs), 7.07-7.14 (2H, m), 7.12 (1H, brs), 7.20-7.26 (2H, m), 7.27-7.33 (2H, m).

(5) Preparation of N-[4-(tert-butyl)benzyl]-N-{3-[4-(trifluoromethoxy)phenoxy]-5-(trifluoromethyl)phenyl}oxamic Acid (Compound No. 55)

The title compound was obtained in the same manner as the Example 4(4) using the following raw material.
Raw material: methyl N-[4-(tert-butyl)benzyl]-N-{3-[4-(trifluoromethoxy)phenoxy]-5-(trifluoromethyl)phenyl}oxamate.
Yield: 71% (white solid).
$^1$H-NMR (DMSO-d$_6$) δ: 1.23 (9H, s), 4.92 (2H, s), 7.04-7.17 (5H, m), 7.26-7.47 (6H, m), 14.45 (1H, brs).

Example 56

Preparation of N-[4-(tert-butyl)benzyl]-N-[2-methyl-4'-(trifluoromethoxy)biphenyl-4-yl]oxamic Acid (Compound No. 56)

(1) Preparation of Methyl N-(3-bromo-4-methylphenyl)oxamate

The title compound was obtained in the same manner as the Example 3(3) using the following raw materials.
Raw materials: 3-bromo-4-methylaniline and methyl chloroglyoxylate.
Yield: 92.5% (white solid).
$^1$H-NMR (CDCl$_3$) δ: 2.38 (3H, s), 3.98 (3H, s), 7.23 (1H, d, J=8.2 Hz), 7.49 (1H, dd, J=2.2, 8.2 Hz), 7.87 (1H, d, J=2.2 Hz), 8.79 (1H, brs).

(2) Preparation of Methyl N-(3-bromo-4-methylphenyl)-N-[4-(tert-butyl)benzyl]oxamate The title compound was obtained in the same manner as the Example 3(4) using the following raw materials.
Raw materials: methyl N-(3-bromo-4-methylphenyl)oxamate and 4-(tert-butyl)benzyl bromide.
Yield: 83.3% (colorless oil).
$^1$H-NMR (CDCl$_3$) δ: 1.30 (9H, s), 2.37 (3H, s), 3.61 (3H, s), 4.87 (2H, s), 6.90 (1H, dd, J=2.2, 8.2 Hz), 7.07-7.21 (3H, m), 7.27 (1H, d, J=2.2 Hz), 7.28-7.38 (2H, m).

(3) Preparation of Methyl N-[4-(tert-butyl)benzyl]-N-[2-methyl-4'-(trifluoromethoxy)biphenyl-5-yl]oxamate The title compound was obtained in the same manner as the Example 1(3) using the following raw materials.
Raw materials: methyl N-(3-bromo-4-methylphenyl)-N-[4-(tert-butyl)benzyl]oxamate and 4-(trifluoromethoxy)phenylboronic acid.
Yield: 73.9% (white solid).
$^1$H-NMR (CDCl$_3$) δ: 1.29 (9H, s), 2.23 (3H, s), 3.58 (3H, s), 4.91 (2H, s), 6.79 (1H, d, J=2.2 Hz), 7.01 (1H, dd, J=2.2, 8.0 Hz), 7.08-7.27 (7H, m), 7.27-7.37 (2H, m).

(4) Preparation of N-[4-(tert-butyl)benzyl]-N-[2-methyl-4'-(trifluoromethoxy)biphenyl-5-yl]oxamic Acid (compound No. 56)

The title compound was obtained in the same manner as the Example 4(4) using the following raw material.
Raw material: methyl N-[4-(tert-butyl)benzyl]-N-[2-methyl-4'-(trifluoromethoxy)biphenyl-5-yl]oxamate Yield: 56.7% (white solid).
$^1$H-NMR (DMSO-d$_6$) δ: 1.23 (9H, s), 2.17 (3H, s), 4.84 (2H, s), 6.90-7.22 (4H, m), 7.22-7.33 (3H, m), 7.33-7.50 (4H, m).

Example 57

Preparation of N-[4-(tert-butyl)benzyl]-N-[2-methyl-4'-(trifluoromethoxy)biphenyl-3-yl]oxamic Acid (Compound No. 57).

(1) Preparation of 3-bromo-N-[4-(tert-butyl)benzyl]-2-methylaniline

The title compound was obtained in the same manner as the Example 1(1) using the following raw materials.
Raw materials: 3-bromo-2-methylaniline and 4-(tert-butyl)benzyl bromide. Yield: 45.5% (white solid).
$^1$H-NMR (CDCl$_3$) δ: 1.32 (9H, s), 1.55 (1H, brs), 2.27 (3H, s), 4.32 (2H, s), 6.61-6.64 (1H, m), 6.94 (1H, t, J=7.8 Hz), 6.98-7.00 (1H, m), 7.28-7.31 (2H, m), 7.37-7.40 (2H, m).

(2) Preparation of Methyl N-(3-bromo-2-methylphenyl)-N-[4-(tert-butyl)benzyl]oxamate The title compound was obtained in the same manner as the Example 3(3) using the following raw materials.
Raw materials: 3-bromo-N-[4-(tert-butyl)benzyl]-2-methylaniline and methyl chloroglyoxylate.
Yield: 95.2% (colorless oil).
$^1$H-NMR (CDCl$_3$) δ: 1.29 (9H, s), 2.24 (3H, s), 3.52 (3H, s), 4.24 (1H, d, J=14.1 Hz), 5.30 (1H, d, J=14.1 Hz), 6.73-6.76 (1H, m), 6.94 (1H, t, J=8.1 Hz), 7.10-7.12 (2H, m), 7.27-7.30 (2H, m), 7.52-7.55 (1H, m).

(3) Preparation of Methyl N-[4-(tert-butyl)benzyl]-N-[2-methyl-4'-(trifluoromethoxy)biphenyl-3-yl]oxamate The title compound was obtained in the same manner as the Example 1(3) using the following raw materials.
Raw materials: methyl N-(3-bromo-2-methylphenyl)-N-[4-(tert-butyl)benzyl]oxamate and 4-(trifluoromethoxy)phenylboronic acid.
Yield: 81.0% (brown oil).
This compound was obtained as a mixture of the rotational isomers.
Major isomer: $^1$H-NMR (CDCl$_3$) δ: 1.31 (9H, s), 2.02 (3H, s), 3.53 (3H, s), 4.34 (1H, d, J=13.8 Hz), 5.30 (1H, d, J=13.8 Hz), 6.85 (1H, dd, J=1.8, 8.1 Hz), 7.10-7.33 (10H, m).
Minor isomer: $^1$H-NMR (CDCl$_3$) δ: 1.29 (9H, s), 2.05 (3H, s), 3.52 (3H, s), 4.60 (1H, d, J=13.8 Hz), 4.84 (1H, d, J=13.8 Hz), 6.74 (1H, dd, J=1.8, 8.1 Hz), 6.81-6.84 (2H, m), 7.08-7.23 (7H, m), 7.54 (1H, dd, J=1.8, 8.1 Hz).

(4) Preparation of N-[4-(tert-butyl)benzyl]-N-[2-methyl-4'-(trifluoromethoxy)biphenyl-3-yl]oxamic Acid (Compound No. 57)

The title compound was obtained in the same manner as the Example 4(4) using the following raw material.
Raw material: methyl N-[4-(tert-butyl)benzyl]-N-[2-methyl-4'-(trifluoromethoxy)biphenyl-3-yl]oxamate Yield: 23.8% (white solid).
This compound was obtained as a mixture of the rotational isomers.
Major isomer: $^1$H-NMR (DMSO-d$_6$) δ: 1.26 (9H, s), 2.07 (3H, s), 4.11 (1H, d, J=14.7 Hz), 5.17 (1H, d, J=14.7 Hz), 6.89-6.93 (1H, m), 7.08-7.18 (3H, m), 7.25-7.43 (7H, m).
Minor isomer: $^1$H-NMR (DMSO-d$_6$) δ: 1.24 (9H, s), 1.73 (3H, s), 4.64 (1H, d, J=14.7 Hz), 4.90 (1H, d, J=14.7 Hz), 6.89-6.93 (1H, m), 7.08-7.18 (3H, m), 7.25-7.43 (7H, m).

Example 58

Preparation of N-[4-(tert-butyl)benzyl]-N-[5-methyl-4'-(trifluoromethoxy)biphenyl-3-yl]oxamic Acid (Compound No. 58)

(1) Preparation of 3-bromo-N-[4-(tert-butyl)benzyl]-5-methylaniline

The title compound was obtained in the same manner as the Example 37(2) using the following raw materials.
Raw materials: 1,3-dibromo-5-methylbenzene and 4-(tert-butyl)benzylamine.
Yield: 84.2% (yellow oil).
$^1$H-NMR (CDCl$_3$) δ: 1.32 (9H, s), 2.23 (3H, s), 3.95 (1H, brs), 4.24 (2H, s), 6.36 (1H, s), 6.60 (1H, s), 6.68 (1H, s), 7.25-7.29 (2H, m), 7.37-7.39 (2H, m).

(2) Preparation of 3-[4-(tert-butyl)benzyl]amino-5-methyl-4'-(trifluoromethoxy)biphenyl The title compound was obtained in the same manner as the Example 1(3) using the following raw materials.
Raw materials: 3-bromo-N-[4-(tert-butyl)benzyl]-5-methylaniline and 4-(trifluoromethoxy)phenylboronic acid.
Yield: 90.9% (brown oil).
$^1$H-NMR (CDCl$_3$) δ: 1.33 (9H, s), 2.33 (3H, s), 4.03 (1H, brs), 4.33 (2H, s), 6.49 (1H, s), 6.62 (1H, s), 6.72 (1H, s), 7.22-7.25 (2H, m), 7.32 (2H, d, J=8.4 Hz), 7.39 (2H, d, J=8.4 Hz), 7.51-7.58 (2H, m).

(3) Preparation of Methyl N-[4-(tert-butyl)benzyl]-N-[5-methyl-4'-(trifluoromethoxy)biphenyl-3-yl]oxamate The title compound was obtained in the same manner as the Example 3(3) using the following raw materials.
Raw materials: 3-[4-(tert-butyl)benzyl]amino-5-methyl-4'-(trifluoromethoxy)biphenyl and methyl chloroglyoxylate.
Yield: 89.3% (brown oil).
$^1$H-NMR (CDCl$_3$) δ: 1.30 (9H, s), 2.37 (3H, s), 3.56 (3H, s), 4.94 (2H, s), 6.90-6.95 (2H, m), 7.16-7.19 (2H, m), 7.21-7.26 (2H, m), 7.30 (1H, brs), 7.32-7.34 (2H, m), 7.38-7.41 (2H, m).

(4) Preparation of N-[4-(tert-butyl)benzyl]-N-[5-methyl-4'-(trifluoromethoxy)biphenyl-3-yl]oxamic Acid (Compound No. 58)

The title compound was obtained in the same manner as the Example 4(4) using the following raw material.
Raw material: methyl N-[4-(tert-butyl)benzyl]-N-[5-methyl-4'-(trifluoromethoxy)biphenyl-3-yl]oxamate Yield: 19.6% (white solid).
$^1$H-NMR (DMSO-d$_6$) δ: 1.27 (9H, s), 2.29 (3H, s), 4.90 (2H, s), 7.11-7.48 (3H, m), 7.26-7.43 (6H, m), 7.63-7.67 (2H, m).

Example 59

Preparation of N-benzyl-N-{4-[4-(tert-butyl)benzyloxy]-4'-(trifluoromethoxy)biphenyl-3-yl}oxamic Acid (Compound No. 59)

(1) Preparation of 4-bromo-1-[4-(tert-butyl)benzyloxy]-2-nitrobenzene

A mixture of 4-(tert-butyl)benzyl bromide (6.252 g, 27.522 mmol), 4-bromo-2-nitrophenol (5.0 g, 22.934 mmol), potassium carbonate (12.679 g, 91.736 mmol) and dimethylformamide (40 ml) was stirred at 50° for 3 hours under argon atmosphere. The reaction mixture was cooled to room temperature, diluted with water and extracted with ethyl acetate. The organic layer was washed with water and saturated brine, and dried over anhydrous sodium sulfate. The residue obtained by evaporation of the solvent under reduced pressure was washed with n-hexane to give the title compound (8.1 g, 97.0%) as a white solid.
$^1$H-NMR (CDCl$_3$) δ: 1.32 (9H, s), 5.19 (2H, s), 7.02 (1H, d, J=8.7 Hz), 7.34-7.43 (4H, m), 7.58 (1H, dd, J=2.7, 8.7 Hz), 7.97 (1H, d, J=2.7 Hz).

(2) Preparation of 4-[4-(tert-butyl)benzyloxy]-3-nitro-4'-(trifluoromethoxy)biphenyl The title compound was obtained in the same manner as the Example 1(3) using the following raw materials.
Raw materials: 4-bromo-[4-(tert-butyl)benzyloxy]-2-nitrobenzene and 4-(trifluoromethoxy)phenylboronic acid.
Yield: 74.6% (pale yellow oil).
$^1$H-NMR (CDCl$_3$) δ: 1.33 (9H, s), 5.26 (2H, s), 7.22 (1H, d, J=8.7 Hz), 7.28-7.58 (8H, m), 7.68 (1H, dd, J=2.4, 8.7 Hz), 8.05 (1H, d, J=2.4 Hz).

(3) Preparation of 3-amino-4-[4-(tert-butyl)benzyloxy]-4'-(trifluoromethoxy)biphenyl The title compound was obtained in the same manner as the Example 3(2) using the following raw material.
Raw material: 4-[4-(tert-butyl)benzyloxy]-3-nitro-4'-(trifluoromethoxy)biphenyl.
Yield: 83.5% (pale yellow solid).
$^1$H-NMR (CDCl$_3$) δ: 1.34 (9H, s), 3.93 (2H, brs), 5.09 (2H, s), 6.87-6.97 (3H, m), 7.22-7.57 (8H, m).

(4) Preparation of 3-benzylamino-4-[4-(tert-butyl)benzyloxy]-4'-(trifluoromethoxy)biphenyl The title compound was obtained in the same manner as the Example 1(1) using the following raw materials.
Raw materials: 3-amino-4-[4-(tert-butyl)benzyloxy]-4'-(trifluoromethoxy)biphenyl and benzyl bromide.
Yield: 93% (yellow oil).
$^1$H-NMR (CDCl$_3$) δ: 1.41 (9H, s), 4.65-4.72 (2H, m), 4.96 (1H, brs), 5.25 (2H, s), 7.02-7.06 (1H, m), 7.15-7.25 (4H, m), 7.26-7.40 (2H, m), 7.56-7.61 (4H, m), 7.64-7.67 (4H, m), 7.89-7.91 (1H, m).

(5) Preparation of Methyl N-benzyl-N-{4-[4-(tert-butyl)benzyloxy]-4'-(trifluoromethoxy)biphenyl-3-yl}oxamate The title compound was obtained in the same manner as the Example 3(3) using the following raw materials.
Raw materials: 3-benzylamino-4-[4-(tert-butyl)benzyloxy]-4'-(trifluoromethoxy)biphenyl and methyl chloroglyoxylate.
Yield: 31% (white solid).
$^1$H-NMR (CDCl$_3$) δ: 1.35 (9H, s), 3.53 (3H, s), 4.44 (1H, d, J=14.4 Hz), 5.10 (2H, s), 5.43 (1H, d, J=14.4 Hz), 7.01-7.05 (2H, m), 7.19-7.26 (7H, m), 7.30-7.36 (4H, m), 7.41-7.45 (3H, m).

(6) Preparation of N-benzyl-N-{4-[4-(tert-butyl)benzyloxy]-4'-(trifluoromethoxy)biphenyl-3-yl}oxamic Acid (Compound No. 59)

The title compound was obtained in the same manner as the Example 4(4) using the following raw material.
Raw material: methyl N-benzyl-N-{4-[4-(tert-butyl)benzyloxy]-4'-(trifluoromethoxy)biphenyl-3-yl}oxamate Yield: 67% (white solid).
This compound was obtained as a mixture of the rotational isomers.
Major isomer: $^1$H-NMR (DMSO-d$_6$) δ: 1.30 (9H, s), 4.19-4.25 (1H, m), 5.21 (2H, s), 5.38-5.44 (1H, m), 7.13-7.26 (6H, m), 7.35-7.53 (10H, m).

Minor isomer: $^1$H-NMR (DMSO-d$_6$) δ: 1.30 (9H, s), 4.90-5.21 (2H, m), 5.15 (2H, s), 7.13-7.26 (6H, m), 7.35-7.53 (10H, m).

Example 60

Preparation of N-benzyl-N-[3,5-dichloro-4'-(trifluoromethoxy)biphenyl-4-yl]oxamic Acid (Compound No. 60)

(1) Preparation of Methyl N-(4-bromo-2,6-dichlorophenyl)oxamate

The title compound was obtained in the same manner as the Example 3(3) using the following raw materials.
Raw materials: 2,6-dichloro-4-bromoaniline and methyl chloroglyoxylate.
Yield: 93.0% (pink solid).
$^1$H-NMR (CDCl$_3$) δ: 4.01 (3H, s), 7.58 (2H, s), 8.51 (1H, brs).

(2) Preparation of Methyl N-(4-bromo-2,6-dichlorophenyl)-N-benzyloxamate

The title compound was obtained in the same manner as the Example 1(1) using the following raw materials.
Raw materials: methyl N-(4-bromo-2,6-dichlorophenyl)oxamate and benzyl bromide.
Yield: 99.9% (red oil).
$^1$H-NMR (CDCl$_3$) δ: 3.69 (3H, s), 4.92 (2H, s), 7.21-7.29 (5H, m), 7.47 (2H, s).

(3) Preparation of Methyl N-benzyl-N-[3,5-dichloro-4'-(trifluoromethoxy)biphenyl-4-yl]oxamate The title compound was obtained in the same manner as the Example 1(3) using the following raw materials.
Raw materials: methyl N-(4-bromo-2,6-dichlorophenyl)-N-benzyloxamate and 4-(trifluoromethoxy)phenylboronic acid.
Yield: 91.6% (red oil).
$^1$H-NMR (CDCl$_3$) δ: 3.69 (3H, s), 4.98 (2H, s), 7.22-7.32 (7H, m), 7.49 (2H, s), 7.54-7.58 (2H, m).

(4) Preparation of N-benzyl-N-[3,5-dichloro-4'-(trifluoromethoxy)biphenyl-4-yl]oxamic Acid (Compound No. 60)

The title compound was obtained in the same manner as the Example 4(4) using the following raw material.
Raw material: methyl N-benzyl-N-[3,5-dichloro-4'-(trifluoromethoxy)biphenyl-4-yl]oxamate.
Yield: 94.5% (white solid).
This compound was obtained as a mixture of the rotational isomers.
Major isomer: $^1$H-NMR (DMSO-d$_6$) δ: 4.76 (2H, s), 7.17-7.22 (4H, m), 7.34-7.37 (1H, m), 7.44 (2H, d, J=8.4 Hz), 7.70-7.75 (2H, m), 7.84-7.88 (2H, m).
Minor isomer: $^1$H-NMR (DMSO-d$_6$) δ: 4.72 (2H, s), 7.17-7.22 (4H, m), 7.34-7.37 (1H, m), 7.44 (2H, d, J=8.4 Hz), 7.70-7.75 (2H, m), 7.84-7.88 (2H, m).

Example 61

Preparation of N-(4-hydroxybenzyl)-N-[4'-(trifluoromethoxy)biphenyl-4-yl]oxamic Acid (Compound No. 61)

(1) Preparation of Methyl N-(4-acetoxybenzyl)-N-(4-bromophenyl)oxamate

The title compound was obtained in the same manner as the Example 3(4) using the following raw materials.
Raw materials: methyl N-(4-bromophenyl)oxamate (compound of Example 4(1)) and 4-(chloromethyl)phenyl acetate.
Yield: 43.9% (colorless oil).
$^1$H-NMR (CDCl$_3$) δ: 2.29 (3H, s), 3.59 (3H, s), 4.90 (2H, s), 6.89-6.98 (2H, m), 6.98-7.08 (2H, m), 7.18-7.26 (2H, m), 7.40-7.50 (2H, m).

(2) Preparation of Methyl N-(4-acetoxybenzyl)-N-[4'-(trifluoromethoxy)biphenyl-4-yl]oxamate The title compound was obtained in the same manner as the Example 1(3) using the following raw materials.
Raw materials: methyl N-(4-acetoxybenzyl)-N-(4-bromophenyl)oxamate and 4-(trifluoromethoxy)boronic acid.
Yield: 26.3% (light brown oil).
$^1$H-NMR (CDCl$_3$) δ: 2.59 (3H, s), 3.59 (3H, s), 4.96 (2H, s), 6.95-7.10 (2H, m), 7.10-7.20 (2H, m), 7.20-7.38 (4H, m), 7.42-7.67 (4H, m).

(3) Preparation of N-(4-hydroxybenzyl)-N-[4'-(trifluoromethoxy)biphenyl-4-yl]oxamic Acid (Compound No. 61).

The title compound was obtained in the same manner as the Example 4(4) using the following raw material.
Raw material: methyl N-(4-acetoxybenzyl)-N-[4'-(trifluoromethoxy)biphenyl-4-yl]oxamate.
Yield: 90.6% (white solid).
$^1$H-NMR (DMSO-d$_6$) δ: 4.79 (2H, s), 6.54-6.74 (2H, m), 6.90-7.36 (4H, m), 7.36-7.48 (2H, m), 7.48-7.65 (2H, m), 7.68-7.84 (2H, m), 9.31 (1H, s).

Example 62

Preparation of N-[4-(tert-butyl)benzyl]-N-[4-methoxyphenyl-4'-(trifluoromethoxy)biphenyl-3-yl]oxamic Acid (Compound No. 62).

(1) Preparation of 4-bromo-2-nitroanisole

4-Bromo-2-nitrophenol (1.00 g, 4.59 mmol) was added in small portions to a suspension of sodium hydride (400 mg, 9.17 mmol) in dimethylformamide (12 ml) at room temperature under argon atmosphere, then the mixture was stirred at room temperature for 30 minutes. A solution of methyl iodide (1.30 g, 9.174 mmol) in dimethylformamide (4 ml) was added to this mixture, and stirred at room temperature for 6 hours. The reaction mixture was diluted with water and extracted with diisopropyl ether. The organic layer was washed with water and saturated brine, and dried over anhydrous sodium sulfate. The solvent was evaporated under reduced pressure to give the title compound (658 mg, 61.8%) as a pale yellow solid.
$^1$H-NMR (CDCl$_3$) δ: 3.96 (3H, s), 6.99 (1H, d, J=9.1 Hz), 7.65 (1R, dd, J=2.5, 9.1 Hz), 7.98 (1H, d, J=2.5 Hz).

(2) Preparation of 2-methoxy-5-bromoaniline

The title compound was obtained in the same manner as the Example 3(2) using the following raw material.
Raw material: 4-bromo-2-nitroanisole.
Yield: 52.1% (brown solid).
$^1$H-NMR (DMSO-d$_6$) δ: 3.74 (3H, s), 5.01 (2H, s), 6.61 (1H, dd, J=2.5, 8.5 Hz), 6.71 (1H, d, J=8.5 Hz), 6.75 (1H, d, J=2.5 Hz).

(3) Preparation of Methyl N-(5-bromo-2-methoxyphenyl)oxamate

The title compound was obtained in the same manner as the Example 3(3) using the following raw materials.
Raw materials: 2-methoxy-5-bromoaniline and methyl chloroglyoxylate.
Yield: 91.0% (light brown solid).
(CDCl$_3$) δ: 3.91 (3H, s), 3.98 (3H, s), 6.79 (1H, d, J=8.5 Hz), 7.25 (1H, d, J=2.5, 8.5 Hz), 8.58 (1H, d, J=2.5 Hz), 9.44 (1H, brs).

(4) Preparation of Methyl N-(5-bromo-2-methoxyphenyl)-N-[4-(tert-butyl)benzyl]oxamate The title compound was obtained in the same manner as the Example 3(4) using the following raw materials.
Raw materials: methyl N-(5-bromo-2-methoxyphenyl)oxamate and 4-(tert-butyl)benzyl bromide.
Yield: 77.8% (pale yellow oil).
$^1$H-NMR (CDCl$_3$) δ: 1.29 (9H, s), 3.60 (3H, s), 3.73 (3H, s), 4.46 (1H, d, J=14.1 Hz), 5.19 (1H, d, J=14.1 Hz), 6.76 (1H, d, J=8.8 Hz), 7.01 (1H, d, J=2.5 Hz), 7.08-7.17 (2H, m), 7.25-7.33 (2H, m), 7.37 (1H, dd, J=2.5, 8.8 Hz).

(5) Preparation of Methyl N-[4-(tert-butyl)benzyl]-N-[4-methoxy-4'-(trifluoromethoxy)biphenyl-3-yl]oxamate The title compound was obtained in the same manner as the Example 1(3) using the following raw materials.
Raw materials: methyl N-(5-bromo-2-methoxyphenyl)-N-[4-(tert-butyl)benzyl]oxamate and 4-(trifluoromethoxy)phenylboronic acid.
Yield: 36.5% (pale yellow solid).
$^1$H-NMR (CDCl$_3$) δ: 1.29 (9H, s), 3.54 (3H, s), 3.85 (3H, s), 4.30 (1H, d, J=14.1 Hz), 5.45 (1H, d, J=14.1 Hz), 6.91 (1H, d, J=2.5 Hz), 6.98 (1H, d, J=8.5 Hz), 7.08-7.22 (4H, m), 7.22-7.40 (4H, m), 7.46 (1H, dd, J=2.5, 8.5 Hz).

(6) Preparation of N-[4-(tert-butyl)benzyl]-N-[4-methoxy-4'-(trifluoromethoxy)biphenyl-3-yl]oxamic Acid (Compound No. 62)

The title compound was obtained in the same manner as the Example 4(4) using the following raw material.
Raw material: methyl N-[4-(tert-butyl)benzyl]-N-[4-methoxy-4'-(trifluoromethoxy)biphenyl-3-yl]oxamate Yield: 74.3% (light orange solid).
This compound was obtained as a mixture of the rotational isomers.
Major isomer: $^1$H-NMR (DMSO-d$_6$) δ: 1.22 (9H, s), 3.83 (3H, s), 4.14-4.50 (1H, m), 5.06-5.42 (1H, m), 7.08-7.15 (2H, m), 7.15-7.22 (2H, m), 7.26-7.33 (2H, m), 7.33-7.42 (2H, m), 7.46-7.56 (2H, m), 7.59 (1H, dd, J=2.5, 8.5 Hz).
Minor isomer: $^1$H-NMR (DMSO-d$_6$) δ: 1.21 (9H, s), 3.76 (3H, s), 4.56-4.88 (2H, m), 6.90-7.64 (11H, m).

Example 63

Preparation of N-(biphenyl-4-yl)-N-[4-(trifluoromethoxy)benzyl]oxamic Acid (Compound No. 63)

(1) Preparation of Methyl N-(4-bromophenyl)-N-[4-(trifluoromethoxy)benzyl]oxamate The title compound was obtained in the same manner as the Example 1(1) using the following raw materials.
Raw materials: methyl N-(4-bromophenyl)oxamate (compound of Example 4(1)) and 4-(trifluoromethoxy)benzyl chloride.
Yield: 99.9% (colorless oil).
$^1$H-NMR (CDCl$_3$) δ: 3.60 (3H, s), 4.91 (2H, s), 6.90-6.95 (2H, m), 7.13-7.16 (2H, m), 7.22-7.27 (2H, m), 7.43-7.50 (2H, m).

(2) Preparation of Methyl N-(biphenyl-4-yl)-N-[4-(trifluoromethoxy)benzyl]oxamate The title compound was obtained in the same manner as the Example 1(3) using the following raw materials.
Raw materials: methyl N-(4-bromophenyl)-N-[4-(trifluoromethoxy)benzyl]oxamate and phenylboronic acid.
Yield: 80.7% (yellow oil).
$^1$H-NMR (CDCl$_3$) δ: 3.59 (3H, s), 4.97 (2H, s), 7.10-7.17 (4H, m), 7.28-7.31 (2H, m), 7.37-7.47 (3H, m), 7.54-7.58 (4H, m).

(3) Preparation of N-(biphenyl-4-yl)-N-[4-(trifluoromethoxy)benzyl]oxamic Acid (Compound No. 63)

The title compound was obtained in the same manner as the Example 4(4) using the following raw material.
Raw material: methyl N-(biphenyl-4-yl)-N-[4-(trifluoromethoxy)benzyl]oxamate.
Yield: 66.3% (white solid).
$^1$H-NMR (DMSO-d$_6$) δ: 4.93 (2H, s), 7.30-7.35 (6H, m), 7.41-7.46 (3H, m), 7.53-7.56 (2H, m), 7.60-7.63 (2H, m).

Example 64

Preparation of N-[4-(tert-butyl)benzyl]-N-[2-methyl-4'-(trifluoromethoxy)biphenyl-4-yl]oxamic Acid (Compound No. 64)

(1) Preparation of 4-amino-2-methyl-4'-(trifluoromethoxy)biphenyl

The title compound was obtained in the same manner as the Example 1(3) using the following raw materials.
Raw materials: 4-bromo-3-methylaniline and 4-(trifluoromethoxy)phenylboronic acid.
Yield: 92% (brown oil).
$^1$H-NMR (CDCl$_3$) δ: 2.20 (3H, s), 3.68 (2H, brs), 6.56-6.63 (2H, m), 7.01 (1H, d, J=8.1 Hz), 7.18-7.32 (4H, m).

(2) Preparation of Methyl N-[2-methyl-4'-(trifluoromethoxy)biphenyl-4-yl]oxamate The title compound was obtained in the same manner as the Example 3(3) using the following raw' materials.
Raw materials: 4-amino-2-methyl-4'-(trifluoromethoxy)biphenyl and methyl chloroglyoxylate.
Yield: 95% (light orange solid).
$^1$H-NMR (CDCl$_3$) δ: 2.28 (3H, s), 3.99 (3H, s), 7.20-7.36 (5H, m), 7.52-7.57 (2H, m), 8.86 (1H, brs).

(3) Preparation of Methyl N-[4-(tert-butyl)benzyl]-N-[2-methyl-4'-(trifluoromethoxy)biphenyl-4-yl]oxamate The title compound was obtained in the same manner as the Example 3(4) using the following raw materials.
Raw materials: methyl N-[2-methyl-4'-(trifluoromethoxy)biphenyl-4-yl]oxamate and 4-(tert-butyl)benzyl bromide.
Yield: 93% (colorless oil).
$^1$H-NMR (CDCl$_3$) δ: 1.30 (9H, s), 2.19 (3H, s), 3.62 (3H, s), 4.94 (2H, s), 6.95 (1H, dd, J=1.8, 8.1 Hz), 7.01 (1H, d, J=1.8 Hz), 7.13 (1H, d, J=8.1 Hz), 7.17-7.36 (8H, m).

(4) Preparation of N-[4-(tert-butyl)benzyl]-N-[2-methyl-4'-(trifluoromethoxy)biphenyl-4-yl]oxamic Acid (Compound No. 64)

The title compound was obtained in the same manner as the Example 4(4) using the following raw material.
Raw material: methyl N-[4-(tert-butyl)benzyl]-N-[2-methyl-4'-(trifluoromethoxy)biphenyl-4-yl]oxamate Yield: 94% (white solid).
$^1$H-NMR (DMSO-d$_6$) δ: 1.23 (9H, s), 2.12 (3H, s), 4.92 (2H, s), 7.06-7.27 (5H, m), 7.29-7.48 (6H, m), 14.08 (1H, brs).

Example 65

Preparation of N-[4-(tert-butyl)benzyl]-N-[2-propoxy-4'-(trifluoromethoxy)biphenyl-5-yl]oxamic Acid (Compound No. 65)

(1) Preparation of 2-chloro-5-nitro-4'-(trifluoromethoxy)biphenyl

The title compound was obtained in the same manner as the Example 1(3) using the following raw materials.
Raw materials: 3-bromo-4-chloro-nitrobenzene and 4-(trifluoromethoxy)phenylboronic acid.
Yield: 99.9% (brown oil).
$^1$H-NMR (CDCl$_3$) δ: 7.33-7.36 (2H, m), 7.48-7.52 (2H, m), 7.67 (1H, d, J=8.7 Hz), 8.18 (1H, dd, J=2.7, 8.7 Hz), 8.23 (1H, d, J=2.7 Hz).

(2) Preparation of 5-nitro-2-propoxy-4'-(trifluoromethoxy)biphenyl

1-Propanol (284 mg, 4.72 mmol) was added dropwise at a slow speed to a suspension of sodium hydride (206 mg, 4.72 mmol) in dimethylformamide (4 ml) at 0° under argon atmosphere, then the mixture was stirred at room temperature for 30 minutes. A solution of 2-chloro-5-nitro-4'-(trifluoromethoxy)biphenyl (1.00 g, 3.15 mmol) in dimethylformamide (2 ml) was added dropwise at a slow speed to this mixture at OD, and then stirred at room temperature for 2 hours. The reaction mixture was diluted with water and extracted with ethyl acetate. The organic layer was washed with saturated brine, and dried over anhydrous sodium sulfate. The residue obtained by evaporation of the solvent under reduced pressure was purified by column chromatography on silica gel (n-hexane:ethyl acetate=6:1) to give the title compound (586g, 54.5%) as a pale yellow solid.
$^1$H-NMR (CDCl$_3$) δ: 0.99 (3H, t, J=7.5 Hz), 1.75-1.85 (2H, m), 4.07 (2H, t, J=6.6 Hz), 7.01-7.04 (1H, m), 7.26-7.30 (2H, m), 7.55-7.60 (2H, m), 8.22-8.26 (2H, m).

(3) Preparation of 5-amino-2-propoxy-4'-(trifluoromethoxy)biphenyl

The title compound was obtained in the same manner as the Example 3(2) using the following raw material.
Raw material: 5-nitro-2-propoxy-4'-(trifluoromethoxy)biphenyl.
Yield: 97.7% (black oil).
$^1$H-NMR (CDCl$_3$) δ: 0.91 (3H, t, J=7.2 Hz), 1.61-1.70 (2H, m), 3.49 (2H, brs), 3.80 (2H, t, J=6.6 Hz), 6.64-6.69 (2H, m), 6.83 (1H, d, J=8.1 Hz), 7.20-7.23 (2H, m), 7.53-7.58 (2H, m).

(4) Preparation of 5-[4-(tert-butyl)benzyl]amino-2-propoxy-4'-(trifluoromethoxy)biphenyl The title compound was obtained in the same manner as the Example 1(1) using the following raw materials.
Raw materials: 5-amino-2-propoxy-4'-(trifluoromethoxy)biphenyl and 4-(tert-butyl)benzyl bromide.
Yield: 12.0% (yellow oil).
$^1$H-NMR (CDCl$_3$) δ: 0.90 (3H, t, J=7.5 Hz), 1.32 (9H, s), 1.60-1.71 (2H, m), 3.79 (2H, t, J=6.3 Hz), 4.09-4.16 (1H, m), 4.27 (2H, s), 6.60-6.63 (2H, m), 6.86 (1H, d, J=8.7 Hz), 7.20-7.23 (2H, m), 7.30-7.33 (2H, m), 7.37-7.40 (2H, m), 7.53-7.56 (2H, m).

(5) Preparation of Methyl N-[4-(tert-butyl)benzyl]-N-[2-propoxy-4'-(trifluoromethoxy)biphenyl-5-yl]oxamate The title compound was obtained in the same manner as the Example 1(2) using the following raw materials.
Raw materials: 5-[4-(tert-butyl)benzyl]amino-2-propoxy-4'-(trifluoromethoxy)biphenyl and methyl chloroglyoxylate.
Yield: 99.9% (colorless oil).
$^1$H-NMR (CDCl$_3$) δ: 0.96 (3H, t, J=7.5 Hz), 1.30 (9H, s), 1.70-1.79 (2H, m), 3.57 (3H, s), 3.89-3.94 (2H, m), 4.88 (2H, s), 6.84-6.87 (2H, m), 7.04 (1H, dd, J=2.4, 8.4 Hz), 7.15-7.19 (4H, m), 7.31-7.39 (4H, m).

(6) Preparation of N-[4-(tert-butyl)benzyl]-N-[2-propoxy-4'-(trifluoromethoxy)biphenyl-5-yl]oxamic Acid (Compound No. 65)

The title compound was obtained in the same manner as the Example 4(4) using the following raw material.
Raw material: methyl N-[4-(tert-butyl)benzyl]-N-[2-propoxy-4'-(trifluoromethoxy)biphenyl-5-yl]oxamate Yield: 69.8% (white solid).
$^1$H-NMR (DMSO-$d_6$) δ: 0.89 (3H, t, J=7.2 Hz), 1.24 (9H, s), 1.61-1.68 (2H, m), 3.90 (2H, t, J=6.0 Hz), 4.81 (2H, s), 6.96-7.13 (4H, m), 7.19-7.22 (1H, m), 7.28-7.37 (4H, m), 7.44-7.54 (2H, m).

Example 66

Preparation of N-[4-(tert-butyl)benzyl]-N-[2-chloro-4'-(trifluoromethoxy)biphenyl-5-yl]oxamic Acid (Compound No. 66)

(1) Preparation of 5-amino-2-chloro-4'-(trifluoromethoxy)biphenyl

The title compound was obtained in the same manner as the Example 3(2) using the following raw material.
Raw material: 2-chloro-5-nitro-4'-(trifluoromethoxy)biphenyl (compound of Example 65(1)).
Yield: 94.5% (yellow oil).
$^1$H-NMR (CDCl$_3$) δ: 3.89 (2H, brs), 6.61-6.65 (2H, m), 7.21-7.27 (3H, m), 7.43-7.46 (2H, m).

(2) Preparation of 5-[4-(tert-butyl)benzyl]amino-2-chloro-4'-(trifluoromethoxy)biphenyl The title compound was obtained in the same manner as the Example 1(1) using the following raw materials.
Raw materials: 5-amino-2-chloro-4'-(trifluoromethoxy)biphenyl and 4-(tert-butyl)benzyl bromide.
Yield: 24.5% (brown oil).
$^1$H-NMR (CDCl$_3$) δ: 1.32 (9H, s), 4.07 (1H, brs), 4.28 (2H, s), 6.55-6.58 (2H, m), 7.22-7.30 (5H, m), 7.37-7.40 (2H, m), 7.42-7.45 (2H, m).

(3) Preparation of Methyl N-[4-(tert-butyl)benzyl]-N-[2-chloro-4'-(trifluoromethoxy)biphenyl-5-yl]oxamate The title compound was obtained in the same manner as the Example 1(2) using the following raw materials.
Raw materials: 5-[4-(tert-butyl)benzyl]amino-2-chloro-4'-(trifluoromethoxy)biphenyl and methyl chloroglyoxylate.
Yield: 76.2% (yellow oil).
$^1$H-NMR (CDCl$_3$) δ: 1.30 (9H, s), 3.61 (3H, s), 4.91 (2H, s), 6.89 (1H, d, J=2.7 Hz), 7.05 (1H, dd, J=2.7, 8.4 Hz), 7.13-7.16 (2H, m), 7.21-7.34 (6H, m), 7.43 (1H, d, J=8.4 Hz).

(4) Preparation of N-[4-(tert-butyl)benzyl]-N-[2-chloro-4'-(trifluoromethoxy)biphenyl-5-yl]oxamic Acid (Compound No. 66).

The title compound was obtained in the same manner as the Example 4(4) using the following raw material.
Raw material: methyl N-[4-(tert-butyl)benzyl]-N-[2-chloro-4'-(trifluoromethoxy)biphenyl-5-yl]oxamate Yield: 76.5% (white solid).
$^1$H-NMR (DMSO-$d_6$) δ: 1.23 (9H, s), 4.91 (2H, s), 7.10-7.18 (2H, m), 7.22-7.33 (4H, m), 7.43-7.54 (5H, m).

Example 67

Preparation of N-[4-(tert-butyl)benzyl]-N-{4-methyl-3-[4-(trifluoromethoxy)phenoxy]phenyl}oxamic Acid (Compound No. 67)

(1) Preparation of 4-methyl-1-nitro-3-[4-(trifluoromethoxy)phenoxy]benzene

A mixture of 2-methyl-5-nitrophenol (765 mg, 5.00 mmol), 4-(trifluoromethoxy)benzeneboronic acid (1.24 g, 6.00 mmol), copper(II) acetate (999 mg, 5.50 mmol), triethylamine (3.48 ml, 25.0 mmol), molecular sieves 4A and dichloromethane (20.0 ml) was stirred at room temperature overnight under argon atmosphere. The reaction mixture was filtered through celite. The residue obtained by evaporation of the solvent of the filtrate under reduced pressure was purified by column chromatography on silica gel (n-hexane:ethyl acetate=20:1) to give the title compound (323 mg, 20.6%) as a colorless oil.
$^1$H-NMR (CDCl$_3$) δ: 2.39 (3H, s), 6.96-7.03 (2H, m), 7.22-7.26 (2H, m), 7.42 (1H, d, J=8.4 Hz), 7.68 (1H, d, J=2.1 Hz), 7.94 (1H, dd, J=2.1, 8.4 Hz).

(2) Preparation of 4-methyl-3-[4-(trifluoromethoxy)phenoxy]aniline

The title compound was obtained in the same manner as the Example 3(2) using the following raw material.
Raw material: 4-methyl-1-nitro-3-[4-(trifluoromethoxy)phenoxy]benzene.
Yield: 99.9% (colorless oil).
$^1$H-NMR (CDCl$_3$) δ: 2.09 (3H, s), 3.58 (2H, brs), 6.26 (1H, d, J=2.1 Hz), 6.44 (1H, dd, J=2.1, 8.1 Hz), 6.86-6.92 (2H, m), 7.02 (1H, d, J=8.1 Hz), 7.10-7.13 (2H, m).

(3) Preparation of Methyl N-{4-methyl-3-[4-(trifluoromethoxy)phenoxy]phenyl}oxamate The title compound was obtained in the same manner as the Example 3(3) using the following raw materials.
Raw materials: 4-methyl-3-[4-(trifluoromethoxy)phenoxy]aniline and methyl chloroglyoxylate.
Yield: 98.7% (white solid).
$^1$H-NMR (CDCl$_3$) δ: 2.22 (3H, s), 3.95 (3H, s), 6.89-6.96 (2H, m), 7.14-7.20 (2H, m), 7.23-7.28 (2H, m), 7.34 (1H, dd, J=2.1, 8.4 Hz), 8.78 (1H, brs).

(4) Preparation of Methyl N-[4-(tert-butyl)benzyl]-N-{4-methyl-3-[4-(trifluoromethoxy)phenoxy]phenyl}oxamate The title compound was obtained in the same manner as the Example 1(1) using the following raw materials.
Raw materials: methyl N-{4-methyl-3-[4-(trifluoromethoxy)phenoxy]phenyl}oxamate and 4-(tert-butyl)benzyl bromide.
Yield: 37.5% (colorless oil).
$^1$H-NMR (CDCl$_3$) δ: 1.27 (9H, s), 2.19 (3H, s), 3.58 (3H, s), 4.86 (2H, s), 6.60 (1H, d, J=2.1 Hz), 6.75-6.80 (2H, m), 6.84 (1H, dd, J=2.1, 8.1 Hz), 7.09-7.16 (4H, m), 7.20 (1H, d, J=8.1 Hz), 7.24-7.29 (2H, m).

(5) Preparation of N-[4-(tert-butyl)benzyl]-N-{4-methyl-3-[4-(trifluoromethoxy)phenoxy]phenyl}oxamic Acid (Compound No. 67)

The title compound was obtained in the same manner as the Example 4(4) using the following raw material.
Raw material: methyl N-[4-(tert-butyl)benzyl]-N-{4-methyl-3-[4-(trifluoromethoxy)phenoxy]phenyl}oxamate Yield: 27.2% (white solid).
¹H-NMR (DMSO-d₆) δ: 1.22 (9H, s), 2.12 (3H, s), 4.84 (2H, s), 6.69 (1H, d, J=2.1 Hz), 6.85-6.91 (2H, m), 7.03 (1H, dd, J=2.1, 8.1 Hz), 7.08 (2H, d, J=8.4 Hz), 7.30 (2H, d, J=8.4 Hz), 7.31-7.37 (3H, m).

Example 68

Preparation of N-[4-(tert-butyl)benzyl]-N-[4-propoxy-4'-(trifluoromethoxy)biphenyl-3-yl]oxamic Acid (Compound No. 68)

(1) Preparation of 4-fluoro-3-nitro-4'-(trifluoromethoxy)biphenyl

The title compound was obtained in the same manner as the Example 1(3) using the following raw materials.
Raw materials: 5-bromo-2-fluoronitrobenzene and 4-(trifluoromethoxy)phenylboronic acid.
Yield: 99.9% (brown oil).
¹H-NMR (CDCl₃) δ: 7.33-7.43 (3H, m), 7.57-7.62 (2H, m), 7.79-7.84 (1H, m), 8.23 (1H, dd, J=2.4, 6.9 Hz).

(2) Preparation of 3-nitro-4-propoxy-4'-(trifluoromethoxy)biphenyl

The title compound was obtained in the same manner as the Example 65(2) using the following raw materials.
Raw materials: 4-fluoro-3-nitro-4'-(trifluoromethoxy)biphenyl and 1-propanol.
Yield: 64.4% (yellow oil).
¹H-NMR (CDCl₃) δ: 1.09 (3H, t, J=7.2 Hz), 1.83-1.96 (2H, m), 4.12 (2H, t, J=6.3 Hz), 7.15 (1H, d, J=8.7 Hz), 7.29-7.32 (2H, m), 7.54-7.59 (2H, m), 7.69 (1H, dd, J=2.4, 8.7 Hz), 8.03 (1H, d, J=2.4 Hz).

(3) Preparation of 3-amino-4-propoxy-4'-(trifluoromethoxy)biphenyl

The title compound was obtained in the same manner as the Example 3(2) using the following raw material.
Raw material: 3-nitro-4-propoxy-4'-(trifluoromethoxy)biphenyl.
Yield: 95.5% (white solid).
¹H-NMR (CDCl₃) δ: 1.07 (3H, t, J=7.5 Hz), 1.81-1.89 (2H, m), 3.90 (2H, brs), 4.00 (2H, t, J=6.0 Hz), 6.83 (1H, d, J=8.4 Hz), 6.88-6.93 (2H, m), 7.22-7.24 (2H, m), 7.51-7.54 (2H, m).

(4) Preparation of Methyl N-[4-propoxy-4'-(trifluoromethoxy)biphenyl-3-yl]oxamate The title compound was obtained in the same manner as the Example 1(2) using the following raw materials.
Raw materials: 3-amino-4-propoxy-4'-(trifluoromethoxy)biphenyl and methyl chloroglyoxylate.
Yield: 97.0% (pale yellow solid).
¹H-NMR (CDCl₃) δ: 1.12 (3H, t, J=7.5 Hz), 1.89-1.96 (2H, m), 3.99 (3H, s), 4.09 (2H, t, J=6.6 Hz), 6.98 (1H, d, J=8.4 Hz), 7.25-7.33 (3H, m), 7.57-7.62 (2H, m), 8.68 (1H, d, J=2.1 Hz), 9.62 (1H, brs).

(5) Preparation of Methyl N-[4-(tert-butyl)benzyl]-N-[4-propoxy-4'-(trifluoromethoxy)biphenyl-3-yl]oxamate The title compound was obtained in the same manner as the Example 1(1) using the following raw materials.
Raw materials: methyl N-[4-propoxy-4'-(trifluoromethoxy)biphenyl-3-yl]oxamate and 4-(tert-butyl)benzyl bromide.
Yield: 88.7% (brown oil).
¹H-NMR (CDCl₃) δ: 1.06 (3H, t, J=7.5 Hz), 1.28 (9H, s), 1.76-1.83 (2H, m), 3.53 (3H, s), 3.89-3.99 (2H, m), 4.39 (1H, d, J=14.4 Hz), 5.38 (1H, d, J=14.4 Hz), 6.94-6.97 (2H, m), 7.13-7.20 (4H, m), 7.26-7.33 (4H, m), 7.41-7.45 (1H, m).

(6) Preparation of N-[4-(tert-butyl)benzyl]-N-[4-propoxy-4∝-(trifluoromethoxy)biphenyl-3-yl]oxamic Acid (Compound No. 68)

The title compound was obtained in the same manner as the Example 4(4) using the following raw material.
Raw material: methyl N-[4-(tert-butyl)benzyl]-N-[4-propoxy-4'-(trifluoromethoxy)biphenyl-3-yl]oxamate Yield: 55.6% (white solid).
This compound was obtained as a mixture of the rotational isomers.
Major isomer: ¹H-NMR (DMSO-d₆) δ: 0.99 (3H, t, J=7.2 Hz), 1.21 (9H, s), 1.69-1.76 (2H, m), 3.90-3.99 (2H, m), 4.40-4.44 (1H, m), 5.18-5.23 (1H, m), 7.09-7.14 (2H, m), 7.25-7.38 (6H, m), 7.46-7.55 (3H, m).
Minor isomer: ¹H-NMR (DMSO-d₆) δ: 0.97-1.04 (3H, m), 1.27 (9H, s), 1.69-1.76 (2H, m), 3.90-3.99 (2H, m), 4.75-4.82 (1H, m), 5.18-5.23 (1H, m), 7.00-7.14 (2H, m), 7.25-7.38 (6H, m), 7.46-7.55 (3H, m).

Example 69

Preparation of N-[4-(tert-butyl)benzyl]-N-[4-butoxy-4'-(trifluoromethoxy)biphenyl-3-yl]oxamic Acid (Compound No. 69)

(1) Preparation of 4-butoxy-3-nitro-4'-(trifluoromethoxy)biphenyl

The title compound was obtained in the same manner as the Example 65(2) using the following raw materials.
Raw materials: 4-fluoro-3-nitro-4'-(trifluoromethoxy)biphenyl (compound of Example 68(1)) and 1-butanol.
Yield: 30.9% (yellow solid).
¹H-NMR (CDCl₃) δ: 0.99 (3H, t, J=7.5 Hz), 1.50-1.58 (2H, m), 1.80-1.88 (2H, m), 4.15 (2H, t, J=6.3 Hz), 7.15 (1H, d, J=8.7 Hz), 7.29-7.32 (2H, m), 7.54-7.59 (2H, m), 7.69 (1H, dd, J=2.4, 6.3 Hz), 8.02 (1H, d, J=2.4 Hz).

(2) Preparation of 3-amino-4-butoxy-4'-(trifluoromethoxy)biphenyl

The title compound was obtained in the same manner as the Example 3(2) using the following raw material.
Raw material: 4-butoxy-3-nitro-4'-(trifluoromethoxy)biphenyl.
Yield: 98.1% (white solid).
¹H-NMR (CDCl₃) δ: 1.00 (3H, t, J=7.5 Hz), 1.47-1.59 (2H, m), 1.78-1.87 (2H, m), 3.90 (2H, brs), 4.04 (2H, t, J=6.3 Hz), 6.83 (1H, d, J=8.4 Hz), 6.88-6.93 (2H, m), 7.21-7.25 (2H, m), 7.50-7.56 (2H, m).

(3) Preparation of Methyl N-[4-butoxy-4'-(trifluoromethoxy)biphenyl-3-yl]oxamate The title compound was obtained in the same manner as the Example 1(2) using the following raw materials.
Raw materials: 3-amino-4-butoxy-4'-(trifluoromethoxy)biphenyl and methyl chloroglyoxylate.
Yield: 94.0% (pale yellow solid).
$^1$H-NMR (CDCl$_3$) δ: 1.03 (3H, t, J=7.2 Hz), 1.53-1.61 (2H, m), 1.84-1.91 (2H, m), 3.99 (3H, s), 4.13 (2H, t, J=6.6 Hz), 6.98 (1H, d, J=8.7 Hz), 7.25-7.33 (3H, m), 7.57-7.62 (2H, m), 8.68 (1H, d, J=2.1 Hz), 9.61 (1H, brs).

(4) Preparation of Methyl N-[4-(tert-butyl)benzyl]-N-[4-butoxy-4'-(trifluoromethoxy)biphenyl-3-yl]oxamate The title compound was obtained in the same manner as the Example 1(1) using the following raw materials.
Raw materials: methyl N-[4-butoxy-4'-(trifluoromethoxy)biphenyl-3-yl]oxamate and 4-(tert-butyl)benzyl bromide.
Yield: 86.6% (colorless oil).
$^1$H-NMR (CDCl$_3$) δ: 0.99 (3H, t, J=7.5 Hz), 1.28 (9H, s), 1.45-1.55 (2H, m), 1.73-1.79 (2H, m), 3.53 (3H, s), 3.95-3.99 (2H, m), 4.38 (1H, d, J=14.4 Hz), 5.38 (1H, d, J=14.4 Hz), 6.94-6.97 (2H, m), 7.13-7.20 (4H, m), 7.26-7.33 (4H, m), 7.41-7.45 (1H, m).

(5) Preparation of N-[4-(tert-butyl)benzyl]-N-[4-butoxy-4'-(trifluoromethoxy)biphenyl-3-yl]oxamic Acid (Compound No. 69)

The title compound was obtained in the same manner as the Example 4(4) using the following raw material.
Raw material: methyl N-[4-(tert-butyl)benzyl]-N-[4-butoxy-4'-(trifluoromethoxy)biphenyl-3-yl]oxamate Yield: 80.4% (white solid).
This compound was obtained as a mixture of the rotational isomers.
Major isomer: $^1$H-NMR (DMSO-d$_6$) δ: 0.95 (3H, t, J=7.2 Hz), 1.24 (9H, s), 1.40-1.48 (2H, m), 1.69-1.74 (2H, m), 3.90-3.99 (2H, m), 4.40-4.44 (1H, m), 5.18-5.23 (1H, m), 7.09-7.14 (2H, m), 7.25-7.38 (6H, m), 7.46-7.55 (3H, m).
Minor isomer: $^1$H-NMR (DMSO-d$_6$) δ: 0.95 (3H, t, J=7.2 Hz), 1.26 (9H, s), 1.40-1.48 (2H, m), 1.69-1.74 (2H, m), 3.90-3.99 (2H, m), 4.78-4.84 (1H, m), 5.18-5.23 (1H, m), 7.00-7.14 (2H, m), 7.25-7.38 (6H, m), 7.46-7.55 (3H, m).

Example 70

Preparation of N-[4-(tert-butyl)benzyl]-N-[2,4-dimethoxy-4'-(trifluoromethoxy)biphenyl-5-yl]oxamic Acid (Compound No. 70)

(1) Preparation of Methyl N-(5-chloro-2,4-dimethoxyphenyl)oxamate

The title compound was obtained in the same manner as the Example 3(3) using the following raw materials.
Raw materials: 5-chloro-2,4-dimethoxyaniline and methyl chloroglyoxylate.
Yield: 52.4% (light purple solid).
$^1$H-NMR (CDCl$_3$) δ: 3.91 (3H, s), 3.94 (3H, s), 3.97 (3H, s), 6.54 (1H, s), 8.46 (1H, s), 9.26 (1H, brs).

(2) Preparation of Methyl N-(5-chloro-2,4-dimethoxyphenyl)-N-[4-(tert-butyl)benzyl]oxamate The title compound was obtained in the same manner as the Example 1(1) using the following raw materials.
Raw materials: methyl N-(5-chloro-2,4-dimethoxyphenyl)oxamate and 4-(tert-butyl)benzyl bromide.
Yield: 87.8% (light purple oil).
$^1$H-NMR (CDCl$_3$) δ: 1.29 (9H, s), 3.59 (3H, s), 3.76 (3H, s), 3.90 (3H, s), 4.36 (1H, d, J=14.1 Hz), 5.19 (1H, d, J=14.1 Hz), 6.45 (1H, s), 6.86 (1H, s), 7.11 (2H, d, J=8.1 Hz), 7.28 (2H, d, J=8.1 Hz).

(3) Preparation of Methyl N-[4-(tert-butyl)benzyl]-N-[2,4-dimethoxy-4'-(trifluoromethoxy)biphenyl-5-yl]oxamate A mixture of methyl N-(5-chloro-2,4-dimethoxyphenyl)-N-[4-(tert-butyl)benzyl]oxamate (800 mg, 1.91 mmol), 4-(trifluoromethoxy)benzeneboronic acid (549 mg, 2.67 mmol), palladium(II) acetate (21 mg, 0.095 mmol), potassium fluoride (332 mg, 5.72 mmol), 2-(di-tert-butylphosphino)biphenyl (57 mg, 0.191 mmol) and tetrahydrofuran (3.0 ml) was refluxed for 5 hours under argon atmosphere. The reaction mixture was cooled to room temperature, diluted with water, and extracted with ethyl acetate. The organic layer was washed with saturated brine and dried over anhydrous sodium sulfate. The residue obtained by evaporation of the solvent under reduced pressure was purified by column chromatography on silica gel (n-hexane:ethyl acetate=2:1) to give the title compound (140 mg, 14%) as a pale yellow oil.
$^1$H-NMR (CDCl$_3$) δ: 1.29 (9H, s), 3.55 (3H, s), 3.84 (3H, s), 3.87 (3H, s), 4.20 (1H, d, J=13.8 Hz), 5.43 (1H, d, J=13.8 Hz), 6.51 (1H, s), 6.62 (1H, s), 7.09-7.15 (4H, m), 7.19-7.24 (2H, m), 7.27-7.32 (2H, m).

(4) Preparation of N-[4-(tert-butyl)benzyl]-N-[2,4-dimethoxy-4'-(trifluoromethoxy)biphenyl-5-yl]oxamic Acid (Compound No. 70)

The title compound was obtained in the same manner as the Example 4(4) using the following raw material.
Raw material: methyl N-[4-(tert-butyl)benzyl]-N-[2,4-dimethoxy-4'-(trifluoromethoxy)biphenyl-5-yl]oxamate Yield: 69.5% (white solid).
This compound was obtained as a mixture of the rotational isomers.
Major isomer: $^1$H-NMR (DMSO-d$_6$) δ: 1.23 (9H, s), 3.83 (3H, s), 3.88 (3H, s), 4.18 (1H, d, J=14.7 Hz), 5.25 (1H, d, J=14.7 Hz), 6.66 (1H, s), 6.82 (1H, s), 7.11 (2H, d, J=8.4 Hz), 7.28-7.35 (6H, m).
Minor isomer: $^1$H-NMR (DMSO-d$_6$) δ: 1.25 (9H, s), 3.80 (3H, s), 3.82 (3H, s), 4.28-4.38 (1H, m), 5.05-5.11 (1H, m), 6.61-7.34 (10H, m).

Example 71

Preparation of N-[4-(tert-butyl)benzyl]-N-{4-chloro-2-[4-(trifluoromethoxy)phenoxy]phenyl}oxamic Acid (Compound No. 71)

(1) Preparation of 4-chloro-2-[4-(trifluoromethoxy)phenoxy]nitrobenzene

The title compound was obtained in the same manner as the Example 11(1) using the following raw materials.
Raw materials: 4-chloro-2-fluoronitrobenzene and 4-(trifluoromethoxy)phenol.

Yield: 99.9% (yellow oil).

$^1$H-NMR (CDCl$_3$) δ: 6.83-6.87 (2H, m), 6.99 (1H, d, J=2.1 Hz), 7.05-7.12 (2H, m), 7.21 (1H, dd, J=2.1, 9.0 Hz), 7.96 (1H, d, J=9.0 Hz).

(2) Preparation of 4-chloro-2-[4-(trifluoromethoxy)phenoxy]aniline

The title compound was obtained in the same manner as the Example 3(2) using the following raw material.

Raw material: 4-chloro-2-[4-(trifluoromethoxy)phenoxy] nitrobenzene.

Yield: 99.9% (yellow oil).

$^1$H-NMR (CDCl$_3$) δ: 3.81 (2H, brs), 6.80-6.84 (2H, m), 6.94-7.01 (3H, m), 7.17-7.20 (2H, m).

(3) Preparation of methyl N-{4-chloro-2-[4-(trifluoromethoxy)phenoxy]phenyl}oxamate The title compound was obtained in the same manner as the Example 1(2) using the following raw materials.

Raw materials: 4-chloro-2-[4-(trifluoromethoxy)phenoxy]aniline and methyl chloroglyoxylate.

Yield: 64.1% (yellow oil).

$^1$H-NMR (CDCl$_3$) δ: 3.96 (3H, s), 6.83 (1H, d, J=2.1 Hz), 7.05-7.13 (2H, m), 7.15 (1H, dd, J=2.1, 9.0 Hz), 7.22-7.26 (2H, m), 8.45 (1H, d, J=9.0 Hz), 9.40 (1H, brs).

(4) Preparation of Methyl N-[4-(tert-butyl)benzyl]-N-{4-chloro-2-[4-(trifluoromethoxy)phenoxy]phenyl}oxamate The title compound was obtained in the same manner as the Example 1(1) using the following raw materials.

Raw materials: methyl N-{4-chloro-2-[4-(trifluoromethoxy)phenoxy]phenyl}oxamate and 4-(tert-butyl)benzyl bromide.

Yield: 99.9% (brown oil).

$^1$H-NMR (CDCl$_3$) δ: 1.27 (9H, s), 3.66 (3H, s), 4.72 (1H, d, J=14.1 Hz), 5.08 (1H, d, J=14.1 Hz), 6.70 (1H, d, J=2.1 Hz), 6.87-6.90 (2H, m), 6.95-7.01 (2H, m), 7.13-7.16 (2H, m), 7.19-7.24 (2H, m), 7.26-7.28 (2H, m).

(5) Preparation of N-[4-(tert-butyl)benzyl]-N-{4-chloro-2-[4-(trifluoromethoxy)phenoxy]phenyl}oxamic Acid (Compound No. 71)

The title compound was obtained in the same manner as the Example 4(4) using the following raw material.

Raw material: methyl N-[4-(tert-butyl)benzyl]-N-{4-chloro-2-[4-(trifluoromethoxy)phenoxy]phenyl}oxamate Yield: 21.3% (light orange solid).

This compound was obtained as a mixture of the rotational isomers.

Major isomer: $^1$H-NMR (DMSO-d$_6$) δ: 1.23 (9H, s), 3.33 (2H, s), 6.18-6.82 (1H, m), 6.96-6.99 (1H, m), 7.03-7.14 (3H, m), 7.20-7.40 (6H, m).

Minor isomer: $^1$H-NMR (DMSO-d$_6$) δ: 1.24 (9H, s), 4.75 (2H, s), 6.18-6.82 (1H, m), 6.96-6.99 (1H, m), 7.03-7.14 (3H, m), 7.20-7.40 (6H, m).

Example 72

Preparation of N-[4-(tert-butyl)benzyl]-N-[5-chloro-4'-(trifluoromethoxy)biphenyl-2-yl]oxamic Acid (Compound No. 72)

(1) Preparation of 2-amino-4'-(trifluoromethoxy)-5-chlorobiphenyl

The title compound was obtained in the same manner as the Example 1(3) using the following raw materials.

Raw materials: 2-bromo-4-chloroaniline and 4-(trifluoromethoxy)phenylboronic acid.

Yield: 95.3% (brown oil).

$^1$H-NMR (CDCl$_3$) δ: 3.71 (2H, brs), 6.70 (1H, d, J=8.4 Hz), 7.08 (1H, d, J=2.4 Hz), 7.12 (1H, dd, J=2.4, 8.4 Hz), 7.27-7.31 (2H, m), 7.44-7.48 (2H, m).

(2) Preparation of 2-[4-(tert-butyl)benzyl]amino-5-chloro-4'-(trifluoromethoxy)biphenyl The title compound was obtained in the same manner as the Example 1(1) using the following raw materials.

Raw materials: 2-amino-4'-(trifluoromethoxy)-5-chlorobiphenyl and 4-(tert-butyl)benzyl bromide.

Yield: 94.3% (brown oil).

$^1$H-NMR (CDCl$_3$) δ: 1.31 (9H, s), 3.84 (1H, brs), 4.28 (2H, s), 6.93-6.95 (1H, m), 7.05 (1H, d, J=2.7 Hz), 7.15 (1H, dd, J=2.7, 8.7 Hz), 7.19-7.25 (2H, m), 7.27-7.31 (2H, m), 7.34-7.36 (2H, m), 7.44-7.47 (2H, m).

(3) Preparation of Methyl N-[4-(tert-butyl)benzyl]-N-[5-chloro-4'-(trifluoromethoxy)biphenyl-2-yl]oxamate The title compound was obtained in the same manner as the Example 1(2) using the following raw materials.

Raw materials: 2-[4-(tert-butyl)benzyl]amino-5-chloro-4'-(trifluoromethoxy)biphenyl and methyl chloroglyoxylate Yield: 95.6% (yellow oil).

$^1$H-NMR (CDCl$_3$) δ: 1.28 (9H, s), 3.42 (1H, d, J=14.4 Hz), 3.67 (3H, s), 5.11 (1H, d, J=14.4 Hz), 6.76 (1H, d, J=8.4 Hz), 6.90-6.95 (2H, m), 7.17 (1H, dd, J=2.4, 8.4 Hz), 7.20-7.24 (2H, m), 7.31-7.34 (2H, m), 7.39 (1H, d, J=2.4 Hz), 7.59-7.62 (2H, m).

(4) Preparation of N-[4-(tert-butyl)benzyl]-N-[5-chloro-4'-(trifluoromethoxy)biphenyl-2-yl]oxamic Acid (Compound No. 72)

The title compound was obtained in the same manner as the Example 4(4) using the following raw material.

Raw material: methyl N-[4-(tert-butyl)benzyl]-N-[5-chloro-4'-(trifluoromethoxy)biphenyl-2-yl]oxamate Yield: 61.5% (white solid).

This compound was obtained as a mixture of the rotational isomers.

Major isomer: $^1$H-NMR (DMSO-d$_6$) δ: 1.21 (9H, s), 3.09 (1H, d, J=14.7 Hz), 4.81 (1H, d, J=14.7 Hz), 6.85-6.88 (2H, m), 7.03 (1H, d, J=8.4 Hz), 7.19-7.21 (2H, m), 7.27 (1H, dd, J=2.7, 8.4 Hz), 7.40 (1H, d, J=2.7 Hz), 7.43-7.46 (2H, m), 8.05-8.08 (2H, m).

Minor isomer: ¹H-NMR (DMSO-d₆) δ: 1.21 (9H, s), 3.89-3.94 (1H, m), 4.55-4.61 (1H, m), 6.93-6.97 (2H, m), 7.09-7.12 (2H, m), 7.19-7.46 (5H, m), 8.05-8.08 (2H, m).

Example 73

Preparation of N-[4-(tert-butyl)benzyl]-N-[2-butoxy-4'-(trifluoromethoxy)biphenyl-5-yl]oxamic Acid (Compound No. 73)

(1) Preparation of 2-butoxy-5-nitro-4'-(trifluoromethoxy)biphenyl

The title compound was obtained in the same manner as the Example 65(2) using the following raw materials.
Raw materials: 2-chloro-5-nitro-4'-(trifluoromethoxy)biphenyl (compound of Example 65(1)) and 1-butanol.
Yield: 87.6% (yellow solid).
¹H-NMR (CDCl₃) δ: 0.94 (3H, t, J=7.2 Hz), 1.39-1.46 (2H, m), 1.72-1.81 (2H, m), 4.10 (2H, t, J=6.6 Hz), 7.03 (1H, dd, J=1.5, 7.8 Hz), 7.26-7.30 (2H, m), 7.55-7.58 (2H, m), 8.22-8.26 (2H, m).

(2) Preparation of 5-amino-2-butoxy-4'-(trifluoromethoxy)biphenyl

The title compound was obtained in the same manner as the Example 3(2) using the following raw material.
Raw material: 2-butoxy-5-nitro-4'-(trifluoromethoxy)biphenyl.
Yield: 91.9% (brown oil).
¹H-NMR (CDCl₃) δ: 0.87 (3H, t, J=7.2 Hz), 1.31-1.41 (2H, m) 1.58-1.67 (2H, m), 3.48 (2H, brs), 3.83 (2H, t, J=6.3 Hz), 6.64-6.68 (2H, m), 6.82 (1H, d, J=8.4 Hz), 7.20-7.23 (2H, m), 7.53-7.55 (2H, m).

(3) Preparation of methyl N-[2-butoxy-4'-(trifluoromethoxy)biphenyl-5-yl]oxamate The title compound was obtained in the same manner as the Example 1(2) using the following raw materials.
Raw materials: 5-amino-2-butoxy-4'-(trifluoromethoxy)biphenyl and methyl chloroglyoxylate.
Yield: 78.7% (white solid).
¹H-NMR (CDCl₃) δ: 0.91 (3H, t, J=7.5 Hz), 1.36-1.43 (2H, m), 1.66-1.73 (2H, m), 3.95-3.99 (5H, m), 6.98 (1H, d, J=8.7 Hz), 7.23-7.27 (2H, m), 7.52 (1H, d, J=2.7 Hz), 7.54-7.57 (2H, m), 7.65 (1H, dd, J=3.0, 8.7 Hz), 8.80 (1H, brs).

(4) Preparation of Methyl N-[4-(tert-butyl)benzyl]-N-[2-butoxy-4'-(trifluoromethoxy)biphenyl-5-yl]oxamate The title compound was obtained in the same manner as the Example 1(1) using the following raw materials.
Raw materials: methyl N-[2-butoxy-4'-(trifluoromethoxy)biphenyl-5-yl]oxamate and 4-(tert-butyl)benzyl bromide.
Yield: 76.9% (colorless oil).
¹H-NMR (CDCl₃) δ: 0.92 (3H, t, J=7.2 Hz), 1.30 (9H, s), 1.36-1.44 (2H, m), 1.66-4.73 (2H, m), 3.57 (3H, s), 3.95 (2H, t, J=6.3 Hz), 4.88 (2H, s), 6.85-6.88 (2H, m), 7.04 (1H, dd, J=2.7, 9.0 Hz), 7.15-7.20 (4H, m), 7.30-7.34 (2H, m), 7.35-7.38 (2H, m).

(5) Preparation of N-[4-(tert-butyl)benzyl]-N-[2-butoxy-4'-(trifluoromethoxy)biphenyl-5-yl]oxamic Acid (Compound No. 73)

The title compound was obtained in the same manner as the Example 4(4) using the following raw material.
Raw material: methyl N-[4-(tert-butyl)benzyl]-N-[2-butoxy-4'-(trifluoromethoxy)biphenyl-5-yl]oxamate Yield: 75.9% (white solid).
¹H-NMR (DMSO-d₆) δ: 0.85 (3H, t, J=7.2 Hz), 1.24 (9H, s), 1.29-1.36 (2H, m), 1.56-1.65 (2H, m), 3.95 (2H, t, J=6.3 Hz), 4.84 (2H, s), 7.02 (1H, d, J=8.7 Hz), 7.09 (1H, d, J=2.4 Hz), 7.12-7.14 (2H, m), 7.19 (1H, dd, J=2.4, 8.7 Hz), 7.28-7.37 (4H, m), 7.48-7.51 (2H, m).

Example 74

Preparation of N-[4-(tert-butyl)benzyl]-N-[4-pentyloxy-4'-(trifluoromethoxy)biphenyl-3-yl]oxamic acid (compound No. 74).

(1) Preparation of 4-pentyloxy-3-nitro-4'-(trifluoromethoxy)biphenyl

The title compound was obtained in the same manner as the Example 65(2) using the following raw materials.
Raw materials: 4-fluoro-3-nitro-4'-(trifluoromethoxy)biphenyl (compound of Example 68(1)) and 1-pentanol.
Yield: 74.9% (brown solid).
¹H-NMR (CDCl₃) δ: 0.95 (3H, t, J=7.2 Hz), 1.39-1.54 (4H, m), 1.82-1.91 (2H, m), 4.11-4.17 (2H, m), 7.15 (1H, d, J=9.0 Hz), 7.29-7.32 (2H, m), 7.55-7.58 (2H, m), 7.70 (1H, dd, J=2.7, 9.0 Hz), 8.02 (1H, d, J=2.7 Hz).

(2) Preparation of 3-amino-4-pentyloxy-4'-(trifluoromethoxy)biphenyl

The title compound was obtained in the same manner as the Example 3(2) using the following raw material.
Raw material: 3-nitro-4-pentyloxy-4'-(trifluoromethoxy)biphenyl.
Yield: 76.8% (yellow solid).
¹H-NMR (CDCl₃) δ: 0.95 (3H, t, J=7.2 Hz), 1.37-1.55 (4H, m), 1.80-1.87 (2H, m), 3.89 (2H, brs), 4.01-4.05 (2H, m), 6.82-6.93 (3H, m), 7.21-7.25 (2H, m), 7.50-7.55 (2H, m).

(3) Preparation of Methyl N-[4-pentyloxy-4'-(trifluoromethoxy)biphenyl-3-yl]oxamate The title compound was obtained in the same manner as the Example 3(3) using the following raw materials.
Raw materials: 3-amino-4-pentyloxy-4'-(trifluoromethoxy)biphenyl and methyl chloroglyoxylate.
Yield: 84.8% (white solid).
¹H-NMR (CDCl₃) δ: 0.97 (3H, t, J=7.2 Hz), 1.40-1.52 (4H, m), 1.86-1.95 (2H, m), 3.99 (3H, s), 4.11 (2H, t, J=6.6 Hz), 6.98 (1H, d, J=8.4 Hz), 7.25-7.33 (3H, m), 7.58-7.61 (2H, m), 8.68 (1H, d, J=2.1 Hz), 9.60 (1H, brs).

(4) Preparation of Methyl N-[4-(tert-butyl)benzyl]-N-[4-pentyloxy-4'-(trifluoromethoxy)biphenyl-3-yl]oxamate The title compound was obtained in the same manner as the Example 1(1) using the following raw materials.

Raw materials: methyl N-[4-pentyloxy-4'-(trifluoromethoxy)biphenyl-3-yl]oxamate and 4-(tert-butyl)benzyl bromide.

Yield: 50.0% (colorless oil).

$^1$H-NMR (CDCl$_3$) δ: 0.95 (3H, t, J=7.2 Hz), 1.28 (9H, s), 1.40-1.49 (4H, m), 1.74-1.81 (2H, m), 3.53 (3H, s), 3.93-3.99 (2H, m), 4.37 (1H, d, J=13.8 Hz), 5.40 (1H, d, J=13.8 Hz), 6.94-6.97 (2H, m), 7.13-7.20 (4H, m), 7.27-7.31 (4H, m), 7.43 (1H, dd, J=2.4, 8.7 Hz).

(5) Preparation of N-[4-(tert-butyl)benzyl]-N-[4-pentyloxy-4'-(trifluoromethoxy)biphenyl-3-yl]oxamic Acid (Compound No. 74)

The title compound was obtained in the same manner as the Example 4(4) using the following raw material.

Raw material: methyl

N-[4-(tert-butyl)benzyl]-N-[4-pentyloxy-4'-(trifluoromethoxy)biphenyl-3-yl]oxamate Yield: 80.4% (white solid).

This compound was obtained as a mixture of the rotational isomers.

Major isomer: $^1$H-NMR (DMSO-d$_6$) δ: 0.90-0.99 (3H, m), 1.21 (9H, s), 1.32-1.50 (4H, m), 1.72-1.78 (2H, m), 3.32-3.40 (1H, m), 4.03-4.07 (2H, m), 4.73-4.78 (1H, m), 7.05-7.09 (3H, m), 7.24-7.27 (2H, m), 7.35-7.38 (3H, m), 7.43-7.46 (1H, m), 7.51-7.54 (2H, m).

Minor isomer: $^1$H-NMR (DMSO-d$_6$) δ: 0.90-0.99 (3H, m), 1.21 (9H, s), 1.32-1.50 (4H, m), 1.72-1.78 (2H, m), 3.96 (2H, t, J=6.3 Hz), 4.21-4.26 (1H, m), 5.22-5.26 (1H, m), 6.94-6.95 (1H, m), 7.05-7.54 (10H, m).

Example 75

Preparation of N-benzyl-N-[4-pentyloxy-4'-(trifluoromethoxy)biphenyl-3-yl]oxamic Acid (Compound No. 75)

(1) Preparation of methyl N-benzyl-N-[4-pentyloxy-4'-(trifluoromethoxy)biphenyl-3-yl]oxamate The title compound was obtained in the same manner as the Example 1(1) using the following raw materials.

Raw materials: methyl N-[4-pentyloxy-4'-(trifluoromethoxy)biphenyl-3-yl]oxamate (compound of Example 74(3)) and benzyl bromide.

Yield: 30.3% (colorless oil).

$^1$H-NMR (CDCl$_3$) δ: 0.95 (3H, t, J=7.2 Hz), 1.34-1.50 (4H, m), 1.75-1.84 (2H, m), 3.54 (3H, s), 3.95-4.00 (2H, m), 4.48 (1H, d, J=14.4 Hz), 5.38 (1H, d, J=14.4 Hz), 6.95 (1H, d, J=8.7 Hz), 7.03 (1H, d, J=2.7 Hz), 7.19-7.29 (7H, m), 7.32-7.35 (2H, m), 7.43 (1H, dd, J=2.7, 8.7 Hz).

(2) Preparation of N-benzyl-N-[4-pentyloxy-4'-(trifluoromethoxy)biphenyl-3-yl]oxamic Acid (Compound No. 75)

The title compound was obtained in the same manner as the Example 4(4) using the following raw material.

Raw material: methyl N-benzyl-N-[4-pentyloxy-4'-(trifluoromethoxy)biphenyl-3-yl]oxamate.

Yield: 43.4% (white solid).

This compound was obtained as a mixture of the rotational isomers.

Major isomer: $^1$H-NMR (DMSO-d$_6$) δ: 0.90-0.95 (3H, m), 1.32-1.50 (4H, m), 1.72-1.79 (2H, m), 3.28-3.30 (1H, m), 4.03-4.07 (2H, m), 4.83-4.88 (1H, m), 7.05-7.26 (6H, m), 7.35-7.39 (3H, m), 7.44-7.55 (3H, m).

Minor isomer: $^1$H-NMR (DMSO-d$_6$) δ: 0.90-0.95 (3H, m), 1.32-1.50 (4H, m), 1.72-1.79 (2H, m), 3.97 (2H, t, J=6.3 Hz), 4.21-4.26 (1H, m), 5.22-5.26 (1H, m), 7.02-7.26 (6H, m), 7.35-7.55 (6H, m).

Example 76

Preparation of N-[4-(tert-butyl)benzyl]-N-[2-(2-carboxyethyl)-4'-(trifluoromethoxy)biphenyl-4-yl]oxamic Acid (Compound No. 76).

(1) Preparation of 4-nitro-4'-(trifluoromethoxy)biphenyl-2-carbaldehyde

The title compound was obtained in the same manner as the Example 70(3) using the following raw materials.

Raw materials: 2-chloro-5-nitrobenzaldehyde and 4-(trifluoromethoxy)phenylboronic acid.

Yield: 39.3% (yellow oil).

$^1$H-NMR (CDCl$_3$) δ: 7.39-7.48 (4H, m), 7.65 (1H, d, J=8.1 Hz), 8.49 (1H, dd, J=2.4, 8.1 Hz), 8.86 (1H, d, J=2.4 Hz), 10.00 (1H, s).

(2) Preparation of Ethyl (E)-3-[4-nitro-4'-(trifluoromethoxy)biphenyl-2-yl]propenoate A solution of triethyl phosphonoacetate (492 mg, 2.19 mmol) in tetrahydrofuran (5 ml) was added dropwise at a slow speed to sodium hydride (95 mg, 2.19 mmol) at room temperature under argon atmosphere, then the mixture was stirred at room temperature for 30 minutes. A solution of 4-nitro-4'-(trifluoromethoxy)biphenyl-2-carbaldehyde (488 mg, 1.56 mmol) in tetrahydrofuran (3 ml) was added dropwise at a slow speed to this mixture at 0°, and then stirred at room temperature for 3 hours. A small amount of saturated aqueous ammonium chloride was added to the reaction mixture. The residue obtained by evaporation of the tetrahydrofuran under reduced pressure was extracted with ethyl acetate. The organic layer was washed with saturated brine, and dried over anhydrous sodium sulfate. The residue obtained by evaporation of the solvent under reduced pressure was washed with methanol to give the title compound (176 mg, 29.6%) as a white solid.

$^1$H-NMR (CDCl$_3$) δ: 1.31 (3H, t, J=7.2 Hz), 4.24 (2H, q, J=7.2 Hz), 6.57 (1H, d, J=16.2 Hz), 7.33-7.38 (4H, m), 7.53 (1H, d, J=8.1 Hz), 7.63 (1H, d, J=16.2 Hz), 8.28 (1H, dd, J=2.4, 8.1 Hz), 8.56 (1H, d, J=2.4 Hz).

(3) Preparation of ethyl 3-[4-amino-4'-(trifluoromethoxy)biphenyl-2-yl]propanoate The title compound was obtained in the same manner as the Example 3(2) using the following raw material.
Raw material: ethyl (E)-3-[4-nitro-4'-(trifluoromethoxy)biphenyl-2-yl]propenoate.
Yield: 96.8% (black oil).
$^1$H-NMR (CDCl$_3$) δ: 1.19 (3H, t, J=7.2 Hz), 2.37-2.42 (2H, m), 2.84 (2H, t, J=8.4 Hz), 3.35 (2H, brs), 4.02-4.10 (2H, m), 6.59 (1H, dd, J=2.4, 8.1 Hz), 6.62 (1H, d, J=2.4 Hz), 6.98 (1H, d, J=8.1 Hz), 7.20-7.23 (2H, m), 7.27-7.31 (2H, m).

(4) Preparation of Methyl N-{2-[2-(ethoxycarbonyl)ethyl]-4'-(trifluoromethoxy)biphenyl-4-yl}oxamate The title compound was obtained in the same manner as the Example 1(2) using the following raw materials.
Raw materials: ethyl 3-[4-amino-4'-(trifluoromethoxy)biphenyl-2-yl]propanoate and methyl chloroglyoxylate.
Yield: 80.1% (white solid).
$^1$H-NMR (CDCl$_3$) δ: 1.16-1.25 (3H, m), 2.43 (2H, t, J=7.2 Hz), 2.92 (2H, t, J=7.2 Hz), 3.96-4.10 (5H, m), 7.20 (1H, d, J=8.4 Hz), 7.25-7.33 (4H, m), 7.55-7.61 (2H, m), 8.90 (1H, brs).

(5) Preparation of Methyl N-[4-(tert-butyl)benzyl]-N-{2-[2-(ethoxycarbonyl)ethyl]-4'-(trifluoromethoxy)biphenyl-4-yl}oxamate The title compound was obtained in the same manner as the Example 1(1) using the following raw materials.
Raw materials: methyl N-{2-[2-(ethoxycarbonyl)ethyl]-4'-(trifluoromethoxy)biphenyl-4-yl}oxamate and 4-(tert-butyl)benzyl bromide.
Yield: 72.7% (colorless oil).
$^1$H-NMR (CDCl$_3$) δ: 1.18 (3H, t, J=7.2 Hz), 1.30 (9H, s), 2.28 (2H, t, J=7.5 Hz), 2.81 (2H, t, J=7.5 Hz), 3.61 (3H, s), 4.04 (2H, q, J=7.2 Hz), 4.93 (2H, s), 6.93 (1H, d, J=2.1 Hz), 7.00 (1H, dd, J=2.1, 8.1 Hz), 7.13 (1H, d, J=8.1 Hz), 7.17-7.19 (2H, m), 7.27-7.35 (6H, m).

(6) Preparation of N-[4-(tert-butyl)benzyl]-N-[2-(2-carboxyethyl)-4'-(trifluoromethoxy)biphenyl-4-yl]oxamic Acid (Compound No. 76)

The title compound was obtained in the same manner as the Example 4(4) using the following raw material.
Raw material: methyl N-[4-(tert-butyl)benzyl]-N-{2-[2-(ethoxycarbonyl)ethyl]-4'-(trifluoromethoxy)biphenyl-4-yl}oxamate Yield: 80.4% (white solid).
$^1$H-NMR (DMSO-d$_6$) δ: 1.25 (9H, s), 2.30 (2H, t, J=7.2 Hz), 2.70 (2H, t, J=7.2 Hz), 4.93 (2H, s), 7.11-7.23 (5H, m), 7.34-7.37 (2H, m), 7.40-7.44 (4H, m), 12.12 (1H, brs).

Example 77

Preparation of N-[4-(tert-butyl)benzyl]-N-[2-(1-ethylpropoxy)-4'-(trifluoromethoxy)biphenyl-5-yl]oxamic Acid (Compound No. 77)

(1) Preparation of 5-nitro-2-(1-ethylpropoxy)-4'-(trifluoromethoxy)biphenyl The title compound was obtained in the same manner as the Example 65(2) using the following raw materials.
Raw materials: 2-chloro-5-nitro-4'-(trifluoromethoxy)biphenyl (compound of Example 65(1)) and 3-pentanol.

Yield: 43.4% (yellow solid).
$^1$H-NMR (CDCl$_3$) δ: 0.89 (6H, t, J=7.8 Hz), 1.64-1.70 (4H, m), 4.31-4.35 (1H, m), 6.98-7.01 (1H, m), 7.26-7.29 (2H, m), 7.53-7.56 (2H, m), 8.19-8.23 (2H, m).

(2) Preparation of 5-amino-2-(1-ethylpropoxy)-4'-(trifluoromethoxy)biphenyl The title compound was obtained in the same manner as the Example 3(2) using the following raw material.
Raw material: 5-nitro-2-(1-ethylpropoxy)-4'-(trifluoromethoxy)biphenyl.
Yield: 99.9% (black oil).
$^1$H-NMR (CDCl$_3$) δ: 0.78 (6H, t, J=7.2 Hz), 1.44-1.54 (4H, m), 3.48 (2H, brs), 3.81-3.88 (1H, m), 6.62-6.67 (2H, m), 6.80-6.84 (1H, m), 7.19-7.22 (2H, m), 7.51-7.55 (2H, m).

(3) Preparation of Methyl N-[2-(1-ethylpropoxy)-4'-(trifluoromethoxy)biphenyl-5-yl]oxamate The title compound was obtained in the same manner as the Example 1(2) using the following raw materials.
Raw materials: 5-amino-2-(1-ethylpropoxy)-4'-(trifluoromethoxy)biphenyl and methyl chloroglyoxylate.
Yield: 99.3% (brown oil).
$^1$H-NMR (CDCl$_3$) δ: 0.84 (6H, t, J=7.5 Hz), 1.55-1.61 (4H, m), 3.97 (3H, s), 4.09-4.13 (1H, m), 6.96 (1H, d, J=9.0 Hz), 7.21-7.27 (2H, m), 7.49 (1H, d, J=2.7 Hz), 7.53-7.67 (2H, m), 7.63 (1H, dd, J=2.7, 9.0 Hz), 8.79 (1H, brs).

(4) Preparation of Methyl N-[4-(tert-butyl)benzyl]-N-[2-(1-ethylpropoxy)-4'-(trifluoromethoxy)biphenyl-5-yl]oxamate The title compound was obtained in the same manner as the Example 1(1) using the following raw materials.
Raw materials: methyl N-[2-(1-ethylpropoxy)-4'-(trifluoromethoxy)biphenyl-5-yl]oxamate and 4-(tert-butyl)benzyl bromide.
Yield: 84.0% (colorless oil).
$^1$H-NMR (CDCl$_3$) δ: 0.84 (6H, t, J=7.5 Hz), 1.30 (9H, s), 1.55-1.61 (4H, m), 3.56 (3H, s), 4.10-4.14 (1H, m), 4.88 (2H, s), 6.82-6.86 (2H, m), 7.02 (1H, dd, J=2.7, 8.7 Hz), 7.15-7.19 (4H, m), 7.31-7.38 (4H, m).

(5) Preparation of N-[4-(tert-butyl)benzyl]-N12-(1-ethylpropoxy)-4'-(trifluoromethoxy)biphenyl-5-yl]oxamic Acid (Compound No. 77)

The title compound was obtained in the same manner as the Example 4(4) using the following raw material.
Raw material: methyl N-[4-(tert-butyl)benzyl]-N-[2-(1-ethylpropoxy)-4'-(trifluoromethoxy)biphenyl-5-yl]oxamate Yield: 81.2% (white solid).
$^1$H-NMR (DMSO-d$_6$) δ: 0.80 (6H, t, J=7.5 Hz), 1.24 (9H, s), 1.50-1.56 (4H, m), 4.17-4.22 (1H, m), 4.78 (2H, s), 6.93-6.97 (1H, m), 7.11-7.19 (4H, m), 7.28-7.36 (4H, m), 7.51-7.54 (2H, m).

Example 78

Preparation of N-[4-(tert-butyl)benzyl]-N-[5-propoxy-4'-(trifluoromethoxy)biphenyl-2-yl]oxamic Acid (Compound No. 78)

(1) Preparation of 5-fluoro-2-nitro-4'-(trifluoromethoxy)biphenyl

The title compound was obtained in the same manner as the Example 1(3) using the following raw materials.
Raw materials: 2-bromo-4-fluoronitrobenzene and 4-(trifluoromethoxy)phenylboronic acid.
Yield: 37.4% (colorless oil).
$^1$H-NMR (CDCl$_3$) δ: 7.10-8.01 (7H, m).

(2) Preparation of 2-nitro-5-propoxy-4'-(trifluoromethoxy)biphenyl

The title compound was obtained in the same manner as the Example 65(2) using the following raw materials.
Raw materials: 5-fluoro-2-nitro-4'-(trifluoromethoxy)biphenyl and 1-propanol.
Yield: 88.2% (yellow oil).
$^1$H-NMR (CDCl$_3$) δ: 1.05 (3H, t, J=7.5 Hz), 1.78-1.92 (2H, m), 4.01 (2H, t, J=6.6 Hz), 6.81 (1H, d, J=2.7 Hz), 6.94 (1H, dd, J=2.7, 9.3 Hz), 7.21-7.35 (4H, m), 8.02 (1H, d, J=9.3 Hz).

(3) Preparation of 2-amino-5-propoxy-4'-(trifluoromethoxy)biphenyl

The title compound was obtained in the same manner as the Example 3(2) using the following raw material.
Raw material: 2-nitro-5-propoxy-4'-(trifluoromethoxy)biphenyl.
Yield: 99.9% (yellow oil).
$^1$H-NMR (CDCl$_3$) δ: 1.02 (3H, t, J=7.5 Hz), 1.71-1.84 (2H, m), 3.45 (2H, brs), 3.87 (2H, t, J=6.6 Hz), 6.71 (1H, d, J=2.7 Hz), 6.72 (1H, d, J=8.7 Hz), 6.79 (1H, dd, J=2.7, 8.7 Hz), 7.26-7.31 (2H, m), 7.46-7.52 (2H, m).

(4) Preparation of Methyl N-[5-propoxy-4'-(trifluoromethoxy)biphenyl-2-yl]oxamate The title compound was obtained in the same manner as the Example 3(3) using the following raw materials.
Raw materials: 2-amino-5-propoxy-4'-(trifluoromethoxy)biphenyl and methyl chloroglyoxylate.
Yield: 41.0% (white solid).
$^1$H-NMR (CDCl$_3$) δ: 1.04 (3H, t, J=7.5 Hz), 1.75-1.88 (2H, m), 3.89 (3H, s), 3.94 (2H, t, J=6.6 Hz), 6.83 (1H, d, J=3.0 Hz), 6.96 (1H, dd, J=3.0, 9.0 Hz), 7.34 (2H, d, J=8.7 Hz), 7.42 (2H, d, J=8.7 Hz), 8.22 (1H, d, J=9.0 Hz), 8.74 (1H, brs).

(5) Preparation of Methyl N-[4-(tert-butyl)benzyl]-N-[5-propoxy-4'-(trifluoromethoxy)biphenyl-2-yl]oxamate The title compound was obtained in the same manner as the Example 1(1) using the following raw materials.
Raw materials: methyl N-[5-propoxy-4'-(trifluoromethoxy)biphenyl-2-yl]oxamate and 4-(tert-butyl)benzyl bromide.
Yield: 91.3% (colorless oil).
$^1$H-NMR (CDCl$_3$) δ: 1.03 (3H, t, J=6.9 Hz), 1.27 (9H, s), 1.77-2.04 (2H, m), 3.40 (1H, d, J=14.4 Hz), 3.65 (3H, s), 3.91 (2H, t, J=6.6 Hz), 5.07 (1H, d, J=14.4 Hz), 6.67 (1H, dd, J=2.7, 8.4 Hz), 6.74 (1H, d, J=8.4 Hz), 6.89 (1H, d, J=2.7 Hz), 6.90-6.96 (2H, m), 7.18-7.23 (2H, m), 7.26-7.32 (2H, m), 7.59-7.65 (2H, m).

(6) Preparation of N-[4-(tert-butyl)benzyl]-N-[5-propoxy-4'-(trifluoromethoxy)biphenyl-2-yl]oxamic Acid (Compound No. 78)

The title compound was obtained in the same manner as the Example 4(4) using the following raw material.
Raw material: methyl N-[4-(tert-butyl)benzyl]-N-[5-propoxy-4'-(trifluoromethoxy)biphenyl-2-yl]oxamate Yield: 43.5% (white solid).
This compound was obtained as a mixture of the rotational isomers.
Major isomer: $^1$H-NMR (DMSO-d$_6$) δ: 0.95 (3H, t, J=7.5 Hz), 1.21 (9H, s), 1.64-1.76 (2H, m), 3.05 (1H, d, J=14.7 Hz), 3.91 (2H, t, J=6.3 Hz), 4.78 (1H, d, J=14.7 Hz), 6.72 (1H, dd, J=3.0, 8.4 Hz), 6.82 (1H, d, J=3.0 Hz), 6.86 (2H, d, J=8.4 Hz), 6.94 (1H, d, J=8.4 Hz), 7.17-7.21 (2H, m), 7.37-7.42 (2H, m), 8.04-8.08 (2H, m).
Minor isomer: $^1$H-NMR (DMSO-d$_6$) δ: 0.93-4.55 (18H, m), 6.78-6.91 (5H, m), 7.06-7.10 (2H, m), 7.25-7.29 (2H, m), 7.32-7.36 (2H, m).

Example 79

Preparation of N-[4-(tert-butyl)benzyl]-N-[4-(1-ethylpropoxy)-4'-(trifluoromethoxy)biphenyl-3-yl]oxamic Acid (Compound No. 79)

(1) Preparation of 3-nitro-4-(1-ethylpropoxy)-4'-(trifluoromethoxy)biphenyl

The title compound was obtained in the same manner as the Example 65(2) using the following raw materials.
Raw materials: 4-fluoro-3-nitro-4'-(trifluoromethoxy)biphenyl (compound of Example 68(1)) and 3-pentanol.
Yield: 85.0% (yellow oil).
$^1$H-NMR (CDCl$_3$) δ: 1.00 (6H, t, J=7.5 Hz), 1.72-1.81 (4H, m), 4.31-4.35 (1H, m), 7.12 (1H, d, J=8.7 Hz), 7.27-7.31 (2H, m), 7.53-7.58 (2H, m), 7.66 (1H, dd, J=2.1, 8.7 Hz), 7.97 (1H, d, J=2.1 Hz).

(2) Preparation of 3-amino-4-(1-ethylpropoxy)-4'-(trifluoromethoxy)biphenyl

The title compound was obtained in the same manner as the Example 3(2) using the following raw material.
Raw material: 3-nitro-4-(1-ethylpropoxy)-4'-(trifluoromethoxy)biphenyl.
Yield: 84.8% (brown solid).
$^1$H-NMR (CDCl$_3$) δ: 0.99 (6H, t, J=7.5 Hz), 1.68-1.77 (4H, m), 3.89 (2H, brs), 4.16-4.20 (1H, m), 6.81-6.92 (3H, m), 7.21-7.25 (2H, m), 7.50-7.53 (2H, m).

(3) Preparation of 3-[4-(tert-butyl)benzyl]amino-4-(1-ethylpropoxy)-4'-(trifluoromethoxy)biphenyl The title compound was obtained in the same manner as the Example 1(1) using the following raw materials.
Raw materials: 3-amino-4-(1-ethylpropoxy)-4'-(trifluoromethoxy)biphenyl and 4-(tert-butyl)benzyl bromide.
Yield: 74.5% (colorless oil).

¹H-NMR (CDCl₃) δ: 0.95-1.04 (6H, m), 1.29 (9H, s), 1.67-1.81 (4H, m), 4.18-4.40 (3H, m), 4.74-4.79 (1H, m), 6.77-6.81 (2H, m), 6.89-6.94 (2H, m), 7.04 (1H, dd, J=2.4, 8.1 Hz), 7.17-7.50 (6H, m).

(4) Preparation of Methyl N-[4-(tert-butyl)benzyl]-N-[4-(1-ethylpropoxy)-4'-(trifluoromethoxy)biphenyl-3-yl]oxamate The title compound was obtained in the same manner as the Example 1(1) using the following raw materials.
Raw materials: 3-[4-(tert-butyl)benzyl]amino-4-(1-ethylpropoxy)-4'-(trifluoromethoxy)biphenyl and methyl chloroglyoxylate.
Yield: 99.9% (brown oil).
¹H-NMR (CDCl₃) δ: 0.94-1.02 (6H, m), 1.29 (9H, s), 1.57-1.78 (4H, m), 3.52 (3H, s), 4.22-4.32 (2H, m), 5.46-5.51 (1H, m), 6.92-6.95 (2H, m), 7.13-7.21 (4H, m), 7.26-7.31 (4H, m), 7.41 (1H, dd, J=2.4, 9.0 Hz).

(5) Preparation of N-[4-(tert-butyl)benzyl]-N-[4-(1-ethylpropoxy)-4'-(trifluoromethoxy)biphenyl-3-yl]oxamic Acid (Compound No. 79)

The title compound was obtained in the same manner as the Example 4(4) using the following raw material.
Raw material: methyl N-[4-(tert-butyl)benzyl]-N-[4-(1-ethylpropoxy)-4'-(trifluoromethoxy)biphenyl-3-yl]oxamate Yield: 45.9% (white solid).
This compound was obtained as a mixture of the rotational isomers.
Major isomer: ¹H-NMR (DMSO-d₆) δ: 0.88-0.96 (6H, m), 1.20 (9H, s), 1.57-1.64 (4H, m), 4.26-5.30 (3H, m), 7.06-7.08 (2H, m), 7.23-7.52 (9H, m).
Minor isomer: ¹H-NMR (DMSO-d₆) δ: 0.88-0.96 (6H, m), 1.20 (9H, s), 1.57-1.64 (4H, m), 4.26-5.30 (3H, m), 6.92-7.08 (2H, m), 7.23-7.52 (9H, m).

Example 80

Preparation of N-[4-(tert-butyl)benzyl]-N-[3'-(trifluoromethoxy)biphenyl-4-yl]oxamic Acid (Compound No. 80)

(1) Preparation of methyl N-[4-(tert-butyl)benzyl]-N-[3'-(trifluoromethoxy)biphenyl-4-yl]oxamate The title compound was obtained in the same manner as the Example 1(3) using the following raw materials.
Raw materials: methyl N-(4-bromophenyl)-N-[4-(tert-butyl)benzyl]oxamate (compound of Example 4(2)) and 3-(trifluoromethyl)phenylboronic acid.
Yield: 96.0% (pale yellow oil).
¹H-NMR (CDCl₃) δ: 1.30 (9H, s), 3.59 (3H, s), 4.95 (2H, s), 7.15-7.25 (5H, m), 7.30-7.34 (2H, m), 7.38-7.55 (5H, m).

(2) Preparation of N-[4-(tert-butyl)benzyl]-N-[3'-(trifluoromethoxy)biphenyl-4-yl]oxamic Acid (Compound No. 80)

The title compound was obtained in the same manner as the Example 4(4) using the following raw material.
Raw material: methyl N-[4-(tert-butyl)benzyl]-N-[3'-(trifluoromethoxy)biphenyl-4-yl]oxamate Yield: 58.2% (white solid).
¹H-NMR (CDCl₃) δ: 1.24 (9H, s), 4.95 (2H, s), 7.17 (2H, d, J=7.8 Hz), 7.31-7.40 (5H, m), 7.58 (1H, t, J=7.8 Hz), 7.60-7.63 (1H, m), 7.68-7.74 (3H, m).

Example 81

Preparation of N-[4-(tert-butyl)benzyl]-N-[2'-(trifluoromethoxy)biphenyl-4-yl]oxamic Acid (Compound No. 81)

(1) Preparation of methyl N-[4-(tert-butyl)benzyl]-N-[2'-(trifluoromethoxy)biphenyl-4-yl]oxamate The title compound was obtained in the same manner as the Example 1(3) using the following raw materials.
Raw materials: methyl N-(4-bromophenyl)-N-[4-(tert-butyl)benzyl]oxamate (compound of Example 4(2)) and 2-(trifluoromethyl)phenylboronic acid.
Yield: 88.3% (pale yellow oil).
¹H-NMR (CDCl₃) δ: 1.30 (9H, s), 3.53 (3H, s), 4.96 (2H, s), 7.11-7.20 (4H, m), 7.29-7.44 (8H, m).

(2) Preparation of N-[4-(tert-butyl)benzyl]-N-[2'-(trifluoromethoxy)biphenyl-4-yl]oxamic Acid (Compound No. 81)

The title compound was obtained in the same manner as the Example 4(4) using the following raw material.
Raw material: methyl N-[4-(tert-butyl)benzyl]-N-[2'-(trifluoromethoxy)biphenyl-4-yl]oxamate.
Yield: 59.5% (white solid).
¹H-NMR (CDCl₃) δ: 1.24 (9H, s), 4.95 (2H, s), 7.13 (2H, d, J=7.8 Hz), 7.29-7.35 (4H, m), 7.44-7.55 (6H, m).

Example 82

Preparation of N-[4'-(tert-butyl)biphenyl-4-yl]-N-[2-(trifluoromethoxy)benzyl]oxamic Acid (Compound No. 82)

(1) Preparation of Methyl N-[4'-(tert-butyl)biphenyl-4-yl]oxamate

The title compound was obtained in the same manner as the Example 70(3) using the following raw materials.
Raw materials: methyl N-(4-bromophenyl)oxamate (compound of Example 4(1)) and 4-(tert-butyl)phenylboronic acid.
Yield: 47.5% (gray solid).
¹H-NMR (CDCl₃) δ: 1.36 (9H, s), 3.99 (3H, s), 7.45-7.54 (4H, m), 7.59-7.72 (4H, m), 8.88 (1H, brs).

(2) Preparation of methyl N-[4'-(tert-butyl)biphenyl-4-yl]-N-[2-(trifluoromethoxy)benzyl]oxamate The title compound was obtained in the same manner as the Example 1(1) using the following raw materials.
Raw materials: methyl N-[4'-(tert-butyl)biphenyl-4-yl]oxamate and 2-(trifluoromethoxy)benzyl bromide.
Yield: 91.1% (colorless oil).
¹H-NMR (CDCl₃) δ: 1.35 (9H, s), 3.58 (3H, s), 5.10 (2H, s), 7.11-7.21 (3H, m), 7.27-7.35 (2H, m), 7.43-7.54 (7H, m).

(3) Preparation of N-[4'-(tert-butyl)biphenyl-4-yl]-N-[2-(trifluoromethoxy)benzyl]oxamic Acid (Compound No. 82)

The title compound was obtained in the same manner as the Example 4(4) using the following raw material.

Raw material: methyl N-[4'-(tert-butyl)biphenyl-4-yl]-N-[2-(trifluoromethoxy)benzyl]oxamate. Yield: 68.7% (white solid).

$^1$H-NMR (DMSO-$d_6$) δ: 1.30 (9H, s), 5.06 (2H, s), 7.27-7.49 (8H, m), 7.54-7.59 (2H, m), 7.62-7.67 (2H, m).

Example 83

Preparation of N-[4'-(tert-butyl)biphenyl-4-yl]-N-[3-(trifluoromethoxy)benzyl]oxamic Acid (Compound No. 83)

(1) Preparation of Methyl N-[4'-(tert-butyl)biphenyl-4-yl]-N-[3-(trifluoromethoxy)benzyl]oxamate The title compound was obtained in the same manner as the Example 1(1) using the following raw materials.

Raw materials: methyl N-[4'-(tert-butyl)biphenyl-4-yl]oxamate (compound of Example 82(1)) and 3-(trifluoromethoxy)benzyl bromide.

Yield: 82.2% (colorless oil).

$^1$H-NMR (CDCl$_3$) δ: 1.35 (9H, s), 3.57 (3H, s), 4.99 (2H, s), 7.07-7.17 (4H, m), 7.22-7.27 (1H, m), 7.35 (1H, t, J=7.8 Hz), 7.44-7.56 (6H, m).

(2) Preparation of N-[4'-(tert-butyl)biphenyl-4-yl]-N-[3-(trifluoromethoxy)benzyl]oxamic Acid (Compound No. 83)

The title compound was obtained in the same manner as the Example 4(4) using the following raw material.

Raw material: methyl N-[4'-(tert-butyl)biphenyl-4-yl]-N-[3-(trifluoromethoxy)benzyl]oxamate.

Yield: 69.6% (white solid).

$^1$H-NMR (DMSO-$d_6$) δ: 1.30 (9H, s), 5.04 (2H, s), 7.18-7.21 (1H, m), 7.24-7.32 (4H, m), 7.45-7.51 (3H, m), 7.54-7.60 (2H, m), 7.63-7.69 (2H, m).

Example 84

Preparation of N-[4'-(tert-butyl)biphenyl-4-yl]-N-(4-chlorobenzyl)oxamic Acid (Compound No. 84)

(1) Preparation of Methyl N-[4'-(tert-butyl)biphenyl-4-yl]-N-(4-chlorobenzyl)oxamate The title compound was obtained in the same manner as the Example 1(1) using the following raw materials.

Raw materials: methyl N-[4'-(tert-butyl)biphenyl-4-yl]oxamate (compound of Example 82(1)) and 4-chlorobenzyl chloride.

Yield: 51.9% (colorless oil).

$^1$H-NMR (CDCl$_3$) δ: 1.35 (9H, s), 3.56 (3H, s), 4.93 (2H, s), 7.06-7.11 (2H, m), 7.17-7.22 (2H, m), 7.25-7.29 (2H, m), 7.44-7.55 (6H, m).

(2) Preparation of N-[4'-(tert-butyl)biphenyl-4-yl]-N-(4-chlorobenzyl)oxamic Acid (Compound No. 84)

The title compound was obtained in the same manner as the Example 4(4) using the following raw material.

Raw material: methyl N-[4'-(tert-butyl)biphenyl-4-yl]-N-(4-chlorobenzyl)oxamate.

Yield: 71.6% (white solid).

$^1$H-NMR (DMSO-$d_6$) δ: 1.30 (9H, s), 4.97 (2H, s), 7.24-7.29 (4H, m), 7.37-7.43 (2H, m), 7.44-7.49 (2H, m), 7.55-7.60 (2H, m), 7.63-7.69 (2H, m).

Example 85

Preparation of N-[4'-(tert-butyl)biphenyl-4-yl]-N-[4-(trifluoromethyl)benzyl]oxamic Acid (Compound No. 85)

(1) Preparation of Methyl N-[4'-(tert-butyl)biphenyl-4-yl]-N-[4-(trifluoromethyl)benzyl]oxamate The title compound was obtained in the same manner as the Example 1(1) using the following raw materials.

Raw materials: methyl N-[4'-(tert-butyl)biphenyl-4-yl]oxamate (compound of Example 82(1)) and 4-(trifluoromethyl)benzyl chloride.

Yield: 52.4% (colorless oil).

$^1$H-NMR (CDCl$_3$) δ: 1.35 (9H, s), 3.58 (3H, s), 5.02 (2H, s), 7.09-7.14 (2H, m), 7.37-7.41 (2H, m), 7.44-7.59 (8H, m).

(2) Preparation of N-[4'-(tert-butyl)biphenyl-4-yl]-N-[4-(trifluoromethyl)benzyl]oxamic Acid (Compound No. 85)

The title compound was obtained in the same manner as the Example 4(4) using the following raw material.

Raw material: methyl N-[4'-(tert-butyl)biphenyl-4-yl]-N-[4-(trifluoromethyl)benzyl]oxamate.

Yield: 73.6% (white solid).

$^1$H-NMR (DMSO-$d_6$) δ: 1.30 (9H, s), 5.08 (2H, s), 7.31 (2H, d, J=8.4 Hz), 7.44-7.50 (4H, m), 7.54-7.60 (2H, m), 7.67 (2H, d, J=8.4 Hz), 7.72 (2H, d, J=8.4 Hz).

Example 86

Preparation of N-(4-butylbenzyl)-N-[4'-(tert-butyl)biphenyl-4-yl]oxamic Acid (Compound No. 86)

(1) Preparation of Methyl N-(4-butylbenzyl)-N-[4'-(tert-butyl)biphenyl-4-yl]oxamate The title compound was obtained in the same manner as the Example 1(1) using the following raw materials.

Raw materials: methyl N-[4'-(tert-butyl)biphenyl-4-yl]oxamate (compound of Example 82(1)) and 4-butylbenzyl chloride (compound of Example 47(1)).

Yield: 32.8% (colorless oil).

$^1$H-NMR (CDCl$_3$) δ: 0.92 (3H, t, J=7.5 Hz), 1.22-1.41 (11H, m), 1.52-1.62 (2H, m), 2.58 (2H, t, J=7.8 Hz), 3.55 (3H, s), 4.93 (2H, s), 7.08-7.17 (6H, m), 7.43-7.53 (6H, m).

(2) Preparation of N-(4-butylbenzyl)-N-[4'-(tert-butyl)biphenyl-4-yl]oxamic Acid (Compound No. 86)

The title compound was obtained in the same manner as the Example 4(4) using the following raw material.

Raw material: methyl N-(4-butylbenzyl)-N-[4'-(tert-butyl)biphenyl-4-yl]oxamate.

Yield: 58.8% (white solid).

$^1$H-NMR (DMSO-$d_6$) δ: 0.87 (3H, t, J=7.5 Hz), 1.21-1.34 (11H, m), 1.46-1.56 (2H, m), 2.53 (2H, t, J=7.5 Hz), 4.93 (2H, s), 7.09-7.16 (4H, m), 7.23-7.28 (2H, m), 7.43-7.49 (2H, m), 7.54-7.60 (2H, m), 7.61-7.67 (2H, m).

Example 87

Preparation of N-[4-(tert-butyl)benzyl]-N-[5-(1-ethylpropoxy)-4'-(trifluoromethoxy)biphenyl-2-yl]oxamic Acid (Compound No. 87)

(1) Preparation of 2-nitro-5-(1-ethylpropoxy)-4'-(trifluoromethoxy)biphenyl The title compound was obtained in the same manner as the Example 65(2) using the following raw materials.
Raw materials: 5-fluoro-2-nitro-4'-(trifluoromethoxy)biphenyl (compound of Example 78(1)) and 3-pentanol.
Yield: 91.4% (brown oil).
$^1$H-NMR (CDCl$_3$) δ: 0.96 (6H, t, J=7.2 Hz), 1.68-1.77 (4H, m), 4.24-4.27 (1H, m), 6.80 (1H, d, J=2.7 Hz), 6.92 (1H, dd, J=2.7, 9.0 Hz), 7.24-7.35 (4H, m), 8.01 (1H, d, J=9.0 Hz).

(2) Preparation of 2-amino-5-(1-ethylpropoxy)-4'-(trifluoromethoxy)biphenyl The title compound was obtained in the same manner as the Example 3(2) using the following raw material.
Raw material: 2-nitro-5-(1-ethylpropoxy)-4'-(trifluoromethoxy)biphenyl.
Yield: 96.3% (brown oil).
$^1$H-NMR (CDCl$_3$) δ: 0.96 (6H, t, J=7.5 Hz), 1.61-1.70 (4H, m), 3.46 (2H, brs), 3.94-3.99 (1H, m), 6.69-6.72 (2H, m), 6.79 (1H, dd, J=2.7, 8.7 Hz), 7.26-7.30 (2H, m), 7.48-7.51 (2H, m).

(3) Preparation of Methyl N-[5-(1-ethylpropoxy)-4'-(trifluoromethoxy)biphenyl-2-yl]oxamate The title compound was obtained in the same manner as the Example 1(2) using the following raw materials.
Raw materials: 2-amino-5-(1-ethylpropoxy)-4'-(trifluoromethoxy)biphenyl and methyl chloroglyoxylate.
Yield: 91.0% (brown oil).
$^1$H-NMR (CDCl$_3$) δ: 0.96 (6H, t, J=7.5 Hz), 1.64-1.71 (4H, m), 3.89 (3H, s), 4.11-4.15 (1H, m), 6.83 (1H, d, J=3.0 Hz), 6.96 (1H, dd, J=3.0, 9.0 Hz), 7.33-7.36 (2H, m), 7.40-7.43 (2H, m), 8.20 (1H, d, J=9.0 Hz), 8.74 (1H, brs).

(4) Preparation of Methyl N-[4-(tert-butyl)benzyl]-N-[5-(1-ethylpropoxy)-4'-(trifluoromethoxy)biphenyl-2-yl]oxamate The title compound was obtained in the same manner as the Example 1(1) using the following raw materials.
Raw materials: methyl N-[5-(1-ethylpropoxy)-4'-(trifluoromethoxy)biphenyl-2-yl]oxamate and 4-(tert-butyl)benzyl bromide.
Yield: 94.9% (colorless oil).
$^1$H-NMR (CDCl$_3$) δ: 0.92-0.97 (6H, m), 1.26 (9H, s), 1.62-1.70 (4H, m), 3.42 (1H, d, J=14.4 Hz), 3.64 (3H, s), 4.08-4.15 (1H, m), 5.05 (1H, d, J=14.4 Hz), 6.66 (1H, dd, J=2.7, 8.7 Hz), 6.75 (1H, d, J=8.7 Hz), 6.88 (1H, d, J=2.7 Hz), 6.93-6.96 (2H, m), 7.18-7.22 (2H, m), 7.25-7.33 (2H, m), 7.60-7.63 (2H, m).

(5) Preparation of N-[4-(tert-butyl)benzyl]-N-[5-(1-ethylpropoxy)-4'-(trifluoromethoxy)biphenyl-2-yl] oxamic Acid (Compound No. 87)

The title compound was obtained in the same manner as the Example 4(4) using the following raw material.
Raw material: methyl N-[4-(tert-butyl)benzyl]-N-[5-(1-ethylpropoxy)-4'-(trifluoromethoxy)biphenyl-2-yl]oxamate
Yield: 76.1% (white solid).
This compound was obtained as a mixture of the rotational isomers.
Major isomer: $^1$H-NMR (DMSO-d$_6$) δ: 0.85-0.91 (6H, m), 1.18-1.21 (9H, m), 1.55-1.62 (4H, m), 3.07 (1H, d, J=14.7 Hz), 4.17-4.24 (1H, m), 4.76 (1H, d, J=14.7 Hz), 6.72 (1H, dd, J=2.7, 8.7 Hz), 6.80 (1H, d, J=2.7 Hz), 6.86-6.88 (2H, m), 6.96 (1H, d, J=8.7 Hz), 7.17-7.20 (2H, m), 7.39-7.41 (2H, m), 8.04-8.07 (2H, m).
Minor isomer: $^1$H-NMR (DMSO-d$_6$) δ: 0.85-0.91 (6H, m), 1.18-1.21 (9H, m), 1.55-1.62 (4H, m), 3.79-3.86 (1H, m), 4.17-4.24 (1H, m), 4.47-4.44 (1H, m), 6.77-6.98 (3H, m), 7.07-7.41 (6H, m), 8.04-8.07 (2H, m).

Example 88

Preparation of N-[4-(tert-butyl)benzyl]-N-[5-diethylamino-4'-(trifluoromethoxy)biphenyl-2-yl]oxamic Acid (Compound No. 88)

(1) Preparation of 5-diethylamino-2-nitro-4'-(trifluoromethoxy)biphenyl

A mixture of 5-fluoro-2-nitro-4'-(trifluoromethoxy)biphenyl (compound of Example 78(1)) (700 mg, 2.32 mmol), diethylamine (339 mg, 4.64 mmol), potassium carbonate (320 mg, 2.32 mmol) and acetonitrile (5 ml) was stirred at 100° for 10 hours under argon atmosphere. The reaction mixture was cooled to room temperature, diluted with water, and extracted with ethyl acetate. The organic layer was washed with saturated brine, and dried over anhydrous sodium sulfate. The residue obtained by evaporation of the solvent under reduced pressure was purified by column chromatography on silica gel (n-hexane:ethyl acetate=10:1) to give the title compound (580 mg, 70.5%) as a yellow solid.
$^1$H-NMR (CDCl$_3$) δ: 1.22 (6H, t, J=6.9 Hz), 3.45 (4H, q, J=6.9 Hz), 6.37 (1H, d, J=3.0 Hz), 6.60 (1H, dd, J=3.0, 9.0 Hz), 7.23-7.33 (4H, m), 8.08 (1H, d, J=9.0 Hz).

(2) Preparation of 2-amino-5-diethylamino-4'-(trifluoromethoxy)biphenyl

The title compound was obtained in the same manner as the Example 3(2) using the following raw material.
Raw material: 5-diethylamino-2-nitro-4'-(trifluoromethoxy)biphenyl.
Yield: 87.5% (yellow solid).
$^1$H-NMR (CDCl$_3$) δ: 1.11 (6H, t, J=6.9 Hz), 3.24 (4H, q, J=6.9 Hz), 3.35 (2H, brs), 6.57 (1H, d, J=2.7 Hz), 6.66-6.75 (2H, m), 7.26-7.29 (2H, m), 7.48-7.52 (2H, m).

(3) Preparation of Methyl N-[5-diethylamino-4'-(trifluoromethoxy)biphenyl-2-yl]oxamate The title compound was obtained in the same manner as the Example 1(2) using the following raw materials.
Raw materials: 2-amino-5-diethylamino-4'-(trifluoromethoxy)biphenyl and methyl chloroglyoxylate.

Yield: 89.5% (colorless oil).
¹H-NMR (CDCl₃) δ: 1.17 (6H, t, J=6.9 Hz), 3.37 (4H, q, J=6.9 Hz), 3.88 (3H, s), 6.53 (1H, d, J=3.0 Hz), 6.72 (1H, dd, J=3.0, 9.0 Hz), 7.31-7.34 (2H, m), 7.37-7.43 (2H, m), 8.08 (1H, d, J=9.0 Hz), 8.63 (1H, brs).

(4) Preparation of Methyl N-[4-(tert-butyl)benzyl]-N-[5-diethylamino-4'-(trifluoromethoxy)biphenyl-2-yl]oxamate The title compound was obtained in the same manner as the Example 1(1) using the following raw materials.
Raw materials: methyl N-[5-diethylamino-4'-(trifluoromethoxy)biphenyl-2-yl]oxamate and 4-(tert-butyl)benzyl bromide.
Yield: 90.7% (yellow oil).
¹H-NMR (CDCl₃) δ: 1.16 (6H, t, J=7.2 Hz), 1.27 (9H, s), 3.30-3.39 (5H, m), 3.65 (3H, s), 5.00 (1H, d, J=14.4 Hz), 6.40 (1H, dd, J=3.0, 9.0 Hz), 6.54 (1H, d, J=3.0 Hz), 6.68 (1H, d, J=9.0 Hz), 6.96-6.99 (2H, m), 7.19-7.22 (2H, m), 7.25-7.30 (2H, m), 7.60-7.62 (2H, m).

(5) Preparation of N-[4-(tert-butyl)benzyl]-N-[5-diethylamino-4'-(trifluoromethoxy)biphenyl-2-yl] oxamic Acid (Compound No. 88)

The title compound was obtained in the same manner as the Example 4(4) using the following raw material.
Raw material: methyl N-[4-(tert-butyl)benzyl]-N-[5-diethylamino-4'-(trifluoromethoxy)biphenyl-2-yl]oxamate Yield: 75.7% (white solid).
¹H-NMR (DMSO-d₆) δ: 1.06 (6H, t, J=7.2 Hz), 1.22 (9H, s), 3.31-3.36 (5H, m), 4.80 (1H, d, J=14.4 Hz), 6.53-6.56 (2H, m), 6.76-6.78 (1H, m), 6.92-6.94 (2H, m), 7.23-7.36 (2H, m), 7.46-7.48 (2H, m), 7.71-7.74 (2H, m).

Example 89

Preparation of N-[4-(tert-butyl)benzyl]-N-[5-isopropoxy-4'-(trifluoromethoxy)biphenyl-2-yl]oxamic Acid (Compound No. 89)

(1) Preparation of 2-nitro-5-isopropoxy-4'-(trifluoromethoxy)biphenyl

The title compound was obtained in the same manner as the Example 65(2) using the following raw materials.
Raw materials: 5-fluoro-2-nitro-4'-(trifluoromethoxy)biphenyl (compound of Example 78(1)) and 2-propanol.
Yield: 99.9% (yellow oil).
¹H-NMR (CDCl₃) δ: 1.39 (6H, d, J=6.0 Hz), 4.63-4.69 (1H, m), 6.79 (1H, d, J=2.7 Hz), 6.92 (1H, dd, J=2.7, 9.0 Hz), 7.24-7.34 (4H, m), 8.01 (1H, d, J=9.0 Hz).

(2) Preparation of 2-amino-5-isopropoxy-4'-(trifluoromethoxy)biphenyl

The title compound was obtained in the same manner as the Example 3(2) using the following raw material.
Raw material: 2-nitro-5-isopropoxy-4'-(trifluoromethoxy) biphenyl.
Yield: 92.1% (yellow oil).

¹H-NMR (CDCl₃) δ: 1.24-1.34 (6H, m), 3.47 (2H, brs), 4.36-4.44 (1H, m), 6.69-6.72 (2H, m), 6.78 (1H, dd, J=2.7, 8.7 Hz), 7.25-7.30 (2H, m), 7.46-7.51 (2H, m).

(3) Preparation of Methyl N-[5-isopropoxy-4'-(trifluoromethoxy)biphenyl-2-yl]oxamate The title compound was obtained in the same manner as the Example 1(2) using the following raw materials.
Raw materials: 2-amino-5-isopropoxy-4'-(trifluoromethoxy)biphenyl and methyl chloroglyoxylate.
Yield: 74.0% (yellow solid).
¹H-NMR (CDCl₃) δ: 1.35 (6H, d, J=6.0 Hz), 3.89 (3H, s), 4.52-4.60 (1H, m), 6.82 (1H, d, J=3.0 Hz), 6.95 (1H, dd, J=3.0, 9.0 Hz), 7.33-7.36 (2H, m), 7.39-7.43 (2H, m), 8.21 (1H, d, J=9.0 Hz), 8.74 (1H, brs).

(4) Preparation of Methyl N-[4-(tert-butyl)benzyl]-N-[5-isopropoxy-4'-(trifluoromethoxy)biphenyl-2-yl]oxamate The title compound was obtained in the same manner as the Example 1(1) using the following raw materials.
Raw materials: methyl N-[5-isopropoxy-4'-(trifluoromethoxy)biphenyl-2-yl]oxamate and 4-(tert-butyl)benzyl bromide.
Yield: 99.9% (colorless oil).
¹H-NMR (CDCl₃) δ: 1.26 (9H, s), 1.32-1.35 (6H, m), 3.40 (1H, d, J=14.4 Hz), 3.65 (3H, s), 4.50-4.56 (1H, m), 5.06 (1H, d, J=14.4 Hz), 6.65 (1H, dd, J=2.7, 8.7 Hz), 6.74 (1H, d, J=8.7 Hz), 6.86 (1H, d, J=2.7 Hz), 6.92-6.95 (2H, m), 7.19-7.22 (2H, m), 7.28-7.31 (2H, m), 7.60-7.63 (2H, m).

(5) Preparation of N-[4-(tert-butyl)benzyl]-N-[5-isopropoxy-4'-(trifluoromethoxy)biphenyl-2-yl]oxamic Acid (Compound No. 89)

The title compound was obtained in the same manner as the Example 4(4) using the following raw material.
Raw material: methyl N-[4-(tert-butyl)benzyl]-N-[5-isopropoxy-4'-(trifluoromethoxy)biphenyl-2-yl]oxamate Yield: 40.1% (white solid).
This compound was obtained as a mixture of the rotational isomers.
Major isomer: ¹H-NMR (DMSO-d₆) δ: 1.15-1.27 (15H, m), 3.03 (1H, d, J=14.7 Hz), 4.56-4.64 (1H, m), 4.76 (1H, d, J=14.7 Hz), 6.70 (1H, dd, J=3.0, 8.7 Hz), 6.78 (1H, d, J=3.0 Hz), 6.84-6.87 (2H, m), 6.94 (1H, d, J=8.7 Hz), 7.17-7.20 (2H, m), 7.38-7.41 (2H, m), 8.05-8.08 (2H, m).
Minor isomer: ¹H-NMR (DMSO-d₆) δ: 1.15-1.27 (15H, m), 3.78-3.82 (1H, m), 4.47-4.51 (1H, m), 4.56-4.64 (1H, m), 6.70 (1H, dd, J=3.0, 8.7 Hz), 6.76-6.78 (1H, m), 6.84-6.87 (2H, m), 6.94 (1H, d, J=8.7 Hz), 7.07-7.41 (4H, m), 8.05-8.08 (2H, m).

Example 90

Preparation of N-benzyl-N-[2-propoxy-4'-(trifluoromethoxy)biphenyl-5-yl]oxamic Acid (Compound No. 90)

(1) Preparation of Methyl N-[2-propoxy-4'-(trifluoromethoxy)biphenyl-5-yl]oxamate The title compound was obtained in the same manner as the Example 3(3) using the following raw materials.
Raw materials: 5-amino-2-propoxy-4'-(trifluoromethoxy) biphenyl (compound of Example 65(3)) and methyl chloroglyoxylate.

Yield: 75.3% (white solid).
¹H-NMR (CDCl₃) δ: 0.96 (3H, t, J=7.5 Hz), 1.68-1.81 (2H, m), 3.93 (2H, t, J=6.3 Hz), 3.97 (3H, s), 6.97 (1H, d, J=9.0 Hz), 7.22-7.27 (2H, m), 7.52 (1H, d, J=2.4 Hz), 7.54-7.59 (2H, m), 7.65 (1H, dd, J=2.4, 9.0 Hz), 8.80 (1H, brs).

(2) Preparation of Methyl N-benzyl-N-[2-propoxy-4'-(trifluoromethoxy)biphenyl-5-yl]oxamate The title compound was obtained in the same manner as the Example 1(1) using the following raw materials.
Raw materials: methyl N-[2-propoxy-4'-(trifluoromethoxy)biphenyl-5-yl]oxamate and benzyl bromide.
Yield: 80.3% (colorless oil).
¹H-NMR (CDCl₃) δ: 0.96 (3H, t, J=7.2 Hz), 1.68-1.77 (2H, m), 3.58 (3H, s), 3.90 (2H, t, J=6.3 Hz), 4.92 (2H, s), 6.82-6.85 (1H, m), 6.96-7.00 (2H, m), 7.19-7.33 (7H, m), 7.39-7.42 (2H, m).

(3) Preparation of N-benzyl-N-[2-propoxy-4'-(trifluoromethoxy)biphenyl-5-yl]oxamic Acid (Compound No. 90).

The title compound was obtained in the same manner as the Example 4(4) using the following raw material.
Raw material: methyl N-benzyl-N-[2-propoxy-4'-(trifluoromethoxy)biphenyl-5-yl]oxamate.
Yield: 57.1% (white solid).
¹H-NMR (DMSO-d₆) δ: 0.88 (3H, t, J=7.2 Hz), 1.60-1.67 (2H, m), 3.88-3.92 (2H, m), 4.84 (2H, s), 6.93-7.04 (2H, m), 7.15-7.30 (6H, m), 7.36-7.38 (2H, m), 7.54-7.57 (2H, m).

Example 91

Preparation of N-[4-(tert-butyl)benzyl]-N-[2-isopropoxy-4'-(trifluoromethoxy)biphenyl-5-yl]oxamic Acid (Compound No. 91)

(1) Preparation of 2-fluoro-5-nitro-4'-(trifluoromethoxy)biphenyl

The title compound was obtained in the same manner as the Example 1(3) using the following raw materials.
Raw materials: 4-(trifluoromethoxy)boronic acid and 3-bromo-4-fluoronitrobenzene.
Yield: 70.8% (white solid).
(CDCl₃) δ: 7.30-7.37 (3H, m), 7.60-7.63 (2H, m), 8.23-8.29 (1H, m), 8.36-8.39 (1H, m).

(2) Preparation of 5-nitro-2-isopropoxy-4'-(trifluoromethoxy)biphenyl

The title compound was obtained in the same manner as the Example 65(2) using the following raw materials.
Raw materials: 2-fluoro-5-nitro-4'-(trifluoromethoxy)biphenyl and 2-propanol.
Yield: 99.9% (yellow solid).
¹H-NMR (CDCl₃) δ: 1.36 (6H, d, J=6.0 Hz), 4.68-4.76 (1H, m), 7.01-7.04 (1H, m), 7.25-7.29 (2H, m), 7.54-7.59 (2H, m), 8.20-8.24 (2H, m).

(3) Preparation of 5-amino-2-isopropoxy-4'-(trifluoromethoxy)biphenyl

The title compound was obtained in the same manner as the Example 3(2) using the following raw material.
Raw material: 5-nitro-2-isopropoxy-4'-(trifluoromethoxy)biphenyl.

Yield: 99.9% (brown oil).
¹H-NMR (CDCl₃) δ: 1.13 (6H, d, J=6.0 Hz), 3.50 (2H, brs), 4.06-4.14 (1H, m), 6.62-6.67 (2H, m), 6.85 (1H, d, J=8.7 Hz), 7.20-7.23 (2H, m), 7.53-7.58 (2H, m).

(4) Preparation of Methyl N-[2-isopropoxy-4'-(trifluoromethoxy)biphenyl-5-yl]oxamate The title compound was obtained in the same manner as the Example 3(3) using the following raw materials.
Raw materials: 5-amino-2-isopropoxy-4'-(trifluoromethoxy)biphenyl and methyl chloroglyoxylate.
Yield: 73.2% (purple solid).
¹H-NMR (CDCl₃) δ: 1.25 (6H, d, J=6.0 Hz), 3.97 (3H, s), 4.41-4.49 (1H, m), 6.99 (1H, d, J=8.7 Hz), 7.22-7.27 (2H, m), 7.51 (1H, d, J=2.7 Hz), 7.55-7.59 (2H, m), 7.64 (1H, dd, J=2.7, 8.7 Hz), 8.80 (1H, brs).

(5) Preparation of Methyl N-[4-(tert-butyl)benzyl]-N-[2-isopropoxy-4'-(trifluoromethoxy)biphenyl-5-yl]oxamate The title compound was obtained in the same manner as the Example 1(1) using the following raw materials.
Raw materials: methyl N-[2-isopropoxy-4'-(trifluoromethoxy)biphenyl-5-yl]oxamate and 4-(tert-butyl)benzyl bromide.
Yield: 89.1% (brown solid).
¹H-NMR (CDCl₃) δ: 1.25-1.33 (15H, m), 3.56 (3H, s), 4.46-4.54 (1H, m), 4.88 (2H, s), 6.86-6.88 (2H, m), 7.03 (1H, dd, J=2.7, 8.7 Hz), 7.16-7.19 (4H, m), 7.31-7.34 (2H, m), 7.35-7.38 (2H, m).

(6) Preparation of N-[4-(tert-butyl)benzyl]-N-[2-isopropoxy-4'-(trifluoromethoxy)biphenyl-5-yl]oxamic Acid (Compound No. 91)

The title compound was obtained in the same manner as the Example 4(4) using the following raw material.
Raw material: methyl N-[4-(tert-butyl)benzyl]-N-[2-isopropoxy-4'-(trifluoromethoxy)biphenyl-5-yl]oxamate Yield: 44.1% (white solid).
¹H-NMR (DMSO-d₆) δ: 1.20-1.24 (15H, m), 4.57-4.65 (1H, m), 4.87 (2H, s), 7.01 (1H, d, J=2.4 Hz), 7.10-7.19 (4H, m), 7.34-7.38 (4H, m), 7.46-7.49 (2H, m).

Example 92

Preparation of N-[2-benzyloxy-4'-(trifluoromethoxy)biphenyl-5-yl]-N-[4-(tert-butyl)benzyl]oxamic Acid (Compound No. 92)

(1) Preparation of 2-benzyloxy-5-nitro-4'-(trifluoromethoxy)biphenyl

The title compound was obtained in the same manner as the Example 65(2) using the following raw materials.
Raw materials: 2-fluoro-5-nitro-4'-(trifluoromethoxy)biphenyl (compound of Example 91(1)) and benzylalcohol.
Yield: 81.4% (white solid).
¹H-NMR (CDCl₃) δ: 5.23 (2H, s), 7.09 (1H, d, J=9.0 Hz), 7.26-7.37 (7H, m), 7.58-7.61 (2H, m), 8.20-8.25 (2H, m).

(2) Preparation of 5-amino-2-benzyloxy-4'-(trifluoromethoxy)biphenyl

The title compound was obtained in the same manner as the Example 3(2) using the following raw material.
Raw material: 2-benzyloxy-5-nitro-4'-(trifluoromethoxy)biphenyl.
Yield: 94.1% (yellow-brown oil).
$^1$H-NMR (CDCl$_3$) δ: 3.51 (2H, brs), 4.91 (2H, s), 6.60-6.69 (2H, m), 6.89 (1H, d, J=8.7 Hz), 7.21-7.32 (7H, m), 7.54-7.57 (2H, m).

(3) Preparation of Methyl N-[2-benzyloxy-4'-(trifluoromethoxy)biphenyl-5-yl]oxamate The title compound was obtained in the same manner as the Example 3(3) using the following raw materials.
Raw materials: 5-amino-2-benzyloxy-4'-(trifluoromethoxy)biphenyl and methyl chloroglyoxylate.
Yield: 78.4% (light orange solid).
$^1$H-NMR (CDCl$_3$) δ: 3.97 (3H, s), 5.08 (2H, s), 7.04 (1H, d, J=9.0 Hz), 7.26-7.36 (7H, m), 7.54-7.66 (4H, m), 8.81 (1H, brs).

(4) Preparation of Methyl N-[2-benzyloxy-4'-(trifluoromethoxy)biphenyl-5-yl]-N-[4-(tert-butyl)benzyl]oxamate The title compound was obtained in the same manner as the Example 1(1) using the following raw materials.
Raw materials: methyl N-[2-benzyloxy-4'-(trifluoromethoxy)biphenyl-5-yl]oxamate and 4-(tert-butyl)benzyl bromide.
Yield: 70.1% (colorless oil).
$^1$H-NMR (CDCl$_3$) δ: 1.30 (9H, s), 3.55 (3H, s), 4.88 (2H, s), 5.07 (2H, s), 6.89 (1H, d, J=3.0 Hz), 6.94 (1H, d, J=8.7 Hz), 7.04 (1H, dd, J=3.0, 8.7 Hz), 7.14-7.19 (4H, m), 7.24-7.41 (9H, m).

(5) Preparation of N-[2-benzyloxy-4'-(trifluoromethoxy)biphenyl-5-yl]-N-[4-(tert-butyl)benzyl]oxamic Acid (Compound No. 92)

The title compound was obtained in the same manner as the Example 4(4) using the following raw material.
Raw material: methyl N-[2-benzyloxy-4'-(trifluoromethoxy)biphenyl-5-yl]-N-[4-(tert-butyl)benzyl]oxamate Yield: 47.5% (white solid).
$^1$H-NMR (DMSO-d$_6$) δ: 1.25 (9H, s), 4.89 (2H, s), 5.13 (2H, s), 7.04-7.24 (5H, m), 7.32-7.38 (9H, m), 7.49-7.53 (2H, m).

Example 93

Preparation of N-[4-(tert-butyl)benzyl]-N-[2-diethylamino-4'-(trifluoromethoxy)biphenyl-5-yl]oxamic Acid (Compound No. 93).

(1) Preparation of 2-diethylamino-5-nitro-4'-(trifluoromethoxy)biphenyl

The title compound was obtained in the same manner as the Example 88(1) using the following raw materials.
Raw materials: 2-fluoro-5-nitro-4'-(trifluoromethoxy)biphenyl (compound of Example 91(1)) and diethylamine.
Yield: 40.1% (yellow oil).
$^1$H-NMR (CDCl$_3$) δ: 0.97 (6H, t, J=7.2 Hz), 3.04 (4H, q, J=7.2 Hz), 7.02 (1H, d, J=9.0 Hz), 7.26-7.03 (2H, m), 7.51-7.56 (2H, m), 8.03 (1H, d, J=2.7 Hz), 8.12 (1H, dd, J=2.7, 9.0 Hz).

(2) Preparation of 5-amino-2-diethylamino-4'-(trifluoromethoxy)biphenyl

The title compound was obtained in the same manner as the Example 3(2) using the following raw material.
Raw material: 2-diethylamine-5-nitro-4'-(trifluoromethoxy)biphenyl.
Yield: 95.1% (yellow-green oil).
$^1$H-NMR (CDCl$_3$) δ: 0.85 (6H, t, J=7.2 Hz), 2.76 (4H, q, J=7.2 Hz), 3.53 (2H, brs), 6.60-6.67 (2H, m), 6.97 (1H, d, J=8.4 Hz), 7.17-7.20 (2H, m), 7.51-7.56 (2H, m).

(3) Preparation of Methyl N-[2-diethylamino-4'-(trifluoromethoxy)biphenyl-5-yl]oxamate The title compound was obtained in the same manner as the Example 3(3) using the following raw materials.
Raw materials: 5-amino-2-diethylamino-4'-(trifluoromethoxy)biphenyl and methyl chloroglyoxylate.
Yield: 85.6% (light green solid).
$^1$H-NMR (CDCl$_3$) δ: 0.89 (6H, t, J=7.2 Hz), 2.85 (4H, q, J=7.2 Hz), 3.97 (3H, s), 7.09 (1H, d, J=8.7 Hz), 7.21-7.24 (2H, m), 7.41 (1H, d, J=2.7 Hz), 7.56-7.59 (2H, m), 7.62 (1H, dd, J=2.7, 8.7 Hz), 8.79 (1H, brs).

(4) Preparation of Methyl N-[4-(tert-butyl)benzyl]-N-[2-diethylamino-4'-(trifluoromethoxy)biphenyl-5-yl]oxamate The title compound was obtained in the same manner as the Example 1(1) using the following raw materials.
Raw materials: methyl N-[2-diethylamino-4'-(trifluoromethoxy)biphenyl-5-yl]oxamate and 4-(tert-butyl)benzyl bromide.
Yield: 88.1% (colorless oil).
$^1$H-NMR (CDCl$_3$) δ: 0.86 (6H, t, J=7.2 Hz), 1.29 (9H, s), 2.83 (4H, q, J=7.2 Hz), 3.54 (3H, s), 4.88 (2H, s), 6.77 (1H, d, J=2.4 Hz), 6.96-6.97 (2H, m), 7.15-7.18 (4H, m), 7.29-7.33 (2H, m), 7.38-7.41 (2H, m).

(5) Preparation of N-[4-(tert-butyl)benzyl]-N-[2-diethylamino-4'-(trifluoromethoxy)biphenyl-5-yl]oxamic Acid (Compound No. 93)

The title compound was obtained in the same manner as the Example 4(4) using the following raw material.
Raw material: methyl N-[4-(tert-butyl)benzyl]-N-[2-diethylamino-4'-(trifluoromethoxy)biphenyl-5-yl]oxamate Yield: 64.7% (white solid).
$^1$H-NMR (DMSO-d$_6$) δ: 0.79 (6H, t, J=7.2 Hz), 1.23 (9H, s), 2.78 (4H, q, J=7.2 Hz), 4.87 (2H, s), 6.88 (1H, d, J=2.1 Hz), 7.07-7.14 (4H, m), 7.32-7.38 (4H, m), 7.48-7.50 (2H, m), 13.93 (1H, brs).

Example 94

Preparation of N-[4-(tert-butyl)benzyl]-N-[2-dimethylamino-4'-(trifluoromethoxy)biphenyl-5-yl]oxamic Acid (Compound No. 94)

(1) Preparation of 2-dimethylamino-5-nitro-4'-(trifluoromethoxy)biphenyl

The title compound was obtained in the same manner as the Example 88(1) using the following raw materials.
Raw materials: 2-fluoro-5-nitro-4'-(trifluoromethoxy)biphenyl (compound of Example 91(1)) and dimethylamine hydrochloride.
Yield: 99.9% (yellow solid).
$^1$H-NMR (CDCl$_3$) δ: 2.71 (6H, s), 6.95 (1H, d, J=9.0 Hz), 7.26-7.30 (2H, m), 7.50-7.55 (2H, m), 8.06 (1H, d, J=3.0 Hz), 8.13 (1H, dd, J=3.0, 9.0 Hz).

(2) Preparation of 5-amino-2-dimethylamino-4'-(trifluoromethoxy)biphenyl

The title compound was obtained in the same manner as the Example 3(2) using the following raw material.
Raw material: 2-dimethylamino-5-nitro-4'-(trifluoromethoxy)biphenyl.
Yield: 99.9% (blue oil).
$^1$H-NMR (CDCl$_3$) δ: 2.44 (6H, s), 3.50 (2H, brs), 6.60 (1H, d, J=2.7 Hz), 6.65 (1H, dd, J=2.7, 8.7 Hz), 6.94 (1H, d, J=8.7 Hz), 7.19-7.22 (2H, m), 7.56-7.60 (2H, m).

(3) Preparation of Methyl N-[2-dimethylamino-4'-(trifluoromethoxy)biphenyl-5-yl]oxamate The title compound was obtained in the same manner as the Example 3(3) using the following raw materials.
Raw materials: 5-amino-2-dimethylamino-4'-(trifluoromethoxy)biphenyl and methyl chloroglyoxylate.
Yield: 82.1% (green solid).
$^1$H-NMR (CDCl$_3$) δ: 2.54 (6H, s), 3.97 (3H, s), 7.05 (1H, d, J=8.7 Hz), 7.23-7.26 (2H, m), 7.40 (1H, d, J=2.7 Hz), 7.56-7.63 (3H, m), 8.78 (1H, brs).

(4) Preparation of Methyl N-[4-(tert-butyl)benzyl]-N-[2-dimethylamino-4'-(trifluoromethoxy)biphenyl-5-yl]oxamate The title compound was obtained in the same manner as the Example 1(1) using the following raw materials.
Raw materials: methyl N-[2-dimethylamino-4'-(trifluoromethoxy)biphenyl-5-yl]oxamate and 4-(tert-butyl)benzyl bromide.
Yield: 66.8% (brown oil).
$^1$H-NMR (CDCl$_3$) δ: 1.29 (9H, s), 2.51 (6H, s), 3.56 (3H, s), 4.86 (2H, s), 6.74 (1H, d, J=2.7 Hz), 6.89 (1H, d, J=8.4 Hz), 6.98 (1H, dd, J=2.7, 8.4 Hz), 7.16-7.20 (4H, m), 7.30-7.33 (2H, m), 7.40-7.43 (2H, m).

(5) Preparation of N-[4-(tert-butyl)benzyl]-N-[2-dimethylamino-4'-(trifluoromethoxy)biphenyl-5-yl]oxamic Acid (Compound No. 94)

The title compound was obtained in the same manner as the Example 4(4) using the following raw material.
Raw material: methyl N-[4-(tert-butyl)benzyl]-N-[2-dimethylamino-4'-(trifluoromethoxy)biphenyl-5-yl]oxamate Yield: 85.5% (white solid).
$^1$H-NMR (DMSO-d$_6$) δ: 1.24 (9H, s), 2.45 (6H, s), 4.85 (2H, s), 6.87 (1H, d, J=2.7 Hz), 7.03 (1H, d, J=8.7 Hz), 7.10-7.15 (3H, m), 7.32-7.35 (2H, m), 7.37-7.40 (2H, m), 7.50-7.53 (2H, m), 13.88 (1H, brs).

Example 95

Preparation of N-[4-(tert-butyl)benzyl]-N-[2-dimethylamino-4-methyl-4'-(trifluoromethoxy)biphenyl-5-yl]oxamic Acid (Compound No. 95)

(1) Preparation of 2-fluoro-5-nitro-4-methyl-4'-(trifluoromethoxy)biphenyl

The title compound was obtained in the same manner as the Example 1(3) using the following raw materials.
Raw materials: 4-(trifluoromethoxy)boronic acid and 5-bromo-4-fluoro-2-methylnitrobenzene.
Yield: 97.9% (orange solid).
$^1$H-NMR (CDCl$_3$) δ: 2.67 (3H, s), 7.15 (1H, d, J=10.8 Hz), 7.31-7.35 (2H, m), 7.57-7.61 (2H, m), 8.17 (1H, d, J=7.5 Hz).

(2) Preparation of 2-dimethylamino-4-methyl-5-nitro-4'-(trifluoromethoxy)biphenyl The title compound was obtained in the same manner as the Example 88(1) using the following raw materials.
Raw materials: 2-fluoro-5-nitro-4-methyl-4'-(trifluoromethoxy)biphenyl and dimethylamine hydrochloride.
Yield: 99.9% (yellow solid).
$^1$H-NMR (CDCl$_3$) δ: 2.68 (9H, s), 6.75 (1H, s), 7.24-7.29 (2H, m), 7.45-7.54 (2H, m), 7.99 (1H, s).

(3) Preparation of 5-amino-2-dimethylamino-4-methyl-4'-(trifluoromethoxy)biphenyl The title compound was obtained in the same manner as the Example 3(2) using the following raw material.
Raw material: 2-dimethylamino-4-methyl-5-nitro-4'-(trifluoromethoxy)biphenyl.
Yield: 93.5% (pale yellow oil).
$^1$H-NMR (CDCl$_3$) δ: 2.21 (3H, s), 2.48 (6H, s), 3.55 (2H, brs), 6.58 (1H, s), 6.89 (1H, s), 7.18-7.29 (2H, m), 7.52-7.59 (2H, m).

(4) Preparation of Methyl N-[2-dimethylamino-4-methyl-4'-(trifluoromethoxy)biphenyl-5-yl]oxamate The title compound was obtained in the same manner as the Example 3(3) using the following raw materials.
Raw materials: 5-amino-2-dimethylamino-4-methyl-4'-(trifluoromethoxy)biphenyl and methyl chloroglyoxylate.
Yield: 70.2% (white solid).
$^1$H-NMR (DMSO-d$_6$) δ: 2.19 (3H, s), 2.48 (6H, s), 3.84 (3H, s), 6.97 (1H, s), 7.11 (1H, s), 7.37-7.42 (2H, m), 7.60-7.65 (2H, m), 10.26 (1H, brs).

(5) Preparation of Methyl N-[4-(tert-butyl)benzyl]-N-[2-dimethylamino-4-methyl-4'-(trifluoromethoxy)biphenyl-5-yl]oxamate The title compound was obtained in the same manner as the Example 1(1) using the following raw materials.

Raw materials: methyl N-[2-dimethylamino-4-methyl-4'-(trifluoromethoxy)biphenyl-5-yl]oxamate and 4-(tert-butyl)benzyl bromide.

Yield: 77.2% (white solid).

$^1$H-NMR (CDCl$_3$) δ: 1.28 (9H, s), 2.20 (3H, s), 2.50 (6H, s), 3.51 (3H, s), 4.12 (1H, d, J=13.8 Hz), 5.40 (1H, d, J=13.8 Hz), 6.38 (1H, s), 6.78 (1H, s), 7.09-7.16 (4H, m), 7.23-7.31 (4H, m).

(6) Preparation of N-[4-(tert-butyl)benzyl]-N-[2-dimethylamino-4-methyl-4'-(trifluoromethoxy)biphenyl-5-yl]oxamic Acid (Compound No. 95)

The title compound was obtained in the same manner as the Example 4(4) using the following raw material.

Raw material: methyl

N-[4-(tert-butyl)benzyl]-N-[2-dimethylamino-4-methyl-4'-(trifluoromethoxy)biphenyl-5-yl]oxamate Yield: 52.6% (white solid).

Major isomer: $^1$H-NMR (DMSO-d$_6$) δ: 1.23 (9H, s), 2.17 (3H, s), 2.45 (6H, s), 4.14 (1H, d, J=13.8 Hz), 5.24 (1H, d, J=13.8 Hz), 6.37 (1H, s), 6.92 (1H, s), 7.08-7.14 (2H, m), 7.27-7.42 (6H, m).

Minor isomer: $^1$H-NMR (DMSO-d$_6$) δ: 1.22 (9H, s), 1.98 (3H, s), 2.44 (6H, s), 4.38-4.47 (1H, m), 4.83-4.92 (1H, m), 6.40 (1H, s), 6.88 (1H, s), 7.08-7.42 (8H, m).

Test Example 1

Human PAI-1 Inhibitory Activity

[Method]

In a 96-well multiplate (black), 1.5 μA of DMSO solution of the present application compound prepared to achieve 80-fold the test concentration (=the final concentration when fluorogenic substrate is added) was diluted with 52.5 μl of pH7.5 Tris buffer. To this solution, 6 μl of 80 nM recombinant human PAI-1 (Molecular Innovations, Inc.) solution prepared by Tris buffer was added, and incubated for 5 minutes at room temperature. Furthermore, 30 μl of 800 IU/ml two-chain tPA (Activity Standard; American diagnostica, inc.) prepared by Tris buffer was added, and the mixed solution was incubated for 15 minutes at room temperature. To this, 30 μl of 400 μM fluorogenic substrate (Pyr-Gly-Arg-MCA; Peptide Institute, Inc.) for tPA prepared by Tris buffer was added and reacted for 30 minutes at room temperature. Every 5 minutes from the reaction start, fluorescence (excitation wavelength=360 nm, emission wavelength=465 nm) was measured using SPECTRAFLUOR (TECAN G.M.B.H.) or GENios (TECAN G.M.B.H.), and increased intensity of fluorescence by 30 minute reaction were measured. Increments of fluorescence by 30 minutes reaction in the presence or absence (tPA alone) of PAI-1 in the control wells (DMSO) were calculated respectively, and their differences ([data in the absence of PAI-1]−[data in the presence of PAI-1]) being PAI-1 activity 100%, the inhibition rates of PAI-1 activity in the presence of the present application compound were obtained.

<Composition of pH7.5 Tris Buffer)

50 mM Tris 150 mM NaCl

10 μg/ml BSA 0.01% Tween80 (SIGMA-ALDRICH Corporation)

[Results]

In the following, inhibition rates of human PAI-1 activity are shown.

TABLE 4

| Compound Number | Inhibition Rate of Human PAI-1 Activity (%) Concentration of Present Application Compound | | | |
|---|---|---|---|---|
| | 25 μM | 10 μM | 5 μM | 2.5 μM |
| 1 | NT | 62 | 27 | 15 |
| 2 | NT | 49 | 22 | 14 |
| 3 | NT | 31 | 15 | NT |
| 4 | NT | 43 | 16 | NT |
| 5 | NT | 43 | 21 | 16 |
| 6 | NT | 12 | 6 | NT |
| 7 | NT | 89 | 58 | 26 |
| 8 | NT | 95 | 75 | 43 |
| 9 | NT | 96 | 82 | 42 |
| 10 | 34 | 10 | NT | NT |
| 11 | 82 | 32 | NT | NT |
| 12 | NT | 92 | 80 | 45 |
| 13 | 75 | 14 | NT | NT |
| 14 | 67 | 6 | NT | NT |
| 15 | 79 | 47 | 16 | NT |
| 16 | 61 | 5 | NT | NT |
| 17 | 61 | 4 | NT | NT |
| 18 | 66 | 59 | 25 | NT |
| 19 | 77 | 31 | 6 | NT |
| 20 | 52 | 5 | NT | NT |
| 21 | 33 | 3 | NT | NT |
| 22 | 22 | 1 | NT | NT |
| 23 | 76 | 22 | 3 | NT |
| 24 | 74 | 35 | 7 | NT |
| 25 | 90 | 73 | 33 | NT |
| 26 | 92 | 80 | 38 | NT |
| 27 | 98 | 55 | 17 | NT |
| 28 | 34 | 3 | NT | NT |
| 29 | 87 | 75 | 33 | NT |
| 30 | 90 | 80 | 35 | NT |
| 31 | 93 | 88 | 41 | NT |
| 32 | 93 | 54 | 20 | NT |
| 33 | 20 | 3 | NT | NT |
| 34 | 81 | 38 | 15 | NT |
| 35 | 38 | 15 | 7 | NT |
| 36 | 67 | 25 | 10 | NT |
| 37 | 96 | 56 | 25 | NT |
| 38 | >99 | 61 | 26 | NT |
| 39 | 92 | 45 | 21 | NT |
| 40 | 68 | 26 | 14 | NT |
| 41 | >99 | 62 | 27 | 11 |
| 42 | >99 | 74 | 30 | 16 |
| 43 | >99 | 84 | 37 | 15 |
| 44 | 96 | 79 | 40 | 15 |
| 45 | 96 | 64 | 27 | 14 |
| 46 | 84 | 79 | 44 | 15 |
| 47 | 87 | 75 | 37 | 12 |
| 48 | NT | 94 | 63 | 29 |
| 49 | 84 | 91 | 59 | 26 |
| 50 | 94 | 73 | 38 | 18 |
| 51 | 81 | 44 | 22 | 9 |
| 52 | 94 | 89 | 58 | 30 |
| 53 | 90 | 95 | 63 | 30 |
| 54 | 91 | 92 | 61 | 26 |
| 55 | 87 | 94 | 66 | 28 |
| 56 | 91 | 94 | 65 | 32 |
| 57 | 91 | 83 | 43 | 18 |
| 58 | 88 | 88 | 56 | 23 |

TABLE 4-continued

| Compound Number | Inhibition Rate of Human PAI-1 Activity (%) Concentration of Present Application Compound | | | |
|---|---|---|---|---|
| | 25 μM | 10 μM | 5 μM | 2.5 μM |
| 59 | NT | 91 | 64 | 29 |
| 60 | 71 | 36 | 19 | NT |
| 61 | 31 | 11 | 10 | NT |
| 62 | 89 | 85 | 56 | 26 |
| 63 | 29 | 11 | NT | NT |
| 64 | 85 | 86 | 59 | 30 |
| 65 | 89 | 87 | 81 | 46 |
| 66 | NT | 91 | 76 | 35 |
| 67 | 88 | 92 | 75 | 40 |
| 68 | 91 | 91 | 73 | 38 |
| 69 | NT | 95 | 87 | 53 |
| 70 | 91 | 91 | 65 | 32 |
| 71 | 87 | 92 | 74 | 46 |
| 72 | 94 | 95 | 80 | 52 |
| 73 | NT | 89 | 81 | 51 |
| 74 | NT | 84 | 84 | 57 |
| 75 | 93 | 94 | 77 | 48 |
| 76 | 64 | 35 | 18 | 3 |
| 77 | 73 | 92 | 90 | 66 |
| 78 | 85 | 95 | 79 | 46 |
| 79 | NT | 89 | 83 | 55 |
| 80 | 92 | 89 | 64 | 37 |
| 81 | 82 | 89 | 64 | 35 |
| 82 | 98 | 94 | 70 | 39 |
| 83 | 97 | 91 | 69 | 42 |
| 84 | >99 | 85 | 58 | 32 |
| 85 | 98 | 80 | 50 | 17 |
| 86 | 89 | 92 | 78 | 46 |
| 87 | NT | 90 | 79 | 49 |
| 88 | NT | 98 | 89 | 65 |
| 89 | 94 | 98 | 81 | 49 |
| 90 | 94 | 70 | 39 | 19 |
| 91 | NT | 96 | 87 | 57 |
| 92 | NT | 95 | 78 | 45 |
| 93 | NT | 84 | 93 | 71 |
| 94 | NT | 93 | 87 | 55 |
| 95 | NT | 92 | 90 | 63 |

NT: Not Tested

Test Example 2

Human PAI-1 Inhibitory Activity

[Method]

Except using the pH7.4 HEPES buffer instead of pH7.5 Tris buffer, and the change of incubation time from 15 minutes to 10 minutes of the mixed solution added by two-chain tPA solution, tests were carried out similarly to the Test Example 1.

<Compotion of pH7.4 HEPES Buffer>

0.1 M HEPES 0.1 M NaCl 1 mM EDTA 0.1% Polyethylene glycol 8,000 (Hampton Research Corporation)

2 mM Dimethyldecylphoshine oxide [Apo-10] (Fluka Corporation)

[Results]

In the following, inhibition rates of human PAI-1 activity are shown.

TABLE 5

| Compound Number | Inhibition Rate of Human PAI-1 Activity (%) Concentration of Present Application Compound | | | |
|---|---|---|---|---|
| | 3 μM | 1 μM | 0.3 μM | 0.1 μM |
| 8 | 86 | 19 | 3 | 1 |
| 9 | 84 | 18 | 2 | 0 |
| 18 | 97 | 30 | 3 | 0 |
| 26 | 99 | 35 | 7 | 0 |
| 48 | 99 | 33 | 0 | 0 |
| 52 | 76 | 18 | 8 | 4 |
| 54 | 96 | 26 | 0 | 0 |
| 56 | 96 | 21 | 10 | 0 |
| 59 | >99 | 68 | 19 | 1 |
| 65 | >99 | 34 | 9 | 0 |
| 66 | >99 | 22 | 9 | 0 |
| 68 | 97 | 33 | 0 | 0 |
| 69 | 97 | 60 | 2 | 4 |
| 70 | 95 | 27 | 3 | 2 |
| 72 | >99 | 35 | 1 | 0 |
| 73 | >99 | 34 | 5 | 2 |
| 74 | 98 | 63 | 7 | 0 |
| 77 | >99 | 38 | 1 | 6 |
| 78 | >99 | 33 | 8 | 11 |
| 79 | >99 | 64 | 13 | 9 |
| 86 | >99 | 66 | 13 | 3 |
| 88 | 99 | 36 | 1 | 10 |
| 91 | 96 | 43 | 16 | 9 |
| 92 | 98 | 64 | 15 | 5 |
| 93 | 98 | 48 | 10 | 0 |
| 94 | 96 | 40 | 2 | 4 |
| 95 | 95 | 54 | 18 | 7 |

From the above results, concentration of the present application compound that inhibits 50% of the human PAI-1 activity ($IC_{50}$) was obtained. The results are shown on the following table.

TABLE 6

| Compound Number | $IC_{50}$ (μM) |
|---|---|
| 8 | 1.63 |
| 9 | 1.71 |
| 18 | 1.25 |
| 26 | 1.17 |
| 48 | 1.14 |
| 52 | 1.84 |
| 54 | 1.32 |
| 56 | 1.40 |
| 59 | 0.66 |
| 65 | 1.15 |
| 66 | 1.14 |
| 68 | 1.18 |
| 69 | 0.88 |
| 70 | 1.32 |
| 72 | 1.06 |
| 73 | 1.13 |
| 74 | 0.82 |
| 77 | 1.04 |
| 78 | 1.08 |
| 79 | 0.74 |
| 86 | 0.73 |
| 88 | 1.13 |

Test Example 3

Rat PAI-1 Inhibitory Activity

[Method]

Similar tests were carried out using recombinant rat PAI-1 (Molecular Innovations, Inc.) instead of recombinant human PAI-1 in the Test Example 2.

[Results]

In the following, inhibition rates of rat PAI-1 activity are shown.

TABLE 7

| Compound Number | Inhibition Rate of Rat PAI-1 Activity (%) Concentration of Present Application Compound | | | |
|---|---|---|---|---|
| | 10 μM | 3 μM | 1 μM | 0.3 μM |
| 8 | 90 | 46 | 14 | 2 |
| 9 | >99 | 50 | 16 | 1 |
| 18 | 88 | 85 | 22 | 0 |
| 26 | 87 | 70 | 14 | 0 |
| 48 | 97 | 61 | 12 | 0 |
| 52 | 97 | 49 | 6 | 0 |
| 54 | 94 | 76 | 11 | 0 |
| 56 | >99 | 71 | 23 | 0 |
| 59 | >99 | >99 | 38 | 7 |
| 65 | 76 | 85 | 17 | 3 |
| 66 | 89 | 83 | 27 | 2 |
| 68 | >99 | 84 | 14 | 0 |
| 69 | >99 | 93 | 32 | 9 |
| 70 | >99 | 66 | 11 | 0 |
| 72 | 96 | 76 | 8 | 0 |
| 73 | 70 | 81 | 26 | 2 |
| 74 | >99 | 98 | 39 | 5 |
| 77 | 75 | 84 | 37 | 0 |
| 78 | 89 | 84 | 12 | 4 |
| 79 | >99 | 97 | 35 | 0 |
| 86 | 88 | 90 | 29 | 3 |
| 88 | 81 | 82 | 12 | 0 |
| 91 | 87 | 78 | 17 | 4 |
| 92 | 67 | 73 | 40 | 8 |
| 93 | 78 | 90 | 26 | 8 |
| 94 | 97 | 77 | 8 | 0 |
| 95 | 97 | 84 | 16 | 2 |

From the above results, concentration of the present application compound that inhibits 50% of the rat PAI-1 activity ($IC_{50}$) was obtained. The results are shown on the following table.

TABLE 8

| Compound Number | $IC_{50}$ (μM) |
|---|---|
| 8 | 3.13 |
| 9 | 2.76 |
| 18 | 1.61 |
| 26 | 2.16 |
| 48 | 2.45 |
| 52 | 3.04 |
| 54 | 2.04 |
| 56 | 1.87 |
| 59 | 1.11 |
| 65 | 1.72 |
| 66 | 1.55 |
| 68 | 1.79 |
| 69 | 1.28 |
| 70 | 2.30 |
| 72 | 2.14 |
| 73 | 1.82 |
| 74 | 1.14 |
| 77 | 1.42 |
| 78 | 1.84 |
| 79 | 1.18 |
| 86 | 1.39 |
| 88 | 1.89 |

Test Example 4

Human PAI-1 Inhibitory Activity

[Method]

100 μl of tPA solution where one-chain recombinant tPA (hereinafter refereed to as tPA; American diagnostica, inc.) diluted with Buffer A to achieve a concentration of 10 μg/ml was added to each well of 96-well plate (Nunc Maxisorp), incubated for one night at 40 to coated with tPA. Then, after suction of tPA solution from the 96-well plate, rinsed successively with Buffer A and Buffer B.

To Buffer B, solutions of the present application compound dissolved with DMSO (final DMSO concentration: 0.2%) and recombinant human PAI-1 (Molecular Innovations, Inc.) were added and blended so that the final concentrations would be 0.1 to 3.0 μM and 50 ng/ml respectively, and were incubated for 15 minutes on ice. These mixed solutions were added to rinsed 96-well plates at 100 μl/well, and incubated for 60 minutes at room temperature. To prepare calibration curve, PAI-1 solutions without the present application compound (solutions where the final concentrations being 100, 50, 25, 12.5, 6.25, 3.13, 1.56 ng/ml PAI-1) were added at 100 μl/well, and were incubated for 60 minutes at room temperature, as standard.

After incubation, the reaction mixture was suction removed, and rinsed each well with Wash Buffer. Next, anti-human PAI-1 monoclonal antibody (PROGEN Inc.) diluted with Buffer C to be 3.0 μg/ml was added to the 96-well plate at 100 μl/well, and incubated for 1 hour at room temperature. After rinsing each well with Wash Buffer, alkaline phosphatase-labeled goat anti-mouse IgG (H+L) (Jackson ImmunoResearch, Inc.) diluted with Buffer D to be 0.12 μg/ml was added at 100 μl/well, and incubated for 1 hour at room temperature. After rinsing each well with Wash Buffer, 1.0 mg/ml p-Nitrophenyl Phosphate (SIGMA) was added to the 96-well plate at 100 μl/well to start the reaction. After 30 to 60 minutes, 25 μl of 0.5 N NaOH was added to stop the reaction, and the absorbance was measured at 405 nm using a multiplate reader (GENios; TECAN G.M.B.H.).

Based on the calibration curve prepared from the standard wells, amounts of PAI-1 bound to tPA in the wells treated with the present application compound were calculated, and the PAI-1 inhibition rates by the present application compounds were obtained by the following equation.

[PAI-1 Inhibition Rate (%)]=[1−(amount of PAI-1 bound to tPA on the well treated with the present application compound)/(amount of PAI-1 bound to tPA on the well treated with PAI-1 solution without present application compound (solution with the final concentration of 50 ng/ml PAI-1)]× 100

<Composition of Buffer A>

0.1 M Tris-HCl-150

150 mM NaCl pH 7.7

<Composition of Buffer B>

50 mM sodium phosphate 0.1 M NaCl 1 mM EDTA pH 6.6

<Composition of Buffer C>

50 mM sodium phosphate 100 mM NaCl pH 7.4

<Composition of Buffer D>

0.01 M Tris-HCl 0.25 M NaCl pH 8.0

<Composition of Wash Buffer>

0.05% Tween 20

0.1% BSA in Buffer A

<Composition of p-Nitrophenyl Phosphate Solution>

1 M Diethanolamine 0.5 mM $MgCl_2$ p-Nitrophenyl phosphate pH 9.8

In the following, inhibition rates of human PAI-1 activities are shown.

TABLE 9

| Compound Number | Inhibition Rate of Human PAI-1 Activity (%) Concentration of Present Application Compound | | | |
|---|---|---|---|---|
| | 3 µM | 1 µM | 0.3 µM | 0.1 µM |
| 8 | 19 | 15 | 5 | 0 |
| 9 | 15 | 3 | 1 | 0 |
| 18 | 32 | 10 | 6 | 0 |
| 54 | 32 | 7 | 0 | 0 |
| 56 | 29 | 9 | 9 | 4 |
| 65 | 49 | 20 | 10 | 0 |
| 66 | 53 | 37 | 15 | 6 |
| 69 | 70 | 30 | 16 | 0 |
| 70 | 55 | 9 | 0 | 0 |
| 74 | 56 | 22 | 6 | 0 |
| 77 | 73 | 34 | 21 | 12 |
| 78 | 33 | 4 | 6 | 0 |
| 79 | 73 | 41 | 18 | 8 |
| 86 | 40 | 17 | 0 | 0 |
| 88 | 36 | 6 | 0 | 0 |

Test Example 5

Anti-thrombotic Activity (Rat AV Shunt Model)

AV shunt model using 7-week old male Crlj:CD(SD) rat was prepared, and anti thrombotic activities when the present application compound was administered orally were examined.

[Method]

(1) Preparation of Administering Solution of Test Compound

Required amount of the test compound was weighed, suspended by adding 0.5% CMC (carboxymethylcellulose)-Na solution little by little, and prepared the solutions so that the final solutions being 2 mg/ml and 6 mg/ml using a graduated cylinder (10 mg/kg and 30 mg/kg solutions, respectively). 5 ml was prepared for 1 course.

(2) Administration

To 7-week old Crlj:CD(SD) male rats, vehicle (0.5% CMC-Na solution) 5 ml/kg or the administering solution of test compound 5 ml/kg (10 mg/kg or 30 mg/kg) was administered orally for 4 days. The administration on the 4th day was carried out about 1 hour before the following perfusion start.

(3) Preparation of AV Shunt Model and Measurement of Thrombus Weight

Put a 6.5 cm silk thread (Matsuda Ika Kogyou; No. 1-0) through in an 8 cm No. 7 polyethylene tube (Hibiki), connect No. 3 tubes (12.5 cm) to both ends via No. 5 tube (1.5 cm), and a catheter for shunt was prepared. On the connected part where the silk thread is through, parafilm was wrapped around to avoid blood leakage.

Rats were anesthetized with pentobarbital (50 mg/kg; intraperitoneally). Saline was filled in the above catheter, and both ends of the catheter were inserted in right carotid artery and left carotid artery, respectively, and blood was circulated. 30 minutes later, the catheter was pinched with forceps to stop blood flow, and tube parts where the silk thread is through were cut and removed. The silk thread was carefully removed from the tubes, remaining wet weight was weighed after removing the liquid phase by filter paper, and further subtraction of the weight of the silk thread, gives the thrombus weight.

(4) Statistical Treatment

For the thrombus weight in each group, an average value ±standard error (S.E.) was calculated. For the significance test between the vehicle administered group and the present application compound administered group, Dunnett's multiple comparison was carried out (significance level 5%). For the test, the SAS System Release 8.2 (TS2M0) for Windows (Registered Trademark) (SAS Institute Inc.) and its coorperative system EXSAS Ver. 7.10 (Arm Systex Co. Ltd.) were employed.

[Results]

The results are shown in the following.

TABLE 10

| Study Compound | Dose (mg/kg/day) | Number of Examples | Thrombus Weight (mg) |
|---|---|---|---|
| Vehicle (0.5% CMC-Na) | — | 5 | 72.7 ± 2.7 |
| Compound Number 8 | 10 | 5 | 56.7 ± 3.8** |

**$p < 0.01$

INDUSTRIAL APPLICABILITY

The compounds of the present invention have inhibitory action against PAI-1. Therefore, the compounds of the present invention are useful as a medicament for preventive and/or therapeutic treatment of diseases caused by an expression of PAI-1 or an enhancement of PAI-1 activity.

What is claimed is:

1. A compound represented by the following formula (I) or a salt thereof:

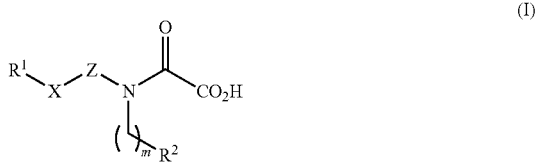

wherein
- $R^1$ represents a $C_{6-10}$ aryl group; or a $C_{6-10}$ aryl group substituted with a group or groups selected from a halogen atom, a cyano group, a nitro group, a $C_{1-6}$ alkyl group, a halogenated $C_{1-6}$ alkyl group, a $C_{1-6}$ alkoxy group, a halogenated $C_{1-6}$ alkoxy group, and a $C_{1-6}$ alkylsulfanyl group,
- $R^2$ represents a $C_{6-10}$ aryl group; or a $C_{6-10}$ aryl group substituted with a group or groups selected from a halogen atom, a hydroxy group, a $C_{1-6}$ alkyl group, a halogenated $C_{1-6}$ alkyl group, a $C_{1-6}$ alkoxy group, a halogenated $C_{1-6}$ alkoxy group, a $C_{1-6}$ alkylsulfanyl group, and a phenyl group,
- X represents a single bond or an oxygen atom,
- Z represents a phenylene group or a substituted phenylene group,
- m represents 0 or 1,
- with the proviso that when $R^1$ is a $C_{6-10}$ aryl group then X is an oxygen atom.

2. The compound according to claim 1 or a salt thereof, wherein Z is a phenylene group; or a phenylene group substituted with a group or groups selected from a halogen atom, a $C_{1-6}$ alkyl group, a halogenated $C_{1-6}$ alkyl group, a carboxy substituted $C_{1-6}$ alkyl group, a $C_{1-6}$ alkoxy group, a halogenated $C_{1-6}$ alkoxy group, a $C_{7-12}$ aralkyloxy group, a $C_{1-6}$ alkyl substituted $C_{7-12}$ aralkyloxy group, and a di-$C_{1-6}$ alkylamino group.

3. A PAI-1 inhibitor which comprises a compound according to claim 1 or a salt thereof.

4. A medicament which comprises a compound according to claim 1 or a pharmacologically acceptable salt thereof.

5. The compound according to claim 1 or a salt thereof, wherein $R^1$ is a $C_{6-10}$ aryl group substituted with a group or groups selected from a halogen atom, a cyano group, a nitro group, a $C_{1-6}$ alkyl group, a halogenated $C_{1-6}$ alkyl group, a $C_{1-6}$ alkoxy group, a halogenated $C_{1-6}$ alkoxy group, and a $C_{1-6}$ alkylsulfanyl group.

6. The compound according to claim 1 or a salt thereof, wherein $R^1$ is a $C_{6-10}$ aryl group substituted with a group or groups selected from a halogenated $C_{1-6}$ alkoxy group and a $C_{1-6}$ alkylsulfanyl group.

7. The compound according to claim 1 or a salt thereof, wherein $R^1$ is a $C_{6-10}$ aryl group substituted with a halogenated $C_{1-6}$ alkoxy group.

* * * * *